US012188088B1

(12) United States Patent
Glezer et al.

(10) Patent No.: US 12,188,088 B1
(45) Date of Patent: Jan. 7, 2025

(54) MULTIPLEXED TARGETED AMPLIFICATION OF POLYNUCLEOTIDES

(71) Applicant: Singular Genomics Systems, Inc, San Diego, CA (US)

(72) Inventors: Eli N. Glezer, Del Mar, CA (US); Daan Witters, San Diego, CA (US); Tung Thanh Le, San Diego, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 0 days.

(21) Appl. No.: 18/335,936

(22) Filed: Jun. 15, 2023

Related U.S. Application Data

(63) Continuation of application No. PCT/US2022/078470, filed on Oct. 20, 2022.

(60) Provisional application No. 63/271,837, filed on Oct. 26, 2021, provisional application No. 63/311,576, filed on Feb. 18, 2022, provisional application No. 63/373,017, filed on Aug. 19, 2022.

(51) Int. Cl.
*C12P 19/34* (2006.01)
*B01L 3/00* (2006.01)
*C12Q 1/6874* (2018.01)

(52) U.S. Cl.
CPC ...... *C12Q 1/6874* (2013.01); *B01L 3/502761* (2013.01); *B01L 2200/0652* (2013.01); *B01L 2200/16* (2013.01); *B01L 2300/0829* (2013.01); *C12Q 2600/16* (2013.01)

(58) Field of Classification Search
USPC .......... 435/6.1, 6.11, 6.12, 91.1, 91.2, 91.51, 435/287.1, 287.2; 436/94, 501; 536/23.1, 24.3, 24.33, 25.3
See application file for complete search history.

(56) References Cited

U.S. PATENT DOCUMENTS

| | | | |
|---|---|---|---|
| 4,318,846 A | 3/1982 | Khanna et al. |
| 4,882,245 A | 11/1989 | Gelorme et al. |
| 4,970,276 A | 11/1990 | Das et al. |
| 5,032,506 A | 7/1991 | Palmer et al. |
| 5,034,506 A | 7/1991 | Summerton et al. |
| 5,066,580 A | 11/1991 | Lee |
| 5,188,934 A | 2/1993 | Menchen et al. |
| 5,235,033 A | 8/1993 | Summerton et al. |
| 5,366,860 A | 11/1994 | Bergot et al. |
| 5,599,675 A | 2/1997 | Brenner |
| 5,641,658 A | 6/1997 | Adams et al. |
| 5,688,648 A | 11/1997 | Mathies et al. |
| 5,750,341 A | 5/1998 | Macevicz |
| 5,763,594 A | 6/1998 | Hiatt et al. |

(Continued)

FOREIGN PATENT DOCUMENTS

| | | |
|---|---|---|
| WO | WO-1989/010977 A1 | 11/1989 |
| WO | WO-1996/007669 A1 | 3/1996 |
| WO | WO-2004/018497 A2 | 3/2004 |
| WO | WO-2017/205336 A1 | 11/2017 |
| WO | WO-2018/148723 A1 | 8/2018 |
| WO | WO-2020/056044 A1 | 3/2020 |

(Continued)

OTHER PUBLICATIONS

"DNA polymerase" from Wikipedia. Printed on Feb. 23, 2024.*

(Continued)

*Primary Examiner* — Frank W Lu
(74) *Attorney, Agent, or Firm* — Mintz, Levin, Cohn, Ferris, Glovsky, Popeo, P.C.; Zachary L. Terranova

(57) ABSTRACT

Disclosed herein, inter alia, are compositions and methods for efficient amplification and sequencing of nucleic acid templates.

21 Claims, 12 Drawing Sheets
Specification includes a Sequence Listing.

(56) References Cited

U.S. PATENT DOCUMENTS

| | | | |
|---|---|---|---|
| 5,800,996 | A | 9/1998 | Lee et al. |
| 5,808,045 | A | 9/1998 | Hiatt et al. |
| 5,847,162 | A | 12/1998 | Lee et al. |
| 5,872,244 | A | 2/1999 | Hiatt et al. |
| 6,060,288 | A * | 5/2000 | Adams .................. C12Q 1/686 |
| | | | 435/6.12 |
| 6,210,891 | B1 | 4/2001 | Nyren et al. |
| 6,218,122 | B1 | 4/2001 | Friend et al. |
| 6,232,465 | B1 | 5/2001 | Hiatt et al. |
| 6,258,540 | B1 | 7/2001 | Lo et al. |
| 6,274,320 | B1 | 8/2001 | Rothberg et al. |
| 6,664,079 | B2 | 12/2003 | Ju et al. |
| 6,724,320 | B2 | 4/2004 | Basson et al. |
| 6,897,012 | B2 | 5/2005 | Hada et al. |
| 6,991,888 | B2 | 1/2006 | Padmanaban et al. |
| 7,057,026 | B2 | 6/2006 | Barnes et al. |
| 7,115,400 | B1 | 10/2006 | Adessi et al. |
| 7,467,632 | B2 | 12/2008 | Lee et al. |
| 7,541,444 | B2 | 6/2009 | Milton et al. |
| 8,003,354 | B2 | 8/2011 | Shen et al. |
| 8,039,817 | B2 | 10/2011 | Feng et al. |
| 8,178,360 | B2 | 5/2012 | Barnes et al. |
| 8,241,573 | B2 | 8/2012 | Banerjee et al. |
| 10,738,072 | B1 | 8/2020 | Graham et al. |
| 2003/0109060 | A1* | 6/2003 | Cook .................. B01J 19/0046 |
| | | | 436/180 |
| 2005/0214812 | A1* | 9/2005 | Li ........................ C12Q 1/6827 |
| | | | 435/6.12 |
| 2008/0000373 | A1 | 1/2008 | Petrucci-Samija et al. |
| 2008/0009420 | A1 | 1/2008 | Schroth et al. |
| 2008/0160559 | A1 | 7/2008 | Carre et al. |
| 2010/0160478 | A1 | 6/2010 | Nilsson et al. |
| 2011/0059865 | A1 | 3/2011 | Smith et al. |
| 2011/0172119 | A1 | 7/2011 | Boutell |
| 2012/0231974 | A1* | 9/2012 | Kim ........................ C40B 50/14 |
| | | | 506/13 |
| 2012/0270305 | A1 | 10/2012 | Reed et al. |
| 2013/0012399 | A1 | 1/2013 | Myers et al. |
| 2013/0344500 | A1 | 12/2013 | Trautman et al. |
| 2015/0079351 | A1 | 3/2015 | Atasoy et al. |
| 2015/0099642 | A1 | 4/2015 | Barany et al. |
| 2016/0310949 | A1 | 10/2016 | Kwang |
| 2017/0022553 | A1 | 1/2017 | Vijayan et al. |
| 2017/0101674 | A1* | 4/2017 | So ........................ C12Q 1/6806 |
| 2018/0216103 | A1* | 8/2018 | Lai ........................ C12Q 1/6806 |
| 2018/0258472 | A1 | 9/2018 | Glezer |
| 2018/0274024 | A1 | 9/2018 | Ju et al. |
| 2018/0361378 | A1* | 12/2018 | Croquette .......... G01N 27/3275 |
| 2019/0048404 | A1 | 2/2019 | Dambacher |
| 2019/0249239 | A1* | 8/2019 | Glökler .................. C40B 20/04 |
| 2019/0355550 | A1 | 11/2019 | Hayworth et al. |
| 2020/0239875 | A1 | 7/2020 | Sabot et al. |
| 2021/0040555 | A1 | 2/2021 | Glezer et al. |
| 2021/0071171 | A1 | 3/2021 | Amorese et al. |
| 2021/0139884 | A1 | 5/2021 | Kellinger et al. |
| 2021/0236651 | A1 | 8/2021 | Mirkin et al. |
| 2021/0317524 | A1 | 10/2021 | Lucero et al. |
| 2021/0373000 | A1 | 12/2021 | Arslan et al. |

FOREIGN PATENT DOCUMENTS

| | | |
|---|---|---|
| WO | WO-2021/133845 A1 | 7/2021 |
| WO | WO-2021/219675 A1 | 11/2021 |
| WO | WO-2022/015913 A1 | 1/2022 |
| WO | WO-2023/130019 A2 | 7/2023 |

OTHER PUBLICATIONS

Aigrain, L. et al. (2016). "Quantitation of next generation sequencing library preparation protocol efficiencies using droplet digital PCR assays—a systematic comparison of DNA library preparation kits for Illumina sequencing," *BMC Genomics* 17(458): 1-11.

Al-Mutairi, N. M. et al. (2019). "Molecular characterization of multidrug-resistant *Mycobacterium tuberculosis* (MDR-TB) isolates identifies local transmission of infection in Kuwait, a country with a low incidence of TB and MDR-TB," *European Journal of Medical Research* 24(38): 1-13.

Arce, S.H. et al. (2013). "Fast and accurate automated cell boundary determination for fluorescence microscopy," *Scientific Reports* 3(2266): 1-6.

Armingol, E. et al. (2021). "Deciphering cell-cell interactions and communication from gene expression," *Nature Reviews Genetics* 22(2): 71-88.

Asp, M. et al. (2020). "Spatially Resolved Transcriptomes—Next Generation Tools for Tissue Exploration," *Bioessays* 42(10): 1900221, pp. 1-16.

Bains, W. et al. (1988). "A novel method for nucleic acid sequence determination," *Journal of theoretical biology* 135(3): 303-307.

Bains, I. et al. (2009). "Quantifying the development of the peripheral naive CD4 T-cell pool in humans," *Immunobiology* 113(22): 5480-5486.

Bentley, D. R. et al. (2008). "Accurate whole human genome sequencing using reversible terminator chemistry," *Nature* 456(7218): 53-59.

Bianchi, D. W. et al. (2012). "Genome-Wide Fetal Aneuploidy Detection by Maternal Plasma DNA Sequencing," *American College of Obstetricians and Gynecologists* 119(5): 1-12.

Carpenter, A. E. et al. (2006). "CellProfiler: image analysis software for identifying and quantifying cell phenotypes," *Genome Biology* 7: R100-100.10.

Chakaya, J. et al. (2021). "Global Tuberculosis Report 2020—Reflections on the Global TB burden, treatment and prevention efforts," *International Journal of Infectious Diseases* 113(Supplement 1): S7-S12.

Chen, A. et al. (2022). "Spatiotemporal transcriptomic atlas of mouse organogenesis using DNA nanoball-patterned arrays," *Cell* 185(10) 1777-1792.

Cho, C. et al. (2021). "Microscopic examination of spatial transcriptome using Seq-Scope," *Cell* 184(13): 3559-3572.

Chung, J. et al. (2019). "Performance evaluation of commercial library construction kits for PCR-based targeted sequencing using a unique molecular identifier," *BMC Genomics* 20(216): 1-10.

Cohen, S. M. (2012). "Postsynthetic Methods for the Functionalization of Metal-Organic Frameworks," *Chemical Reviews* 112(2): 970-1000.

Dennis Lo, Y. M. et al. (2007). "Digital PCR for the molecular detection of fetal chromosomal aneuploidy," 104(32): 13116-13121.

Drmanac, S. et al. (1998). "Accurate sequencing by hybridization for DNA diagnostics and individual genomics," *Nature biotechnology* 16(1): 54-58.

Eminaga, S. et al. (2013). "Quantification of microRNA Expression with Next-Generation Sequencing," *Current Protocols in Molecular Biology* 4(4.17).

Fodor, S. P. et al. (1991). "Light-directed, spatially addressable parallel chemical synthesis," *Science* 251(4995): 767-773.

Furukawa, H. et al. (2013). "The chemistry and applications of metal-organic frameworks," *Science* 341(6149): 1230444.

Ganusov, V. V. et al. (2007) "Do most lymphocytes in humans really reside in the gut?," *Trends in Immunology* 28(12): 514-518.

Ghanta, S. et al. (2010). "Non-Invasive Prenatal Detection of Trisomy 21 Using Tandem Single Nucleotide Polymorphisms," *PLoS One* 5(10): e13184, pp. 1-10.

Haas, K.-H. et al. (1999). "Synthesis, properties and applications of inorganic-organic copolymers (ORMOCER® s)," *Current Opinion in Solid State and Materials Science* 4(6): 571-580.

Haque, I. S. et al. (2017). "Challenges in Using ctDNA to Achieve Early Detection," bioRxiv 237578 [Preprint]. 2017 [cited Jul. 14, 2023] Available from https://doi.org/10.1101/237578.

International Search Report and Written Opinion mailed on Feb. 23, 2023, for PCT application PCT/US2022/078470, filed Oct. 20, 2022, 20 pages.

Kannan, K. et al. (2011). "Recurrent chimeric RNAs enriched in human prostate cancer identified by deep sequencing," *PNAS* 108(22): 9172-9177.

(56) References Cited

OTHER PUBLICATIONS

Klevebring, D. et al. (2014). "Evaluation of Exome Sequencing to Estimate Tumor Burden in Plasma," *PLoS One* 9(8): e104417, pp. 1-10.

Kucharik, M. et al. (2020). "Non-invasive prenatal testing (NIPT) by low coverage genomic sequencing: Detection limits of screened chromosomal microdeletions," *PLoS One* 15(8): 1-15.

Lee, J. et al. (2022). "Recent advances in spatially resolved transcriptomics: challenges and opportunities," *BMC Reports* 55(3): 113-124.

Macosko, E. Z. et al. (2015). "Highly Parallel Genome-wide Expression Profiling of Individual Cells Using Nanoliter Droplets," *Cell* 161(5): 1202-1214.

Maher, C.A. et al. (2009). "Chimeric transcript discovery by paired-end transcriptome sequencing," *PNAS* 106:12353-8 Maher, C.A. et al. (2009). "Transcriptome sequencing to detect fusions in cancer," *Nature* 458(7234): 97-101.

Mandelboum, S. et al. (2019). "Recurrent functional misinterpretation of RNA-seq data caused by sample-specific gene length bias," *PLoS Biology* 17(11): e3000481, pp. 1-15.

Matthias, M. et al. (1992). "Synthesis and Selective Cleavage of an Oligodeoxynucleotide Containing a Bridged Non-Chiral Internucleotide 3'-Phosphoramidate Linkage," *Tetrahedron Letters* 33(48): 7319-22.

McCabe, M. J. et al. (2019). "Development and validation of a targeted gene sequencing panel for application to disparate cancers," *Scientific Reports* 9(17052).

McKellar, D. W. et al. (2022). "In situ polyadenylation enables spatial mapping of the total transcriptome," bioRxiv 2022.04.20.488964 [Preprint] 2022. [cited Jul. 14, 2023] Available from https://doi.org/10.1101/2022.04.20.488964.

Norton, M. E. et al. (2015). "Cell-free DNA Analysis for Noninvasive Examination of Trisomy," *The New England Journal of Medicine* 372(17): 1589-1597.

Pietrasz, D. et al. (2017). "Plasma Circulating Tumor DNA in Pancreatic Cancer Patients Is a Prognostic Marker," *American Association for Cancer Research* 23 (1): 116-123.

Quail, M. A. et al. (2008). "A large genome centre's improvements to the Illumina sequencing system," *Nature Methods* 5(12): 1005-1010.

Quan, P. L. et al. (2018). "dPCR: A Technology Review," *Sensors* 18(4): 1271, pp. 1-27.

Raman, L. et al. (Feb. 28, 2019, e-published Dec. 19, 2018). "WisecondorX: improved copy number detection for routine shallow whole-genome sequencing," *Nucleic Acids Research* 47(4): 1605-1614.

Reda, M. et al. (2020). "Implementation and use of whole exome sequencing for metastatic solid cancer," *EBioMedicine* 51: 102624, pp. 1-8.

Rodriques, S. G. et al. (2019). "Slide-seq: A scalable technology for measuring genome-wide expression at high spatial resolution," *Science* 363(6434): 1463-1467.

Ronaghi, M. et al. (1996). "Real-time DNA sequencing using detection of pyrophosphate release," *Analytical Biochemistry* 242(1): 84-90.

Ronaghi, M. et al. (1998). "A sequencing method based on real-time pyrophosphate," *Science* 281(5375): 363-365.

Ronaghi, M. (2001). "Pyrosequencing sheds light on DNA sequencing," *Genome research* 11(1): 3-11.

Salmen, F. et al. (2018). "Barcoded solid-phase RNA capture for Spatial Transcriptomics profiling in mammalian tissue sections," *Nature Protocols* 13: 2501-2534.

Sarantopoulou, D. et al. (2019). "Comparative evaluation of RNA-Seq library preparation methods for strand-specificity and low input," *Scientific Reports* 9(13477).

Shendure, J. et al. (2005). "Accurate multiplex polony sequencing of an evolved bacterial genome," *Science* 309(5741): 1728-1732.

Southworth, M. W. et al. (1996). "Cloning of thermostable DNA polymerases from hyperthermophilic marine Archaea with emphasis on *Thermococcus* sp. 9 degrees N-7 and mutations affecting 3'-5' exonuclease activity," *PNAS* 93(11): 5281-5285.

Steingart, K. R. et al. (2014). "Xpert® MTB/RIF assay for pulmonary tuberculosis and rifampicin resistance in adults," *Cochrane Database of Systematic Reviews* 1: CD009593, pp. 1-134.

Tsao, D. S. et al. (2019). "A novel high-throughput molecular counting method with single basepair resolution enables accurate single-gene NIPT," *Scientific Reports* 9(14382): 1-14.

Van Schendel, R. V. et al. (2017). "Implementing non-invasive prenatal testing for aneuploidy in a national healthcare system: global challenges and national solutions," *BMC Health Services Research* 17(670): 1-10.

Vickovic, S. et al. (2019). "High-definition spatial transcriptomics for in situ tissue profiling," *Nature Methods* 16(10): 987-990.

Villacampa, E. G. et al. (2021). "Genome-wide spatial expression profiling in formalin-fixed tissues," *Cell Genomics 1* 100065: 1-24.

Viscardi, M. J. et al. (2022). "Poly(a) selection introduces bias and undue noise in direct RNA-sequencing," *BMC Genomics* 23(350): 1-10.

Vogelstein, B. et al. (2013). "Cancer Genome Landscapes," *Science* 339(6127): 1546-1558.

Walker, J. W. et al. (1988). "Photolabile 1-(2-nitrophenyl) ethyl phosphate esters of adenine nucleotide analogs. Synthesis and mechanism of photolysis," *Journal of the American Chemical Society* 110(21): 7170-7177.

Yaari, G. et al. (2015). "Practical guidelines for B-cell receptor repertoire sequencing analysis," *Genome Medicine* 7(121): 1-14.

Yang, S. et al. (2004). "PCR-based diagnostics for infectious diseases: uses, limitations, and future applications in acute-care settings," *The Lancet Infectious Diseases* 4(6): 337-348.

Yang, L. et al. (2011). "Genomewide characterization of non-polyadenylated RNAs," *Genome Biology* 12(R16): 1-14.

Yang, S. R. et al. (2020). "Integrated genomic characterization of ERBB2/HER2 alterations in invasive breast carcinoma: a focus on unusual FISH groups," *Modern Pathology* 33(8): 1546-1556.

Zhang, D. et al. (2018). "Preparation and Surface Properties Study of Novel Fluorine-Containing Methacrylate Polymers for Coating," *Materials* 11(2258): 1-14.

Zhao, Q. et al. (2011). "Optimizing de novo transcriptome assembly from short-read RNA-Seq data: a comparative study," *BMC Bioinformatics* 12(14): 1-12.

Zhou, C. et al. (2021). "Estimating tumor mutational burden across multiple cancer types using whole-exome sequencing," *Annals of Translational Medicine* 5(12): 1005-1010.

\* cited by examiner 2 distinct bead populations

Target 1     Target 2

MULTIPLEXED TARGETED AMPLIFICATION OF POLYNUCLEOTIDES

CROSS-REFERENCES TO RELATED APPLICATIONS

This application is a continuation of International Application No. PCT/US2022/078470, filed Oct. 20, 2022, which claims the benefit of U.S. Provisional Application No. 63/271,837, filed Oct. 26, 2021, U.S. Provisional Application No. 63/311,576, filed Feb. 18, 2022, and U.S. Provisional Application No. 63/373,017, filed Aug. 19, 2022, each of which are incorporated herein by reference in their entirety and for all purposes.

SEQUENCE LISTING

The instant application contains a Sequence Listing, which has been submitted electronically in ASCII format and is hereby incorporated by reference in its entirety. Said ASCII copy, created on Jun. 5, 2023, is named 051385-559C01US_ST26.xml and is 6,415 bytes in size.

BACKGROUND

In next-generation sequencing (NGS) applications, the ligation of exogenous adapters to pools of different target polynucleotides prior to sequencing is typically required. For example, a genomic polynucleotide sample is fragmented, end-repaired, and A-tailed, with purification steps occurring between most or all steps, all prior to ligation of an adapter at each end. The exogenous adapters are useful for immobilizing the target polynucleotides on a solid support and also serving as primer binding sites to initiate amplification and/or sequencing reactions. However, standard library preparation is both reagent- and time-consuming, and often is inefficient. For example, when ligating blunt end adapters to each end of the target polynucleotide the ligation efficiency of amplifiable and sequence-able products is less than about 50%. Disclosed herein, inter alia, are solutions to these and other problems in the art.

BRIEF SUMMARY

In an aspect is provided a solid support including two or more wells, wherein each well includes a first plurality of immobilized oligonucleotides and a second plurality of immobilized oligonucleotides, wherein one or more of the immobilized oligonucleotides of the first plurality include a first sequence capable of hybridizing to a first endogenous region of a target polynucleotide, and wherein one or more of the immobilized oligonucleotides of the second plurality include a second sequence capable of hybridizing to the complement of a second region of the target polynucleotide.

In an aspect is provided a particle including a first plurality of immobilized oligonucleotides and a second plurality of immobilized oligonucleotides, wherein one or more of the immobilized oligonucleotides of the first plurality include a first sequence capable of hybridizing to a first endogenous region of a target polynucleotide, and wherein one or more of the immobilized oligonucleotides of the second plurality include a second sequence capable of hybridizing to the complement of a second region of the target polynucleotide.

In an aspect is provided a solid support including a first well and a second well, wherein the first well includes a plurality of immobilized oligonucleotides including a first sequence capable of hybridizing to an endogenous region of a first target polynucleotide, and a plurality of immobilized oligonucleotides including a second sequence capable of hybridizing to the complement of an endogenous region of the first target polynucleotide; and wherein the second well includes a plurality of immobilized oligonucleotides including a third sequence capable of hybridizing to an endogenous region of a second target polynucleotide, and a plurality of immobilized oligonucleotides including a fourth sequence capable of hybridizing to the complement of an endogenous region of the second target polynucleotide; wherein the first target polynucleotide and second target polynucleotide are different.

In an aspect is provided a method of immobilizing a first oligonucleotide and a second oligonucleotide to a particle, the method including: i) annealing a first primer to the first oligonucleotide, wherein the first primer includes, from 5' to 3', a bioconjugate reactive moiety and a first primer binding sequence, and wherein the first oligonucleotide includes, from 3' to 5', a sequence complementary to the first primer binding sequence and a sequence capable of hybridizing to the complement of the first endogenous region of the target polynucleotide; ii) annealing a second primer to the second oligonucleotide, wherein the second primer includes, from 5' to 3', a bioconjugate reactive moiety and a second primer binding sequence, and wherein the second oligonucleotide includes, from 3' to 5', a sequence complementary to the second primer binding sequence and a sequence capable of hybridizing to the second region of the target polynucleotide; iii) extending the first and second primers with a polymerase to generate first and second extension products, thereby forming a first double-stranded oligonucleotide and a second double-stranded oligonucleotide; iv) contacting the bioconjugate moiety of the double-stranded oligonucleotides with a particle including one or more complementary bioconjugate moieties and forming a bioconjugate linker, thereby immobilizing the first oligonucleotide and the second oligonucleotide to the particle.

BRIEF DESCRIPTION OF THE DRAWINGS

FIG. 1A depicts an array for immobilized targeted capture of polynucleotides. The array includes multiple features; within each feature there is a plurality of a first type of immobilized oligonucleotides (solid bar) and a plurality of a second type of immobilized oligonucleotides (striped bar), collectively referred to as a set of primers. One primer type is complementary to a first sequence of the nucleic acid fragment, whereas the second primer type is homologous to a second sequence of the fragment, indicated in the figure as different color/textures. Each feature on the array can include a different set of primers. Polynucleotide fragments are allowed to contact the array. If the fragment includes a complementary region to one of the immobilized oligonucleotides in the set, it is captured by hybridizing to the first type of immobilized oligonucleotide under suitable conditions. In the presence of a polymerase (depicted as a cloud in FIG. 1B) and nucleotides, the immobilized oligonucleotide is extended to generate a complement of a portion of the captured fragment.

FIG. 3A illustrates an embodiment of an array as a patterned array, wherein the set of immobilized oligonucleotides occupy distinct features surrounded by interstitial regions of the surface (e.g., a well). FIG. 3B illustrates and embodiment of an array as a patterned array, wherein the set of immobilized oligonucleotides are immobilized to particles, wherein at least one particle occupies a feature.

FIG. 5C depicts a feature containing immobilized oligonucleotide that includes a first type of immobilized oligonucleotide that includes a primer binding sequence (e.g., PB1) along with a complementary target capture sequence (TC'), a second type of immobilized oligonucleotides that includes a second primer binding sequence (PB2) and a sequence homologous to a sequence of the target fragment, and also includes additional immobilized oligonucleotide binding sequences (e.g., PB1 and PB2).

FIG. 6A depicts a first immobilized oligonucleotide (PB1) and a second immobilized oligonucleotide (PB2). A first oligo containing a target capture sequence (i.e., a sequence complementary to a target, T1') and a region of complementarity to the first immobilized oligonucleotide (PB1') is allowed to contact the immobilized oligonucleotides. Similarly, a second oligo containing a target capture sequence (i.e., a sequence complementary to a target, T2') and a region of complementarity to the second immobilized oligonucleotide (PB2') is brought into contact with the immobilized oligonucleotides. A polymerase (not shown) extends the first and second immobilized oligonucleotide to generate immobilized oligonucleotides (FIG. 6B). For example, following primer extension the first immobilized oligonucleotide contains a first primer binding sequence (PB1) and a target sequence (T1) and the second immobilized oligonucleotide contains a second primer binding sequence (PB2) and a different target sequence (T2). The primer binding sequences each independently include a complementary sequence to one or more primers (e.g., an amplification primer, a sequencing primer, or both).

FIG. 7A depicts a feature of a substrate containing with immobilized targeted capture of polynucleotides containing two different target capture sequences (T1 and T2). A first immobilized oligonucleotide includes a first primer binding sequence (PB1) and a first target capture sequence (T1). A second immobilized oligonucleotide includes a second primer binding sequence (PB2) and a second target capture sequence (T2). A sample of polynucleotides containing i) a complementary sequence to the first immobilized oligonucleotide (T1') and the target sequence (T2); or a complementary sequence to the second immobilized oligonucleotide (T2') and the target sequence (T1) is allowed to contact the feature. In the presence of a polymerase and nucleotides, the immobilized oligonucleotides are extended to immobilize the complement of the sample polynucleotide to the substrate (FIG. 7B). FIG. 7C depicts a first amplification cycle, whereby the immobilized complements anneal to immobilized oligonucleotides and are extended to generate immobilized sample polynucleotides (FIG. 7D). This solid phase amplification process is repeated to yield features containing a plurality of immobilized sample polynucleotides. For clarity, two immobilized sample polynucleotides are shown in FIG. 7E.

FIG. 9A shows that as the concentration of the input DNA is increased the detected clusters become brighter and more populated. Following amplification, the clusters were quantified by introducing a nucleic acid stain (e.g., SYBR® Gold stain available from Thermo Fisher, Catalog #511494 or a FAM (6-fluorescein amidite) labeled oligonucleotide) in the presence of a buffer and allowed to incubate with the amplicons for 10 minutes. After a wash, the substrate containing the stained amplicons was imaged and subjected to post-processing analysis to determine cluster size and brightness. FIG. 9B depicts two distinct populations of particles, the first population includes a plurality of particles, wherein each particle includes a first sequence complementary to a first endogenous region of a target polynucleotide (i.e., Target 1). The second population includes a plurality of particles, wherein each particle includes a first sequence complementary to a different endogenous region (i.e., different than Target 1) of a target polynucleotide (i.e., Target 2). A nucleic acid stain complementary to either Target 1 or Target 2 was hybridized to the respective particles imaged and subjected to post-processing analysis to determine cluster size and brightness, as shown in FIG. 9B. The particles were then subjected to sequencing. Base calling accuracy, measured by the Phred quality score (Q score), is the most common metric used to assess the accuracy of a sequencing platform. It indicates the probability that a given base is called incorrectly by the sequencer. For example, if the base calling algorithm assigns a Q score of 30 (Q30) to a base, this is equivalent to the probability of an incorrect base call 1 in 1000 times. FIG. 9C reports on the sequencing quality scores for two different target polynucleotides prepared according to the methods described herein.

FIG. 10A depicts a first oligonucleotide (PB1) and a second oligonucleotide (PB2), wherein each oligonucleotide includes on the 5' end a bioconjugate reactive moiety (e.g., a dibenzocyclooctyne (DBCO) moiety), depicted as a sphere. A first oligo containing a target capture sequence (i.e., a sequence complementary to a target, T1') and a region of complementarity to the first labeled oligonucleotide (PB1') is allowed to contact the labeled oligonucleotide. Similarly, a second oligo containing a target capture sequence (i.e., a sequence complementary to a target, T2') and a region of complementarity to the second labeled oligonucleotide (PB2') is brought into contact with the labeled oligonucleotide. A polymerase (not shown) extends the first and second labeled oligonucleotides to generate double-stranded labeled oligonucleotides. For example, following primer extension the first labeled oligonucleotide contains a first primer binding sequence (PB1) and a target sequence (T1) and the second labeled oligonucleotide contains a second primer binding sequence (PB2) and a different target sequence (T2). The primer binding sequences each independently include a complementary sequence to one or more primers (e.g., an amplification primer, a sequencing primer, or both). Subsequently, the double-stranded oligonucleotides are covalently linked to a solid support that includes complementary bioconjugate reactive moieties (e.g., an azide moiety) thereby forming a bioconjugate linker and covalently binding the oligonucleotide to the solid support, as shown in FIG. 10B. In embodiments, the first oligonucleotide and the second oligonucleotide independently include different bioconjugate reactive moieties (e.g., the first oligonucleotide includes DBCO and the second oligonucleotide includes an amino). Following surface deposition, chemical and/or heat denaturation is applied to release the non-immobilized strand, leaving behind the immobilized target capture solid support.

DETAILED DESCRIPTION

Figure 1A:
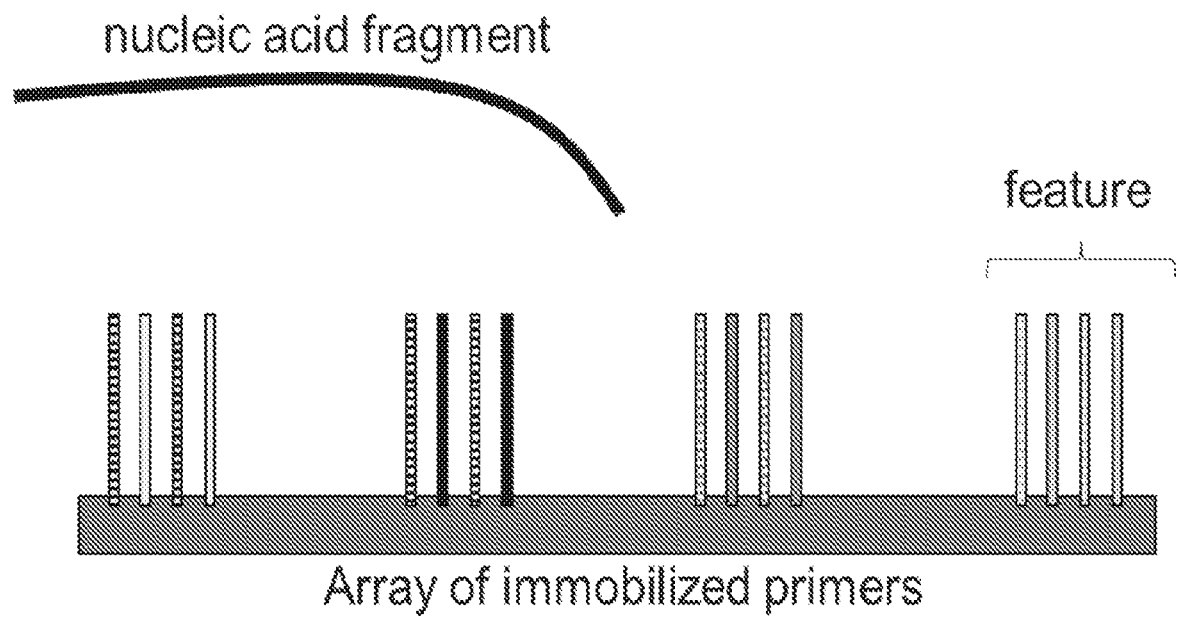
FIGS. 1A-1B illustrate an embodiment of the method described herein.

The aspects and embodiments described herein relate to compositions and methods for efficient amplification and sequencing of nucleic acid templates while minimizing library preparation reagents, techniques, and methods.

I. Definitions

All patents, patent applications, articles and publications mentioned herein, both supra and infra, are hereby expressly incorporated herein by reference in their entireties.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms "a", "an", and "the" include the plural reference unless the context clearly indicates otherwise. Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein, the term "control" or "control experiment" is used in accordance with its plain and ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

As used herein, the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can also be a physical association. In some instances, two or more associated species are "tethered", "coated", "attached", or "immobilized" to one another or to a common solid or semisolid support (e.g. a receiving substrate). An association may refer to a relationship, or connection, between two entities. Associated may refer to the relationship between a sample and the DNA molecules, RNA molecules, or polynucleotides originating from or derived from that sample. These relationships may be encoded in oligonucleotide barcodes, as described herein. A polynucleotide is associated with a sample if it is an endogenous polynucleotide, i.e., it occurs in the sample at the time the sample is obtained, or is derived from an endogenous polynucleotide. For example, the RNAs endogenous to a cell are associated with that cell. cDNAs resulting from reverse transcription of these RNAs, and DNA amplicons resulting from PCR amplification of the cDNAs, contain the sequences of the RNAs and are also associated with the cell. The polynucleotides associated with a sample need not be located or synthesized in the sample, and are considered associated with the sample even after the sample has been destroyed (for example, after a cell has been lysed). Barcoding can be used to determine which polynucleotides in a mixture are associated with a particular sample.

As used herein, the term "complement" is used in accordance with its plain and ordinary meaning and refers to a nucleotide (e.g., RNA nucleotide or DNA nucleotide) or a sequence of nucleotides capable of base pairing with a complementary nucleotide or sequence of nucleotides (e.g., Watson-Crick base pairing). As described herein and commonly known in the art the complementary (matching) nucleotide of adenosine is thymidine and the complementary (matching) nucleotide of guanosine is cytosine. Thus, a complement may include a sequence of nucleotides that base paired with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence. As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, sequences in a pair of complementary sequences form portions of a single polynucleotide with non-base-pairing nucleotides (e.g., as in a hairpin or loop structure, with or without an overhang) or portions of separate polynucleotides. In embodiments, one or both sequences in a pair of complementary sequences form portions of longer polynucleotides, which may or may not include additional regions of complementarity.

As used herein, the term "contacting" is used in accordance with its plain ordinary meaning and refers to the process of allowing at least two distinct species (e.g., chemical compounds including biomolecules, particles, solid supports, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme. In some embodiments contacting includes allowing a particle described herein to interact with an array.

As may be used herein, the terms "nucleic acid," "nucleic acid molecule," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may include natural nucleic acid sequences and variants thereof, artificial nucleic acid sequences, or a combination of such sequences. As may be used herein, the terms "nucleic acid oligomer" and "oligonucleotide" are used interchangeably and are intended to include, but are not limited to, nucleic acids having a length of 200 nucleotides or less. In some embodiments, an oligonucleotide is a nucleic acid having a length of 2 to 200 nucleotides, 2 to 150 nucleotides, 5 to 150 nucleotides or 5 to 100 nucleotides. The terms "polynucleotide," "oligonucleotide," "oligo" or the like refer, in the usual and customary sense, to a linear sequence of nucleotides. Oligonucleotides are typically from about 5, 6, 7, 8, 9, 10, 12, 15, 25, 30, 40, 50 or more nucleotides in length, up to about 100 nucleotides in length. In some embodiments, an oligonucleotide is a primer configured for extension by a polymerase when the primer is annealed completely or partially to a complementary nucleic acid template. A primer is often a single stranded nucleic acid. In certain embodiments, a primer, or portion thereof, is substantially complementary to a portion of an adapter. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides. In some embodiments, an oligonucleotide may be immobilized to a solid support.

As used herein, the terms "polynucleotide primer" and "primer" refers to any polynucleotide molecule that may hybridize to a polynucleotide template, be bound by a polymerase, and be extended in a template-directed process for nucleic acid synthesis (e.g., amplification and/or sequencing). The primer may be a separate polynucleotide from the polynucleotide template, or both may be portions of the same polynucleotide (e.g., as in a hairpin structure having a 3' end that is extended along another portion of the polynucleotide to extend a double-stranded portion of the hairpin). Primers (e.g., forward or reverse primers) may be attached to a solid support. A primer can be of any length depending on the particular technique it will be used for. For example, PCR primers are generally between 10 and 40 nucleotides in length. The length and complexity of the nucleic acid fixed onto the nucleic acid template may vary. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides. One of skill can adjust these factors to provide optimum hybridization and signal production for a given hybridization procedure. The primer permits the addition of a nucleotide residue thereto, or oligonucleotide or polynucleotide synthesis therefrom, under suitable conditions. In an embodiment the primer is a DNA primer, i.e., a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment the primer is an RNA primer. In embodiments, a primer is hybridized to a target polynucleotide. A "primer" is complementary to a polynucleotide template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

As used herein, the term "primer binding sequence" refers to a polynucleotide sequence that is complementary to at least a portion of a primer (e.g., a sequencing primer or an amplification primer). Primer binding sequences can be of any suitable length. In embodiments, a primer binding sequence is about or at least about 10, 15, 20, 25, 30, or more nucleotides in length. In embodiments, a primer binding sequence is 10-50, 15-30, or 20-25 nucleotides in length. The primer binding sequence may be selected such that the primer (e.g., sequencing primer) has the preferred characteristics to minimize secondary structure formation or minimize non-specific amplification, for example having a length of about 20-30 nucleotides; approximately 50% GC content, and a Tm of about 55° C. to about 65° C.

As used herein, a platform primer is a primer oligonucleotide immobilized or otherwise bound to a solid support (i.e. an immobilized oligonucleotide). Examples of platform primers include P7 and P5 primers, or S1 and S2 sequences, or the reverse complements thereof. A "platform primer binding sequence" refers to a sequence or portion of an oligonucleotide that is capable of binding to a platform primer (e.g., the platform primer binding sequence is complementary to the platform primer). In embodiments, a platform primer binding sequence may form part of an adapter. In embodiments, a platform primer binding sequence is complementary to a platform primer sequence. In embodiments, a platform primer binding sequence is complementary to a primer.

As used herein, the term "capture domain" refers to an oligonucleotide sequence (e.g., an oligonucleotide sequence included in a primer, for example a surface-immobilized capture primer). The capture domain may be any suitable domain capable of hybridizing to RNA or a transcript thereof, such as mRNA. In some embodiments, the capture domain includes a poly-T oligonucleotide. A poly-T oligonucleotide includes a series of consecutive deoxythymidine residues linked by phosphodiester bonds. A poly-T oligonucleotide is capable of hybridizing to the poly-A tail of mRNA. In some embodiments, the capture domain may further include additional sequences to facilitate the capture of a particular RNA (e.g., mRNA) corresponding to select genes or groups of genes. Such a capture primer may be selected or designed based on sequence of the RNA it is desired to capture. Accordingly, the capture primer may be a sequence-specific capture primer as described herein. In some embodiments, the capture domain may target DNA, instead of RNA. In some embodiments, the capture domain may target non-specific or specific DNA sequences. For example, the capture domain may include a nucleic acid sequence to facilitate the capture of a target DNA sequence. The type of target may depend on the specific capture domain used and/or the presence of additional capture moieties on the substrate. For example, capture domains including a poly-dT tail are suited for spatial detection of RNA with poly-A tail. RNA that does not have poly-A tail may be labeled with poly-A before being captured by the substrate. Capture domains including a nucleic acid sequence against a target DNA sequence are useful for spatial detection of DNA. Substrates include a capture primer and an additional capture moiety (e.g. an antibody targeting protein or DNA/RNA probes targeting specific nucleic acid sequence) are useful for multiplex detection of nucleic acid and non-nucleic acid targets.

As used herein, the term "spatial barcode" refers to a known nucleic acid sequence that allows the location of a biological molecule with which the barcode is associated to be resolved. A barcode can be a spatial barcode. The barcode or spatial barcode may be associated with an oligonucleotide as described herein (e.g., a capture oligonucleotide or capture probe). The barcodes can be designed for precision sequence performance, e.g., GC content between 40% and 60%, no homo-polymer runs longer than two, no self-complementary stretches longer than 3, and be comprised of sequences not present in a human genome reference. A barcode sequence can be at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 bases. A barcode sequence can be at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 bases. A barcode sequence can be about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 bases. An oligonucleotide (e.g., primer or adapter) can include about, more than, less than, or at least 1, 2, 3, 4, 5, 6, 7, 8, 9, or 10 different barcodes. Barcodes can be of sufficient length and include sequences that can be sufficiently different to allow the identification of the spatial position of each biological molecule based on barcode(s) with which each biological molecule is associated. In some cases, each barcode is, for example, four deletions or insertions or substitutions away from any other barcode in an array. The oligonucleotides in each array spot on the barcoded oligonucleotide array can include the same barcode sequence and oligonucleotides in different array spots can include different barcode sequences. The barcode sequence used in one array spot can be different from the barcode sequence in any other array spot. Alternatively, the barcode sequence used in one array spot can be the same as the barcode sequence used in another array spot, as long as the two array spots are not adjacent. Barcode sequences corresponding to particular array spots can be known from the controlled synthesis of the array. Alternatively, barcode sequences corresponding to particular array spots can be known by retrieving and sequencing material from particular array spots. In embodiments, the spatial barcode sequence is indicative of the location of the immobilized capture probe on the solid support to within about 2 µm, about 1 µm, about 0.5 µm, about 0.2 µm, or about 0.1 µm.

The order of elements within a nucleic acid molecule is typically described herein from 5' to 3'. In the case of a double-stranded molecule, the "top" strand is typically shown from 5' to 3', according to convention, and the order of elements is described herein with reference to the top strand.

Nucleic acids, including e.g., nucleic acids with a phosphorothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The term "messenger RNA" or "mRNA" refers to an RNA that is without introns and is capable of being translated into a polypeptide. The term "RNA" refers to any ribonucleic acid, including but not limited to mRNA, tRNA (transfer RNA), rRNA (ribosomal RNA), and/or noncoding RNA (such as lncRNA (long noncoding RNA)). The term "cDNA" refers to a DNA that is complementary or identical to an RNA, in either single stranded or double stranded form.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

As used herein, the terms "analogue" and "analog", in reference to a chemical compound, refers to compound having a structure similar to that of another one, but differing from it in respect of one or more different atoms, functional groups, or substructures that are replaced with one or more other atoms, functional groups, or substructures. In the context of a nucleotide, a nucleotide analog refers to a compound that, like the nucleotide of which it is an analog, can be incorporated into a nucleic acid molecule (e.g., an extension product) by a suitable polymerase, for example, a DNA polymerase in the context of a nucleotide analogue. The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphorothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, e.g., see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

As used herein, a "native" nucleotide is used in accordance with its plain and ordinary meaning and refers to a naturally occurring nucleotide that does not include an exogenous label (e.g., a fluorescent dye, or other label) or chemical modification such as may characterize a nucleotide analog. Examples of native nucleotides useful for carrying out procedures described herein include: dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate); and dUTP (2'-deoxyuridine-5'-triphosphate).

In embodiments, the nucleotides of the present disclosure use a cleavable linker to attach the label to the nucleotide. The use of a cleavable linker ensures that the label can, if required, be removed after detection, avoiding any interfering signal with any labelled nucleotide incorporated subsequently. The use of the term "cleavable linker" is not meant to imply that the whole linker is required to be removed from the nucleotide base. The cleavage site can be located at a position on the linker that ensures that part of the linker remains attached to the nucleotide base after cleavage. The linker can be attached at any position on the nucleotide base provided that Watson-Crick base pairing can still be carried out. In the context of purine bases, it is preferred if the linker is attached via the 7-position of the purine or the preferred deazapurine analogue, via an 8-modified purine, via an N-6 modified adenosine or an N-2 modified guanine. For pyrimidines, attachment is preferably via the 5-position on cytidine, thymidine or uracil and the N-4 position on cytosine.

The term "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. A cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$)). A chemically cleavable linker is non-enzymatically cleavable. In embodiments, the cleavable linker is cleaved by contacting the cleavable linker with a cleaving agent. In embodiments, the cleaving agent is a phosphine containing reagent (e.g., TCEP or THPP), sodium dithionite ($Na_2S_2O_4$), weak acid, hydrazine ($N_2H_4$), Pd(0), or light-irradiation (e.g., ultraviolet radiation). In embodiments, cleaving includes removing. A "cleavable site" or "scissile linkage" in the context of a polynucleotide is a site which allows controlled cleavage of the polynucleotide strand (e.g., the linker, the primer, or the polynucleotide) by chemical, enzymatic, or photochemical means known in the art and described herein. A scissile site may refer to the linkage of a nucleotide between two other nucleotides in a nucleotide strand (i.e., an internucleosidic linkage). In embodiments, the scissile linkage can be located at any position within the one or more nucleic acid molecules, including at or near a terminal end (e.g., the 3' end of an oligonucleotide) or in an interior portion of the one or more nucleic acid molecules. In embodiments, conditions suitable for separating a scissile linkage include a modulating the pH and/or the temperature. In embodiments, a scissile site can include at least one acid-labile linkage. For example, an acid-labile linkage may include a phosphoramidate linkage. In embodiments, a phosphoramidate linkage can be hydrolysable under acidic conditions, including mild acidic conditions such as trifluoroacetic acid and a suitable temperature (e.g., 30° C.), or other conditions known in the art, for example Matthias Mag, et al Tetrahedron Letters, Volume 33, Issue 48, 1992, 7319-7322. In embodiments, the scissile site can include at least one photolabile internucleosidic linkage (e.g., o-nitrobenzyl linkages, as described in Walker et al, J. Am. Chem. Soc. 1988, 110, 21, 7170-7177), such as o-nitrobenzyloxymethyl or p-nitrobenzyloxymethyl group(s). In embodiments, the scissile site includes at least one uracil nucleobase. In embodiments, a uracil nucleobase can be cleaved with a uracil DNA glycosylase (UDG) or Formamidopyrimidine DNA Glycosylase Fpg. In embodiments, the scissile linkage site includes a sequence-specific nicking site having a nucleotide sequence that is recognized and nicked by a nicking endonuclease enzyme or a uracil DNA glycosylase. A cleavable site may also be referred to herein as a "cleavage domain" or "cleavable domain".

As used herein, the term "modified nucleotide" refers to nucleotide modified in some manner. Typically, a nucleotide contains a single 5-carbon sugar moiety, a single nitrogenous base moiety and 1 to three phosphate moieties. In embodiments, a nucleotide can include a blocking moiety and/or a label moiety. A blocking moiety on a nucleotide prevents formation of a covalent bond between the 3' hydroxyl moiety of the nucleotide and the 5' phosphate of another nucleotide. A blocking moiety on a nucleotide can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. In embodiments, the blocking moiety is attached to the 3' oxygen of the nucleotide and is independently —$NH_2$, —CN, —$CH_3$, $C_2$-$C_6$ allyl (e.g., —$CH_2$—CH=$CH_2$), methoxyalkyl (e.g., —$CH_2$—O—$CH_3$), or —$CH_2N_3$. A label moiety of a modified nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both. Examples of nucleotide analogues include, without limitation, 7-deaza-adenine, 7-deaza-guanine, the analogues of deoxynucleotides shown herein, analogues in which a label is attached through a cleavable linker to the 5-position of cytosine or thymine or to the 7-position of deaza-adenine or deaza-guanine, and analogues in which a small chemical moiety is used to cap the OH group at the 3'-position of deoxyribose. Nucleotide analogues and DNA polymerase-based DNA sequencing are also described in U.S. Pat. No. 6,664,079, which is incorporated herein by reference in its entirety for all purposes. Non-limiting examples of detectable labels include labels including fluorescent dyes, biotin, digoxin, haptens, and epitopes. In general, a dye is a molecule, compound, or substance that can provide an optically detectable signal, such as a colorimetric, luminescent, bioluminescent, chemiluminescent, phosphorescent, or fluorescent signal. In embodiments, the dye is a fluorescent dye. Non-limiting examples of dyes, some of which are commercially available, include CF dyes (Biotium, Inc.), Alexa Fluor dyes (Thermo Fisher), DyLight dyes (Thermo Fisher), Cy dyes (GE Healthscience), IRDyes (Li-Cor Biosciences, Inc.), and HiLyte dyes (Anaspec, Inc.). In embodiments, the label is a fluorophore.

In some embodiments, a nucleic acid includes a label. As used herein, the term "label" or "labels" is used in accordance with their plain and ordinary meanings and refer to molecules that can directly or indirectly produce or result in a detectable signal either by themselves or upon interaction with another molecule. Non-limiting examples of detectable labels include fluorescent dyes, biotin, digoxin, haptens, and epitopes. In general, a dye is a molecule, compound, or substance that can provide an optically detectable signal, such as a colorimetric, luminescent, bioluminescent, chemiluminescent, phosphorescent, or fluorescent signal. In embodiments, the label is a dye. In embodiments, the dye is a fluorescent dye. Non-limiting examples of dyes, some of which are commercially available, include CF dyes (Biotium, Inc.), Alexa Fluor dyes (Thermo Fisher), DyLight dyes (Thermo Fisher), Cy dyes (GE Healthscience), IRDyes (Li-Cor Biosciences, Inc.), and HiLyte dyes (Anaspec, Inc.). In embodiments, a particular nucleotide type is associated with a particular label, such that identifying the label identifies the nucleotide with which it is associated. In embodiments, the label is luciferin that reacts with luciferase to produce a detectable signal in response to one or more bases being incorporated into an elongated complementary strand, such as in pyrosequencing. In embodiment, a nucleotide includes a label (such as a dye). In embodiments, the label is not associated with any particular nucleotide, but detection of the label identifies whether one or more nucleotides having a known identity were added during an extension step (such as in the case of pyrosequencing). Examples of detectable agents (i.e., labels) include imaging agents, including fluorescent and luminescent substances, molecules, or compositions, including, but not limited to, a variety of organic or inorganic small molecules commonly referred to as "dyes," "labels," or "indicators." Examples include fluorescein, rhodamine, acridine dyes, Alexa dyes, and cyanine dyes. In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent molecule (e.g., acridine dye, cyanine, dye, fluorine dye, oxazine dye, phenanthridine dye, or rhodamine dye). The term "cyanine" or "cyanine moiety" as described herein refers to a detectable moiety containing two nitrogen groups separated by a polymethine chain. In embodiments, the cyanine moiety has 3 methine structures (i.e., cyanine 3 or Cy3). In embodiments, the cyanine moiety has 5 methine structures (i.e., cyanine 5 or Cy5). In embodiments, the cyanine moiety has 7 methine structures (i.e., cyanine 7 or Cy7).

The term "nucleoside" refers, in the usual and customary sense, to a glycosylamine including a nucleobase and a five-carbon sugar (ribose or deoxyribose). Non-limiting examples of nucleosides include cytidine, uridine, adenosine, guanosine, thymidine and inosine. Nucleosides may be modified at the base and/or the sugar. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g., polynucleotides contemplated herein include any types of RNA, e.g., mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site www.ncbi.nlm.nih.gov/BLAST/or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

As used herein, the term "removable" group, e.g., a label or a blocking group or protecting group, is used in accordance with its plain and ordinary meaning and refers to a chemical group that can be removed from a nucleotide analogue such that a DNA polymerase can extend the nucleic acid (e.g., a primer or extension product) by the incorporation of at least one additional nucleotide. Removal may be by any suitable method, including enzymatic, chemical, or photolytic cleavage. Removal of a removable group, e.g., a blocking group, does not require that the entire removable group be removed, only that a sufficient portion of it be removed such that a DNA polymerase can extend a nucleic acid by incorporation of at least one additional nucleotide using a nucleotide or nucleotide analogue. In general, the conditions under which a removable group is removed are compatible with a process employing the removable group (e.g., an amplification process or sequencing process).

As used herein, the terms "reversible blocking groups" and "reversible terminators" are used in accordance with their plain and ordinary meanings and refer to a blocking moiety located, for example, at the 3' position of a modified nucleotide and may be a chemically cleavable moiety such as an allyl group, an azidomethyl group or a methoxymethyl group, or may be an enzymatically cleavable group such as a phosphate ester. Non-limiting examples of nucleotide blocking moieties are described in applications WO 2004/018497, WO 96/07669, U.S. Pat. Nos. 7,057,026, 7,541,444, 5,763,594, 5,808,045, 5,872,244 and 6,232,465 the contents of which are incorporated herein by reference in their entirety. The nucleotides may be labelled or unlabeled. They may be modified with reversible terminators useful in methods provided herein and may be 3'-O-blocked reversible or 3'-unblocked reversible terminators. In nucleotides with 3'-O-blocked reversible terminators, the blocking group —OR [reversible terminating (capping) group] is linked to the oxygen atom of the 3'-OH of the pentose, while the label is linked to the base, which acts as a reporter and can be cleaved. The 3'-O-blocked reversible terminators are known in the art, and may be, for instance, a 3'-ONH$_2$ reversible terminator, a 3'-O-allyl reversible terminator, or a 3'-O-azidomethyl reversible terminator. In embodiments, the reversible terminator moiety is attached to the 3'-oxygen of the nucleotide, having the formula:

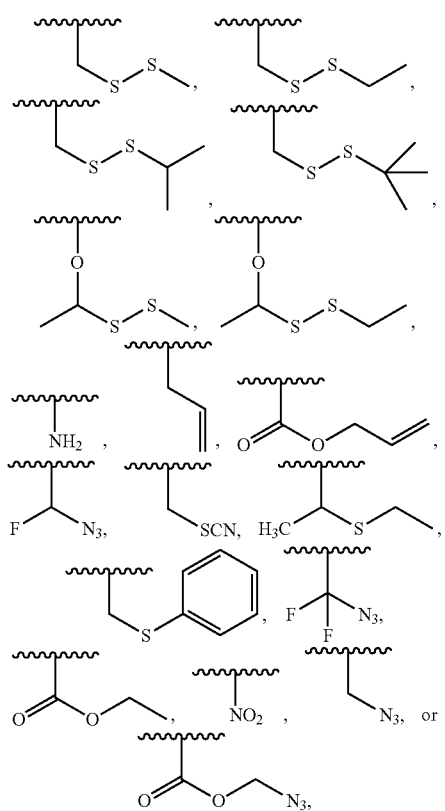

wherein the 3' oxygen of the nucleotide is not shown in the formulae above. The term "allyl" as described herein refers to an unsubstituted methylene attached to a vinyl group (i.e., —CH═CH$_2$). In embodiments, the reversible terminator moiety is

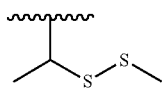 [SMILES: *C(C)SSC]

as described in U.S. Pat. No. 10,738,072, which is incorporated herein by reference for all purposes. For example, a nucleotide including a reversible terminator moiety may be represented by the formula:

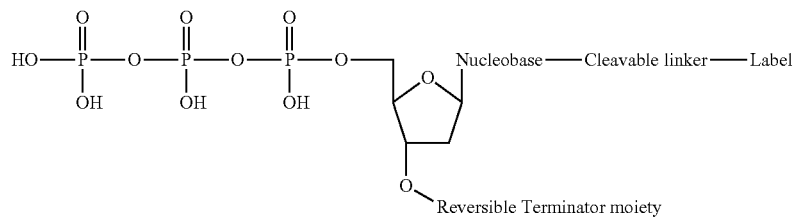

where the nucleobase is adenine or adenine analogue, thymine or thymine analogue, guanine or guanine analogue, or cytosine or cytosine analogue.

In some embodiments, a nucleic acid (e.g., an immobilized oligonucleotide) includes a molecular identifier or a molecular barcode. As used herein, the term "molecular barcode" (which may be referred to as a "tag", a "barcode", a "molecular identifier", an "identifier sequence" or a "unique molecular identifier" (UMI)) refers to any material (e.g., a nucleotide sequence, a nucleic acid molecule feature) that is capable of distinguishing an individual molecule in a large heterogeneous population of molecules. In embodiments, a barcode is unique in a pool of barcodes that differ from one another in sequence, or is uniquely associated with a particular sample polynucleotide in a pool of sample polynucleotides. In embodiments, every barcode in a pool of adapters is unique, such that sequencing reads including the barcode can be identified as originating from a single sample polynucleotide molecule on the basis of the barcode alone. In other embodiments, individual barcode sequences may be used more than once, but adapters including the duplicate barcodes are associated with different sequences and/or in different combinations of barcoded adaptors, such that sequence reads may still be uniquely distinguished as originating from a single sample polynucleotide molecule on the basis of a barcode and adjacent sequence information (e.g., sample polynucleotide sequence, and/or one or more adjacent barcodes). In embodiments, barcodes are about or at least about 5, 6, 7, 8, 9, 10, 15, 20, 25, 30, 40, 50, 75 or more nucleotides in length. In embodiments, barcodes are shorter than 20, 15, 10, 9, 8, 7, 6, or 5 nucleotides in length. In embodiments, barcodes are about 10 to about 50 nucleotides in length, such as about 15 to about 40 or about 20 to about 30 nucleotides in length. In a pool of different barcodes, barcodes may have the same or different lengths. In general, barcodes are of sufficient length and include sequences that are sufficiently different to allow the identification of sequencing reads that originate from the same sample polynucleotide molecule. In embodiments, each barcode in a plurality of barcodes differs from every other barcode in the plurality by at least three nucleotide positions, such as at least 3, 4, 5, 6, 7, 8, 9, 10, or more nucleotide positions. In some embodiments, substantially degenerate barcodes may be known as random. In some embodiments, a barcode may include a nucleic acid sequence from within a pool of known sequences. In some embodiments, the barcodes may be pre-defined.

In embodiments, a nucleic acid (e.g., an adapter or primer) includes a sample barcode. In general, a "sample barcode" is a nucleotide sequence that is sufficiently different from other sample barcode to allow the identification of the sample source based on sample barcode sequence(s) with which they are associated. In embodiments, a plurality of nucleotides (e.g., all nucleotides from a particular sample source, or sub-sample thereof) are joined to a first sample barcode, while a different plurality of nucleotides (e.g., all nucleotides from a different sample source, or different subsample) are joined to a second sample barcode, thereby associating each plurality of polynucleotides with a different sample barcode indicative of sample source. In embodiments, each sample barcode in a plurality of sample barcodes differs from every other sample barcode in the plurality by at least three nucleotide positions, such as at least 3, 4, 5, 6, 7, 8, 9, 10, or more nucleotide positions. In some embodiments, substantially degenerate sample barcodes may be known as random. In some embodiments, a sample barcode may include a nucleic acid sequence from within a pool of known sequences. In some embodiments, the sample barcodes may be pre-defined. In embodiments, the sample barcode includes about 1 to about 10 nucleotides. In embodiments, the sample barcode includes about 3, 4, 5, 6, 7, 8, 9, or about 10 nucleotides. In embodiments, the sample barcode includes about 3 nucleotides. In embodiments, the sample barcode includes about 5 nucleotides. In embodiments, the sample barcode includes about 7 nucleotides. In embodiments, the sample barcode includes about 10 nucleotides. In embodiments, the sample barcode includes about 6 to about 10 nucleotides.

As used herein, the term "biomolecule" refers to an agent (e.g., a compound, macromolecule, or small molecule), and the like derived from a biological system (e.g., an organism). The biomolecule may contain multiple individual components that collectively construct the biomolecule, for example, in embodiments, the biomolecule is a polynucleotide wherein the polynucleotide is composed of nucleotide monomers. The biomolecule may be or may include DNA, RNA, organelles, carbohydrates, lipids, proteins, or any combination thereof. These components may be extracellular. In some examples, the biomolecule may be referred to as a clump or aggregate of combinations of components. In some instances, the biomolecule may include one or more constituents of a cell but may not include other constituents of the cell. In embodiments, a biomolecule is a molecule produced by a biological system (e.g., an organism). In embodiments, a biomolecule may be referred to as an analyte. Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In embodiments, the analytes within a cell can be localized to subcellular locations, including, for example, organelles, e.g., mitochondria, Golgi apparatus, endoplasmic reticulum, chloroplasts, endocytic vesicles, exocytic vesicles, vacuoles, lysosomes, etc. In embodiments, analyte(s) can be peptides or proteins, including antibodies and/or enzymes. In embodiments, an analyte can be detected indirectly, such as through detection of an intermediate agent, for example, a ligation product or an analyte capture agent (e.g., an oligonucleotide-conjugated antibody), such as those described herein.

As used herein, the term "biological system" refers to a virus, cell, cell derivative, cell nucleus, cell organelle, cell constituent and the like derived from a biological sample. Examples of a cell organelle include, without limitation, a nucleus, endoplasmic reticulum, a ribosome, a Golgi apparatus, an endoplasmic reticulum, a chloroplast, an endocytic vesicle, an exocytic vesicle, a vacuole, and a lysosome. The biological system (e.g., an organism) may contain multiple individual components, such as viruses, cells, cell derivatives, cell nuclei, cell organelles and cell constituents, including combinations of different of these and other components. The biological system may include DNA, RNA, organelles, proteins, or any combination thereof. These components may be extracellular. In some examples, the biological system may be referred to as a clump or aggregate of combinations of components. In some instances, the biological system may include one or more constituents of a cell but may not include other constituents of the cell. An example of such constituents include nucleus or an organelle. A cell may be a live or viable cell. The live cell may be capable of being cultured, for example, being cultured when enclosed in a gel or polymer matrix or cultured when including a gel or polymer matrix. A biological system may include a single cell and/or a single nuclei from a cell.

As used herein, the term "DNA polymerase" and "nucleic acid polymerase" are used in accordance with their plain ordinary meanings and refer to enzymes capable of synthesizing nucleic acid molecules from nucleotides (e.g., deoxyribonucleotides). Exemplary types of polymerases that may be used in the compositions and methods of the present disclosure include the nucleic acid polymerases such as DNA polymerase, DNA- or RNA-dependent RNA polymerase, and reverse transcriptase. In some cases, the DNA polymerase is 9° N polymerase or a variant thereof, E. Coli DNA polymerase I, Bacteriophage T4 DNA polymerase, Sequenase, Taq DNA polymerase, DNA polymerase from *Bacillus stearothermophilus*, Bst 2.0 DNA polymerase, 9° N polymerase (exo-)A485L/Y409V, Phi29 DNA Polymerase (φ29 DNA Polymerase), T7 DNA polymerase, DNA polymerase II, DNA polymerase III holoenzyme, DNA polymerase IV, DNA polymerase V, VentR DNA polymerase, Therminator™ II DNA Polymerase, Therminator™ III DNA Polymerase, or or Therminator™ IX DNA Polymerase. In embodiments, the polymerase is a protein polymerase. Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol R DNA polymerase, Pol µ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g. Therminator γ, 9° N polymerase (exo-), Therminator II, Therminator III, or Therminator IX). In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044). In embodiments, the polymerase is an enzyme described in US 2021/0139884.

As used herein, the term "exonuclease activity" is used in accordance with its ordinary meaning in the art, and refers to the removal of a nucleotide from a nucleic acid by an enzyme (e.g. DNA polymerase, a lambda exonuclease, Exo I, Exo III, T5, Exo V, Exo VII or the like). For example, during polymerization, nucleotides are added to the 3' end of the primer strand. Occasionally a DNA polymerase incorporates an incorrect nucleotide to the 3'-OH terminus of the primer strand, wherein the incorrect nucleotide cannot form a hydrogen bond to the corresponding base in the template strand. Such a nucleotide, added in error, is removed from the primer as a result of the 3' to 5' exonuclease activity of the DNA polymerase. In embodiments, exonuclease activity may be referred to as "proofreading." When referring to 3'-5' exonuclease activity, it is understood that the DNA polymerase facilitates a hydrolyzing reaction that breaks phosphodiester bonds at the 3' end of a polynucleotide chain to excise the nucleotide. In embodiments, 3'-5' exonuclease activity refers to the successive removal of nucleotides in single-stranded DNA in a 3'→5' direction, releasing deoxyribonucleoside 5'-monophosphates one after another. Methods for quantifying exonuclease activity are known in the art, see for example Southworth et al, PNAS Vol 93, 8281-8285 (1996). In embodiments, 5'-3' exonuclease activity refers to the successive removal of nucleotides in double-stranded DNA in a 5'→3' direction. In embodiments, the 5'-3' exonuclease is lambda exonuclease. For example, lambda exonuclease catalyzes the removal of 5' mononucleotides from duplex DNA, with a preference for 5' phosphorylated double-stranded DNA. In other embodiments, the 5'-3' exonuclease is *E. coli* DNA Polymerase I.

As used herein, the term "incorporating" or "chemically incorporating," when used in reference to a primer and cognate nucleotide, refers to the process of joining the cognate nucleotide to the primer or extension product thereof by formation of a phosphodiester bond.

As used herein, the term "selective" or "selectivity" or the like of a compound refers to the compound's ability to discriminate between molecular targets. For example, a chemical reagent may selectively modify one nucleotide type in that it reacts with one nucleotide type (e.g., cytosines) and not other nucleotide types (e.g., adenine, thymine, or guanine). When used in the context of sequencing, such as in "selectively sequencing," this term refers to sequencing one or more target polynucleotides from an original starting population of polynucleotides, and not sequencing non-target polynucleotides from the starting population. Typically, selectively sequencing one or more target polynucleotides involves differentially manipulating the target polynucleotides based on known sequence. For example, target polynucleotides may be hybridized to a probe oligonucleotide that may be labeled (such as with a member of a binding pair) or bound to a surface. In embodiments, hybridizing a target polynucleotide to a probe oligonucleotide includes the step of displacing one strand of a double-stranded nucleic acid. Probe-hybridized target polynucleotides may then be separated from non-hybridized polynucleotides, such as by removing probe-bound polynucleotides from the starting population or by washing away polynucleotides that are not bound to a probe. The result is a selected subset of the starting population of polynucleotides, which is then subjected to sequencing, thereby selectively sequencing the one or more target polynucleotides.

As used herein, the term "template polynucleotide" refers to any polynucleotide molecule that may be bound by a polymerase and utilized as a template for nucleic acid synthesis. A template polynucleotide may be a target polynucleotide. In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction. A target polynucleotide is not necessarily any single molecule or sequence. For example, a target polynucleotide may be any one of a plurality of target polynucleotides in a reaction, or all polynucleotides in a given reaction, depending on the reaction conditions. For example, in a nucleic acid amplification reaction with random primers, all polynucleotides in a reaction may be amplified. As a further example, a collection of targets may be simultaneously assayed using polynucleotide primers directed to a plurality of targets in a single reaction. In the context of selective sequencing, "target polynucleotide(s)" refers to the subset of polynucleotide(s) to be sequenced from within a starting population of polynucleotides.

In embodiments, a target polynucleotide is a cell-free polynucleotide. In general, the terms "cell-free," "circulating," and "extracellular" as applied to polynucleotides (e.g. "cell-free DNA" (cfDNA) and "cell-free RNA" (cfRNA)) are used interchangeably to refer to polynucleotides present in a sample from a subject or portion thereof that can be isolated or otherwise manipulated without applying a lysis step to the sample as originally collected (e.g., as in extraction from cells or viruses). Cell-free polynucleotides are thus unencapsulated or "free" from the cells or viruses from which they originate, even before a sample of the subject is collected. Cell-free polynucleotides may be produced as a byproduct of cell death (e.g., apoptosis or necrosis) or cell shedding, releasing polynucleotides into surrounding body fluids or into circulation. Accordingly, cell-free polynucleotides may be isolated from a non-cellular fraction of blood (e.g., serum or plasma), from other bodily fluids (e.g., urine), or from non-cellular fractions of other types of samples.

As used herein, the terms "specific", "specifically", "specificity", or the like of a compound refers to the compound's ability to cause a particular action, such as binding, to a particular molecular target with minimal or no action to other proteins in the cell.

As used herein, the terms "bind" and "bound" are used in accordance with their plain and ordinary meanings and refer to an association between atoms or molecules. The association can be direct or indirect. For example, bound atoms or molecules may be directly bound to one another, e.g., by a covalent bond or non-covalent bond (e.g., electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). As a further example, two molecules may be bound indirectly to one another by way of direct binding to one or more intermediate molecules, thereby forming a complex. As used herein, the term "attached" refers to the state of two things being joined, fastened, adhered, connected or bound to each other. For example, a sample such as a cell or tissue, can be attached to a material, such as a hydrogel, polymer, or solid support, by a covalent or non-covalent bond. In embodiments, attachment is a covalent attachment.

"Specific binding" is where the binding is selective between two molecules. A particular example of specific binding is that which occurs between an antibody and an antigen. Typically, specific binding can be distinguished from non-specific when the dissociation constant (KD) is less than about $1\times10^{-5}$ M or less than about $1\times10^{-6}$ M or $1\times10^{-7}$ M. Specific binding can be detected, for example, by ELISA, immunoprecipitation, coprecipitation, with or without chemical crosslinking, two-hybrid assays and the like.

As used herein, the terms "sequencing", "sequence determination", "determining a nucleotide sequence", and the like include determination of a partial or complete sequence information (e.g., a sequence) of a polynucleotide being sequenced, and particularly physical processes for generating such sequence information. That is, the term includes sequence comparisons, consensus sequence determination, contig assembly, fingerprinting, and like levels of information about a target polynucleotide, as well as the express identification and ordering of nucleotides in a target polynucleotide. The term also includes the determination of the identification, ordering, and locations of one, two, or three of the four types of nucleotides within a target polynucleotide. In some embodiments, a sequencing process described herein includes contacting a template and an annealed primer with a suitable polymerase under conditions suitable for polymerase extension and/or sequencing. The sequencing methods are preferably carried out with the target polynucleotide arrayed on a solid substrate. Multiple target polynucleotides can be immobilized on the solid support through linker molecules, or can be attached to particles, e.g., microspheres, which can also be attached to a solid substrate. In embodiments, the solid substrate is in the form of a chip, a bead, a well, a capillary tube, a slide, a wafer, a filter, a fiber, a porous media, or a column. In embodiments, the solid substrate is gold, quartz, silica, plastic, glass, diamond, silver, metal, or polypropylene. In embodiments, the solid substrate is porous.

As used herein, the terms "solid support" and "substrate" and "solid surface" refers to discrete solid or semi-solid surface. A solid support may encompass any type of solid, porous, or hollow sphere, ball, cylinder, or other similar configuration composed of plastic, ceramic, metal, or polymeric material (e.g., hydrogel) onto which a nucleic acid may be immobilized (e.g., covalently or non-covalently). A solid support may include a discrete particle that may be spherical (e.g., microspheres) or have a non-spherical or irregular shape, such as cubic, cuboid, pyramidal, cylindrical, conical, oblong, or disc-shaped, and the like. Solid supports may be in the form of discrete particles, which alone does not imply or require any particular shape. The term "particle" means a small body made of a rigid or semi-rigid material. The body can have a shape characterized, for example, as a sphere, oval, microsphere, or other recognized particle shape whether having regular or irregular dimensions. As used herein, the term "discrete particles" refers to physically distinct particles having discernible boundaries. The term "particle" does not indicate any particular shape. The shapes and sizes of a collection of particles may be different or about the same (e.g., within a desired range of dimensions, or having a desired average or minimum dimension). A particle may be substantially spherical (e.g., microspheres) or have a non-spherical or irregular shape, such as cubic, cuboid, pyramidal, cylindrical, conical, oblong, or disc-shaped, and the like. In embodiments, the particle has the shape of a sphere, cylinder, spherocylinder, or ellipsoid. Discrete particles collected in a container and contacting one another will define a bulk volume containing the particles, and will typically leave some internal fraction of that bulk volume unoccupied by the particles, even when packed closely together. In embodiments, cores and/or core-shell particles are approximately spherical. As used herein the term "spherical" refers to structures which appear substantially or generally of spherical shape to the human eye, and does not require a sphere to a mathematical standard. In other words, "spherical" cores or particles are generally spheroidal in the sense of resembling or approximating to a sphere. In embodiments, the diameter of a spherical core or particle is substantially uniform, e.g., about the same at any point, but may contain imperfections, such as deviations of up to 1, 2, 3, 4, 5 or up to 10%. Because cores or particles may deviate from a perfect sphere, the term "diameter" refers to the longest dimension of a given core or particle. Likewise, polymer shells are not necessarily of perfect uniform thickness all around a given core. Thus, the term "thickness" in relation to a polymer structure (e.g., a shell polymer of a core-shell particle) refers to the average thickness of the polymer layer.

A "nanoparticle," as used herein, is a particle wherein the longest diameter is less than or equal to 1000 nanometers. Nanoparticles may be composed of any appropriate material. For example, nanoparticle cores may include appropriate metals and metal oxides thereof (e.g., a metal nanoparticle core), carbon (e.g., an organic nanoparticle core) silicon and oxides thereof (e.g., a silicon nanoparticle core) or boron and oxides thereof (e.g., a boron nanoparticle core), or mixtures thereof. Nanoparticles may be composed of at least two distinct materials, one material (e.g., silica or a MOF carrier) forms the core and the other material forms the shell (e.g., copolymer) surrounding the core. In embodiments, the nanoparticle is composed of a copolymer described herein. In embodiments, a particle may be referred to as a nanoparticle, and vice versa. The term "silica nanoparticle" is used according to its plain and ordinary meaning and refers to a nanoparticle containing Si atoms (e.g., in a tetrahedral coordination) with 4 oxygen atoms surrounding a central Si atom. A person of ordinary skill in the art would recognize that the silica nanoparticle typically includes terminal oxygen atoms (e.g., the oxygens on the surface of the nanoparticle) that are hydroxyl moieties. A silica nanoparticle is a particle wherein the longest diameter is typically less than or equal to 1000 nanometers including a matrix of silicon-oxygen bonds. In embodiments, a nanoparticle has a shortest diameter greater than or equal to 1 nanometer (e.g., diameter from 1 to 1000 nanometers). In embodiments, the silica nanoparticle is mesoporous. In embodiments, the silica nanoparticle is nonporous. A functionalized particle, as used herein, may refer to the post hoc conjugation (i.e., conjugation after the formation of the particle) of a moiety to a functional group on the surface of a particle. For example, a silica particle may be further functionalized to include additional atoms (e.g., nitrogen) or chemical entities (e.g., polymeric moieties or bioconjugate group). For example, when the silica nanoparticle is further functionalized with a nitrogen containing compound, one of the surface oxygen atoms surrounding the Si atom may be replaced with a nitrogen containing moiety. For example, a silica particle may be functionalized by reacting an unmodified silica nanoparticle with APTMS, APTES, or AHAMTES to generate an amine functionalized silica particle. The amine group may serve as a bioconjugate reactive moiety. In contrast to a functionalized particle, an unmodified particle refers to a particle which has not been further functionalized. Thus, for example, an unmodified particle does not include a nitrogen containing moiety (e.g., terminal amine moieties). For example, an unmodified silica nanoparticle refers to a silica nanoparticle as synthesized without post hoc functionalization. As used herein, the terms "bare particle" and "unmodified particle" are synonymous and interchangeable. In embodiments, an unmodified silica nanoparticle includes terminal oxygen atoms (e.g., the oxygens on the surface of the nanoparticle) that are hydroxyl moieties. In embodiments, the terminal oxygen atoms of the unmodified silica nanoparticle are —OH or salts thereof (e.g., —O— moieties).

As used herein, the term "MOF" is used in accordance with its ordinary meaning in the art and refers to a metal-organic framework. A MOF is a type of porous material comprised of metal containing nodes and organic ligands linked through coordination bonds. The structure and topology of MOFs can be designed and tailored so that the MOF can form one-, two-, or three-dimensional structures. The modular nature of MOFs allows for great synthetic tunability so properties such as porosity, stability, particle morphology and conductivity can be tailored for specific applications including encapsulation or release of guest molecules. The organic ligands used in MOFs are also referred to as "linkers" and are typically mono-, di-, tri-, or tetravalent ligands. The choice of metal and linker dictates the structure and properties of the MOF. For example, the metal's coordination preference can influence the size and shape of the pores in the MOF through the metal's preference for number and orientation of binding ligands. A MOF typically has potential voids between the organic ligands which make them valuable in applications such as drug delivery, biostorage and bio-catalysis. Further MOFs can undergo post-synthetic modification to further tune properties through swapping, altering or removing linker or node components in the framework. The MOF can be modified using a "modulator" or "modulating agent". The modulator competes with the organic linkers to bind to the metal center. In doing so, this prevents formation of impurities and slows down the reaction, allowing for increased reproducibility and crystallinity of the final product. Compounds that can act as modulators include but are not limited to CTAB, 1-methylimidazole, sodium formate and n-butylamine. A MOF can be degraded to release the compound(s) and/or material(s) encapsulated by the MOF. A MOF can be degraded in response to changes in pH, temperature or light.

Examples of MOF structures are zinc imidazolate framework (e.g., ZIF-8), Zr based MOFs, mesoporous iron (III) carboxylate MIL-100(Fe).

As used herein, the term "ZIF-8" refers to a zeolitic imidazolate framework, which is a type of MOF. A ZIF-8 is composed of metal cation $Zn^{2+}$ linked to the 2-methylimidazolate ligand species. On-demand release of material (i.e., controlled degradation) from a ZIF-8 carrier occurs in the presence of an external stimulus such as pH and at high efficiency (up to 100%) and/or at high temperature conditions. The ZIF-8 can be degraded by lowering the pH with an acid such as HCl, or by raising the pH with a base such as NaOH, and/or in the presence of degrading compounds such as phosphate, thereby eroding or dissolving the MOF.

Lengths and sizes of nanoparticles and functionalized particles as described herein may be measured using Transmission Electron Microscopy. For example, transmission electron microscopy measurements of the various particle samples may be drop coated (5 µL) onto 200 mesh copper EM grids, air-dried and imaged using a FEI Tecnai 12 TEM equipped with a Gatan Ultrascan 2K CCD camera at an accelerating voltage of 120 kV. The average size distributions of the particles may then be obtained from the TEM images using Image J software that were plotted using software (e.g., Origin Pro 8) to obtain the histogram size distributions of the particles. In embodiment, the length of a nanoparticle refers to the longest dimension of the particle.

As used herein, the term "core" refers to a polymer within which polynucleotide primers are attached, and that is surrounded by a "shell polymer" to which no polynucleotide primers are attached. The presence of the polynucleotide primer within the core permits a nucleic acid amplification reaction to take place, while the shell polymer provides a physical barrier between amplification reactions in adjacent cores. The cores are "surrounded" by the shell polymer in the sense that the shell polymer completely covers each core, and no core is in direct contact with any other core. The shell layer may enclose (e.g., surround, encapsulate, envelope) a core. In embodiments, each core surrounded by the shell polymer forms a discrete particle, the outer surface of which is defined by the shell polymer. In embodiments, the shells of discrete core-shell particles suspended in a container (e.g., a well, tube, or flow cell) expands, to fill any space between adjacent particles. In such cases, the boundaries of individual particles may no longer be readily discernable, but each core remains separated from each other by the shell polymer surrounding each, which can be readily observed by, e.g., detecting products of a nucleic acid amplification reaction. The core polymer may itself surround a solid support particle, such as a glass, ceramic, metal, silica, magnetic, or paramagnetic particle (e.g., a 500 nm silica nanoparticle). Solid support particles may be composed of any appropriate material. In embodiments, the support particle is an amorphous solid. In embodiments, the support particle is a crystalline solid. For example, solid support particles may include appropriate metals and metal oxides thereof (a metal particle core), carbon (an organic particle core) silica and oxides thereof (a silica particle core) or boron and oxides thereof (a boron particle core). For example, the core/shell layers may be formed around a supporting bead (alternatively referred to as a support particle), for example, a silica, magnetic, or paramagnetic bead. The term "support particle" as used herein may refer to any particle or substance having a diameter in the micrometer range, such as a "microparticle," which typically has a diameter of approximately 1 µm and higher, or a "nanoparticle," which typically has a diameter of 1 nm to 1 µm. The core, optionally including a solid silica support particle, may be referred to herein as a nanoparticle core wherein the longest diameter is less than 1000 nanometers. Lengths and sizes of particles and their surrounding cores as described herein may be measured using Transmission Electron Microscopy (TEM). The term "silica" is used according to its plain and ordinary meaning and refers to a composition (e.g., a solid composition such as a particle) containing oxides of silicon such as Si atoms (e.g., in a tetrahedral coordination) with 4 oxygen atoms surrounding a central Si atom. A silica support particle may refer to a particle including a matrix of silicon-oxygen bonds.

A solid support may further include a polymer or hydrogel on the surface to which the primers are attached (e.g., the primers are covalently attached to the polymer, wherein the polymer is in direct contact with the solid support). Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefin copolymers, polyimides etc.), nylon, ceramics, resins, Zeonor, silica or silica-based materials including silicon and modified silicon, carbon, metals, inorganic glasses, optical fiber bundles, photopatternable dry film resists, UV-cured adhesives and polymers. The solid supports for some embodiments have at least one surface located within a flow cell. The solid support, or regions thereof, can be substantially flat. The solid support can have surface features such as wells, pits, channels, ridges, raised regions, pegs, posts or the like. The term solid support is encompassing of a substrate (e.g., a flow cell) having a surface including a polymer coating covalently attached thereto. In embodiments, the solid support is a flow cell. The term "flow cell" as used herein refers to a chamber including a solid surface across which one or more fluid reagents can be flowed. Examples of flow cells and related fluidic systems and detection platforms that can be readily used in the methods of the present disclosure are described, for example, in Bentley et al., Nature 456:53-59 (2008). In certain embodiments a substrate includes a surface (e.g., a surface of a flow cell, a surface of a tube, a surface of a chip), for example a metal surface (e.g., steel, gold, silver, aluminum, silicon and copper). In some embodiments a substrate (e.g., a substrate surface) is coated and/or includes functional groups and/or inert materials. In certain embodiments a substrate includes a bead, a chip, a capillary, a plate, a membrane, a wafer (e.g., silicon wafers), a comb, or a pin for example. In some embodiments a substrate includes a bead and/or a nanoparticle. A substrate can be made of a suitable material, non-limiting examples of which include a plastic or a suitable polymer (e.g., polycarbonate, poly(vinyl alcohol), poly(divinylbenzene), polystyrene, polyamide, polyester, polyvinylidene difluoride (PVDF), polyethylene, polyurethane, polypropylene, and the like), borosilicate, glass, nylon, Wang resin, Merrifield resin, metal (e.g., iron, a metal alloy, sepharose, agarose, polyacrylamide, dextran, cellulose and the like or combinations thereof. In some embodiments a substrate includes a magnetic material (e.g., iron, nickel, cobalt, platinum, aluminum, and the like). In certain embodiments a substrate includes a magnetic bead (e.g., DYNABEADS®, hematite, AMPure XP). Magnets can be used to purify and/or capture nucleic acids bound to certain substrates (e.g., substrates including a metal or magnetic material).

As used herein, the term "channel" refers to a passage in or on a substrate material that directs the flow of a fluid. A channel may run along the surface of a substrate, or may run through the substrate between openings in the substrate. A channel can have a cross section that is partially or fully surrounded by substrate material (e.g., a fluid impermeable substrate material). For example, a partially surrounded cross section can be a groove, trough, furrow or gutter that inhibits lateral flow of a fluid. The transverse cross section of an open channel can be, for example, U-shaped, V-shaped, curved, angular, polygonal, or hyperbolic. A channel can have a fully surrounded cross section such as a tunnel, tube, or pipe. A fully surrounded channel can have a rounded, circular, elliptical, square, rectangular, or polygonal cross section. A microfluidic flow channel is characterized by cross-sectional dimensions less than 1000 microns. Usually at least one, and preferably all, cross-sectional dimensions are greater than 500 microns.

As used herein, the term "polymer" refers to macromolecules having one or more structurally unique repeating units. The repeating units are referred to as "monomers," which are polymerized for the polymer. Typically, a polymer is formed by monomers linked in a chain-like structure. A polymer formed entirely from a single type of monomer is referred to as a "homopolymer." A polymer formed from two or more unique repeating structural units may be referred to as a "copolymer." A polymer may be linear or branched, and may be random, block, polymer brush, hyperbranched polymer, bottlebrush polymer, dendritic polymer, or polymer micelles. The term "polymer" includes homopolymers, copolymers, tripolymers, tetra polymers and other polymeric molecules made from monomeric subunits. Copolymers include alternating copolymers, periodic copolymers, statistical copolymers, random copolymers, block copolymers, linear copolymers and branched copolymers. The term "polymerizable monomer" is used in accordance with its meaning in the art of polymer chemistry and refers to a compound that may covalently bind chemically to other monomer molecules (such as other polymerizable monomers that are the same or different) to form a polymer.

Polymers can be hydrophilic, hydrophobic, or amphiphilic, as known in the art. Thus, "hydrophilic polymers" are substantially miscible with water and include, but are not limited to, polyethylene glycol and the like. "Hydrophobic polymers" are substantially immiscible with water and include, but are not limited to, polyethylene, polypropylene, polybutadiene, polystyrene, polymers disclosed herein, and the like. "Amphiphilic polymers" have both hydrophilic and hydrophobic properties and are typically copolymers having hydrophilic segment(s) and hydrophobic segment(s). Polymers include homopolymers, random copolymers, and block copolymers, as known in the art. The term "homopolymer" refers, in the usual and customary sense, to a polymer having a single monomeric unit. The term "copolymer" refers to a polymer derived from two or more monomeric species. The term "random copolymer" refers to a polymer derived from two or more monomeric species with no preferred ordering of the monomeric species. The term "block copolymer" refers to polymers having two or homopolymer subunits linked by covalent bond. Thus, the term "hydrophobic homopolymer" refers to a homopolymer which is hydrophobic. The term "hydrophobic block copolymer" refers to two or more homopolymer subunits linked by covalent bonds and which is hydrophobic.

As used herein, the term "hydrogel" refers to a three-dimensional polymeric structure that is substantially insoluble in water, but which is capable of absorbing and retaining large quantities of water to form a substantially stable, often soft and pliable, structure. In embodiments, water can penetrate in between polymer chains of a polymer network, subsequently causing swelling and the formation of a hydrogel. In embodiments, hydrogels are super-absorbent (e.g., containing more than about 90% water) and can be comprised of natural or synthetic polymers. In some embodiments, the hydrogel polymer includes 60-90% fluid, such as water, and 10-30% polymer. In certain embodiments, the water content of hydrogel is about 70-80%.

Hydrogels may be prepared by cross-linking hydrophilic biopolymers or synthetic polymers. Thus, in some embodiments, the hydrogel may include a crosslinker. As used herein, the term "crosslinker" refers to a molecule that can form a three-dimensional network when reacted with the appropriate base monomers. Examples of the hydrogel polymers, which may include one or more crosslinkers, include but are not limited to, hyaluronans, chitosans, agar, heparin, sulfate, cellulose, alginates (including alginate sulfate), collagen, dextrans (including dextran sulfate), pectin, carrageenan, polylysine, gelatins (including gelatin type A), agarose, (meth)acrylate-oligolactide-PEO-oligolactide-(meth)acrylate, PEO—PPO-PEO copolymers (Pluronics), poly(phosphazene), poly(methacrylates), poly(N-vinylpyrrolidone), PL(G)A-PEO-PL(G)A copolymers, poly(ethylene imine), polyethylene glycol (PEG)-thiol, PEG-acrylate, acrylamide, N,N'-bis(acryloyl)cystamine, PEG, polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), bisacrylamide, diacrylate, diallylamine, triallylamine, divinyl sulfone, diethyleneglycol diallyl ether, ethyleneglycol diacrylate, polymethyleneglycol diacrylate, polyethyleneglycol diacrylate, trimethylopropoane trimethacrylate, ethoxylated trimethylol triacrylate, or ethoxylated pentaerythritol tetracrylate, or combinations thereof. Thus, for example, a combination may include a polymer and a crosslinker, for example polyethylene glycol (PEG)-thiol/PEG-acrylate, acrylamide/N,N'-bis(acryloyl)cystamine (BACy), or PEG/polypropylene oxide (PPO). In embodiments, the hydrogel includes chemical crosslinks (e.g., intermolecular or intramolecular joining of two or more molecules by a covalent bond) and may be referred to as a chemical hydrogel. In embodiments, the hydrogel includes physical crosslinks (e.g., intermolecular or intramolecular joining of two or more molecules by a non-covalent bond) and may be referred to as a physical hydrogel. In embodiments, the physical hydrogel include one or more crosslinks including hydrogen bonds, hydrophobic interactions, and/or polymer chain entanglements.

The term "array" as used herein, refers to a container (e.g., a microplate, tube, or flow cell) including a plurality of features (e.g., wells). For example, an array may include a container with a plurality of wells. In embodiments, the array is a microplate. In embodiments, the array is a flow cell.

The term "microplate," "microtiter plate," "multiwell container," or "multiwell plate" as used herein, refers to a substrate including a surface, the surface including a plurality of chambers or wells separated from each other by interstitial regions on the surface. In embodiments, the microplate has dimensions as provided and described by American National Standards Institute (ANSI) and Society for Laboratory Automation And Screening (SLAS); for example the tolerances and dimensions set forth in ANSI SLAS 1-2004 (R2012); ANSI SLAS 2-2004 (R2012); ANSI SLAS 3-2004 (R2012); ANSI SLAS 4-2004 (R2012); and ANSI SLAS 6-2012, which are incorporated herein by reference. The dimensions of the microplate as described herein and the arrangement of the reaction chambers may be compatible with an established format for automated laboratory equipment. In embodiments, the device described herein provides methods for high-throughput screening. High-throughput screening (HTS) refers to a process that uses a combination of modem robotics, data processing and control software, liquid handling devices, and/or sensitive detectors, to efficiently process a large amount of (e.g., thousands, hundreds of thousands, or millions) samples in biochemical, genetic, or pharmacological experiments, either in parallel or in sequence, within a reasonably short period of time (e.g., days). Preferably, the process is amenable to automation, such as robotic simultaneous handling of 96 samples, 384 samples, 1536 samples or more. A typical HTS robot tests up to 100,000 to a few hundred thousand compounds per day. The samples are often in small volumes, such as no more than 1 mL, 500 µl, 200 µl, 100 µl, 50 µl or less. Through this process, one can rapidly identify active compounds, small molecules, antibodies, proteins, or polynucleotides in a cell.

The reaction chambers may be provided as wells, for example an array or microplate may contain 2, 4, 6, 12, 24, 48, 96, 384, or 1536 sample wells. In embodiments, the 96 and 384 wells are arranged in a 2:3 rectangular matrix. In embodiments, the 24 wells are arranged in a 3:8 rectangular matrix. In embodiments, the 48 wells are arranged in a 3:4 rectangular matrix. In embodiments, the reaction chamber is a microscope slide (e.g., a glass slide about 75 mm by about 25 mm). In embodiments the slide is a concavity slide (e.g., the slide includes a depression). In embodiments, the slide includes a coating for enhanced cell adhesion (e.g., poly-L-lysine, silanes, carbon nanotubes, polymers, epoxy resins, or gold). In embodiments, the microplate is about 5 inches by about 3.33 inches, and includes a plurality of 5 mm diameter wells. In embodiments, the microplate is about 5 inches by about 3.33 inches, and includes a plurality of 6 mm diameter wells. In embodiments, the microplate is about 5 inches by about 3.33 inches, and includes a plurality of 7 mm diameter wells. In embodiments, the microplate is about 5 inches by about 3.33 inches, and includes a plurality of 7.5 mm diameter wells. In embodiments, the microplate is 5 inches by 3.33 inches, and includes a plurality of 7.5 mm diameter wells. In embodiments, the microplate is about 5 inches by about 3.33 inches, and includes a plurality of 8 mm diameter wells. In embodiments, the microplate is a flat glass or plastic tray in which an array of wells are formed, wherein each well can hold between from a few microliters to hundreds of microliters of fluid reagents and samples.

The term "surface" is intended to mean an external part or external layer of a substrate. The surface can be in contact with another material such as a gas, liquid, gel, polymer, organic polymer, second surface of a similar or different material, metal, or coat. The surface, or regions thereof, can be substantially flat. The substrate and/or the surface can have surface features such as wells, pits, channels, ridges, raised regions, pegs, posts or the like.

The term "well" refers to a discrete concave feature in a substrate having a surface opening that is completely surrounded by interstitial region(s) of the surface. Wells can have any of a variety of shapes at their opening in a surface including but not limited to round, elliptical, square, polygonal, or star shaped (i.e., star shaped with any number of vertices). The cross section of a well taken orthogonally with the surface may be curved, square, polygonal, hyperbolic, conical, or angular. The wells of a microplate are available in different shapes, for example F-Bottom: flat bottom; C-Bottom: bottom with minimal rounded edges; V-Bottom: V-shaped bottom; or U-Bottom: U-shaped bottom. In embodiments, the well is substantially square. In embodiments, the well is square. In embodiments, the well is F-bottom. In embodiments, the microplate includes 24 substantially round flat bottom wells. In embodiments, the microplate includes 48 substantially round flat bottom wells. In embodiments, the microplate includes 96 substantially round flat bottom wells. In embodiments, the microplate includes 384 substantially square flat bottom wells. The wells (alternatively referred to as reaction chambers) of a solid support and/or support insert may contain 2, 4, 6, 12, 24, 48, 96, 384, or 1536 sample wells. In embodiments, the 96 and 384 wells are arranged in a 2:3 rectangular matrix. In embodiments, the 24 wells are arranged in a 3:8 rectangular matrix. In embodiments, the 48 wells are arranged in a 3:4 rectangular matrix. In embodiments, the solid support is a microscope slide (e.g., a glass slide about 75 mm by about 25 mm). In embodiments the slide is a concavity slide (e.g., the slide includes a depression). In embodiments, the slide includes a coating for enhanced cell adhesion (e.g., poly-L-lysine, silanes, carbon nanotubes, polymers, epoxy resins, or gold). In embodiments, the solid support is about 5 inches by about 3.33 inches, and includes a plurality of 5 mm diameter wells. In embodiments, the solid support is about 5 inches by about 3.33 inches, and includes a plurality of 6 mm diameter wells. In embodiments, the solid support is about 5 inches by about 3.33 inches, and includes a plurality of 7 mm diameter wells. In embodiments, the solid support is about 5 inches by about 3.33 inches, and includes a plurality of 7.5 mm diameter wells. In embodiments, the solid support is 5 inches by 3.33 inches, and includes a plurality of 7.5 mm diameter wells. In embodiments, the solid support is about 5 inches by about 3.33 inches, and includes a plurality of 8 mm diameter wells. In embodiments, the solid support insert is a flat glass or plastic tray in which an array of wells are formed, wherein each well can hold between from a few microliters to hundreds of microliters of fluid reagents and samples. In embodiments, the solid support is a flat glass or plastic tray in which an array of wells are formed, wherein each well can hold between from a few microliters to hundreds of microliters of fluid reagents and samples. In embodiments, the solid support has a rectangular shape that measures 127.7 mm+0.5 mm in length by 85.4 mm±0.5 mm in width, and includes 6, 12, 24, 48, or 96 wells, wherein each well has an average diameter of about 5-7 mm. In embodiments, the solid support has a rectangular shape that measures 127.7 mm±0.5 mm in length by 85.4 mm+0.5 mm in width, and includes 6, 12, 24, 48, or 96 wells, wherein each well has an average diameter of about 6 mm. In embodiments, the solid support includes an array of femtoliter wells, array of nanoliter wells, or array of microliter wells. In embodiments, the wells in an array may all have substantially the same volume. The array of wells may have a volume up to 100 e.g., about 0.1 femtoliter, 1 femtoliter, 10 femtoliter, 25 femtoliter, 50 femtoliter, 100 femtoliter, 0.1 pL, 1 pL, 10 pL, 25 pL, 50 pL, 100 pL, 0.1 nL, 1 nL, 10 nL, 25 nL, 50 nL, 100 nL, 0.1 microliter, 1 microliter, 10 microliter, 25 microliter, 50 microliter, or 100 microliter.

The term "nanowell" refers to a discrete concave feature or depression in a substrate having a surface opening that is completely surrounded by interstitial region(s) of the surface, wherein the diameter of the feature is less than or equal to 1000 nanometers.

The discrete regions (i.e., features, wells) of the microplate may have defined locations in a regular array, which may correspond to a rectilinear pattern, circular pattern, hexagonal pattern, or the like. In embodiments, the pattern of wells includes concentric circles of regions, spiral patterns, rectilinear patterns, hexagonal patterns, and the like. In embodiments, the pattern of wells is arranged in a rectilinear or hexagonal pattern A regular array of such regions is advantageous for detection and data analysis of signals collected from the arrays during an analysis. These discrete regions are separated by interstitial regions. As used herein, the term "interstitial region" refers to an area in a substrate or on a surface that separates other areas of the substrate or surface. For example, an interstitial region can separate one concave feature of an array from another concave feature of the array. The two regions that are separated from each other can be discrete, lacking contact with each other. In another example, an interstitial region can separate a first portion of a feature from a second portion of a feature. In embodiments the interstitial region is continuous whereas the features are discrete, for example, as is the case for an array of wells in an otherwise continuous surface. The separation provided by an interstitial region can be partial or full separation. In embodiments, interstitial regions have a surface material that differs from the surface material of the wells (e.g., the interstitial region contains a photoresist and the surface of the well is glass). In embodiments, interstitial regions have a surface material that is the same as the surface material of the wells (e.g., both the surface of the interstitial region and the surface of well contain a polymer or copolymer).

As used herein, the term "sequencing cycle" is used in accordance with its plain and ordinary meaning and refers to incorporating one or more nucleotides (e.g., nucleotide analogues) to the 3' end of a polynucleotide with a polymerase, and detecting one or more labels that identify the one or more nucleotides incorporated. In embodiments, one nucleotide (e.g., a modified nucleotide) is incorporated per sequencing cycle. The sequencing may be accomplished by, for example, sequencing by synthesis, pyrosequencing, and the like. In embodiments, a sequencing cycle includes extending a complementary polynucleotide by incorporating a first nucleotide using a polymerase, wherein the polynucleotide is hybridized to a template nucleic acid, detecting the first nucleotide, and identifying the first nucleotide. In embodiments, to begin a sequencing cycle, one or more differently labeled nucleotides and a DNA polymerase can be introduced. Following nucleotide addition, signals produced (e.g., via excitation and emission of a detectable label) can be detected to determine the identity of the incorporated nucleotide (based on the labels on the nucleotides). Reagents can then be added to remove the 3' reversible terminator and to remove labels from each incorporated base. Reagents, enzymes, and other substances can be removed between steps by washing. Cycles may include repeating these steps, and the sequence of each cluster is read over the multiple repetitions.

As used herein, the term "extension" or "elongation" is used in accordance with their plain and ordinary meanings and refer to synthesis by a polymerase of a new polynucleotide strand complementary to a template strand by adding free nucleotides (e.g., dNTPs) from a reaction mixture that are complementary to the template in the 5'-to-3' direction. Extension includes condensing the 5'-phosphate group of the dNTPs with the 3'-hydroxy group at the end of the nascent (elongating) DNA strand.

As used herein, the term "sequencing read" is used in accordance with its plain and ordinary meaning and refers to an inferred sequence of nucleotide bases (or nucleotide base probabilities) corresponding to all or part of a single polynucleotide fragment. A sequencing read may include 10, 20, 30, 40, 50, 60, 70, 80, 90, 100, 150, 200, 250, or more nucleotide bases. Reads of length 20-40 base pairs (bp) are referred to as ultra-short. Typical sequencers produce read lengths in the range of 100-500 bp. Read length is a factor which can affect the results of biological studies. For example, longer read lengths improve the resolution of de novo genome assembly and detection of structural variants. In embodiments, a sequencing read includes reading a barcode and a template nucleotide sequence. In embodiments, a sequencing read includes reading a template nucleotide sequence. In embodiments, a sequencing read includes reading a barcode and not a template nucleotide sequence. In embodiments, a sequencing read includes a computationally derived string corresponding to the detected label. In some embodiments, a sequencing read may include 500, 600, 700, 800, 900, 1,000, 1,100, 1,200, 1,300, 1,400, 1,500, or more nucleotide bases. In embodiments, a sequencing read is a string of characters representing the sequence of nucleotides. In embodiments, the length of a sequencing read corresponds to the length of the target sequence. In embodiments, the length of a sequencing read corresponds to the number of sequencing cycles. A sequencing read may be subjected to initial processing (often termed "pre-processing") prior to annotation. Pre-processing includes filtering out low-quality sequences, sequence trimming to remove continuous low-quality nucleotides, merging paired-end sequences, or identifying and filtering out PCR repeats using known techniques in the art. The sequenced reads may then be assembled and aligned using bioinformatic algorithms known in the art. A sequencing read may be aligned to a reference sequence. In embodiments, a sequencing read includes a computationally derived string corresponding to the detected complementary nucleotide (e.g., a labeled nucleotide). The sequence reads are optionally stored in an appropriate data structure for further evaluation. In embodiments, a first sequencing reaction can generate a first sequencing read. The first sequencing read can provide the sequence of a first region of the polynucleotide fragment. In some embodiments, the nucleic acid template is optionally subjected to one or more additional rounds of sequencing using additional sequencing primers, thereby generating additional sequencing reads. In embodiments, generating a sequencing read includes reading a barcode and a template nucleotide sequence. In embodiments, generating a sequencing read includes reading a template nucleotide sequence. In embodiments, generating a sequencing read includes reading a barcode and not a template nucleotide sequence. In embodiments, a sequencing read is about 25 nucleotide bases. In embodiments, a sequencing read is about 35 nucleotide bases. In embodiments, a sequencing read is about 45 nucleotide bases. In embodiments, a sequencing read is about 55 nucleotide bases. In embodiments, a sequencing read is about 65 nucleotide bases. In embodiments, a sequencing read is about 75 nucleotide bases. In embodiments, a sequencing read is about 85 nucleotide bases.

A "gene" refers to a polynucleotide sequence that is capable of conferring biological function after being transcribed and/or translated. Functionally, a genome is subdivided into genes. Each gene is a nucleic acid sequence that encodes an RNA or polypeptide. A gene is transcribed from DNA into RNA, which can either be non-coding (ncRNA) with a direct function, or an intermediate messenger (mRNA) that is then translated into protein. Typically a gene includes multiple sequence elements, such as for example, a coding element (i.e., a sequence that encodes a functional protein), non-coding element, and regulatory element. Each element may be as short as a few bp to 5 kb. In embodiments, the gene is the protein coding sequence of RNA. Non-limiting examples of genes include developmental genes (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogenes (e.g., ABL1, BCL1, BCL2, BCL6, CBFA2, CBL, CSF1R, ERBA, ERBB, EBRB2, ETS1, ETS1, ETV6, FGR, FOS, FYN, HCR, HRAS, JUN, KRAS, LCK, LYN, MDM2, MLL, MYB, MYC, MYCL1, MYCN, NRAS, PIM1, PML, RET, SRC, TAL1, TCL3, and YES); tumor suppressor genes (e.g., APC, BRCA1, BRCA2, MADH4, MCC, NF1, NF2, RB1, TP53, and WT1); and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases). In embodiments, a gene includes at least one mutation associated with a disease or condition mediated by a mutant form of the gene.

The term "genetic locus," or "locus" as used herein refers to a genome or target polynucleotide, specifically a contiguous subregion or segment of the genome or target polynucleotide. As used herein, genetic locus, or locus, may refer to the position of a nucleotide, a gene, or a portion of a gene in a genome, including mitochondrial DNA, or it may refer to any contiguous portion of genomic sequence whether or not it is within, or associated with, a gene. In one aspect, a genetic locus refers to any portion of genomic sequence, including mitochondrial DNA, from a single nucleotide to a segment of few hundred nucleotides, e.g. 100-300, in length. Usually, a particular genetic locus may be identified by its nucleotide sequence, or the nucleotide sequence, or sequences, of one or both adjacent or flanking regions. In another aspect, a genetic locus refers to the expressed nucleic acid product of a gene, such as an RNA molecule or a cDNA copy thereof.

The term "multiplexing" as used herein refers to an analytical method in which the presence and/or amount of multiple targets, e.g., multiple nucleic acid target sequences, can be assayed simultaneously by using the methods and devices as described herein, each of which has at least one different detection characteristic, e.g., fluorescence characteristic (for example excitation wavelength, emission wavelength, emission intensity, FWHM (full width at half maximum peak height), or fluorescence lifetime) or a unique nucleic acid or protein sequence characteristic. As used herein, the term "multiplex" is used to refer to an assay in which multiple (i.e. at least two) different biomolecules are assayed at the same time, and more particularly in the same aliquot of the sample, or in the same reaction mixture. In embodiments, more than two different biomolecules are assayed at the same time. In embodiments, at least 2, 4, 6, 8, 10, 20, 50, 100, 200, 300, 400, 500, 600, 700, 800, 900, 1000, 1100, 1200, 1300, 1400 or 1500 or more biomolecules are detected according to the present method.

As used herein, the term "adjacent," refers to two nucleotide sequences in a nucleic acid, can refer to nucleotide sequences separated by 0 to about 20 nucleotides, more specifically, in a range of about 1 to about 10 nucleotides, or to sequences that directly abut one another. As those of skill in the art appreciate, two nucleotide sequences that that are to ligated together will generally directly abut one another.

As used herein, the terms "incubate," and "incubation" refer collectively to altering the temperature of an object in a controlled manner such that conditions are sufficient for conducting the desired reaction. Thus, it is envisioned that the terms encompass heating a receptacle (e.g., a microplate) to a desired temperature and maintaining such temperature for a fixed time interval. Also included in the terms is the act of subjecting a receptacle to one or more heating and cooling cycles (i.e., "temperature cycling" or "thermal cycling"). While temperature cycling typically occurs at relatively high rates of change in temperature, the term is not limited thereto, and may encompass any rate of change in temperature.

Complementary single stranded nucleic acids and/or substantially complementary single stranded nucleic acids can hybridize to each other under hybridization conditions, thereby forming a nucleic acid that is partially or fully double stranded. All or a portion of a nucleic acid sequence may be substantially complementary to another nucleic acid sequence, in some embodiments. As referred to herein, "substantially complementary" refers to nucleotide sequences that can hybridize with each other under suitable hybridization conditions. Hybridization conditions can be altered to tolerate varying amounts of sequence mismatch within complementary nucleic acids that are substantially complementary. Substantially complementary portions of nucleic acids that can hybridize to each other can be 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other. In some embodiments substantially complementary portions of nucleic acids that can hybridize to each other are 100% complementary. Nucleic acids, or portions thereof, that are configured to hybridize to each other often include nucleic acid sequences that are substantially complementary to each other.

"Hybridize" shall mean the annealing of a nucleic acid sequence to another nucleic acid sequence (e.g., one single-stranded nucleic acid (such as a primer) to another nucleic acid) based on the well-understood principle of sequence complementarity. In an embodiment the other nucleic acid is a single-stranded nucleic acid. In some embodiments, one portion of a nucleic acid hybridizes to itself, such as in the formation of a hairpin structure. The propensity for hybridization between nucleic acids depends on the temperature and ionic strength of their milieu, the length of the nucleic acids and the degree of complementarity. The effect of these parameters on hybridization is described in, for example, Sambrook J., Fritsch E. F., Maniatis T., Molecular cloning: a laboratory manual, Cold Spring Harbor Laboratory Press, New York (1989). As used herein, hybridization of a primer, or of a DNA extension product, respectively, is extendable by creation of a phosphodiester bond with an available nucleotide or nucleotide analogue capable of forming a phosphodiester bond, therewith. For example, hybridization can be performed at a temperature ranging from 15° C. to 95° C. In some embodiments, the hybridization is performed at a temperature of about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., or about 95° C. In other embodiments, the stringency of the hybridization can be further altered by the addition or removal of components of the buffered solution.

As used herein, "specifically hybridizes" refers to preferential hybridization under hybridization conditions where two nucleic acids, or portions thereof, that are substantially complementary, hybridize to each other and not to other nucleic acids that are not substantially complementary to either of the two nucleic acids. For example, specific hybridization includes the hybridization of a primer or capture nucleic acid to a portion of a target nucleic acid (e.g., a template, or adapter portion of a template) that is substantially complementary to the primer or capture nucleic acid. In some embodiments nucleic acids, or portions thereof, that are configured to specifically hybridize are often about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more or 100% complementary to each other over a contiguous portion of nucleic acid sequence. A specific hybridization discriminates over non-specific hybridization interactions (e.g., two nucleic acids that a not configured to specifically hybridize, e.g., two nucleic acids that are 80% or less, 70% or less, 60% or less or 50% or less complementary) by about 2-fold or more, often about 10-fold or more, and sometimes about 100-fold or more, 1000-fold or more, 10,000-fold or more, 100,000-fold or more, or 1,000,000-fold or more. Two nucleic acid strands that are hybridized to each other can form a duplex which includes a double stranded portion of nucleic acid.

A nucleic acid can be amplified by a suitable method. The term "amplification," "amplified," or "amplifying" as used herein refers to subjecting a target nucleic acid in a sample to a process that linearly or exponentially generates amplicon nucleic acids having the same or substantially the same (e.g., substantially identical) nucleotide sequence as the target nucleic acid, or segment thereof, and/or a complement thereof (which may be referred to herein as an "amplification product" or "amplification products"). In some embodiments an amplification reaction includes a suitable thermal stable polymerase. Thermal stable polymerases are known in the art and are stable for prolonged periods of time, at temperature greater than 80° C. when compared to common polymerases found in most mammals. In certain embodiments the term "amplification," "amplified," or "amplifying" refers to a method that includes a polymerase chain reaction (PCR). Conditions conducive to amplification (i.e., amplification conditions) are well known and often include at least a suitable polymerase, a suitable template, a suitable primer or set of primers, suitable nucleotides (e.g., dNTPs), a suitable buffer, and application of suitable annealing, hybridization and/or extension times and temperatures. In certain embodiments an amplified product (e.g., an amplicon) can contain one or more additional and/or different nucleotides than the template sequence, or portion thereof, from which the amplicon was generated (e.g., a primer can contain "extra" nucleotides (such as a 5' portion that does not hybridize to the template), or one or more mismatched bases within a hybridizing portion of the primer).

As used herein, bridge-PCR (bPCR) amplification is a method for solid-phase amplification as exemplified by the disclosures of U.S. Pat. Nos. 5,641,658; 7,115,400; and U.S. Patent Publ. No. 2008/0009420, each of which is incorporated herein by reference in its entirety. Bridge-PCR involves repeated polymerase chain reaction cycles, cycling between denaturation, annealing, and extension conditions and enables controlled, spatially-localized, amplification, to generate amplification products (e.g., amplicons) immobilized on a solid support in order to form arrays comprised of colonies (or "clusters") of immobilized nucleic acid molecule.

As used herein, the terms "cluster" and "colony" are used interchangeably to refer to a discrete site on a solid support that includes a plurality of immobilized polynucleotides and a plurality of immobilized complementary polynucleotides. The term "clustered array" refers to an array formed from such clusters or colonies. In this context the term "array" is not to be understood as requiring an ordered arrangement of clusters. The term "array" is used in accordance with its ordinary meaning in the art, and refers to a population of different molecules that are attached to one or more solid-phase substrates such that the different molecules can be differentiated from each other according to their relative location. An array can include different molecules that are each located at different addressable features on a solid-phase substrate. The molecules of the array can be nucleic acid primers, nucleic acid probes, nucleic acid templates or nucleic acid enzymes such as polymerases or ligases. Arrays useful in the invention can have densities that ranges from about 2 different features to many millions, billions or higher. The density of an array can be from 2 to as many as a billion or more different features per square cm. For example an array can have at least about 100 features/$cm^2$, at least about 1,000 features/$cm^2$, at least about 10,000 features/$cm^2$, at least about 100,000 features/$cm^2$, at least about 10,000,000 features/$cm^2$, at least about 100,000,000 features/$cm^2$, at least about 1,000,000,000 features/$cm^2$, at least about 2,000,000,000 features/$cm^2$ or higher. In embodiments, the arrays have features at any of a variety of densities including, for example, at least about 10 features/$cm^2$, 100 features/$cm^2$, 500 features/$cm^2$, 1,000 features/$cm^2$, 5,000 features/$cm^2$, 10,000 features/$cm^2$, 50,000 features/$cm^2$, 100,000 features/$cm^2$, 1,000,000 features/$cm^2$, 5,000,000 features/$cm^2$, or higher.

As used herein, the term "rolling circle amplification (RCA)" refers to a nucleic acid amplification reaction that amplifies a circular nucleic acid template (e.g., single-stranded DNA circles) via a rolling circle mechanism. Rolling circle amplification reaction is initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). The rolling circle amplification typically produces concatemers including tandem repeat units of the circular nucleic acid template sequence. The rolling circle amplification may be a linear RCA (LRCA), exhibiting linear amplification kinetics (e.g., RCA using a single specific primer), or may be an exponential RCA (ERCA) exhibiting exponential amplification kinetics. Rolling circle amplification may also be performed using multiple primers (multiply primed rolling circle amplification or MPRCA) leading to hyper-branched concatemers. For example, in a double-primed RCA, one primer may be complementary, as in the linear RCA, to the circular nucleic acid template, whereas the other may be complementary to the tandem repeat unit nucleic acid sequences of the RCA product. Consequently, the double-primed RCA may proceed as a chain reaction with exponential (geometric) amplification kinetics featuring a ramifying cascade of multiple-hybridization, primer-extension, and strand-displacement events involving both the primers. This often generates a discrete set of concatemeric, double-stranded nucleic acid amplification products. The rolling circle amplification may be performed in-vitro under isothermal conditions using a suitable nucleic acid polymerase such as Phi29 DNA polymerase. RCA may be performed by using any of the DNA polymerases that are known in the art (e.g., a Phi29 DNA polymerase, a Bst DNA polymerase, or SD polymerase).

A nucleic acid can be amplified by a thermocycling method or by an isothermal amplification method. In some embodiments a rolling circle amplification method is used. In some embodiments amplification takes place on a solid support (e.g., within a flow cell) where a nucleic acid, nucleic acid library or portion thereof is immobilized. In certain sequencing methods, a nucleic acid library is added to a flow cell and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support.

In some embodiments solid phase amplification includes a nucleic acid amplification reaction including only one species of oligonucleotide primer immobilized to a surface or substrate. In certain embodiments solid phase amplification includes a plurality of different immobilized oligonucleotide primer species. In some embodiments solid phase amplification may include a nucleic acid amplification reaction including one species of oligonucleotide primer immobilized on a solid surface and a second different oligonucleotide primer species in solution. Multiple different species of immobilized or solution-based primers can be used. Non-limiting examples of solid phase nucleic acid amplification reactions include interfacial amplification, bridge PCR amplification, emulsion PCR, WildFire amplification (e.g., US patent publication US20130012399), the like or combinations thereof.

Provided herein are methods and compositions for analyzing a sample (e.g., sequencing nucleic acids within a sample). A sample (e.g., a sample including nucleic acid) can be obtained from a suitable subject. A sample can be isolated or obtained directly from a subject or part thereof. In some embodiments, a sample is obtained indirectly from an individual or medical professional. A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. A fluid or tissue sample from which nucleic acid is extracted may be acellular (e.g., cell-free). Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may include cells or tissues that are normal, healthy, diseased (e.g., infected), and/or cancerous (e.g., cancer cells). A sample obtained from a subject may include cells or cellular material (e.g., nucleic acids) of multiple organisms (e.g., virus nucleic acid, fetal nucleic acid, bacterial nucleic acid, parasite nucleic acid).

In some embodiments, a sample includes one or more nucleic acids, or fragments thereof. A sample can include nucleic acids obtained from one or more subjects. In some embodiments a sample includes nucleic acid obtained from a single subject. In some embodiments, a sample includes a mixture of nucleic acids. A mixture of nucleic acids can include two or more nucleic acid species having different nucleotide sequences, different fragment lengths, different origins (e.g., genomic origins, cell or tissue origins, subject origins, the like or combinations thereof), or combinations thereof.

A subject can be any living or non-living organism, including but not limited to a human, non-human animal, plant, bacterium, fungus, virus or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a human subject. A subject can be a patient (e.g., a human patient). In some embodiments a subject is suspected of having a genetic variation or a disease or condition associated with a genetic variation.

The methods and kits of the present disclosure may be applied, mutatis mutandis, to the sequencing of RNA, or to determining the identity of a ribonucleotide.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., packaging, buffers, written instructions for performing a method, etc.) from one location to another. For example, kits include one or more enclosures (e.g., boxes) containing the relevant reaction reagents and/or supporting materials. As used herein, the term "fragmented kit" refers to a delivery system including two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits.

The terms "bioconjugate group," "bioconjugate reactive moiety," and "bioconjugate reactive group" refer to a chemical moiety which participates in a reaction to form a bioconjugate linker (e.g., covalent linker). Non-limiting examples of bioconjugate reactive groups and the resulting bioconjugate reactive linkers may be found in the Bioconjugate Table below:

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
|---|---|---|
| activated esters | amines/anilines | carboxamides |
| acrylamides | thiols | thioethers |
| acyl azides | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

As used herein, the term "bioconjugate reactive moiety" and "bioconjugate reactive group" refers to a moiety or group capable of forming a bioconjugate (e.g., covalent linker) as a result of the association between atoms or molecules of bioconjugate reactive groups. The association can be direct or indirect. For example, a conjugate between a first bioconjugate reactive group (e.g., —NH$_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine). Useful bioconjugate reactive groups used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds; (n) azides coupled to alkynes using copper catalyzed cycloaddition click chemistry; (o) biotin conjugate can react with avidin or strepavidin to form a avidin-biotin complex or streptavidin-biotin complex.

The term "covalent linker" is used in accordance with its ordinary meaning and refers to a divalent moiety which connects at least two moieties to form a molecule. The term "non-covalent linker" is used in accordance with its ordinary meaning and refers to a divalent moiety which includes at least two molecules that are not covalently linked to each other but are capable of interacting with each other via a non-covalent bond (e.g., electrostatic interactions (e.g., ionic bond, hydrogen bond, halogen bond) or van der Waals interactions (e.g., dipole-dipole, dipole-induced dipole, London dispersion). In embodiments, the non-covalent linker is the result of two molecules that are not covalently linked to each other that interact with each other via a non-covalent bond.

The term "adapter" as used herein refers to any synthetic oligonucleotide that can be attached (e.g., by ligation, hybridization, or transposition) to a nucleic acid molecule, thereby generating nucleic acid products that can be sequenced on a sequencing platform (e.g., an Illumina or Singular Genomics sequencing platform). In embodiments, adapters include two reverse complementary oligonucleotides forming a double-stranded structure. In embodiments, an adapter includes two oligonucleotides that are complementary at one portion and mismatched at another portion, forming a Y-shaped or fork-shaped adapter that is double stranded at the complementary portion and has two overhangs at the mismatched portion. Since Y-shaped adapters have a complementary, double-stranded region, they can be considered a special form of double-stranded adapters. When this disclosure contrasts Y-shaped adapters and double stranded adapters, the term "double-stranded adapter" or "blunt-ended" is used to refer to an adapter having two strands that are fully complementary, substantially (e.g., more than 90% or 95%) complementary, or partially complementary. In embodiments, adapters include sequences that bind to sequencing primers. In embodiments, adapters include sequences that bind to immobilized oligonucleotides (e.g., P7 and P5 sequences) or reverse complements thereof. In embodiments, the adapter is substantially non-complementary to the 3' end or the 5' end of any target polynucleotide present in the sample. In embodiments, the adapter can include a sequence that is substantially identical, or substantially complementary, to at least a portion of a primer, for example a universal primer. In embodiments, the adapter can include an index sequence (also referred to as barcode or tag) to assist with downstream error correction, identification or sequencing. In embodiments, the adapter includes a synthetic sequence (e.g., optimized for a particular property, such as a melting temperature and/or the percentage of guanine and cytosines. In embodiments, an adapter is an engineered sequence that typically include sites for restriction endonuclease recognition and/or cutting and sites for primer binding (e.g., for amplifying or sequencing the library constructs).

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed within the invention. The upper and lower limits of any such smaller range (within a more broadly recited range) may independently be included in the smaller ranges, or as particular values themselves, and are also encompassed within the invention, subject to any specifically excluded limit in the stated range. Where the stated range includes one or both of the limits, ranges excluding either or both of those included limits are also included in the invention.

Provided herein are methods, systems, and compositions for analyzing a sample (e.g., sequencing nucleic acids within a sample) in situ. The term "in situ" is used in accordance with its ordinary meaning in the art and refers to a sample surrounded by at least a portion of its native environment, such as may preserve the relative position of two or more elements. For example, an extracted human cell obtained is considered in situ when the cell is retained in its local microenvironment so as to avoid extracting the target (e.g., nucleic acid molecules or proteins) away from their native environment. An in situ sample (e.g., a cell) can be obtained from a suitable subject. An in situ cell sample may refer to a cell and its surrounding milieu, or a tissue. A sample can be isolated or obtained directly from a subject or part thereof. In embodiments, the methods described herein (e.g., sequencing a plurality of target nucleic acids of a cell in situ) are applied to an isolated cell (i.e., a cell not surrounded by least a portion of its native environment). For the avoidance of any doubt, when the method is performed within a cell (e.g., an isolated cell) the method may be considered in situ. In some embodiments, a sample is obtained indirectly from an individual or medical professional. A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may include cells or tissues that are normal, healthy, diseased (e.g., infected), and/or cancerous (e.g., cancer cells). A sample obtained from a subject may include cells or cellular material (e.g., nucleic acids) of multiple organisms (e.g., virus nucleic acid, fetal nucleic acid, bacterial nucleic acid, parasite nucleic acid). A sample may include a cell and RNA transcripts. A sample can include nucleic acids obtained from one or more subjects. In some embodiments a sample includes nucleic acid obtained from a single subject. A subject can be any living or non-living organism, including but not limited to a human, non-human animal, plant, bacterium, fungus, virus, or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a plant. In some embodiments, a subject is a human subject. A subject can be a patient (e.g., a human patient). In some embodiments a subject is suspected of having a genetic variation or a disease or condition associated with a genetic variation. A "tissue section" as used herein refers to a portion of a biological tissue derived from a biological sample, typically from an organism (e.g., a human or animal subject or patient).

As used herein, the term "fresh," generally in the context of a fresh tissue means that the tissue has recently been obtained from an organism, generally before any subsequent fixation steps, for example, flash freezing or chemical fixation. In embodiments, a fresh tissue is obtained from an organism about 1 second up to about 20 minutes before any fixation steps are performed. In embodiments, a fresh tissue is obtained from an organism about 1 second up to about 60 seconds before any fixation steps are performed. In embodiments, a fresh tissue is obtained from an organism about 30 seconds up to about 60 seconds before any fixation steps are performed. In embodiments, a fresh tissue is obtained from an organism about 1 minutes up to about 20 minutes before any fixation steps are performed. In embodiments, a fresh tissue is obtained from an organism about 1 minutes up to about 10 minutes before any fixation steps are performed. In embodiments, a fresh tissue is obtained from an organism about 1 minutes up to about 5 minutes before any fixation steps are performed. In embodiments, a fresh tissue is obtained from an organism about 30 seconds, about 1 minute, about 2 minutes, about 3 minutes, about 4 minutes, about 5 minutes, about 10 minutes, about 15 minutes, or about 20 minutes before any fixation steps are performed.

As used herein, the term "fix," refers to formation of covalent bonds, such as crosslinks, between biomolecules or within molecules. The process of fixing tissue samples or biological samples (e.g., cells and nuclei) for example, is called "fixation." The agent that causes fixation is generally referred to as a "fixative" or "fixing agent." "Fixed biological samples" (e.g., fixed cells or nuclei) or "fixed tissues" refers to biological samples (e.g., cells or nuclei) or tissues that have been in contact with a fixative under conditions sufficient to allow or result in formation of intra- and inter-molecular crosslinks between biomolecules in the biological sample. Fixation may be reversed and the process of reversing fixation may be referred to as "un-fixing" or "decrosslinking." Unfixing or decrosslinking refers to breaking or reversing the formation of covalent bonds in biomolecules formed by fixatives. In some examples, the tissue fixed is fresh tissue. In some examples, the tissue fixed may be frozen tissue. In some examples, the tissue fixed may not be dissociated. In some examples, the tissue fixed may be dissociated or partially dissociated (e.g., chopped, cut). In some examples, tissue that has been rapidly frozen and, perhaps, cut or chopped into pieces (e.g., small enough to fit into a tube or container used for fixation) may be used. In some examples, tissue may be dissociated or partially dissociated (e.g., cut, chopped) before or during fixation. In some examples, tissue that is fixed may not be dissociated. The frozen biological tissue can be fixed using a fixing agent, which is suitably an organic fixing agent. Suitable organic fixing agents include without limitation alcohols, ketones, aldehydes (e.g., glutaraldehyde), cross-linking agents, disuccinimidyl suberate (DSS), dimethylsuberimidate (DMS), formalin, dimethyladipimidate (DMA), dithiobis(-succinimidyl propionate) (DSP), disuccinimidyl tartrate (DST), ethylene glycol bis (succinimidyl succinate) (EGS), bis(sulfosuccinimidyl)suberate (BS3) and combinations thereof. A particularly suitable fixing agent is a formaldehyde-based fixing agent such as formalin, which is a mixture of formaldehyde and water. The formalin may include about 1% to about 15% by weight formaldehyde and about 85% to about 99% by weight water, suitable about 2% to about 8% by weight formaldehyde and about 92% to about 98% by weight water, or about 4% by weight formaldehyde and about 96% by weight water. In some examples, tissues may be fixed in 4% paraformaldehyde. Other suitable fixing agents will be appreciated by those of ordinary skill in the art (e.g., International PCT App. No. PCT/US2020/066705, which is incorporated herein by reference in its entirety).

As used herein, the term "permeable" refers to a property of a substance that allows certain materials to pass through the substance. "Permeable" may be used to describe a biological sample, such as a cell or nucleus, in which analytes in the biological sample can leave the biological sample. "Permeabilize" is an action taken to cause, for example, a biological sample (e.g., a cell) to release its analytes. In some examples, permeabilization of a biological sample is accomplished by affecting the integrity (e.g., compromising) of a biological sample membrane (e.g., a cellular or nuclear membrane) such as by application of a protease or other enzyme capable of disturbing a membrane allowing analytes to diffuse out of the biological sample.

As used herein, the term "single biological sample", such as a single cell or a single nucleus generally refers to a biological sample that is not present in an aggregated form or clump. Single biological samples, such as cells and/or nuclei may be the result of dissociating a tissue sample.

As used herein, the term "disease state" is used in accordance with its plain and ordinary meaning and refers to any abnormal biological or aberrant state of a cell or organism. The presence of a disease state may be identified by the same collection of biological constituents used to determine the cell's biological state. In general, a disease state will be detrimental to a biological system. A disease state may be a consequence of, inter alia, an environmental pathogen, for example a viral infection (e.g., HIV/AIDS, hepatitis B, hepatitis C, influenza, measles, etc.), a bacterial infection, a parasitic infection, a fungal infection, or infection by some other organism. A disease state may also be the consequence of some other environmental agent, such as a chemical toxin or a chemical carcinogen. As used herein, a disease state further includes genetic disorders wherein one or more copies of a gene is altered or disrupted, thereby affecting its biological function. Exemplary genetic diseases include, but are not limited to polycystic kidney disease, familial multiple endocrine neoplasia type I, neurofibromatoses, Tay-Sachs disease, Huntington's disease, sickle cell anemia, thalassemia, and Down's syndrome, as well as others (see, e.g., The Metabolic and Molecular Bases of Inherited Diseases, 7th ed., McGraw-Hill Inc., New York). Other exemplary diseases include, but are not limited to, cancer, hypertension, Alzheimer's disease, neurodegenerative diseases, and neuropsychiatric disorders such as bipolar affective disorders or paranoid schizophrenic disorders. Disease states are monitored to determine the level or severity (e.g., the stage or progression) of one or more disease states of a subject and, more specifically, detect changes in the biological state of a subject which are correlated to one or more disease states (see, e.g., U.S. Pat. No. 6,218,122, which is incorporated by reference herein in its entirety). In embodiments, methods provided herein are also applicable to monitoring the disease state or states of a subject undergoing one or more therapies. Thus, the present disclosure also provides, in some embodiments, methods for determining or monitoring efficacy of a therapy or therapies (i.e., determining a level of therapeutic effect) upon a subject. In embodiments, methods of the present disclosure can be used to assess therapeutic efficacy in a clinical trial, e.g., as an early surrogate marker for success or failure in such a clinical trial. Within eukaryotic cells, there are hundreds to thousands of signaling pathways that are interconnected. For this reason, perturbations in the function of proteins within a cell have numerous effects on other proteins and the transcription of other genes that are connected by primary, secondary, and sometimes tertiary pathways. This extensive interconnection between the function of various proteins means that the alteration of any one protein is likely to result in compensatory changes in a wide number of other proteins. In particular, the partial disruption of even a single protein within a cell, such as by exposure to a drug or by a disease state which modulates the gene copy number (e.g., a genetic mutation), results in characteristic compensatory changes in the transcription of enough other genes that these changes in transcripts can be used to define a "signature" of particular transcript alterations which are related to the disruption of function, e.g., a particular disease state or therapy, even at a stage where changes in protein activity are undetectable.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer. A protein may refer to a protein expressed in a cell.

A polypeptide, or a cell is "recombinant" when it is artificial or engineered, or derived from or contains an artificial or engineered protein or nucleic acid (e.g., non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

As used herein, a "single cell" refers to one cell. Single cells useful in the methods described herein can be obtained from a tissue of interest, or from a biopsy, blood sample, or cell culture. Additionally, cells from specific organs, tissues, tumors, neoplasms, or the like can be obtained and used in the methods described herein. In general, cells from any population can be used in the methods, such as a population of prokaryotic or eukaryotic organisms, including bacteria or yeast.

As used herein, the term "tissue" is used in accordance with its plain and ordinary meaning and refers to an organization of cells in a structure, where the structure generally functions as a unit in an organism (e.g., mammals) and may carry out specific functions. In some examples, cells in a tissue are configured in a mass and may not be free from one another. This disclosure describes methods of obtaining single biological samples (e.g., cells or nuclei) from tissues that can be used in various single biological samples (e.g., single-cell/nucleus) workflows. In some examples, blood cells (e.g., lymphocytes) can be considered a tissue. However, blood cells, like lymphocytes, generally are free from one another in the blood. The methods disclosed herein can be used to process those cells to obtain cells and/or nuclei, although dissociation steps may not be necessary when using those types of tissues. Generally, any type of tissue can be used in the methods described herein. Examples of tissues that may be used in the disclosed methods include, but are not limited to connective, epithelial, muscle and nervous tissue. In some examples, the tissues are from mammals. Tissues that contain any type of cells may be used. For example, tissues from abdomen, bladder, brain, esophagus, heart, intestine, kidney, liver, lung, lymph node, olfactory bulb, ovary, pancreas, skin, spleen, stomach, testicle, and the like. The tissue may be normal or tumor tissue (e.g., malignant). This example is not meant to be limiting. Although the conditions used in the disclosed may not be identical for different types of tissue, the methods may be applied to any tissue. The tissues used in the disclosed methods may be in various states. In some examples, the tissues used in the disclosed methods may be fresh, frozen, or fixed.

The term "cellular component" is used in accordance with its ordinary meaning in the art and refers to any organelle, nucleic acid, protein, or analyte that is found in a prokaryotic, eukaryotic, archaeal, or other organismic cell type. Examples of cellular components (e.g., a component of a cell) include RNA transcripts, proteins, membranes, lipids, and other analytes. In embodiments, a cellular component is a biomolecule.

As used herein the term "determine" can be used to refer to the act of ascertaining, establishing or estimating. A determination can be probabilistic. For example, a determination can have an apparent likelihood of at least 50%, 75%, 90%, 95%, 98%, 99%, 99.9% or higher. In some cases, a determination can have an apparent likelihood of 100%. An exemplary determination is a maximum likelihood analysis or report. As used herein, the term "identify," when used in reference to a thing, can be used to refer to recognition of the thing, distinction of the thing from at least one other thing or categorization of the thing with at least one other thing. The recognition, distinction or categorization can be probabilistic. For example, a thing can be identified with an apparent likelihood of at least 50%, 75%, 90%, 95%, 98%, 99%, 99.9% or higher. A thing can be identified based on a result of a maximum likelihood analysis. In some cases, a thing can be identified with an apparent likelihood of 100%.

The term "protein-specific binding agent" refers to an agent to a protein or polypeptide molecule, or portion thereof, capable of selectively binding or interacting with a protein. In embodiments, a protein-specific binding agent specifically binds a particular protein (e.g., a protein antigen or epitope thereof). In embodiments a protein-specific binding agent is an immunoglobulin (IgA, IgD, IgE, IgG, or IgM). Intact immunoglobulins, also known as antibodies, are typically tetrameric glycosylated proteins composed of two light (L) chains of approximately 25 kDa each, and two heavy (H) chains of approximately 50 kDa each. In embodiments, the protein binding moiety is an antigen-specific antibody. Non-limiting examples of protein-specific binding agent encompassed within the term "antigen-specific antibody" used herein include: (i) an Fab fragment, a monovalent fragment consisting of the VL, VH, CL and CH1 domains; (ii) an F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment, which consists of a VH domain; and (vi) an isolated CDR. Furthermore, although the two domains of the Fv fragment, VL and VH, are coded for by separate genes, they may be recombinantly joined by a synthetic linker, creating a single protein chain in which the VL and VH domains pair to form monovalent molecules (known as single chain Fv (scFv)). The most commonly used linker is a 15-residue (Gly4Ser)3 peptide, but other linkers are also known in the art. Single chain antibodies are also intended to be encompassed within the terms "protein-specific binding agent," of an antibody. The antibody can also be a polyclonal antibody, monoclonal antibody, chimeric antibody, antigen-binding fragment, Fc fragment, single chain antibodies, or any derivatives thereof. In embodiments, the protein-specific binding agent is the antigen-binding site (e.g., fragment antigen-binding (Fab) variable region) of an antibody. The term "antigen-binding site" of an antibody (or simply "antibody portion"), as used herein, refers to one or more fragments of an antibody that retains the ability to specifically bind to an antigen. It has been shown that the antigen-binding function of an antibody can be performed by fragments of a full-length antibody.

An "antibody" (Ab) is a protein that binds specifically to a particular substance, known as an "antigen" (Ag). An "antibody" or "antigen-binding fragment" is an immunoglobulin that binds a specific "epitope." The term encompasses polyclonal, monoclonal, and chimeric antibodies. In nature, antibodies are generally produced by lymphocytes in response to immune challenge, such as by infection or immunization. An "antigen" (Ag) is any substance that reacts specifically with antibodies or T lymphocytes (T cells). An antibody may include the entire antibody as well as any antibody fragments capable of binding the antigen or antigenic fragment of interest. Examples include complete antibody molecules, antibody fragments, such as Fab, F(ab')2, CDRs, VL, VH, and any other portion of an antibody which is capable of specifically binding to an antigen. Antibodies used herein are immunospecific for, and therefore specifically and selectively bind to, for example, proteins either detected (e.g., biological targets of interest) or used for detection (e.g., probes containing oligonucleotide barcodes) in the methods and devices as described herein.

The term "nucleic acid sequencing device" and the like means an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, detection systems, data collection and/or integration systems, for the purpose of determining the nucleic acid sequence of a template polynucleotide. Nucleic acid sequencing devices may further include valves, pumps, and specialized functional coatings on interior walls. Nucleic acid sequencing devices may include a receiving unit, or platen, that orients the flow cell such that a maximal surface area of the flow cell is available to be exposed to an optical lens. Other nucleic acid sequencing devices include those provided by Singular Genomics™ (e.g., the G4™ system), Illumina™ (e.g., HiSeq™, MiSeq™, NextSeq™, or NovaSeq™ systems), Life Technologies™ (e.g., ABI PRISM™, or SOLiD™ systems), Pacific Biosciences (e.g., systems using SMRT™ Technology such as the Sequel™ or RS II™ systems), or Qiagen (e.g., Genereader™ system). Nucleic acid sequencing devices may further include fluidic reservoirs (e.g., bottles), valves, pressure sources, pumps, sensors, control systems, valves, pumps, and specialized functional coatings on interior walls. In embodiments, the device includes a plurality of a sequencing reagent reservoirs and a plurality of clustering reagent reservoirs. In embodiments, the clustering reagent reservoir includes amplification reagents (e.g., an aqueous buffer containing enzymes, salts, and nucleotides, denaturants, crowding agents, etc.) In embodiments, the reservoirs include sequencing reagents (such as an aqueous buffer containing enzymes, salts, and nucleotides); a wash solution (an aqueous buffer); a cleave solution (an aqueous buffer containing a cleaving agent, such as a reducing agent); or a cleaning solution (a dilute bleach solution, dilute NaOH solution, dilute HCl solution, dilute antibacterial solution, or water). The fluid of each of the reservoirs can vary. The fluid can be, for example, an aqueous solution which may contain buffers (e.g., saline-sodium citrate (SSC), ascorbic acid, tris(hydroxymethyl)aminomethane or "Tris"), aqueous salts (e.g., KCl or $(NH_4)_2SO_4$)), nucleotides, polymerases, cleaving agent (e.g., tri-n-butyl-phosphine, triphenyl phosphine and its sulfonated versions (i.e., tris(3-sulfophenyl)-phosphine, TPPTS), and tri(carboxyethyl)phosphine (TCEP) and its salts, cleaving agent scavenger compounds (e.g., 2'-Dithiobisethanamine or 11-Azido-3,6,9-trioxaundecane-1-amine), chelating agents (e.g., EDTA), detergents, surfactants, crowding agents, or stabilizers (e.g., PEG, Tween, BSA). Non-limited examples of reservoirs include cartridges, pouches, vials, containers, and eppendorf tubes. In embodiments, the device is configured to perform fluorescent imaging. In embodiments, the device includes one or more light sources (e.g., one or more lasers). In embodiments, the illuminator or light source is a radiation source (i.e., an origin or generator of propagated electromagnetic energy) providing incident light to the sample. A radiation source can include an illumination source producing electromagnetic radiation in the ultraviolet (UV) range (about 200 to 390 nm), visible (VIS) range (about 390 to 770 nm), or infrared (IR) range (about 0.77 to 25 microns), or other range of the electromagnetic spectrum. In embodiments, the illuminator or light source is a lamp such as an arc lamp or quartz halogen lamp. In embodiments, the illuminator or light source is a coherent light source. In embodiments, the light source is a laser, LED (light emitting diode), a mercury or tungsten lamp, or a super-continuous diode. In embodiments, the light source provides excitation beams having a wavelength between 200 nm to 1500 nm. In embodiments, the laser provides excitation beams having a wavelength of 405 nm, 470 nm, 488 nm, 514 nm, 520 nm, 532 nm, 561 nm, 633 nm, 639 nm, 640 nm, 800 nm, 808 nm, 912 nm, 1024 nm, or 1500 nm. In embodiments, the illuminator or light source is a light-emitting diode (LED). The LED can be, for example, an Organic Light Emitting Diode (OLED), a Thin Film Electroluminescent Device (TFELD), or a Quantum dot based inorganic organic LED. The LED can include a phosphorescent OLED (PHOLED). In embodiments, the nucleic acid sequencing device includes an imaging system (e.g., an imaging system as described herein). The imaging system capable of exciting one or more of the identifiable labels (e.g., a fluorescent label) linked to a nucleotide and thereafter obtain image data for the identifiable labels. The image data (e.g., detection data) may be analyzed by another component within the device. The imaging system may include a system described herein and may include a fluorescence spectrophotometer including an objective lens and/or a solid-state imaging device. The solid-state imaging device may include a charge coupled device (CCD) and/or a complementary metal oxide semiconductor (CMOS). The system may also include circuitry and processors, including systems using microcontrollers, reduced instruction set computers (RISC), application specific integrated circuits (ASICs), field programmable gate array (FPGAs), logic circuits, and any other circuit or processor capable of executing functions described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. In embodiments, the device includes a thermal control assembly useful to control the temperature of the reagents.

The term "isolated" means altered or removed from the natural state. For example, a nucleic acid or a polypeptide naturally present in a living animal is not isolated, but the same nucleic acid or polypeptide partially or completely separated from the coexisting materials of its natural state is isolated. An isolated nucleic acid or protein can exist in substantially purified form, or can exist in a non-native environment such as, for example, a host cell. In embodiments, "isolated" refers to a nucleic acid, polynucleotide, polypeptide, protein, or other component that is partially or completely separated from components with which it is normally associated (other proteins, nucleic acids, cells, etc.).

As used herein, a "plurality" refers to two or more.

As used herein the terms "automated" and "semi-automated" mean that the operations are performed by system programming or configuration with little or no human interaction once the operations are initiated, or once processes including the operations are initiated.

The term "image" is used according to its ordinary meaning and refers to a representation of all or part of an object. The representation may be an optically detected reproduction. For example, an image can be obtained from fluorescent, luminescent, scatter, or absorption signals. The part of the object that is present in an image can be the surface or other xy plane of the object. Typically, an image is a 2 dimensional representation of a 3 dimensional object. An image may include signals at differing intensities (i.e., signal levels). An image can be provided in a computer readable format or medium. An image is derived from the collection of focus points of light rays coming from an object (e.g., the sample), which may be detected by any image sensor.

As used herein, the term "signal" is intended to include, for example, fluorescent, luminescent, scatter, or absorption impulse or electromagnetic wave transmitted or received. Signals can be detected in the ultraviolet (UV) range (about 200 to 390 nm), visible (VIS) range (about 391 to 770 nm), infrared (IR) range (about 0.771 to 25 microns), or other range of the electromagnetic spectrum. The term "signal level" refers to an amount or quantity of detected energy or coded information. For example, a signal may be quantified by its intensity, wavelength, energy, frequency, power, luminance, or a combination thereof. Other signals can be quantified according to characteristics such as voltage, current, electric field strength, magnetic field strength, frequency, power, temperature, etc. Absence of signal is understood to be a signal level of zero or a signal level that is not meaningfully distinguished from noise.

The term "xy coordinates" refers to information that specifies location, size, shape, and/or orientation in an xy plane. The information can be, for example, numerical coordinates in a Cartesian system. The coordinates can be provided relative to one or both of the x and y axes or can be provided relative to another location in the xy plane (e.g., a fiducial). The term "xy plane" refers to a 2-dimensional area defined by straight line axes x and y. When used in reference to a detecting apparatus and an object observed by the detector, the xy plane may be specified as being orthogonal to the direction of observation between the detector and object being detected.

"Synthetic" agents refer to non-naturally occurring agents, such as enzymes or nucleotides derived or constructed using human-made techniques. For example, s synthetic DNA polymerases refer to non-naturally occurring DNA polymerases such as those constructed by synthetic methods, mutated parent DNA polymerases such as truncated DNA polymerases and fusion DNA polymerases. Synthetic oligonucleotides such as adapter sequences or primers, include a human-designed sequence, typically configured to maximize yield and minimize off-target products, without introducing any biases. Examples of synthetic oligonucleotide sequences include P5, P7, or complementary sequences thereof (i.e., P5' or P7'). The P5 and P7 primers are used on the surface of commercial flow cells for sequencing on various Illumina platforms, as described in U.S. Patent Publication No. 2011/0059865 A1.

The term "library" merely refers to a collection or plurality of template nucleic acid molecules which share common sequences at their 5' ends (e.g., the first end) and common sequences at their 3' ends (e.g., the second end). In embodiments, a population of template nucleic acid molecules form a library.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

II. Compositions & Kits

In an aspect is provided a solid support including a first plurality of immobilized oligonucleotides and a second plurality of immobilized oligonucleotides, wherein one or more of the immobilized oligonucleotides of the first plurality include a first sequence capable of hybridizing to a first endogenous region of a target polynucleotide, and wherein one or more of the immobilized oligonucleotides of the second plurality include a second sequence capable of hybridizing to the complement of a second region of the target polynucleotide. In embodiments, one or more of the second plurality include a second sequence capable of hybridizing to the complement of a second endogenous region of the target polynucleotide. In embodiments, the target polynucleotide is a single stranded polynucleotide. In embodiments, the first endogenous region of a target polynucleotide and the complement of a second region of the target polynucleotide are in reference to the same strand of the target polynucleotide.

In an aspect is provided a solid support including two or more wells, wherein each well includes a first plurality of immobilized oligonucleotides and a second plurality of immobilized oligonucleotides, wherein one or more of the immobilized oligonucleotides of the first plurality include a first sequence capable of hybridizing to a first endogenous region of a target polynucleotide, and wherein one or more of the immobilized oligonucleotides of the second plurality include a second sequence capable of hybridizing to the complement of a second region of the target polynucleotide. In embodiments, one or more of the second plurality include a second sequence capable of hybridizing to the complement of a second endogenous region of the target polynucleotide.

In an aspect is provided a solid support including a first well and a second well, wherein the first well includes a plurality of immobilized oligonucleotides including a first sequence capable of hybridizing to an endogenous region of a first target polynucleotide, and a plurality of immobilized oligonucleotides including a second sequence capable of hybridizing to the complement of an endogenous region of the first target polynucleotide; and wherein the second well includes a plurality of immobilized oligonucleotides including a third sequence capable of hybridizing to an endogenous region of a second target polynucleotide, and a plurality of immobilized oligonucleotides including a fourth sequence capable of hybridizing to the complement of an endogenous region of the second target polynucleotide; wherein the first target polynucleotide and second target polynucleotide are different.

In an aspect is provided a multiwell container (e.g., a microplate) including a plurality of sample wells, wherein the sample wells are about 1 mm to about 10 mm in diameter, (e.g., 3.6 mm in diameter, or 6.8 mm in diameter), and wherein one or more of the sample wells include a plurality of nanowells, wherein the nanowells are about 0.5 µm to about 2 µm in diameter. In embodiments, each nanowell includes a first plurality of immobilized oligonucleotides and a second plurality of immobilized oligonucleotides, including a first sequence capable of hybridizing to a first endogenous region of a target polynucleotide, and wherein one or more of the second plurality include a second sequence capable of hybridizing to the complement of a second region of the target polynucleotide. In embodiments, the nanowells are separated by interstitial space, wherein the interstitial space includes a resist (e.g., a photoresist or nanoimprint resist including a crosslinked polymer matrix).

In as aspect is provided a particle including a first plurality of immobilized oligonucleotides and a second plurality of immobilized oligonucleotides, wherein one or more of the first plurality include a first sequence capable of hybridizing to a first endogenous region of a target polynucleotide, and wherein one or more of the second plurality include a second sequence capable of hybridizing to the complement of a second region of the target polynucleotide. In embodiments, one or more of the second plurality include a second sequence capable of hybridizing to the complement of a second endogenous region of the target polynucleotide. In embodiments, the 3' end of the first sequence is complementary to the first endogenous region of the target polynucleotide, and the 3' end of the second sequence is complementary to the complement of the second region of the target polynucleotide. In embodiments, the 3' end of the first sequence is complementary to the first endogenous region of the target polynucleotide, and the 3' end of the second sequence is complementary to the complement of the second endogenous region of the target polynucleotide. As used herein, "immobilized" refers to a covalent linkage to a solid support (e.g., a particle) via a linker (i.e., a covalent linker). For example, an immobilized oligonucleotide refers to an oligonucleotide covalently linked to a solid support (e.g., covalently linked at the 5'-end of the oligonucleotide). In embodiments, an immobilized oligonucleotide is covalently linked to the particle via a linker. In embodiments, the linker includes a cleavable site. In embodiments, the linker does not include a cleavable site.

In as aspect is provided a particle including a first plurality of immobilized oligonucleotides and a second plurality of immobilized oligonucleotides, wherein each of the first plurality include a first sequence complementary to a first endogenous region of a target polynucleotide, and wherein each of the second plurality include a second sequence identical to a second region of the target polynucleotide. In embodiments, each of the second plurality include a second sequence identical to a second endogenous region of the target polynucleotide.

In an aspect is provided a particle including a first plurality of immobilized oligonucleotides and a second plurality of immobilized oligonucleotides, wherein one or more of the immobilized oligonucleotides of the first plurality include a first sequence capable of hybridizing to a first endogenous region of a target polynucleotide, and wherein one or more of the immobilized oligonucleotides of the second plurality include a second sequence capable of hybridizing to the complement of a second region of the target polynucleotide.

In as aspect is provided a particle including a first plurality of immobilized oligonucleotides and a second plurality of immobilized oligonucleotides, wherein each of the first plurality include a first sequence complementary to a first endogenous region of a target polynucleotide, and wherein each of the second plurality include a second sequence homologous (e.g., at least 80% identical) to a second region of the target polynucleotide. In embodiments, each of the second plurality include a second sequence homologous (e.g., at least 80% identical) to a second endogenous region of the target polynucleotide.

In an aspect is provided a solid support for spatial detection of nucleic acids in a cell and/or tissue sample (e.g., spatial detection of nucleic acids in situ). In embodiments, the solid support for spatial detection of nucleic acids is a microplate (e.g., a microplate array). In embodiments, the solid support is a slide (e.g., a glass slide). In embodiments, the solid support includes a flow cell. In embodiments, the solid support includes a first plurality of immobilized oligonucleotides (e.g., a first plurality of immobilized capture probes) and a second plurality of immobilized oligonucleotides (e.g., a second plurality of immobilized capture probes), wherein one or more of the first plurality include a first sequence capable of hybridizing to a first endogenous region of a target polynucleotide, and wherein one or more of the second plurality include a second sequence capable of hybridizing to the complement of a second region of the target polynucleotide. In embodiments, one or more of the second plurality include a second sequence capable of hybridizing to the complement of a second endogenous region of the target polynucleotide. In embodiments, the solid support includes a tissue sample.

As used herein, "capable of hybridizing" is used in accordance with its ordinary meaning in the art and refers to two oligonucleotides that, under suitable conditions, can form a duplex (e.g., Watson-Crick pairing) which includes a double-stranded portion of nucleic acid. Such conditions, known in the art and described herein, depend upon, for example, the nature of the nucleotide sequence, temperature, and buffer conditions. The stringency of hybridization can be influenced by various parameters, including degree of identity and/or complementarity between the polynucleotides (or any target sequences within the polynucleotides) to be hybridized; melting point of the polynucleotides and/or target sequences to be hybridized, referred to as "Tm"; parameters such as salts, buffers, pH, temperature, GC % content of the polynucleotide and primers, and/or time. Typically, hybridization is favored in lower temperatures and/or increased salt concentrations, as well as reduced concentrations of organic solvents. Some exemplary conditions suitable for hybridization include incubation of the polynucleotides to be hybridized in solutions having sodium salts, such as NaCl, sodium citrate and/or sodium phosphate. In some embodiments, hybridization or wash solutions can include about 10-75% formamide and/or about 0.01-0.7% sodium dodecyl sulfate (SDS). In some embodiments, a hybridization solution can be a stringent hybridization solution which can include any combination of 50% formamide, 5×SSC (0.75 M NaCl, 0.075 M sodium citrate), 50 mM sodium phosphate (pH 6.8), 0.1% sodium pyrophosphate, 5×Denhardt's solution, 0.1% SDS, and/or 10% dextran sulfate. In some embodiments, the hybridization or washing solution can include BSA (bovine serum albumin). In some embodiments, hybridization or washing can be conducted at a temperature range of about 20-25° C., or about 25-30° C., or about 30-35° C., or about 35-40° C., or about 40-45° C., or about 45-50° C., or about 50-55° C., or higher. In some embodiments, hybridization or washing can be conducted for a time range of about 1-10 minutes, or about 10-20 minutes, or about 20-30 minutes, or about 30-40 minutes, or about 40-50 minutes, or about 50-60 minutes, or longer. In some embodiments, hybridization or wash conditions can be conducted at a pH range of about 5-10, or about pH 6-9, or about pH 6.5-8, or about pH 6.5-7.

As used herein, "endogenous" is used in accordance with its ordinary meaning in the art and refers to an internal origin. For example, an endogenous gene sequence (also referred to herein as an endogenous region) is a polynucleotide sequence found within the original polynucleotide sequence. In embodiments, an endogenous gene sequence is a polynucleotide sequence found within the original polynucleotide sequence in a biological sample. In embodiments, the endogenous region includes a gene or a fragment thereof. In embodiments, the first endogenous region includes a gene or a fragment thereof. In embodiments, the second endogenous region includes a gene or a fragment thereof. In embodiments, both the first endogenous region and the second endogenous region include a gene or a fragment thereof. In embodiments, the endogenous region includes mRNA. In embodiments, the endogenous region includes genomic DNA (e.g., exons, single nucleotide polymorphisms, mutable regions and/or highly conserved regions). In embodiments, the endogenous region includes a genetic locus. In embodiments, the endogenous region includes autosomal DNA and/or mitochondrial DNA. In embodiments, the endogenous region includes a portion of a gene, a regulatory sequence, genomic DNA, cDNA, RNA including mRNA, miRNA, or rRNA. In embodiments, an endogenous region may refer to the post hoc ligation (i.e., ligation after the fragmentation) of an exogenous sequence to one of the ends of the target polynucleotide. In embodiments, an endogenous region of a target polynucleotide is a sequence of the target polynucleotide present prior to fragmentation. In embodiments, the endogenous region of a target polynucleotide is not an adapter sequence. In embodiments, the endogenous region of a target polynucleotide does not include a universal priming binding sequence. In embodiments, the endogenous region does not include the P5, P7, or complementary sequences thereof (i.e., P5' or P7'). The P5 and P7 primers are used on the surface of commercial flow cells for sequencing on various Illumina platforms. The P5 and P7 adapter sequences are described in U.S. Patent Publication No. 2011/0059865 A1, which is incorporated herein by reference in its entirety. The terms P5 and P7 may be used when referring to amplification primers, e.g., universal primers. The terms P5' (P5 prime) and P7' (P7 prime) refer to the complement of P5 and P7, respectively. In embodiments, an endogenous sequence is not a synthetic sequence. In embodiments, an endogenous sequence is a sequence found in nature. In embodiments, an endogenous sequence is not a synthetic or engineered sequence.

In embodiments, the second sequence is homologous to a second endogenous region of the target polynucleotide. In embodiments, the second sequence is 80%, 90%, 95%, 99%, or 100% homologous to a second region of the target polynucleotide. In embodiments, the second sequence is 80% homologous to a second region of the target polynucleotide. In embodiments, the second sequence is 90% homologous to a second region of the target polynucleotide. In embodiments, the second sequence is 95% homologous to a second region of the target polynucleotide. In embodiments, the second sequence is 99% homologous to a second region of the target polynucleotide. In embodiments, the second sequence is 95% homologous to a second region of the target polynucleotide. In embodiments, the second sequence is 100% homologous to a second region of the target polynucleotide. In embodiments, the second sequence is about 80% to about 100%, about 90% to about 100%, about 95% to about 100%, or about 99% to about 100% homologous to a second region of the target polynucleotide. In embodiments, the second sequence is at least 80%, at least 90%, at least 95%, at least 99%, or 100% homologous to a second region of the target polynucleotide. In embodiments, the second region of the target polynucleotide is an endogenous region of the target polynucleotide. In embodiments, the second region of the target polynucleotide is the endogenous region of the target polynucleotide.

In embodiments, each of the first plurality of immobilized oligonucleotides include a first sequence capable of hybridizing to a first endogenous region of a target polynucleotide, and each of the second plurality include a second sequence capable of hybridizing to the complement of a second region of the target polynucleotide. In embodiments, each of the second plurality include a second sequence capable of hybridizing to the complement of a second endogenous region of the target polynucleotide. In embodiments, one or more of the first plurality of immobilized oligonucleotides include a first sequence capable of hybridizing to a first endogenous region of a target polynucleotide, and one or more of the second plurality include a second sequence capable of hybridizing to the complement of a second region of the target polynucleotide. In embodiments, one or more of the second plurality include a second sequence capable of hybridizing to the complement of a second endogenous region of the target polynucleotide. In embodiments, two or more of the first plurality of immobilized oligonucleotides include a first sequence capable of hybridizing to a first endogenous region of a target polynucleotide, and two or more of the second plurality include a second sequence capable of hybridizing to the complement of a second region of the target polynucleotide. In embodiments, two or more of the second plurality include a second sequence capable of hybridizing to the complement of a second endogenous region of the target polynucleotide.

In embodiments, the first endogenous region is about 10 to 100 nucleotides in length. In embodiments, the first endogenous region is between 10 and 40 nucleotides in length. The length and complexity may vary. In embodiments, the first endogenous region is about 200 nucleotides or less. In embodiments, the first endogenous region is about 10 to 150 nucleotides, 15 to 150 nucleotides, 5 to 100 nucleotides, 5 to 50 nucleotides or 10 to 50 nucleotides. In embodiments, the second endogenous region is about 10 to 100 nucleotides in length. In embodiments, the second endogenous region is between 10 and 40 nucleotides in length. The length and complexity may vary. In embodiments, the second endogenous region is about 200 nucleotides or less. In embodiments, the second endogenous region is about 10 to 150 nucleotides, 15 to 150 nucleotides, 5 to 100 nucleotides, 5 to 50 nucleotides or 10 to 50 nucleotides. The gap between the two regions (i.e., the first endogenous region and the second endogenous region) may be from a few base pairs up to 5,000 base pairs or more. The gap size may be from 10 base pairs to 2,000 base pairs, or 50-500 base pairs. In embodiments, the gap size may be from any combination of 50, 75, 100, 125, 150, 175, 200, or 225 base pairs to 150, 200, 250, 300, 350, 400, 450 or 500 base pairs in length.

In embodiments, the second sequence is identical to a second endogenous region of the target polynucleotide. In embodiments, the second sequence is 80%, 90%, 95%, 99%, or 100% identical to a second region of the target polynucleotide. In embodiments, the second sequence is 80% identical to a second region of the target polynucleotide. In embodiments, the second sequence is 90% identical to a second region of the target polynucleotide. In embodiments, the second sequence is 95% identical to a second region of the target polynucleotide. In embodiments, the second sequence is 99% identical to a second region of the target polynucleotide. In embodiments, the second sequence is 95% identical to a second region of the target polynucleotide. In embodiments, the second sequence is 100% identical to a second region of the target polynucleotide. In embodiments, the second sequence is about 80% to about 100%, about 90% to about 100%, about 95% to about 100%, or about 99% to about 100% identical to a second region of the target polynucleotide. In embodiments, the second sequence is at least 80%, at least 90%, at least 95%, at least 99%, or 100% identical to a second region of the target polynucleotide. In embodiments, the second region of the target polynucleotide is an endogenous region of the target polynucleotide. In embodiments, the second region of the target polynucleotide is the endogenous region of the target polynucleotide.

In embodiments, the first sequence and the second sequence further each independently include a primer binding sequence (i.e., a nucleic acid sequence having complementarity to a primer). In embodiments, the first plurality of immobilized oligonucleotides further includes a plurality of primer binding sequences. In embodiments, the second plurality of immobilized oligonucleotides further includes a plurality of primer binding sequences. In embodiments, the primer binding sequence may be an amplification primer binding sequence. In embodiments, primer binding sequence may be a sequencing primer binding sequence.

In embodiments, the primer binding sequence of the immobilized oligonucleotides of the first plurality includes a different primer binding sequence than the primer binding sequence of the immobilized oligonucleotides of the second plurality. In embodiments, the primer binding sequence is common (e.g., identical or universal) to the immobilized oligonucleotides of the array such that all of the immobilized nucleotides may initiate amplification by annealing and extending the same primer.

In embodiments, the first sequence includes, from 5' to 3', one or more primer binding sequences and sequence complementary to a first endogenous region of the target polynucleotide. In embodiments, the first sequence includes, from 5' to 3', a primer binding sequence and sequence complementary to a first endogenous region of the target polynucleotide.

In embodiments, the second sequence includes, from 5' to 3', a primer binding sequence and a second sequence homologous (e.g., at least 80% identical) to a second region of the target polynucleotide. In embodiments, the second sequence includes, from 5' to 3', a primer binding sequence and a second sequence homologous to a second region of the target polynucleotide, wherein the second sequence is 80%, 90%, 95%, 99%, or 100% homologous to a second region of the target polynucleotide. In embodiments, the second sequence is 80% homologous to a second region of the target polynucleotide. In embodiments, the second sequence is 90% homologous to a second region of the target polynucleotide. In embodiments, the second sequence is 95% homologous to a second region of the target polynucleotide. In embodiments, the second sequence is 99% homologous to a second region of the target polynucleotide. In embodiments, the second sequence is 95% homologous to a second region of the target polynucleotide. In embodiments, the second sequence is 100% homologous to a second region of the target polynucleotide. In embodiments, the second sequence is about 80% to about 100%, about 90% to about 100%, about 95% to about 100%, or about 99% to about 100% homologous to a second region of the target polynucleotide. In embodiments, the second sequence is at least 80%, at least 90%, at least 95%, at least 99%, or 100% homologous to a second region of the target polynucleotide. In embodiments, the second region of the target polynucleotide is an endogenous region of the target polynucleotide. In embodiments, the second region of the target polynucleotide is the endogenous region of the target polynucleotide.

In embodiments, the second sequence includes, from 5' to 3', a primer binding sequence and a second sequence identical to a second region of the target polynucleotide. In embodiments, the second sequence includes, from 5' to 3', a primer binding sequence and a second sequence identical (e.g., at least 80% identical) to a second region of the target polynucleotide, wherein the second sequence is 80%, 90%, 95%, 99%, or 100% identical to a second region of the target polynucleotide. In embodiments, the second sequence is 80% identical to a second region of the target polynucleotide. In embodiments, the second sequence is 90% identical to a second region of the target polynucleotide. In embodiments, the second sequence is 95% identical to a second region of the target polynucleotide. In embodiments, the second sequence is 99% identical to a second region of the target polynucleotide. In embodiments, the second sequence is 95% identical to a second region of the target polynucleotide. In embodiments, the second sequence is 100% identical to a second region of the target polynucleotide. In embodiments, the second sequence is about 80% to about 100%, about 90% to about 100%, about 95% to about 100%, or about 99% to about 100% identical to a second region of the target polynucleotide. In embodiments, the second sequence is at least 80%, at least 90%, at least 95%, at least 99%, or 100% identical to a second region of the target polynucleotide. In embodiments, the second region of the target polynucleotide is an endogenous region of the target polynucleotide. In embodiments, the second region of the target polynucleotide is the endogenous region of the target polynucleotide.

In embodiments, each of the first plurality of immobilized capture probes and the second plurality of immobilized capture probes further include a capture domain and a spatial barcode. The plurality of capture probes may be arranged in clusters on the solid support, each cluster including the first plurality of immobilized capture probes and the second plurality of immobilized capture probes. In some embodiments, each capture probe in a cluster includes the same spatial barcode, and the spatial barcode for each cluster is unique relative to the other clusters. In embodiments, the spatial barcode of the first and second plurality of capture probes located in one cluster is different for the spatial barcode of the first and second plurality of capture probes located in another cluster (e.g., no two or more clusters contain first and second pluralities of capture probes including the same spatial barcode sequence). In embodiments, the capture domain for each capture probe is the same within each cluster. As used herein, a "domain" or "region" may be used interchangeably and refer to a sequence of nucleotides, typically associated with some function (e.g., capturing a target).

In some embodiments, the capture domain is located at the 3' end of the capture probe and includes a free 3' end that can be extended, e.g. by template dependent polymerization, to form an extended capture probe as described herein. In some embodiments, the capture domain includes a nucleotide sequence that is capable of hybridizing to nucleic acid, e.g. RNA or other analyte, present in the cells of the tissue sample contacted with the array. In some embodiments, the capture domain can be selected or designed to bind selectively or specifically to a target nucleic acid. For example, the capture domain can be selected or designed to capture mRNA by way of hybridization to the mRNA poly(A) tail. Thus, in some embodiments, the capture domain includes a poly(T) DNA oligonucleotide, i.e., a series of consecutive deoxythymidine residues linked by phosphodiester bonds, which is capable of hybridizing to the poly(A) tail of mRNA. In some embodiments, the capture domain can include nucleotides that are functionally or structurally analogous to a poly(T) tail. For example, a poly(U) oligonucleotide or an oligonucleotide included of deoxythymidine analogues. In some embodiments, the capture domain includes at least 10, 11, 12, 13, 14, 15, 16, 17, 18, 19, or 20 nucleotides. In some embodiments, the capture domain includes at least 25, 30, or 35 nucleotides.

In some embodiments, random sequences, e.g., random hexamers or similar sequences, can be used to form all or a part of the capture domain. For example, random sequences can be used in conjunction with poly(T) (or poly(T) analogue) sequences. Thus, where a capture domain includes a poly(T) (or a "poly(T)-like") oligonucleotide, it can also include a random oligonucleotide sequence (e.g., "poly(T)-random sequence" probe). This can, for example, be located 5' or 3' of the poly(T) sequence, e.g. at the 3' end of the capture domain. The poly(T)-random sequence probe can facilitate the capture of the mRNA poly(A) tail. In some embodiments, the capture domain can be an entirely random sequence. In some embodiments, degenerate capture domains can be used.

In some embodiments, the capture domain includes a DNA sequence complementary to a nucleotide sequence of a target nucleic acid. In embodiments, a single cluster (e.g., a single cluster including each of the first plurality of capture probes and the second plurality of capture probes) could have multiple different capture domains to capture different sequences. In some embodiments, different clusters have different capture domains.

In some embodiments, the capture domain includes nucleotides which are functionally or structurally analogous to poly-T and retain the functional property of binding to poly-A. For example, the capture domain may include a poly-U oligonucleotide. In some embodiments, the capture domain is nonspecific (e.g., intended to capture all RNAs containing a poly-A tail). In some embodiments, the capture domain may further include additional sequences, such as random sequences, to facilitate the capture of specific subtypes of RNA. In some embodiments, the capture domain may further include additional sequences to capture a desired subtype of RNA, such as mRNA or rRNA. In some embodiments, the capture domain for each primer is the same. In some embodiments, the capture domain for one or more probes is different from the capture domain from at least one other probe. Additional embodiments of capture domains may be found, for example, in PCT Publication No. WO2022/015913 and U.S. Patent Pub. No. 2021/0317524, each of which is incorporated herein by reference in its entirety.

The capture domain can be based on a particular gene sequence or particular motif sequence or common/conserved sequence, that it is designed to capture (i.e., a sequence-specific capture domain). Thus, in some embodiments, the capture domain is capable of binding selectively to a desired sub-type or subset of nucleic acid, for example a particular type of RNA, such as mRNA, rRNA, tRNA, SRP RNA, tmRNA, snRNA, snoRNA, SmY RNA, scaRNA, gRNA, RNase P, RNase MRP, TERC, SL RNA, aRNA, cis-NAT, crRNA, lncRNA, miRNA, piRNA, siRNA, shRNA, tasiRNA, rasiRNA, 7SK, eRNA, ncRNA or other types of RNA. In a non-limiting example, the capture domain can be capable of binding selectively to a desired subset of ribonucleic acids, for example, microbiome RNA, such as 16S rRNA.

In some embodiments, a capture domain includes an "anchor" or "anchoring sequence", which is a sequence of nucleotides that is designed to ensure that the capture domain hybridizes to the intended biological analyte. In some embodiments, an anchor sequence includes a sequence of nucleotides, including a 1-mer, 2-mer, 3-mer or longer sequence. In some embodiments, the short sequence is random. For example, a capture domain including a poly(T) sequence can be designed to capture an mRNA. In such embodiments, an anchoring sequence can include a random 3-mer (e.g., GGG) that helps ensure that the poly(T) capture domain hybridizes to an mRNA. In some embodiments, an anchoring sequence can be VN, N, or NN. Alternatively, the sequence can be designed using a specific sequence of nucleotides. In some embodiments, the anchor sequence is at the 3' end of the capture domain. In some embodiments, the anchor sequence is at the 5' end of the capture domain.

In some embodiments, capture domains of capture probes are blocked prior to contacting the biological sample with the array, and blocking probes are used when the nucleic acid in the biological sample is modified prior to its capture on the array. In some embodiments, the blocking probe is used to block or modify the free 3' end of the capture domain. In some embodiments, blocking probes can be hybridized to the capture probes to mask the free 3' end of the capture domain, e.g., hairpin probes or partially double stranded probes. In some embodiments, the free 3' end of the capture domain can be blocked by chemical modification, e.g., addition of an azidomethyl group as a chemically reversible capping moiety such that the capture probes do not include a free 3' end. Blocking or modifying the capture probes, particularly at the free 3' end of the capture domain, prior to contacting the biological sample with the array, prevents modification of the capture probes, e.g., prevents the addition of a poly(A) tail to the free 3' end of the capture probes.

Non-limiting examples of 3' modifications include dideoxy C-3' (3'-ddC), 3' inverted dT, 3' C3 spacer, 3'Amino, and 3' phosphorylation. In some embodiments, the nucleic acid in the biological sample can be modified such that it can be captured by the capture domain. For example, an adaptor sequence (including a binding domain capable of binding to the capture domain of the capture probe) can be added to the end of the nucleic acid, e.g., fragmented genomic DNA. In some embodiments, this is achieved by ligation of the adaptor sequence or extension of the nucleic acid. In some embodiments, an enzyme is used to incorporate additional nucleotides at the end of the nucleic acid sequence, e.g., a poly(A) tail. In some embodiments, the capture probes can be reversibly masked or modified such that the capture domain of the capture probe does not include a free 3' end. In some embodiments, the 3' end is removed, modified, or made inaccessible so that the capture domain is not susceptible to the process used to modify the nucleic acid of the biological sample, e.g., ligation or extension.

In some embodiments, the capture domain of the capture probe is modified to allow the removal of any modifications of the capture probe that occur during modification of the nucleic acid molecules of the biological sample. In some embodiments, the capture probes can include an additional sequence downstream of the capture domain, i.e., 3' to the capture domain, namely a blocking domain.

In some embodiments, the capture domain of the capture probe can be a non-nucleic acid domain. Examples of suitable capture domains that are not exclusively nucleic-acid based include, but are not limited to, proteins, peptides, aptamers, antigens, antibodies, and molecular analogs that mimic the functionality of any of the capture domains described herein.

In some embodiments, the capture probes include a cleavage domain. In some embodiments, the cleavage domain is 3' of the capture domain, such that the capture domain is not exposed until the cleavage domain is cleaved. For example, the cleavage domain may include a binding site (e.g., a restriction site) for a restriction endonuclease. Other examples of cleavage domains include labile chemical bonds such as, but not limited to, ester linkages (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)). In some embodiments, the cleavage domain includes a poly(U) sequence which can be cleaved by a mixture of Uracil DNA glycosylase (UDG) and the DNA glycosylase-lyase Endonuclease VIII, commercially known as the USER™ enzyme. Releasable capture probes can be available for reaction once released. Thus, for example, an activatable capture probe can be activated by releasing the capture probes from a feature. The cleavage domain may be intact (e.g., un-cleaved) during binding of the capture probes to the surface of the substrate and cluster generation. Following cluster generation and/or determination of the location of each cluster on the substrate (e.g., by sequencing of the spatial barcode), an enzyme may be added to induce cleavage of the cleavage domain. For example, a restriction endonuclease (e.g., XbaI, DraI, etc.) may be added to cut the cleavage domain and one or more wash steps may optionally be performed, thus exposing the capture domain.

In some embodiments, cleavage of the cleavage domain may allow for exposure of additional domain(s). For example, cleavage of the cleavage domain may expose the capture domain (e.g., a sequence capable of hybridizing to a target polynucleotide).

In some embodiments, a cleavage domain is absent from the capture probe. Examples of substrates with attached capture probes lacking a cleavage domain are described for example in Macosko et al., (2015) Cell 161, 1202-1214, the entire contents of which are incorporated herein by reference.

Capture domains including a nucleic acid sequence against a target DNA sequence are useful for spatial detection of DNA. Substrates including a capture probe and an additional capture moiety (e.g., an antibody targeting protein or DNA/RNA probes targeting specific nucleic acid sequence) are useful for multiplex detection of nucleic acid and non-nucleic acid targets.

In embodiments the capture probe further includes a spatial barcode. The spatial barcode may be an oligonucleotide of any suitable length. A spatial barcode can be part of an analyte, or independent from an analyte (i.e., part of the capture probe). A spatial barcode can be a tag attached to an analyte (e.g., a nucleic acid molecule) or a combination of a tag in addition to an endogenous characteristic of the analyte (e.g., size of the analyte or end sequence(s)). A spatial barcode can be unique. In some embodiments where the spatial barcode is unique, the spatial barcode functions both as a spatial barcode and as a unique molecular identifier (UMI), associated with one particular capture probe.

Spatial barcodes can have a variety of different formats. For example, spatial barcodes can include polynucleotide spatial barcodes, random nucleic acid sequences, and synthetic nucleic acid sequences. In some embodiments, a spatial barcode is attached to an analyte in a reversible or irreversible manner. In some embodiments, a spatial barcode is added to, for example, a fragment of a DNA or RNA sample before, during, and/or after sequencing of the sample. In some embodiments, a spatial barcode allows for identification and/or quantification of individual sequencing-reads. In some embodiments, a spatial barcode is a used as a fluorescent barcode for which fluorescently labeled oligonucleotide probes hybridize to the spatial barcode.

In some embodiments, the spatial barcode is a nucleic acid sequence that does not substantially hybridize to analyte nucleic acid molecules in a biological sample. In some embodiments, the spatial barcode has less than 80% sequence identity (e.g., less than 70%, 60%, 50%, or less than 40% sequence identity) to the nucleic acid sequences across a substantial part (e.g., 80% or more) of the nucleic acid molecules in the biological sample.

In some embodiments, the spatial barcode includes 10-50 nucleotides. The spatial barcode sequences can include from about 6 to about 20 or more nucleotides within the sequence of the capture probes. In some embodiments, the length of a spatial barcode sequence can be about 6, 7, 8, 9, 10, 11, 12, 13, 14, 15, 16, 17, 18, 19, 20 nucleotides or longer. In some embodiments, the length of a spatial barcode sequence can be at least about 6, 7, 8, 9, 10, 11, 12, 13, 14, 15, 16, 17, 18, 19, 20 nucleotides or longer. In some embodiments, the length of a spatial barcode sequence is at most about 6, 7, 8, 9, 10, 11, 12, 13, 14, 15, 16, 17, 18, 19, 20 nucleotides or shorter. For example, the spatial barcode may include 10, 11, 12, 13, 14, 15, 16, 17, 18, 19, 20, 21, 22, 23, 24, 25, 26, 27, 28, 29, 30, 31, 31, 32, 33, 34, 35, 36, 37, 38, 39, 40, 41, 42, 43, 44, 45, 46, 47, 48, 49, or 50 nucleotides. In particular embodiments, the spatial barcode includes 20 nucleotides. The spatial barcode can be a first spatial barcode, and the capture probe can include a second spatial barcode different from the first spatial barcode. For multiple capture probes that are attached to a common array feature, the one or more spatial barcode sequences of the multiple capture probes can include sequences that are the same for all capture probes coupled to the feature, and/or sequences that are different across all capture probes coupled to the feature.

In embodiments, the capture probe includes a spatial barcode sequence, a capture domain, and a cleavage domain. In embodiments, the capture probe further includes one or more sequencing primer binding sequences. In embodiments, the capture probe further includes one or more platform primer binding sequences. In embodiments, the capture probe includes, from 5' to 3', a spatial barcode sequence, a capture domain, and a cleavage domain. In embodiments, the capture probe includes, from 5' to 3', a capture domain, a spatial barcode sequence, and a cleavage domain. In embodiments, at least one sequencing primer binding sequence is located upstream of the one or more spatial barcodes.

Capture probes attached to a single array feature can include identical (or common) spatial barcode sequences, different spatial barcode sequences, or a combination of both. Capture probes attached to a feature can include multiple sets of capture probes. Capture probes of a given set can include identical spatial barcode sequences. The identical spatial barcode sequences can be different from spatial barcode sequences of capture probes of another set.

The plurality of capture probes can include spatial barcode sequences (e.g., nucleic acid barcode sequences) that are associated with specific locations on a spatial array. For example, a first plurality of capture probes can be associated with a first region, based on a spatial barcode sequence common to the capture probes within the first region, and a second plurality of capture probes can be associated with a second region, based on a spatial barcode sequence common to the capture probes within the second region. The second region may or may not be associated with the first region. Additional pluralities of capture probes can be associated with spatial barcode sequences common to the capture probes within other regions. In some embodiments, the spatial barcode sequences can be the same across a plurality of capture probe molecules.

In some embodiments, multiple different spatial barcodes are incorporated into a single arrayed capture probe. For example, a mixed but known set of spatial barcode sequences can provide a stronger address or attribution of the spatial barcodes to a given spot or location, by providing duplicate or independent confirmation of the identity of the location. In some embodiments, the multiple spatial barcodes represent increasing specificity of the location of the particular array point.

A capture probe of the plurality of capture probes can include a universal molecular identifier (UMI). In some embodiments, a barcode includes both a UMI and a spatial barcode. In some embodiments, a barcode includes two or more sub-barcodes that together function as a single barcode. For example, a polynucleotide barcode can include two or more polynucleotide sequences (e.g., sub-barcodes) that are separated by one or more non-barcode (i.e., non-identifying) sequences.

In embodiments, each well does not include any other oligonucleotides other than the first plurality of immobilized oligonucleotides and the second plurality of immobilized oligonucleotides.

In embodiments, the solid support includes 96, 384, 1536, 2, 4, 6, 12, 24, or 48 wells. In embodiments, the solid support includes 2 wells. In embodiments, the solid support includes 4 wells. In embodiments, the solid support includes 6 wells. In embodiments, the solid support includes 12 wells. In embodiments, the solid support includes 24 wells. In embodiments, the solid support includes 48 wells. In embodiments, the solid support includes 96 wells. In embodiments, the solid support includes 384 wells. In embodiments, the solid support includes 1536 wells. In embodiments, each well is about 5 mm to about 8 mm in diameter. In embodiments, each well is about 5 mm, about 6 mm, about 7 mm, or about 8 mm in diameter.

In embodiments, one or more wells include a first sequence complementary to a first endogenous region of different target polynucleotides. In embodiments, a plurality of wells include a first sequence complementary to a first endogenous region of different target polynucleotides. In embodiments, each of the wells include a first sequence complementary to a first endogenous region of different target polynucleotides.

In embodiments, the solid support includes a plurality of wells (e.g., a billion or more wells). In embodiments, the wells (e.g., each well) is separated from each other by about 0.2 m to about 2.0 m. In embodiments, the wells (e.g., each well) is separated from each other by about 0.3 μm to about 2.0 μm. In embodiments, the wells (e.g., each well) is separated from each other by about 0.4 μm to about 2.0 μm. In embodiments, the wells (e.g., each well) is separated from each other by about 0.5 μm to about 2.0 μm. In embodiments, the wells (e.g., each well) is separated from each other by about 1.0 μm to about 2.0 μm. In embodiments, the wells (e.g., each well) is separated from each other by about 1.0 μm to about 1.5 μm. In embodiments, the wells of the solid support are all the same size. In embodiments, the solid support includes wells that are from about 0.1 μm to about 3 μm in diameter. In embodiments, the solid support includes wells that are from about 0.2 μm to about 3 μm in diameter. In embodiments, the solid support includes wells that are from about 0.3 μm to about 3 μm in diameter. In embodiments, the solid support includes wells that are from about 0.4 μm to about 3 μm in diameter. In embodiments, the solid support includes wells that are from about 0.5 μm to about 3 μm in diameter. In embodiments, the solid support includes wells that are from about 0.6 μm to about 3 μm in diameter. In embodiments, the solid support includes wells that are from about 0.7 μm to about 3 μm in diameter. In embodiments, the solid support includes wells that are from about 0.8 jam to about 3 μm in diameter. In embodiments, the solid support includes wells that are from about 0.9 μm to about 3 μm in diameter. In embodiments, the solid support includes wells that are from about 1.0 jam to about 3 μm in diameter. In embodiments, the solid support includes wells that are from about 0.1 μm to about 2 μm in diameter. In embodiments, the solid support includes wells that are from about 0.2 μm to about 2 μm in diameter. In embodiments, the solid support includes wells that are from about 0.3 μm to about 2 μm in diameter. In embodiments, the solid support includes wells that are from about 0.4 μm to about 2 μm in diameter. In embodiments, the solid support includes wells that are from about 0.5 μm to about 2 μm in diameter. In embodiments, the solid support includes wells that are from about 0.6 μm to about 2 μm in diameter. In embodiments, the solid support includes wells that are from about 0.7 μm to about 2 μm in diameter. In embodiments, the solid support includes wells that are from about 0.8 μm to about 2 μm in diameter. In embodiments, the solid support includes wells that are from about 0.9 μm to about 2 μm in diameter. In embodiments, the solid support includes wells that are from about 1.0 μm to about 2 μm in diameter. In embodiments, the solid support includes wells that are from about 1.0 μm to about 1.5 μm in diameter. In embodiments, the solid support includes wells that are about 0.1 μm to about 2 μm in depth. In embodiments, the solid support includes wells that are about 0.2 μm to about 2 μm in depth. In embodiments, the solid support includes wells that are about 0.3 μm to about 2 µm in depth. In embodiments, the solid support includes wells that are about 0.4 µm to about 2 µm in depth. In embodiments, the solid support includes wells that are about 0.5 µm to about 2 µm in depth. In embodiments, the solid support includes wells that are about 0.6 µm to about 2 µm in depth. In embodiments, the solid support includes wells that are about 0.7 µm to about 2 µm in depth. In embodiments, the solid support includes wells that are about 0.8 µm to about 2 µm in depth. In embodiments, the solid support includes wells that are about 0.9 µm to about 2 µm in depth. In embodiments, the solid support includes wells that are about 1.0 µm to about 2 µm in depth. In embodiments, the solid support includes wells that are about 0.1 µm to about 1.5 µm in depth. In embodiments, the solid support includes wells that are about 0.2 µm to about 1.5 µm in depth. In embodiments, the solid support includes wells that are about 0.3 µm to about 1.5 µm in depth. In embodiments, the solid support includes wells that are about 0.4 µm to about 1.5 µm in depth. In embodiments, the solid support includes wells that are about 0.5 µm to about 1.5 µm in depth. In embodiments, the solid support includes wells that are about 0.6 µm to about 1.5 µm in depth. In embodiments, the solid support includes wells that are about 0.7 µm to about 1.5 µm in depth. In embodiments, the solid support includes wells that are about 0.8 µm to about 1.5 µm in depth. In embodiments, the solid support includes wells that are about 0.9 µm to about 1.5 µm in depth. In embodiments, the solid support includes wells that are about 1.0 µm to about 1.5 µm in depth. In embodiments, one or more wells are different sizes (e.g., one population of wells are 1.0 µm in diameter, and a second population are 0.5 µm in diameter). In embodiments, the solid support is a glass slide about 75 mm by about 25 mm. In embodiments, the solid support includes a resist (e.g., a photoresist or nanoimprint resist including a cross-linked polymer matrix attached to the solid support).

In embodiments, each well includes a plurality of nanowells. In embodiments, each nanowell is about 0.1 µm to about 2.0 µm in depth, and wherein the nanowells are about 0.1 µm to about 2.0 m in diameter. In embodiments, each nanowell is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 µm in depth. In embodiments, each nanowell is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 µm in diameter.

In embodiments, density of wells on the solid support may be tuned. For example, in embodiments, the multiwell container includes a density of at least about 100 wells per mm², about 1,000 wells per mm², about 0.1 million wells per mm², about 1 million wells per mm², about 2 million wells per mm², about 5 million wells per mm², about 10 million wells per mm², about 50 million wells per mm², or more. In embodiments, the multiwell container includes no more than about 50 million wells per mm², about 10 million wells per mm², about 5 million wells per mm², about 2 million wells per mm², about 1 million wells per mm², about 0.1 million wells per mm², about 1,000 wells per mm², about 100 wells per mm², or less. In embodiments, the solid support includes about 500, 1,000, 2,500, 5,000, or about 25,000 wells per mm². In embodiments, the solid support includes about $1 \times 10^6$ to about $1 \times 10^{12}$ wells. In embodiments, the solid support includes about $1 \times 10^7$ to about $1 \times 10^{12}$ wells. In embodiments, the solid support includes about $1 \times 10^8$ to about $1 \times 10^{12}$ wells. In embodiments, the solid support includes about $1 \times 10^6$ to about $1 \times 10^9$ wells. In embodiments, the solid support includes about $1 \times 10^9$ to about $1 \times 10^{10}$ wells. In embodiments, the solid support includes about $1 \times 10^7$ to about $1 \times 10^9$ wells. In embodiments, the solid support includes about $1 \times 10^8$ to about $1 \times 10^8$ wells. In embodiments, the solid support includes about $1 \times 10^6$ to about $1 \times 10^8$ wells. In embodiments, the solid support includes about $1 \times 10^6$, $1 \times 10^7$, $1 \times 10^8$, $1 \times 10^9$, $1 \times 10^{10}$, $1 \times 10^{11}$, $1 \times 10^{12}$, $5 \times 10^{12}$, or more wells. In embodiments, the solid support includes about $1.8 \times 10^9$, $3.7 \times 10^9$, $9.4 \times 10^9$, $1.9 \times 10^{10}$, or about $9.4 \times 10^{10}$ wells. In embodiments, the solid support includes about $1 \times 10^6$ or more wells. In embodiments, the solid support includes about $1 \times 10^7$ or more wells. In embodiments, the solid support includes about $1 \times 10^8$ or more wells. In embodiments, the solid support includes about $1 \times 10^9$ or more wells. In embodiments, the solid support includes about $1 \times 10^{10}$ or more wells. In embodiments, the solid support includes about $1 \times 10^{11}$ or more wells. In embodiments, the solid support includes about $1 \times 10^{12}$ or more wells. In embodiments, the solid support is a glass slide. In embodiments, the solid support is a about 75 mm by about 25 mm. In embodiments, the solid support includes one, two, three, or four channels.

In embodiments, at least 1%, 5%, 10%, 15%, 20%, 25% or more of the wells include a first sequence complementary to a first endogenous region of different target polynucleotides. In embodiments, at least 10%, 20%, 30%, 40%, 50% or more of the wells include a first sequence complementary to a first endogenous region of different target polynucleotides. In embodiments, at least 50%, 75%, 90%, 95%, 99% or more of the wells include a first sequence complementary to a first endogenous region of different target polynucleotides.

In embodiments, each well further includes one or more immobilized target polynucleotides, each including from 5' to 3', the target polynucleotide sequence or a complement thereof, and a sequence complementary the second sequence.

In embodiments, each well further includes a plurality of bioconjugate reactive moieties. In embodiments, each well includes a polymer coating. In embodiments, the polymer coating includes a plurality of bioconjugate reactive moieties. In embodiments, each well further includes a plurality of azide moieties, alkyne moieties, dibenzocyclooctyne (DBCO) moieties, epoxy moieties, or isocyanate moieties.

In embodiments, the particle is bound to a solid support. In embodiments, the particle is in contact with a solid support. In embodiments, the particle is non-covalently bound to a solid support. In embodiments, the particle is covalently bound to a solid support. In embodiments, the particle is bound to a discrete site on a solid support. In embodiments, the particle is in a well of a multiwell container (e.g., a microwell or nanowell container). In embodiments, the particle is in a well of an array.

In embodiments, the target polynucleotide does not include a universal adapter (e.g., an exogenous adapter). The term "universal adapter" is used to refer to an adapter of a plurality of sequencing adapters having one or more universal sequences. Typically, the plurality of sequencing adapters is configured to be attached to (e.g., by ligation, hybridization, or transposition) target polynucleotides to provide adapter-target polynucleotides in a sequencing process for determining sequences of the target nucleic acids. In embodiments, all universal adapters in a sequencing process are identical, and can be attached to target nucleic acids having different characteristics, such as different sample sources, different organisms, different cell types, etc. Index sequences that are used to index sample sources are sample-specific sequences.

In embodiments, the target polynucleotide does not include a universal primer binding sequence. As used herein, the term "universal primer binding sequence" refers to a polynucleotide sequence that is common to two or more nucleic acid molecules where the molecules also have regions of sequence that differ from each other. Non-limiting examples of universal primer binding sites include sequences that are identical to or complementary to P5 and P7 primers, for example, P5: 5'-AATGATACGGCGAC-CACCG (SEQ ID NO: 5), or the complement thereof, and P7: 5'-CAAGCAGAAGACGGCATACGA (SEQ ID NO: 6), or the complement thereof. In embodiments, the target polynucleotide does not include a P5 sequence, or complement thereof. In embodiments, the target polynucleotide does not include a P7 sequence, or complement thereof. In embodiments, the target polynucleotide does not include a P5 sequence and/or P7 sequence, or complements thereof. In embodiments, the target polynucleotide does not include SEQ ID NO: 5, or a complement thereof. In embodiments, the target polynucleotide does not include SEQ ID NO: 6, or a complement thereof. In embodiments, the target polynucleotide does not include SEQ ID NO: 5 and/or SEQ ID NO: 6, or complements thereof. For example, the target polynucleotide is not ligated to an adapter including a universal primer binding sequence, therefore the target polynucleotide does not include a universal primer binding sequence. Following extension of the immobilized oligonucleotide and generation of an immobilized complement of the target polynucleotide, the immobilized complement includes any primer binding sequence present on the immobilized oligonucleotide. In embodiments, the first endogenous region of the target polynucleotide does not include a universal primer binding sequence. In embodiments, the first endogenous region of the target polynucleotide does not include an adapter. In embodiments, the second region of the target polynucleotide does not include a universal primer binding sequence. In embodiments, the second region of the target polynucleotide does not include an adapter. In embodiments, the second endogenous region of the target polynucleotide does not include a universal primer binding sequence. In embodiments, the second endogenous region of the target polynucleotide does not include an adapter. In embodiments, the first region of the target polynucleotide does not include a synthetic sequence.

The target polynucleotide molecules may be treated chemically or enzymatically either prior or subsequent to any fragmentation processes, and prior to or subsequent to the step of enrichment using the probe libraries or probe amplicons. Such fragmentation methods are known in the art and can utilize standard methods (Sambrook and Russell, Molecular Cloning, A Laboratory Manual, third edition). Random fragmentation is designed to produce fragments irrespective of the sequence identity or position of nucleotides including and/or surrounding the break. More particularly, the random fragmentation can be by mechanical means such as nebulization or sonication. The fragments can be about 50 base pairs in length to about 1500 base pairs in length. In embodiments, the target polynucleotides are 50-700 base pairs in length, or 50-400 base pairs in length. In embodiments, the target polynucleotides are about 100-300 base pairs in length. In the methods described herein, the nucleic acid samples may be fragmented prior to hybridization on the array, or may be used without fragmentation. The samples may be subjected to an amplification reaction prior to use, for example a whole sample amplification technique such as random primer extension.

In embodiments, the particle further includes one or more immobilized target polynucleotides, each including from 5' to 3', the target polynucleotide sequence or a complement thereof, and a sequence complementary the second sequence.

In embodiments, each particle further includes a plurality of bioconjugate reactive moieties. In embodiments, the particle includes a polymer coating. In embodiments, the polymer coating includes a plurality of bioconjugate reactive moieties. In embodiments, each particle further includes a plurality of azide moieties, alkyne moieties, dibenzocyclooctyne (DBCO) moieties, epoxy moieties, or isocyanate moieties.

In embodiments, the average longest dimension of the particle is from about 100 nm to about 3000 nm. In embodiments, the average longest dimension of the particle is from about 100 nm to about 1000 nm. In embodiments, the average longest dimension of the particle is from about 150 nm to about 600 nm. In some embodiments, the average longest dimension of the particle is from about 200 nm to about 1000 nm. In embodiments, the average longest dimension of the particle is from about 150 nm to about 600 nm. In some embodiments, the average longest dimension of the particle is from about 350 nm to about 600 nm. In some embodiments, the average longest dimension of the particle is from about 400 nm to about 500 nm. In some embodiments, the average longest dimension of the particle is from about 500 nm to about 1200 nm. In some embodiments, the average longest dimension of the particle is from about 1000 nm to about 1500 nm. In some embodiments, the average longest dimension of the particle is from about 1500 nm to about 2500 nm. In some embodiments, the average longest dimension of the particle is from about 2500 nm to about 3000 nm. In some embodiments, the average longest dimension of the particle is about 500 nm. In some embodiments, the average longest dimension of the particle is about 400 nm. In some embodiments, the average longest dimension of the particle is about 400 nm, 450 nm, 500 nm, or 550 nm. In embodiments, the average longest dimension of the particle is at least, about, or at most 100, 200, 300, 400, 500, 600, 700, 800, 900, 1000 nm or a number or a range between any two of these values. In embodiments, the average longest dimension of the particle is at least, about, or at most 1000, 1100, 1200, 1300, 1400, 1500, 1600, 1700, 1800, 1900, 2000, 2100, 2200, 2300, 2400, 2500, 2600, 2700, 2800, 2900, 3000 nm or a number or a range between any two of these values.

In embodiments, the particle includes glass, ceramic, metal, silica, magnetic material, or a paramagnetic material. In embodiments, the particle includes silica, magnetic material, or a paramagnetic material. In embodiments, the particle is silica particle.

In embodiments, the particle is a polymer particle including polymerized units of polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, polyethylene glycol (PEG)-thiol/PEG-acrylate, acrylamide/N,N'-bis(acryloyl) cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly (vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof. In embodiments, the particle is a hydrogel polymer particle.

In some embodiments, a crosslinker forms a disulfide bond in the hydrogel polymer, thereby linking hydrogel polymers. In some embodiments, the hydrogel polymers form a hydrogel matrix having pores (for example, a porous hydrogel matrix). These pores are capable of retaining sufficiently large genetic material within the hydrogel bead, for example, long DNA fragments, but allow small materials, such as reagents, to pass through the pores, thereby passing in and out of the hydrogel beads. In some embodiments, the pore size is finely tuned by varying the ratio of the concentration of polymer to the concentration of crosslinker. In some embodiments, the ratio of polymer to crosslinker is 30:1, 25:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:15, 1:20, or 1:30, or a ratio within a range defined by any two of the aforementioned ratios. In some embodiments, additional functions such as DNA primer, or charged chemical groups can be grafted to polymer matrix to meet the requirements of different applications.

As used herein, the term "porosity" means the fractional volume (dimension-less) of a hydrogel that is composed of open space, for example, pores or other openings. Therefore, porosity measures void spaces in a material and is a fraction of volume of voids over the total volume, as a percentage between 0 and 100% (or between 0 and 1). Porosity of the hydrogel may range from 0.5 to 0.99, from about 0.75 to about 0.99, or from about 0.8 to about 0.95.

The hydrogels can have any pore size. As used herein, the term "pore size" refers to a diameter or an effective diameter of a cross-section of the pores. The term "pore size" can also refer to an average diameter or an average effective diameter of a cross-section of the pores, based on the measurements of a plurality of pores. The effective diameter of a cross-section that is not circular equals the diameter of a circular cross-section that has the same cross-sectional area as that of the non-circular cross-section. In some embodiments, the hydrogel can be swollen when the hydrogel is hydrated. The sizes of the pores size can then change depending on the water content in the hydrogel. In some embodiments, the pores of the hydrogel can have a pore of sufficient size to retain genetic material within the hydrogel but allow reagents to pass through.

In some embodiments, the crosslinker is a reversible crosslinker. In some embodiments, a reversible crosslinker is capable of reversibly crosslinking the hydrogel polymer and is capable of being un-crosslinked in the presence of a cleaver. In some embodiments, a crosslinker can be cleaved by the presence of a reducing agent, by elevated temperature, or by an electric field. In some embodiments, the reversible crosslinker may be N,N'-bis(acryloyl)cystamine, a reversible crosslinker for polyacrylamide gels, wherein a disulfide linkage may be broken in the presence of a suitable reducing agent. In some embodiments, contacting the crosslinker with a reducing agent cleaves the disulfide bonds of the crosslinker, breaking down the hydrogel beads. The hydrogel beads degrade, and release the contents, such as nucleic acids that were retained therein. In some embodiments, the crosslinker is cleaved by increasing the temperature to greater than 50, 55, 60, 65, 70, 75, 80, 85, 90, 95, or 100° C. In some embodiments, the crosslinker is cleaved by contacting the hydrogel beads with a reducing agent. In some embodiments, the reducing agents include phosphine compounds, water soluble phosphines, nitrogen containing phosphines and salts and derivatives thereof, dithioerythritol (DTE), dithiothreitol (DTT) (cis and trans isomers, respectively, of 2,3-dihydroxy-1,4-dithiolbutane), 2-mercaptoethanol or 3-mercaptoethanol (BME), 2-mercaptoethanol or aminoethanethiol, glutathione, thioglycolate or thioglycolic acid, 2,3-dimercaptopropanol, tris(2-carboxyethyl)phosphine (TCEP), tris(hydroxymethyl)phosphine (THP), or P-[tris(hydroxymethyl)phosphine] propionic acid (THPP).

In some embodiments, elevating the temperature to increase diffusion or contacting with a reducing agent degrades the crosslinker, thereby releasing encapsulated genetic material from the hydrogel bead.

In embodiments, the particle includes a particle core and a particle shell, wherein the particle shell includes a plurality of bioconjugate reactive moieties, wherein each of the bioconjugate reactive moieties and each of the immobilized oligonucleotides include a linker binding the bioconjugate reactive moieties and oligonucleotide to the particle core. In embodiments, the particle core includes glass, ceramic, metal, silica, magnetic material, or a paramagnetic material, and further wherein the particle shell includes polymerized units of polyacrylamide (AAm), glicydyl methacrylate (GMA), glicydyl methacrylate (GMA)-azide, polyethylene glycol methacrylate (PEGMA), polyethylene glycol methacrylate (PEGMA), isocyanatoethyl methacrylate (IEM), or a copolymer thereof.

In embodiments, the particle core includes glass, ceramic, metal, silica, magnetic material, or a paramagnetic material. The particle core may be an inorganic particle core. The inorganic particle core may be a metal particle core. When the particle core is a metal, the metal may be titanium, zirconium, gold, silver, platinum, cerium, arsenic, iron, aluminum or silicon. The metal particle core may be titanium, zirconium, gold, silver, or platinum and appropriate metal oxides thereof. In embodiments, the particle core is titanium oxide, zirconium oxide, cerium oxide, arsenic oxide, iron oxide, aluminum oxide, or silicon oxide. The metal oxide particle core may be titanium oxide or zirconium oxide. The particle may be titanium. The particle may be gold. The particle may be silicon dioxide. The particle may be silica. In embodiments, the particle core is in the form of a bead. For example, the core/shell layers may be formed around a supporting structure, for example, a silica, magnetic, or paramagnetic bead. In some embodiments, the composition includes a solid bead support (which itself may include a magnetic core and an encapsulating polymer layer), a functional core layer around the bead for primer attachment, and a shell polymer layer in which no amplification reactions take place. In embodiments, the particle is a silica particle includes a magnetic core, and a copolymer shell. In embodiments, the particle shell is chemically distinct from the particle core.

In some embodiments, the particle shell includes polymerized units of polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, polyethylene glycol (PEG)-thiol/PEG-acrylate, acrylamide/N,N'-bis(acryloyl)cystamine (BACy), PEG/polypropylene oxide (PPO), polyacrylic acid, poly (hydroxyethyl methacrylate) (PHEMA), poly(methyl methacrylate) (PMMA), poly(N-isopropylacrylamide) (PNI-PAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof. In embodiments, the particle shell includes polymerized units of polyacrylamide (AAm), glicydyl methacrylate (GMA), glicydyl methacrylate (GMA)-azide, polyethylene glycol methacrylate (PEGMA), polyethylene glycol methacrylate (PEGMA), isocyanatoethyl methacrylate (IEM), or a copolymer thereof. In embodiments, the particle shell includes polymerized units of 3-azido-2-hydroxypropyl methacrylate, 2-azido-3-hydroxypropyl methacrylate, 2-(((2-azidoethoxy)carbonyl)amino)ethyl methacrylate, 3-azido-2-hydroxypropyl acrylate, 2-azido-3-hydroxypropyl acrylate, or 2-(((2-azidoethoxy)carbonyl)amino)ethyl acrylate. In embodiments, the particle shell includes polymerized units of 3-azido-2-hydroxypropyl methacrylate, 2-azido-3-hydroxypropyl methacrylate, or 2-(((2-azidoethoxy)carbonyl)amino)ethyl methacrylate. In embodiments, the particle shell includes polymerized units of 3-azido-2-hydroxypropyl methacrylate. In embodiments, the particle shell includes polymerized units of 3-azido-2-hydroxypropyl methacrylate 2-azido-3-hydroxypropyl methacrylate. In embodiments, the particle shell includes polymerized units of 3-azido-2-hydroxypropyl methacrylate 2-(((2-azidoethoxy)carbonyl)amino)ethyl methacrylate.

In embodiments, the particle shell is permeable to a polymerase. In embodiments, the polymer particle is permeable to a polymerase. In embodiments, the particle shell is permeable to an amplification reaction mixture and/or a sequencing reaction mixture. In embodiments, the polymer particle is permeable to an amplification reaction mixture and/or a sequencing reaction mixture. In embodiments, the particle shell is permeable to a sequencing reaction mixture. In embodiments, the polymer particle is permeable to a sequencing reaction mixture. In embodiments, the polymer particle and shell polymer are permeable to a polymerase for amplifying the target polynucleotide. In embodiments, the shell polymer has a higher permeability than the core (e.g., the particle core is substantially less permeable than the particle shell). In embodiments, the polymer shell is permeable to a polymerase for amplifying the target polynucleotide, such that the interface of the core is in contact with the polymerase. The term "sequencing reaction mixture" refers to an aqueous mixture that contains the agents and reagents necessary to allow addition of a nucleotide to a polynucleotide strand by a polymerase (e.g., addition of a dNTP or dNTP analogue to a DNA strand by a DNA polymerase). Exemplary mixtures of agents and reagents include buffers (e.g., saline-sodium citrate (SSC), tris(hydroxymethyl)aminomethane or "Tris"), salts (e.g., KCl or $(NH_4)_2SO_4$)), nucleotides (e.g., modified nucleotides), polymerases, cleaving agent (e.g., tri-n-butyl-phosphine, triphenyl phosphine and its sulfonated versions (i.e., tris(3-sulfophenyl)-phosphine, TPPTS), and tri(carboxyethyl)phosphine (TCEP) and its salts, cleaving agent scavenger compounds (e.g., 2'-Dithiobisethanamine or 11-Azido-3,6,9-trioxaundecane-1-amine), detergents and/or crowding agents (e.g., PEG, Tween, BSA). In embodiments, the modified nucleotides are reversibly terminated nucleotides linked to fluorescent dyes, such that the identity of a nucleotide added in a sequencing reaction can be identified based on the fluorescent dye with which it is associated. The term "amplification reaction mixture" refers to an aqueous mixture that contains the agents and reagents necessary to make one or more copies of a nucleic acid. Exemplary components include a polymerase, a nucleic acid template, a suitable primer or set of primers, suitable nucleotides (e.g., dNTPs), and a suitable buffer.

In an aspect is a particle including a degradable particle core; a polymer shell surrounding the degradable particle core; and a plurality of oligonucleotide moieties covalently attached to the particle via a polymeric bioconjugate linker. In embodiments, the polymer shell includes a plurality of polymerized units of shell monomers and a plurality of oligonucleotide moieties wherein each oligonucleotide moiety is covalently attached to the polymer shell via a bioconjugate linker. In embodiments, the polymeric bioconjugate linker is the product of a reaction between the two bioconjugate group (e.g., click chemistry group). In embodiments, the polymeric bioconjugate linker is formed between a first reactive moiety and a second reactive moiety as described herein.

In embodiments, each particle includes a plurality of oligonucleotide moieties covalently attached to said particle via a polymeric bioconjugate linker. In embodiments, the polymeric bioconjugate linker is formed through a reaction between a particle polymer (e.g., a polymer covalently attached to the surface of the particle) including a first bioconjugate reactive moiety and an oligonucleotide including a second bioconjugate reactive moiety. In embodiments, the average longest dimension of the particle is from about 100 nm to about 3000 nm. In embodiments, each particle includes a plurality of oligonucleotide moieties covalently attached to said particle via a bioconjugate linker, wherein the polymeric bioconjugate linker is formed through a reaction between a particle polymer (e.g., a polymer covalently attached to the surface of the particle) including a first bioconjugate reactive moiety (e.g., an azide) and an oligonucleotide including a second bioconjugate reactive moiety (e.g., DBCO).

In embodiments, the oligonucleotide moiety includes a DBCO bioconjugate reactive moiety that reacts with an azide bioconjugate reactive moiety on the particle polymer and forms a bioconjugate linker that covalently links the oligonucleotide moiety to the particle polymer, for example according to the following scheme:

Scheme 1.

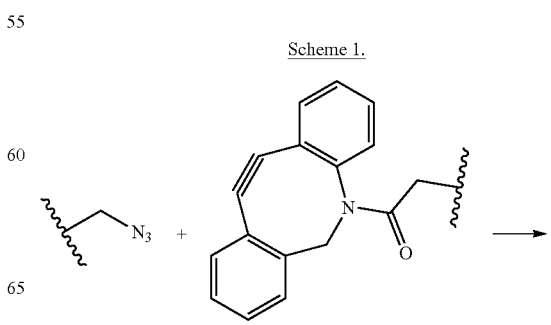

-continued

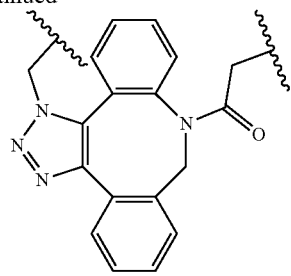

An example mechanism of the bioconjugate covalent linker former by reacting a DBCO containing oligonucleotide with a particle containing an azide moiety, wherein the "⸹" refers to the attachment point to the oligonucleotide moiety and the particle polymer, respectively.

In embodiments, the particle includes a degradable particle core surrounded by a polymer shell wherein the polymer shell is functionalized for primer attachment. In embodiments, the particle comprises a degradable particle core surrounded by a polymer shell wherein the polymer shell includes a plurality of polymerized units of shell monomers and one or more shell monomers includes an oligonucleotide moiety covalently linked to the shell monomer. In embodiments, the particle (e.g., a nanoparticle) includes a plurality of oligonucleotide moieties covalently attached to the polymer shell via a bioconjugate linker, wherein the bioconjugate linker is formed via a reaction between a particle polymer including a first bioconjugate reactive moiety and an oligonucleotide including a second bioconjugate reactive moiety as described herein. In embodiments, the particle includes a plurality of particle polymers (e.g., a polymer or copolymer described herein). In embodiments, the particle polymer is a brush polymer. In embodiments, the plurality of particle polymers are not covalently crosslinked. In embodiments, the plurality of particle polymers are covalently crosslinked.

In embodiments, the particle includes a metal-organic framework (MOF) particle. In embodiments, the particle has a degradable particle core that includes a metal-organic framework (MOF) particle. In embodiments, the degradable particle core includes a polystyrene (PS) particle, or polymethyl methacrylate (PMMA) particle, or latex particle. In embodiments, the MOF particle is any metal-organic framework particle that can be degraded by a change in external conditions, including a change in pH, temperature, or other chemical degrading agent. In embodiments, the MOF particle is a Zeolitic Imidazolate Framework 8 (ZIF-8) particle. In embodiments, the MOF particle is UiO-66. In embodiments, the MOF particle is a Zr based MOFs, mesoporous iron (III) carboxylate MIL-100(Fe). In embodiments, the degrading the degradable particle core does not destroy or damage the oligonucleotide. In embodiments, the MOF particle is as described in Furukawa et al. (see Science, vol. 341, No. 6149, 1230444, 2013) or Cohen (see Chem. Reviews, Vol. 112, No. 2, p. 970-1000, 2012).

In embodiments, the MOF particle is synthesized by joining metal-containing units, also known as secondary building units (SBUs), with organic linkers using reticular synthesis. In embodiments, the MOF particle may vary in size and nature of its structure without changing its underlying topology. In embodiments, the MOF particle may be post-synthetically modified so that organic units and metal-organic complexes may be incorporated by reactions with linkers so that the reactivity of the pores is changed. In embodiments, the MOF particle may be multivariate wherein multiple organic functionalities are incorporated within a single framework.

In embodiments, the MOF particle is MOF-5; MOF-177 [$Zn_4O(BTB)_2$ wherein BTB=4, 4',4"-benzene-1,3,5-triyl-bribenzoate]; MOF-200 [$Zn_4O(BBC)_2$ wherein $BBC^{3-}$ is 4,4',4"-(benzene-1,3,5-triyl-tris(benzene-4,1-diyl)tribenzoate]; MOF-210 [$(Zn_4O)_3(BTE)_4(BPDC)_3$ wherein BTE=4, 4',4"-(benzene-1,3,5-triyl-tris(ethyne-2,1-diyl))tribenzoate and BPDC=bipheyl-4,4'-dicarboxylate]; NU-110[$Cu_3$(BHEHPI) wherein $BHEHPI^{6-}$ is 5,5',5"-((((benzene-1,3,5-triyltris(benzene-4,1-diyl))tris(ethyne-2,1-diyl))-tris(benzene-4,1,-diyl))tris(ethyne-2,1-diyl))triisophthalate]; IRMOF-1; IRMOF-16 [$Zn_4O(TPDC)_3$ wherein $TPDC^{2-}$ is terphenyl-5,5"-dicarboxylate]; MOF-180 [$Zm_4O(BTE)_2$], HKUST-1 [$Cu_3(BTC)_2$ wheren $BTC^{3-}$ is benzene-1,3,5-tricarboxylate]; MOF-399 [$Zn_3(TPBTM)$ wherein $TPBTM^{6-}$ is 5,5',5"-((benzene-1,3,5-tricarbonyl)tris(azanediyl))triisophthalate]; $Cu_3(TPBTM)$; $Cu_3(TDPAT)$ wherein $TDPAT^{6-}$ is 5,5',5"-(1,3,5-triazine-2,4,6-triyl)tris(azanediyl)triisophthalate; NOTT-112 [$Cu_3(BTPI)$] wherein $BTPI^{6-}$ is 5,5',5"-(benzene-1,3,5-triyl-tris)benzene-4,1-diyl))triisophthalate]; NOTT-116, also known as PCN-68, [$Cu_3(PTEI)$ wherein $PTEI^{6-}$ is 5,5',5"-((benzene-1,3,5-triyl-trisbenzene-4,1-diyl)tris(ethyne-2,1-diyl))triisophthalate]; PCN-61 [$Cu_3(BTEI)$ wherein $BTEI^{6-}$ is 5,5',5"-(benzene-1,3,5-triyl-tris(ethyne-2,1-diyl))triisophthalate]; PCN-66 [$Cu_3$(NTEI) wherein $NTEI^{6-}$ is 5,5',5"-((nitrilotris(benzene-4,1-diyl))tris(ethyne-2,1-diyl))triisophthalate]; PCN-69, also known as NOTT-119, [$Cu_3(BTTI)$ wherein $BTTI^{6-}$ is 5,5',5"=(benzene-1,3,5-triyl-tris(biphenyl-4,4'-dyl))triisophthalate]; PCN-610, also known as NU-100, [$Cu_3(TTEI)$ wherein $TTEI^{6-}$ is 5,5',5"-(((benzene-1,3,5-triyl-tris(ethyne-2,1-diyl))tris(benzene-4,1-diyl))tris(ethyne-2,1-diyl))triisophthalate]; NU-108 [$Cu_3(BTETCA)$ wherein $BTETCA^{6-}$ is 5,5"",5""'-(benzene-1,3,5-triyl-tris(ethyne-2,1-diyl))tris((([1,1':3'1"-terphenyl]-4,4"-dicarboxylate))]; NU-109 [$Cu_3$(BNETPI) wherein $BNETPI^{6-}$ is 5,5',5"-(((benzene-1,3,5-triyl-tris(ethyne-2,1-diyl))tris(benzene-4,1-diyl))tris(buta-1,3-diyne-4,1-diyl))triisophthalate]; NU-110 and NU-111 [$Cu_3$(BHEI), wherein $BHEI^{6-}$ is 5,5',5"-(benzene-1,3,5-ytiyl-tris(buta-1,3-diyne-4,1-diyl))triisophthalate]. In embodiments, the MOF particle is $M_3(BTC)_2$ wherein M is Zn(II), Fe(II), Mo(II), Cr(II) and Ru(II), MOF-74 [$M_2(DOT)$ wherein DOT is dioxidoterephthalate using divalent metal ions such as Mg, Co, Ni and Mn and $M^{21}$ is Zn or Mg]. In embodiments, the MOF particle is IRMOF-74-I, IRMOF-74-II, IRMOF-74-III, IRMOF-74-IV, IRMOF-74-V, IRMOF-74-VI, IRMOF-74-VII, IRMOF-74-VIII, IRMOF-74-IX, IRMOF-74-X and IRMOF-74-XI. In embodiments, the MOF particle is MTV-MOF-5, $Ag_6(OH_2)(H_2O_4)(TIPA)$s, PCN-14, MOF-2, MOF-11, MOF-73 or POST-1. In embodiments the MOF particle is UiO-66, MOT-525, MOF-545, MOF-11, IRMOF-3, UCMC-1-$NH_2$, MIL-101, Mn-BTT, MOF-48, PIZA-3, MIL-101(Cr), MIL-53, MIL-68, MOF-5, NU-100, Ni-MOF-74, Mg-MOF-74, Fe-MOF-74, MOF-508, MOF-1001, CPM-7 or CPM-24. In embodiments, the MOF particle is MOF-LIC-1, DMOF-1, UMCM-1, ZIF-90, STAM-1, SNU-30, CAU-1, or SIM-1. In embodiments the MOF particle is ZIF-8, also known as $Zn(MIm)_2$ wherein MIm is 2-methylimidazolate.

In embodiments, the degradable particle core can be removed to release material through the presence of an external stimulus. In embodiments, the external stimulus is a change in pH. In embodiments, the pH is altered with a base to degrade the particle core. In embodiments, the base is NaOH. In embodiments, the pH is altered with an acid to degrade the particle core. In embodiments, the external stimulus is the presence of a compound such as phosphate. In embodiments, degrading the particle core causes the release of the polymer shell. In embodiments, the degradable particle core is degraded under conditions that would not degrade and/or alter an oligonucleotide. In embodiments, the mass of the degradable particle core reduces upon incubation and/or contact with the external stimulus.

In embodiments, the degradable particle core is contacted with about 0.1 to 1.0 M solution of an acid or base. In embodiments, the degradable particle core is contacted with about 0.1 to 0.5 M solution of an acid or base solution. In embodiments, the degradable particle core is contacted with about 0.1 M solution of an acid or base solution. In embodiments, the degradable particle core is contacted with about 0.2 M solution of an acid or base solution. In embodiments, the degradable particle core is contacted with about 0.3 M solution of an acid or base solution. In embodiments, the degradable particle core is contacted with about 0.4 M solution of an acid or base solution. In embodiments, the degradable particle core is contacted with about 0.5 M solution of an acid or base solution. In embodiments, the degradable particle core is contacted with about 0.6 M solution of an acid or base solution. In embodiments, the degradable particle core is contacted with about 0.7 M solution of an acid or base solution. In embodiments, the degradable particle core is contacted with about 0.8 M solution of an acid or base solution. In embodiments, the degradable particle core is contacted with about 0.9 M solution of an acid or base solution. In embodiments, the degradable particle core is contacted with about 1.0 M solution of an acid or base solution. In embodiments, the degradable particle core is contacted with about 0.1 M solution of an acid solution. In embodiments, the degradable particle core is contacted with about 0.1 M solution of HCl. In embodiments, the degradable particle core is contacted with about 0.2 M solution of an acid solution. In embodiments, the degradable particle core is contacted with about 0.2 M solution of HCl. In embodiments, the degradable particle core is contacted with about 0.3 M solution of an acid solution. In embodiments, the degradable particle core is contacted with about 0.3 M solution of HCl. In embodiments, the degradable particle core is contacted with about 0.4 M solution of an acid solution. In embodiments, the degradable particle core is contacted with about 0.4 M solution of HCl. In embodiments, the degradable particle core is contacted with about 0.5 M solution of an acid solution. In embodiments, the degradable particle core is contacted with about 0.5 M solution of HCl. In embodiments, the degradable particle core is contacted with about 0.6 M solution of an acid solution. In embodiments, the degradable particle core is contacted with about 0.6 M solution of HCl. In embodiments, the degradable particle core is contacted with about 0.7 M solution of an acid solution. In embodiments, the degradable particle core is contacted with about 0.7 M solution of HCl. In embodiments, the degradable particle core is contacted with about 0.8 M solution of an acid solution. In embodiments, the degradable particle core is contacted with about 0.8 M solution of HCl. In embodiments, the degradable particle core is contacted with about 0.9 M solution of an acid solution. In embodiments, the degradable particle core is contacted with about 0.9 M solution of HCl. In embodiments, the degradable particle core is contacted with about 1.0 M solution of an acid solution. In embodiments, the degradable particle core is contacted with about 1.0 M solution of HCl. In embodiments, the degradable particle core is contacted with about 0.1 M solution of a base solution. In embodiments, the degradable particle core is contacted with about 0.1 M solution of NaOH solution. In embodiments, the degradable particle core is contacted with about 0.2 M solution of a base solution. In embodiments, the degradable particle core is contacted with about 0.2 M solution of NaOH solution. In embodiments, the degradable particle core is contacted with about 0.3 M solution of a base solution. In embodiments, the degradable particle core is contacted with about 0.3 M solution of NaOH solution. In embodiments, the degradable particle core is contacted with about 0.4 M solution of a base solution. In embodiments, the degradable particle core is contacted with about 0.4 M solution of NaOH solution. In embodiments, the degradable particle core is contacted with about 0.5 M solution of a base solution. In embodiments, the degradable particle core is contacted with about 0.5 M solution of NaOH solution. In embodiments, the degradable particle core is contacted with about 0.6 M solution of a base solution. In embodiments, the degradable particle core is contacted with about 0.6 M solution of NaOH solution. In embodiments, the degradable particle core is contacted with about 0.7 M solution of a base solution. In embodiments, the degradable particle core is contacted with about 0.7 M solution of NaOH solution. In embodiments, the degradable particle core is contacted with about 0.8 M solution of a base solution. In embodiments, the degradable particle core is contacted with about 0.8 M solution of NaOH solution. In embodiments, the degradable particle core is contacted with about 0.9 M solution of a base solution. In embodiments, the degradable particle core is contacted with about 0.9 M solution of NaOH solution. In embodiments, the degradable particle core is contacted with about 1.0 M solution of a base solution. In embodiments, the degradable particle core is contacted with about 1.0 M solution of NaOH solution.

In embodiments, the degradable particle core is contacted with an acid or base solution to degrade the particle core. In embodiments, degrading the particle core causes the release of the polymer shell. In embodiments, the degradable particle core is contacted with an acid or base solution for about 10 sec to about 20 min. In embodiments, the degradable particle core is contacted with an acid or base solution for about 30 sec to about 15 min. In embodiments, the degradable particle core is contacted with an acid or base solution for about 1 min to about 10 min. In embodiments, the degradable particle core is contacted with an acid or base solution for about 2 min to about 8 min. In embodiments, the degradable particle core is contacted with an acid or base solution for about 1 min, 2 min, 3 min, 4 min, 5 min, 6 min, 7 min, 8 min, 9 min or 10 min. In embodiments, the degradable particle core is contacted with an acid or base solution for about 5 min, 6 min, 7 min, 8 min, 9 min or 10 min.

In embodiments, a plurality of oligonucleotide moieties is covalently attached to said particle via a polymeric bioconjugate linker. In embodiments, the polymeric bioconjugate linker is formed through a reaction between a particle polymer (e.g., a polymer covalently attached to the surface of the particle) including a first bioconjugate reactive moiety and an oligonucleotide including a second bioconjugate reactive moiety. In embodiments, the polymeric bioconjugate linker is formed before the degradable particle core is contacted with an external stimulus (e.g. acid or base solution which degrades the particle core). In embodiments, the polymeric bioconjugate linker is formed after the degradable particle core is contacted with an external stimulus (e.g. acid or base solution which degrades the particle core).

In embodiments, the particle has a polymer shell surrounding the degradable particle core. In embodiments, the polymer shell includes polymerized units of polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, polyethylene glycol (PEG)-thiol/PEG-acrylate, acrylamide/N,N'-bis(acryloyl) cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly (vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), glicydyl methacrylate (GMA) azide, hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof. In embodiments, the polymer shell includes polymerized units of polyethylene glycol methacrylate (PEGMA) and glicydyl methacrylate (GMA). In embodiments, the polymer shell includes polymerized units of polyethylene glycol methacrylate (PEGMA) and isocyanatoethyl methacrylate (IEM). In embodiments, the polymer shell includes polymerized units of glicydyl methacrylate azide (GMA azide) and polyethylene glycol methacrylate (PEGMA).

In embodiments, the particles are non-covalently attached to the wells. In embodiments, the particles are physiosorbed to the wells. In embodiments, the particles are covalently attached to the wells. In embodiments, each particle attaches to the polymer layer of the surface (e.g., non-covalently attach to the polymer layer). In embodiments, the particles contact the well and remain attached without any additional means for attachment (e.g., hybridization of complementary oligonucleotides immobilized on the solid support). In embodiments, the solid support does not include immobilized oligonucleotides.

In embodiments, the particle does not include any other oligonucleotides other than the first plurality of immobilized oligonucleotides and the second plurality of immobilized oligonucleotides.

In an aspect is provided a plurality of particles, wherein each of the particles is a particle as described herein. In embodiments, one or more particles include a first sequence complementary to a first endogenous region of different target polynucleotides. In embodiments, one or more particles of the plurality include a first sequence complementary to a first endogenous region of different target polynucleotides. In embodiments, each of the particles of the plurality include a first sequence complementary to a first endogenous region of different target polynucleotides. In embodiments, the plurality of particles include different particles, wherein the particles differ from each other by the different target polynucleotides.

In embodiments, at least 1%, 5%, 10%, 15%, 20%, 25% or more of the particles include a first sequence complementary to a first endogenous region of different target polynucleotides. In embodiments, at least 10%, 20%, 30%, 40%, 50% or more of the particles include a first sequence complementary to a first endogenous region of different target polynucleotides. In embodiments, at least 50%, 75%, 90%, 95%, 99% or more of the particles include a first sequence complementary to a first endogenous region of different target polynucleotides.

In embodiments, each particle of the plurality is bound (e.g., covalently linked) to a solid support. In embodiments, each particle of the plurality is non-covalently bound to a solid support. In embodiments, each particle of the plurality is arrayed on a solid support. In embodiments, each particle of the plurality is non-covalently attached to the wells. In embodiments, each particle of the plurality is physiosorbed to the wells. In embodiments, each particle attaches to the polymer layer of the surface (e.g., non-covalently attach to the polymer layer).

In embodiments, the microplate (e.g., a microplate array) includes 2, 4, 6, 12, 24, 48, 96, 384 or 1536 wells. In embodiments, the microplate array includes 24, 48, 96, or 384 wells. In embodiments, the microplate array includes 24 wells. In embodiments, the microplate array includes 48 wells. In embodiments, the microplate array includes 96 wells. In embodiments, the microplate array includes 384 wells. In embodiments, the dimensions of the microplate conform to the standards provided by the American National Standards Institute (ANSI) and Society For Laboratory Automation And Screening (SLAS); for example the tolerances and dimensions set forth in ANSI SLAS 1-2004 (R2012); ANSI SLAS 2-2004 (R2012); ANSI SLAS 3-2004 (R2012); ANSI SLAS 4-2004 (R2012); and ANSI SLAS 6-2012. In embodiments, the microplate has a rectangular shape that measures 127.7 mm±0.5 mm in length by 85.4 mm±0.5 mm in width, and includes 6, 12, 24, 48, or 96 wells. In embodiments, the microplate has a rectangular shape that measures 127.7 mm±0.5 mm in length by 85.4 mm±0.5 mm in width, and includes 6, 12, 24, 48, or 96 wells, wherein each well has an average diameter of about 5-7 mm. In embodiments, the microplate has a rectangular shape that measures 127.7 mm±0.5 mm in length by 85.4 mm±0.5 mm in width, and includes 6, 12, 24, 48, or 96 wells, wherein each well has an average diameter of about 6 mm.

In embodiments, the microplate includes wells that are formatted for compatibility with automated reagent loading equipment (e.g., pipetting robots) that exists and are in common usage in laboratories and manufacturing facilities.

In embodiments, the microplate and wells are comprised of the same material. Though typically glass, suitable microplate materials may include polymeric materials, plastics, silicon, quartz (fused silica), Borofloat® glass, silica, silica-based materials, carbon, metals, an optical fiber or optical fiber bundles, sapphire, or plastic materials such as COCs and epoxies. The material can be selected based on properties desired for a particular use. For example, materials that are transparent to a desired wavelength of radiation are useful for analytical techniques that will utilize radiation of the desired wavelength. Conversely, it may be desirable to select a material that does not pass radiation of a certain wavelength (e.g., being opaque, absorptive, or reflective). In embodiments, at least a portion of the bottom of the wells is transparent and the sides (i.e., walls) of the wells are opaque. In embodiments, the material of the microplate is selected due to the ability to conduct thermal energy. In embodiments, the microplate and wells as used herein may be referred to as the receiving substrate.

In embodiments, the microplate includes a plurality of wells. In embodiments, each well includes about 10,000 to 100,000 cells per well. In embodiments, each well includes at least 1,000, 2,000, 3,000, 4,000, 5,000, 6,000, 7,000, 8,000, 9,000 or at least 10,000 cells per well. In embodiments, each well includes about 10,000, 20,000, 30,000, 40,000, 50,000, 60,000, 70,000, 80,000, 90,000 or at least 100,000 cells per well.

In embodiments, the well contains a gel and/or a polymeric matrix. The term "gel" in this context refers to a semi-rigid solid that is permeable to liquids and gases. Exemplary gels include, but are not limited to, those having a colloidal structure, such as agarose; polymer mesh structure, such as gelatin; or cross-linked polymer structure, such as polyacrylamide or a derivative thereof. Analytes, such as polynucleotides, can be attached to a gel or polymer material via covalent or non-covalent means. Exemplary methods and reactants for attaching nucleic acids to gels are described, for example, in US 2011/0059865 which is incorporated herein by reference. The analytes, sample, tissue, or cell can include nucleic acids and the nucleic acids can be attached to the gel or polymer via their 3' oxygen, 5' oxygen, or at other locations along their length such as via a base moiety of the 3' terminal nucleotide, a base moiety of the 5' nucleotide, and/or one or more base moieties elsewhere in the molecule. In embodiments, the microplate includes a polymer layer (alternatively referred to as a polymer coating). In embodiments, the microplate includes a polymer layer, wherein the polymer layer includes an amphiphilic copolymer. The term "amphiphilic copolymer" is used in accordance with its ordinary meaning and refers to a copolymer composed of polymerized hydrophilic (e.g., PEG monomers) and hydrophobic monomers (e.g., alkoxysilyl or (poly(propylene oxide) monomers). Amphiphilic copolymers can have both hydrophilic and hydrophobic properties. In embodiments, the polymer layer includes an amphiphilic acrylate copolymer or amphiphilic methacrylate copolymer. In embodiments, the amphiphilic polymer includes a poloxamer. In some embodiments, the poloxamer is a polyoxyethylene-polyoxypropylene copolymer.

In embodiments, the solid support is subjected to lithographic patterning methods (e.g., nanolithographic to microlithographic patterning). Typically features smaller than 10 micrometers are considered microlithographic, and features smaller than 100 nanometers are considered nanolithographic. Lithographic techniques make use of masks or templates to transfer patterns over a large area simultaneously. A powerful microfabrication technique is photolithography, i.e. the lithography using a UV light source and a photosensitive material as resist. As the name suggests, the photoresist (alternatively referred to as a resist) is an active material layer that can be patters by selective exposure and must "resist" chemical/physical attach of the underlying substrate. In embodiments, the solid support includes a glass substrate having a surface coated in silsesquioxane resist (e.g., polyhedral oligosilsesquioxanemethacrylate (POSS)), an epoxy-based polymer resist (e.g., SU-8 as described in U.S. Pat. No. 4,882,245), poly(vinylpyrrolidone-vinyl acrylic acid) copolymer resist (e.g., as described in U.S. Pat. No. 7,467,632), or novolaks resist, bisazides resist, or a combination thereof (e.g., as described in U.S. Pat. No. 4,970,276). In embodiments, the solid support includes a photoresist. In embodiments, the solid support includes a photoresist. In embodiments, the solid support includes a photoresist and polymer layer, wherein the photoresist is between the solid support and the polymer layer. In embodiments the photoresist is on the interstitial areas and not the surface of the wells. Suitable photoresist compositions are known in the art, such as, for example the compositions and resins described in U.S. Pat. Nos. 6,897,012; 6,991,888; 4,882,245; 7,467,632; 4,970,276, each of which is incorporated herein by reference in their entirety. In embodiments, the solid support includes a photoresist and polymer layer, wherein the photoresist is covalently attached to the solid support and covalently attached to the polymer layer.

In embodiments, the solid support includes a resist. For example, the solid support surface, but not the surface of the wells, is coated in an organically modified ceramic polymer (ORMOCER®, registered trademark of Fraunhofer-Gesellschaft zur Forderung der angewandten Forschung e. V. in Germany). Organically modified ceramics contain organic side chains attached to an inorganic siloxane backbone. Several ORMOCER® polymers are now provided under names such as "Ormocore", "Ormoclad" and "Ormocomp" by Micro Resist Technology GmbH. In embodiments, the solid support includes a resist as described in Haas et al Volume 351, Issues 1-2, 30 Aug. 1999, Pages 198-203, US 2015/0079351A1, US 2008/0000373, or US 2010/0160478, each of which is incorporated herein by reference.

In embodiments, the solid support includes a polymer layer. In embodiments, the polymer layer includes polymerized units of alkoxysilyl methacrylate, alkoxysilyl acrylate, alkoxysilyl methylacrylamide, alkoxysilyl methylacrylamide, or a copolymer thereof. In embodiments, the polymer layer includes polymerized units of alkoxysilyl methacrylate. In embodiments, the polymer layer includes polymerized units of alkoxysilyl acrylate. In embodiments, the polymer layer includes polymerized units of alkoxysilyl methylacrylamide. In embodiments, the polymer layer includes polymerized units of alkoxysilyl methylacrylamide. In embodiments, the polymer layer includes glycidyloxypropyl-trimethyloxysilane. In embodiments, the polymer layer includes methacryloxypropyl-trimethoxysilane. In embodiments, the polymer layer includes polymerized units of

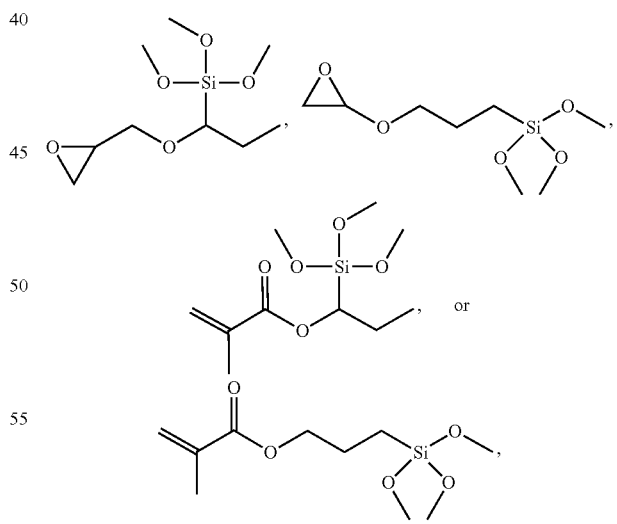

or a copolymer thereof.

In embodiments, the solid support includes a passivated polymer layer (alternatively referred to as a passivated polymer coating). In embodiments, the solid support comprises a passivated polymer layer, wherein the passivated polymer layer includes an amphiphilic copolymer. The term "amphiphilic copolymer" is used in accordance with its ordinary meaning and refers to a copolymer composed of polymerized hydrophilic (e.g., PEG monomers and hydrophobic monomers (e.g., alkoxysilyl or (poly(propylene oxide) monomers). The term "amphiphilic copolymer" is used in accordance with its ordinary meaning and refers to a copolymer composed of polymerized hydrophilic (e.g., PEG monomers or HEMA monomers) and hydrophobic monomers (e.g., alkoxysilyl or (poly(propylene oxide) monomers). Amphiphilic copolymers can have both hydrophilic and hydrophobic properties. In embodiments, the polymer layer includes an amphiphilic acrylate copolymer or amphiphilic methacrylate copolymer.

In embodiments, the solid support include an inert substrate or matrix (e.g. glass slides, polymer beads, etc.) which has been "functionalized", for example by application of a layer or coating of an intermediate material including reactive groups which permit covalent attachment to biomolecules, such as polynucleotides. Examples of such supports include, but are not limited to, polyacrylamide hydrogels supported on an inert substrate such as glass. In embodiments, the biomolecules (e.g. polynucleotides) may be directly covalently attached to the intermediate material (e.g. the hydrogel), but the intermediate material may itself be non-covalently attached to the substrate or matrix (e.g. the glass substrate). The term "covalent attachment to a solid support" is to be interpreted accordingly as encompassing this type of arrangement. Examples of solid phases, or surfaces, may be a planar array made from, for example, glass, silica or plastic microscope slides or similar materials, beads or an array of beads on a surface. The surface may additionally include one, two or more immobilized oligonucleotides.

In embodiments, the amphiphilic polymer includes a poloxamer. In some embodiments, the solid support includes a poloxamer layer. In some embodiments, the poloxamer is a polyoxyethylene-polyoxypropylene copolymers. In some embodiments, the poloxamer is poloxamer 101, poloxamer 105, poloxamer 108, poloxamer 122, poloxamer 123, poloxamer 124, poloxamer 181, poloxamer 182, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403, and poloxamer 407. In embodiments, the poloxamer is poloxamer 184, poloxamer 188, poloxamer 338, or poloxamer 407 (also known as F127).

In embodiments, the solid support includes a polymer layer, wherein the polymer layer includes a brush copolymer or a comb polymer. A comb polymer includes a main polymer chain with two or more three-way branch points and linear side chains. A brush polymer includes a main polymer chain with linear, unbranched side chains and where one or more of the branch points has four-way functionality or larger.

In some embodiments, the solid support includes a hydrophobic polymer layer. In embodiments, the solid support includes a perfluorinated polymer. In embodiments, the solid support includes a polyfluorinated polymer. In embodiments, the solid support includes polymerized units of a fluorine-containing methacrylate (e.g., $CH_2=C(CH_3)COOC-(CF_3)_2CF_2CF_2CF_3$). Non-limiting examples and synthetic protocols of fluorine-containing methacrylate monomers may be found in Zhang, D., (2018). Materials (Basel, Switzerland), 11(11), 2258 (2018), which is incorporated herein by reference. In embodiments, the fluorinated polymer is an amorphous (non-crystalline) fluoropolymer (e.g., CYTOP® from Bellex), a crystalline fluoropolymer, or a fluoropolymer having both amorphous and crystalline domains.

In some embodiments, the solid support includes a hydrophilic polymer layer. In some embodiments, the hydrophilic polymer is a silane functionalized polymer. In some embodiments, the silane functionalized polymer is a silane functionalized polyethylene glycol (S1-PEG) polymer or a silane functionalized poly(acrylamide) (S1-PAm).

Figure 7A:
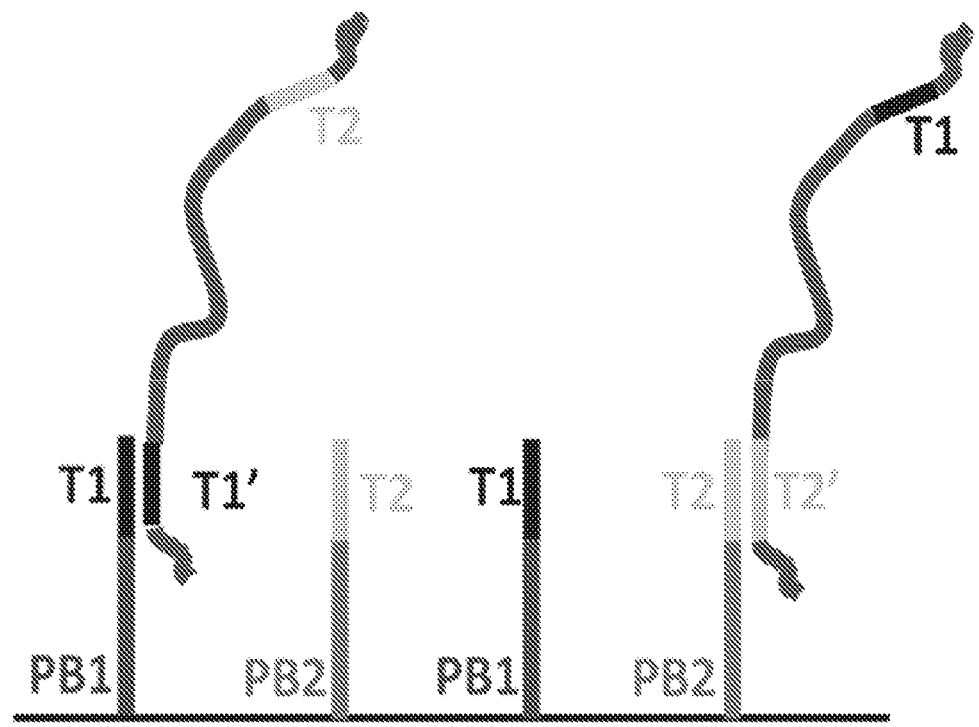
FIGS. 7A-7E illustrate an embodiment of the method described herein.
Figure 7B:
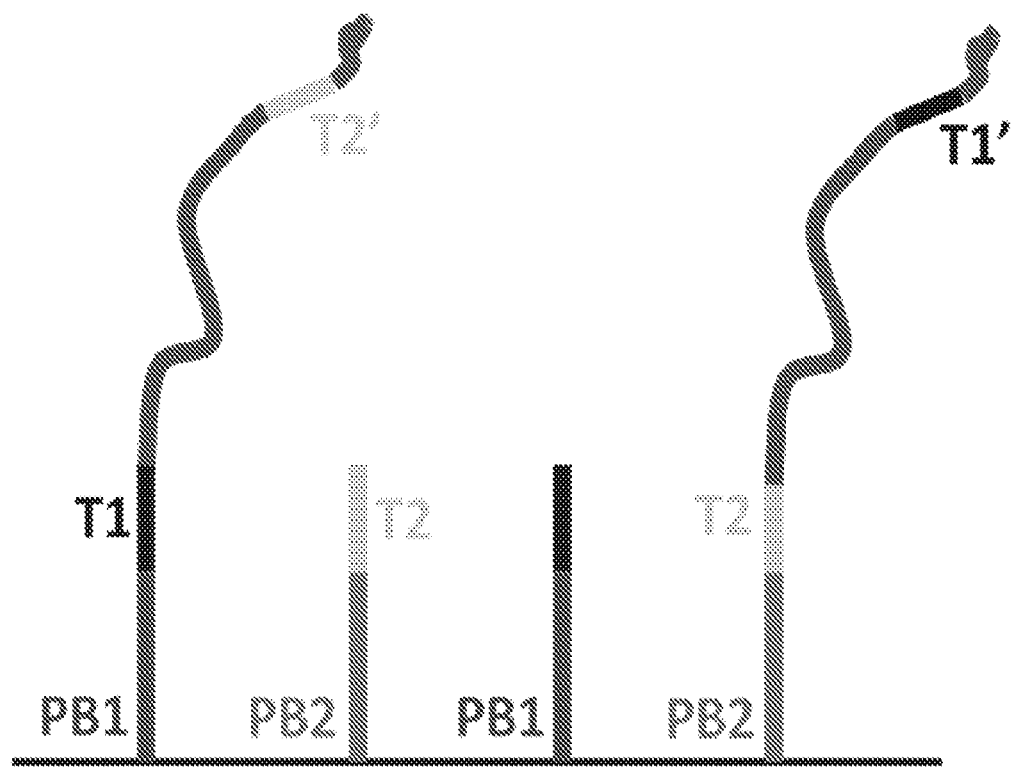
Figure 7C:
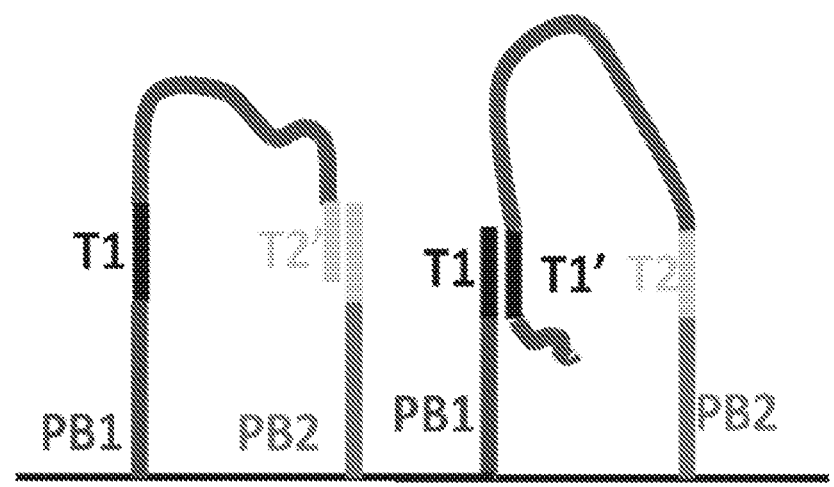
Figure 7D:
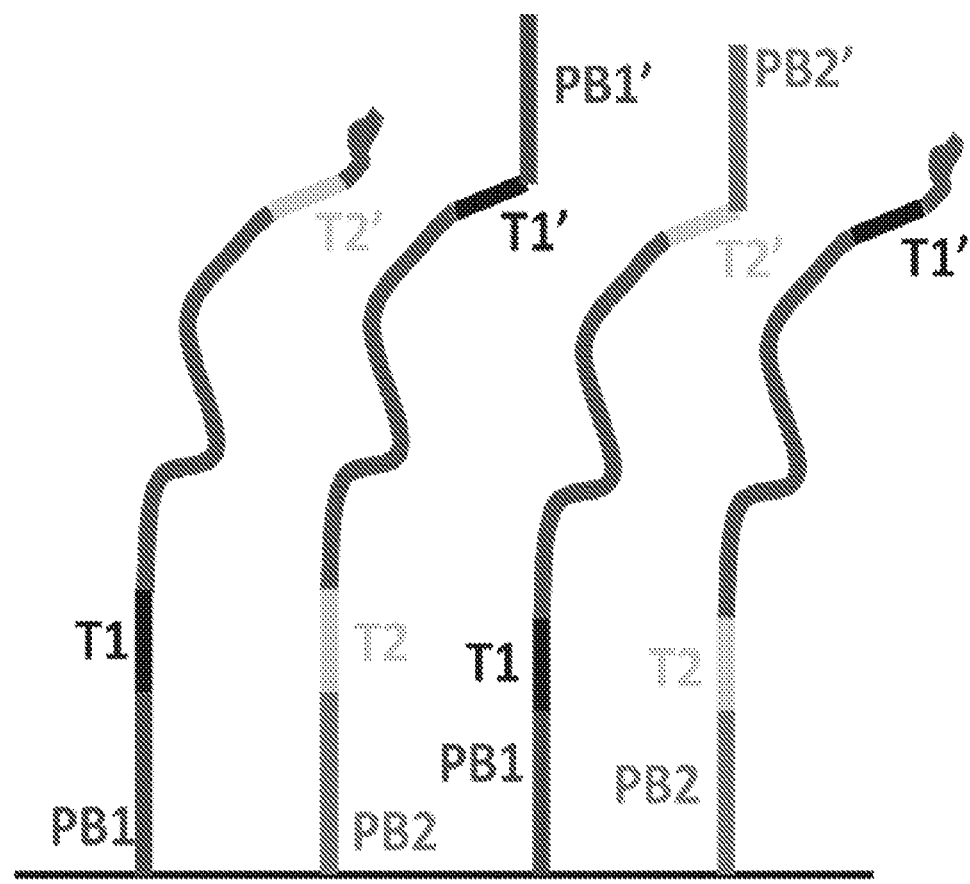
Figure 7E:
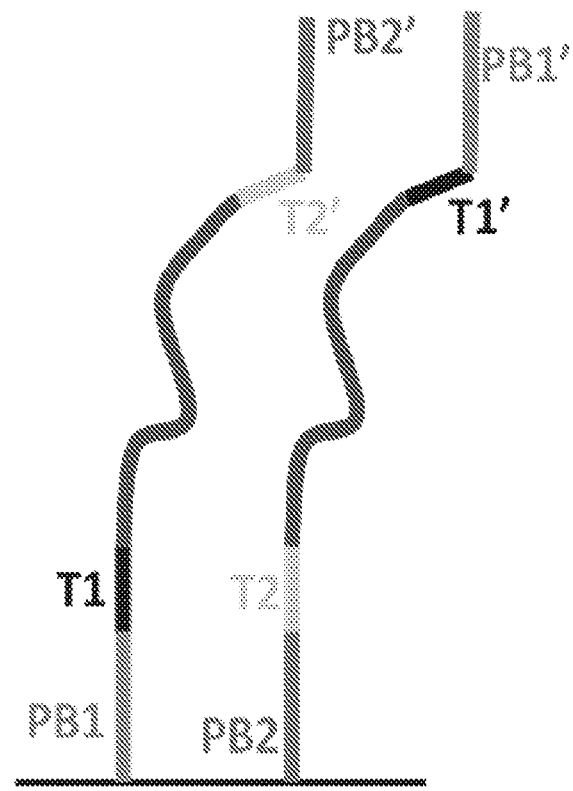
Figure 8:
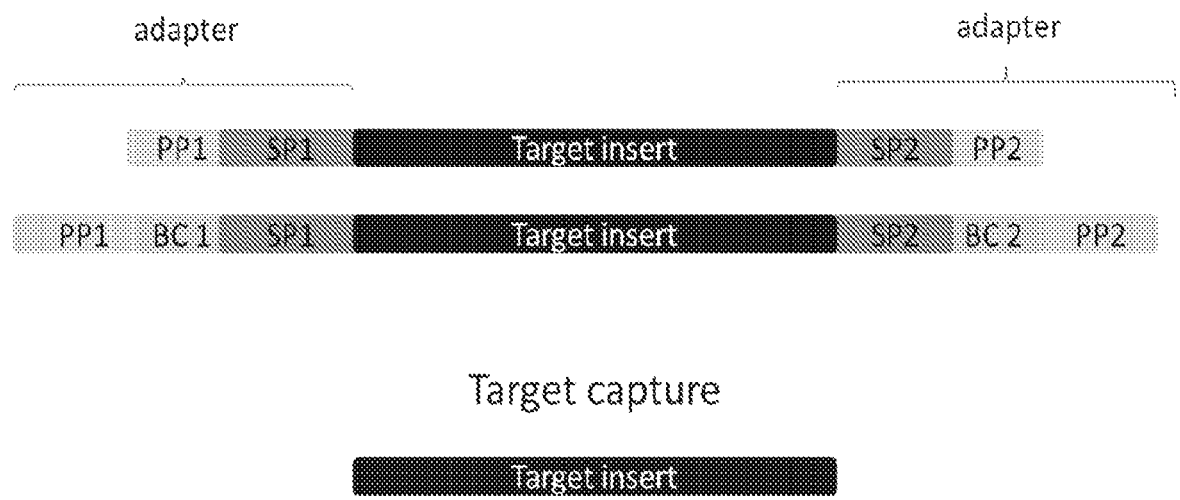
FIG. 8. An illustration of the different polynucleotides used as input for traditional sequencing platforms (top) compared to the input for the target capture methods described herein (bottom). Typically, a target insert requires adapter ligation to render it usable on commercial sequencing platforms. An adapter (e.g., an exogenous adapter) may include a platform primer sequence (PP1 and PP2) such as the universal P5 and P7 sequences, a sequencing primer binding sequence (SP1 and SP2), and optionally one or two barcode/indexes (BC1 and BC2). In contrast, employing the methods described herein requires no adapter ligation to the input polynucleotide.
Figure 9A:
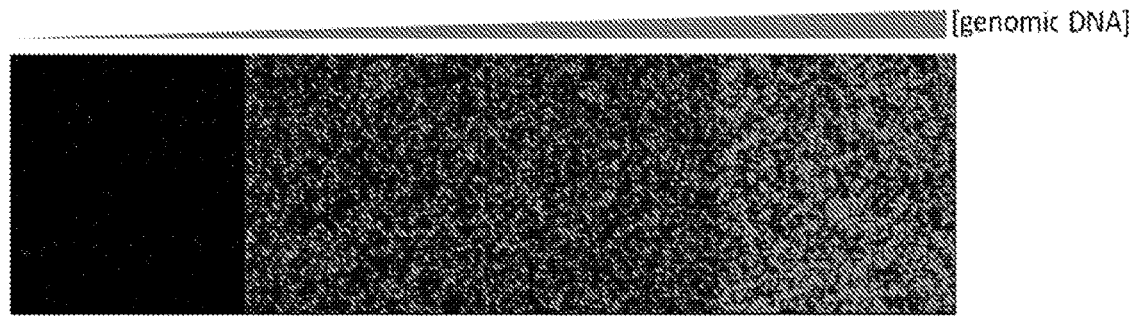
FIGS. 9A-9C. Titrating the amount of genomic input results in greater amplification.
Figure 9B:
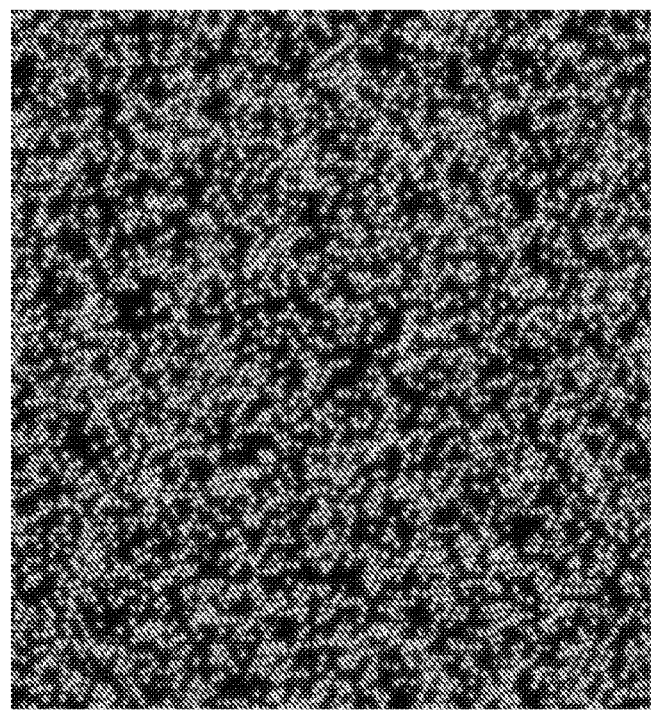
Figure 9B:
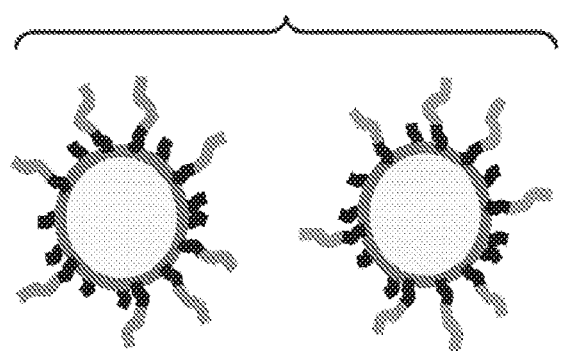
Figure 9C:
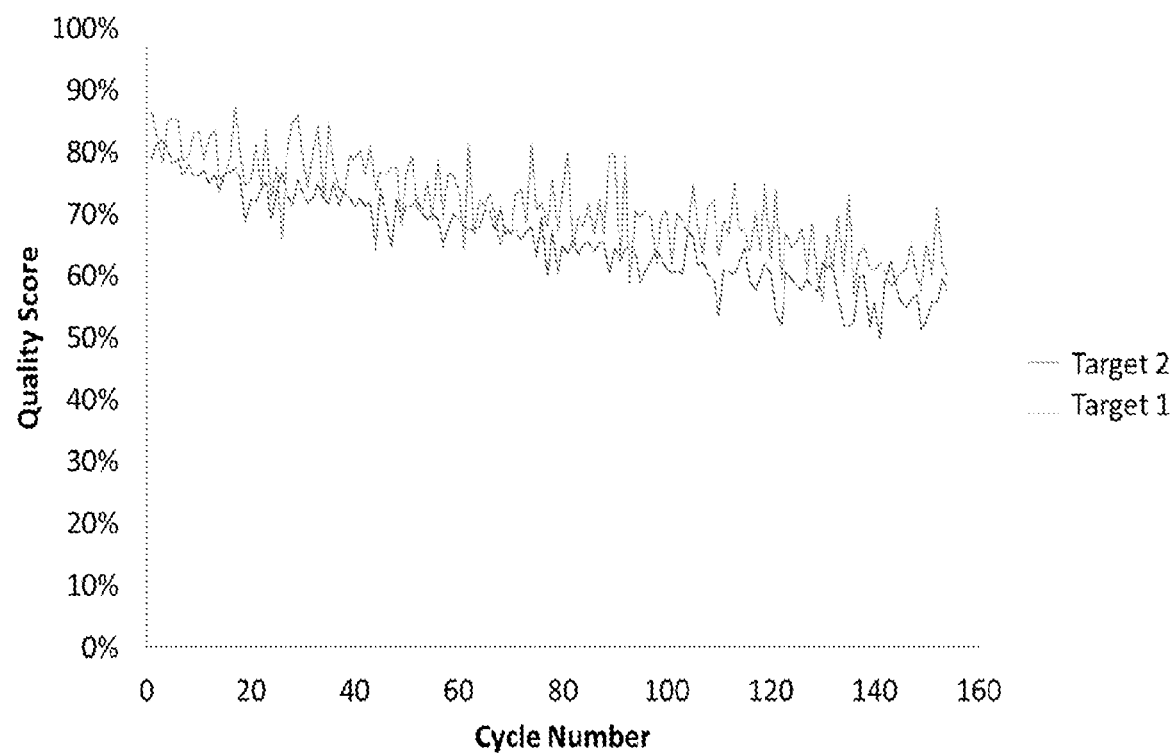

In embodiments, the polymer layer or the amphiphilic polymer includes polymerized units of alkoxysilyl polymers. In embodiments, the polymer layer includes polymerized units of alkoxysilyl polymers (e.g., TMSPM) and polymerized units of polyethylene glycol methacrylate (PEGMA); see for example an embodiment of such a copolymer in FIG. 7B. In embodiments, the amphiphilic copolymer includes polymerized units of alkoxysilyl polymers and polymerized units of polyethylene glycol methacrylate (PEGMA), or polyethylene glycol acrylate (PEGA). In embodiments, the amphiphilic copolymer includes polymerized units of 3-(trimethoxysilyl)propyl methacrylate (TMSPM), 3-(trimethoxysilyl)propyl methacrylate (TMSPA) and polymerized units of polyethylene glycol methacrylate (PEGMA), or polyethylene glycol acrylate (PEGA). In embodiments, the amphiphilic copolymer includes polymerized units of 3-(trimethoxysilyl)propyl methacrylate (TMSPM) and polymerized units of polyethylene glycol methacrylate (PEGMA).

In embodiments, one or more particles of the plurality is in a well of a multiwell container. In embodiments, each well of the multiwell container includes one or more of the same particles including the same immobilized oligonucleotides. In embodiments, one or more wells of the multiwell container include different particles including different immobilized oligonucleotides. For example, different wells of the multiwell container may have different particles, but within each well the one or more particles are all the same and include the same immobilized oligonucleotides.

In embodiments, greater than 50%, 60%, 70%, 80%, 90% or 95% of the wells include a particle. In some embodiments, greater than 50% of the wells include a particle. In some embodiments, greater than 60% of the wells include a particle. In some embodiments, greater than 70% of the wells include a particle. In some embodiments, greater than 80% of the wells include a particle. In some embodiments, greater than 90% of the wells include a particle. In some embodiments, greater than 90%, 91%, 92%, 93%, 94%, 95%, 96%, 97%, 98%, or 99% of the wells include a particle. In some embodiments, about 50%, 60%, 70%, 80%, 90% or 95% of the wells include a particle. In some embodiments, about 50% of the wells include a particle. In some embodiments, about 60% of the wells include a particle. In some embodiments, about 70% of the wells include a particle. In some embodiments, about 80% of the wells include a particle. In some embodiments, about 90% of the wells include a particle. In some embodiments, about 90%, 91%, 92%, 93%, 94%, 95%, 96%, 97%, 98%, or 99% of the wells include a particle.

In some embodiments, the interstitial regions are substantially free of oligonucleotides. In some embodiments, the interstitial regions are substantially free of particles.

In embodiments, each of the wells are separated from each other by about 0.2 μm to about 2.0 m. In some embodiments, the wells of the array are separated from each other by about 0.7 μm to about 1.5 μm. In some embodiments, the wells of the array are separated from each other by at least or at most 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 µm. In some embodiments, the wells of the array are from about 0.2 µm to about 2 µm in diameter, and wherein the wells of the array are about 0.5 µm to about 2 µm in depth. In some embodiments, the wells of the array are from about 0.2 µm to about 2 µm in diameter, and wherein the wells of the array are about 0.5 µm to about 1.5 µm in depth. In some embodiments, the wells of the array are separated from each other by about 1 mm to about 10 mm. In embodiments, the well is about 3 mm in diameter. In embodiments, the well is about 3.6 mm in diameter. In embodiments, the well is about 4 mm in diameter. In embodiments, the well is about 5 mm in diameter. In embodiments, the well is about 6 mm in diameter. In embodiments, the well is about 6.5 mm in diameter. In embodiments, the well is about 7 mm in diameter. In embodiments, the well is about 7.5 mm in diameter. In embodiments, the well is about 8 mm in diameter. In embodiments, the well is 5 mm in diameter. In embodiments, the well is 6 mm in diameter. In embodiments, the well is 6.5 mm in diameter. In embodiments, the well is 7 mm in diameter. In embodiments, the well is 7.5 mm in diameter. In embodiments, the well is 8 mm in diameter. In embodiments, the well is about 6 to 12 mm in depth. In embodiments, the depth of the well is measured from the bottom of the well to the top of the array. In embodiments, the depth of the well is measured from the bottom of the well to the top of the interstitial region. In embodiments, the depth of the well is measured from the bottom of the well to the top of the photoresist. In embodiments, the array is a nanoarray which can have nanowells having a diameter sufficient to allow only one particle into the well. It is understood that the size of the nanowell will be dependent upon the size of the particle. In some embodiments, the diameter of the nanowells is less than 700 nm, less than 600 nm, less than 500 nm, less than 400 nm, less than 300 nm, less than 200 nm, or less than 100 nm. It is also understood that the size of the wells on the array can be of various sizes and will ultimately depend on the systems and/or apparatus used to analyze later reactions.

In embodiments, each well of the solid support is separated by an interstitial region. In embodiments, the interstitial regions include a polymer layer as described herein (e.g., an amphiphilic copolymer). In embodiments, the solid support further includes a photoresist, wherein the photoresist does not contact the bottom of the well. In embodiments, the polymer layer is substantially free of oligonucleotide moieties. In embodiments, the solid support does not include a polymer (e.g., the solid support is a patterned glass slide). In embodiments, the wells do not include a polymer (e.g., an amphiphilic polymer as described herein) prior to particle loading.

In embodiments, each of the wells are from about 0.2 µm to about 2 µm in diameter, and wherein the wells are about 0.5 µm to about 2 µm in depth. In embodiments, each the wells are from about 0.2 m, about 0.3 m, about 0.4 m, about 0.5 m, about 0.6 m, about 0.7 µm, about 0.8 µm, about 0.9 µm, about 1.0 µm, about 1.1 µm, about 1.2 µm, about 1.3 m, about 1.4 µm, about 1.5 µm, about 1.6 µm, about 1.7 µm, about 1.8 µm, about 1.9 µm, or about 2 µm in diameter, and wherein the wells are about 0.5 µm, about 0.6 µm, about 0.7 µm, about 0.8 m, about 0.9 m, about 1.0 m, about 1.1 µm, about 1.2 µm, about 1.3 µm, about 1.4 m, about 1.5 µm, about 1.6 µm, about 1.7 µm, about 1.8 µm, about 1.9 µm, or about 2 µm in depth.

In embodiments, each particle is bound to a discrete site on solid support, wherein each discrete site of the solid support is separated by an interstitial region. In embodiments, each of the particles is immobilized at a discrete site. In further embodiments, each discrete site is separated by an interstitial region.

In an aspect is provided a solid support including the plurality of particles as described herein. In embodiments, the solid support is an array. In embodiments, the array is a multiwell plate. In embodiments, the array is within a flow cell. In embodiments, the solid support is a flow cell.

In embodiments, the solid support includes about 0.2 wells to about 4.0 wells per $\mu m^2$. In embodiments, the solid support includes about 0.2 wells to about 0.8 wells per $\mu m^2$. In embodiments, the solid support includes about 0.8 wells to about 1.2 wells per $\mu m^2$. In embodiments, the solid support includes about 1.2 wells to about 2.0 wells per $\mu m^2$. In embodiments, the solid support includes about 2.0 wells to about 3.0 wells per $\mu m^2$. In embodiments, the solid support includes about 3.0 wells to about 4.0 wells per $\mu m^2$. In embodiments, the solid support includes about 0.2, about 0.4, about 0.6, about 0.8, about 1.0, about 1.2, about 1.4, about 1.6, about 1.8, about 2.0, about 2.2, about 2.4, about 2.6, about 2.8, about 3.0, about 3.2, about 3.4, about 3.6 about 3.8, or about 4.0 wells per $\mu m^2$. In embodiments, the solid support includes about 0.2 wells per $\mu m^2$. In embodiments, the solid support includes about 0.6 wells per $\mu m^2$. In embodiments, the solid support includes about 1.0 wells per $\mu m^2$. In embodiments, the solid support includes about 1.2 wells per $\mu m^2$. In embodiments, the solid support includes about 1.8 wells per $\mu m^2$. In embodiments, the solid support includes about 2.4 wells per $\mu m^2$. In embodiments, the solid support includes about 3.0 wells per $\mu m^2$. In embodiments, the solid support includes about 4.0 wells per $\mu m^2$.

In embodiments, there is at least one particle per well. In embodiments, there is one particle per well. In embodiments, each well contains a plurality of particles (e.g., wherein the well is at least twice the diameter of the longest dimension of the particle).

The arrays and solid supports for some embodiments have at least one surface located within a flow cell. Flow cells provide a convenient format for housing an array of clusters produced by the methods described herein, in particular when subjected to an SBS or other detection technique that involves repeated delivery of reagents in cycles.

In an aspect is provided a microfluidic device including the plurality of particles as described herein. In an aspect is provided a microfluidic device included a solid support as described herein. In embodiments, the microfluidic device includes a flow cell. In embodiments, the microfluidic device includes an imaging system or detection apparatus. Any of a variety of detection apparatus can be configured to detect the reaction vessel or solid support where reagents interact. Examples include luminescence detectors, surface plasmon resonance detectors and others known in the art. Exemplary systems having fluidic and detection components that can be readily modified for use in a system herein include, but are not limited to, those set forth in U.S. Pat. Nos. 8,241,573, 8,039,817; or US Pat. App. Pub. No. 2012/0270305 A1, each of which is incorporated herein by reference. In embodiments, the microfluidic device further includes one or more excitation lasers.

In embodiments, the microfluidic device is a nucleic acid sequencing device. Nucleic acid sequencing devices utilize excitation beams to excite labeled nucleotides in the DNA containing sample to enable analysis of the base pairs present within the DNA. Many of the next-generation sequencing (NGS) technologies use a form of sequencing by synthesis (SBS), wherein modified nucleotides are used along with an enzyme to read the sequence of DNA templates in a controlled manner. In embodiments, sequencing includes a sequencing by synthesis event, where individual nucleotides are identified iteratively (e.g., incorporated and detected into a growing complementary strand, as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. Nos. 10,738,072, 7,541,444 and 7,057,026. Once such a modified nucleotide has been incorporated into the growing polynucleotide chain complementary to the region of the template being sequenced, there is no free 3'-OH group available to direct further sequence extension and therefore the polymerase cannot add further nucleotides. Once the identity of the base incorporated into the growing chain has been determined, the 3' reversible terminator may be removed to allow addition of the next successive nucleotide. In embodiments, the nucleic acid sequencing device utilizes the detection of four different nucleotides that include four different labels.

In embodiments, each of the immobilized oligonucleotides of the first plurality includes a first primer binding sequence, and wherein each of the immobilized oligonucleotides of the second plurality includes a second primer binding sequence. The first primer binding sequence and/or second primer binding sequence may include a platform primer binding sequence or a sequencing primer binding sequence, or complement thereof. Platform primer binding sequences and sequencing primer binding sequences are known in the art. For example, sequences used for cluster generation and sequencing on a sequencing device (e.g., the G4™ sequencing platform) include SP2': 5'-GATCG-GAAGAGCACACGTCTGAACTCCAGTC (SEQ ID NO: 1), S2': 5'-AGTGGTTGGTGAGGGTCATCTCGCTGGAG (SEQ ID NO:2), S1: 5'-ACAAAGGCAGC-CACGCACTCCTTCCCTGT (SEQ ID NO:3), and SP1: ACACTCTTTCCCTACACGACGCTCTTCCGATCT (SEQ ID NO:4), or a complement thereof. Primer binding sites can be of any suitable length. In embodiments, a primer binding site is about or at least about 10, 15, 20, 25, 30, or more nucleotides in length. In embodiments, a primer binding site is 10-50, 15-30, or 20-25 nucleotides in length. The primer binding site may be selected such that the primer (e.g., sequencing primer) has the following properties, for example having a length of about 20-30 nucleotides; approximately 50% GC content, and a Tm of about 55° C. to about 65° C.

In embodiments, the first primer binding sequence of the first plurality includes, at the 3' end, a region complementary to the first oligonucleotide probe, and wherein the second primer binding sequence of the second plurality includes, at the 3' end, a region complementary to the second oligonucleotide probe.

In embodiments, a subset of the plurality of particles include a first plurality of immobilized oligonucleotides including the same sequence complementary to a region of the target polynucleotide.

In embodiments, the shell diameter is about 0.1-10 microns, 0.25-5 microns, 0.5-2 microns, 1 micron, or a number or a range between any two of these values. In embodiments, the particle shell diameter is at least, about, or at most 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 µm or a number or a range between any two of these values. In embodiments, the core diameter is about 150-700 nanometers, and/or the shell diameter is about 0.25-5 µm (microns).

In some embodiments, each of the plurality of bioconjugate reactive moieties include an amine moiety, aldehyde moiety, alkyne moiety, azide moiety, carboxylic acid moiety, dibenzocyclooctyne (DBCO) moiety, tetrazine moiety, epoxy moiety, isocyanate moiety, furan moiety, maleimide moiety, thiol moiety, or transcyclooctene (TCO) moiety. In some embodiments, each of the plurality of bioconjugate reactive moieties include an amine moiety, azide moiety, dibenzocyclooctyne (DBCO) moiety, epoxy moiety, or isocyanate moiety. In embodiments, each of the plurality of bioconjugate reactive moieties include an amine moiety, azide moiety, alkyne moiety, dibenzocyclooctyne (DBCO) moiety, epoxy moiety, or isocyanate moiety.

In embodiments, the oligonucleotide (alternatively referred to herein as primer or polynucleotide primer) is covalently attached to the polymer of the particle (i.e., generating an immobilized oligonucleotide). In embodiments, the 5' end of the oligonucleotide contains a functional group that is tethered to the polymer (i.e., the particle shell polymer or the polymer particle). Non-limiting examples of covalent attachment include amine-modified oligonucleotides reacting with epoxy or isothiocyanate groups on the polymer, succinylated oligonucleotides reacting with aminophenyl or aminopropyl functional groups on the polymer, dibenzocycloctyne-modified oligonucleotides reacting with azide functional groups on the polymer (or vice versa), trans-cyclooctyne-modified oligonucleotides reacting with tetrazine or methyl tetrazine groups on the polymer (or vice versa), disulfide modified oligonucleotides reacting with mercapto-functional groups on the polymer, amine-functionalized oligonucleotides reacting with carboxylic acid groups on the polymer via 1-ethyl-3-(3-dimethylaminopropyl)-carbodiimide hydrochloride (EDC) chemistry, thiol-modified oligonucleotides attaching to a polymer via a disulfide bond or maleimide linkage, alkyne-modified oligonucleotides attaching to a polymer via copper-catalyzed click reactions to azide functional groups on the polymer, and acrydite-modified oligonucleotides polymerizing with free acrylic acid monomers on the polymer to form polyacrylamide or reacting with thiol groups on the polymer. In embodiments, the oligonucleotide is attached to the polymer through electrostatic binding. For example, the negatively charged phosphate backbone of the primer may be bound electrostatically to positively charged monomers in the polymer.

In embodiments, each particle includes multiple copies of one or more immobilized oligonucleotide. In embodiments, the one or more immobilized oligonucleotide include at least two different primers attached to the polymer (e.g., a forward and a reverse primer), each of which may be present in multiple copies. In embodiments, about or at most about 50%, 40%, 30%, 25%, 20%, 15%, 10%, 5%, or less of the monomers in the polymer of each particle are attached to a copy of the oligonucleotide. In embodiments, about 1-25%, about 2-20%, about 3-15%, about 4-14%, or about 5-12% of the monomers in the polymer of each particle are attached to a copy of the oligonucleotide, or a number or a range between any two of these values. In embodiments, about 5-10% of the monomers in the polymer of each particle are attached to a copy of the oligonucleotide. In embodiments, two different oligonucleotides are attached to the particle (e.g., a forward and a reverse primer), which facilitates generating multiple amplification products from the first extension product or a complement thereof. In embodiments, four different oligonucleotides are attached to the particle (e.g., a first forward and a first reverse primer, and a second forward and a second reverse primer), which facilitates generating multiple amplification products from a first extension product or a complement thereof, and a second extension product or a complement thereof. In embodiments, more than four different oligonucleotides are attached to the particle. In embodiments, more than six different oligonucleotides are attached to the particle. In embodiments, more than eight different oligonucleotides are attached to the particle. In embodiments, more than ten different oligonucleotides are attached to the particle. In embodiments, 2, 4, 6, 8, 10, or more different oligonucleotides are attached to the particle.

In some embodiments, the immobilized oligonucleotide is about 5 to about 50 nucleotides in length. In some embodiments, the immobilized oligonucleotide is about 5 to about 40 nucleotides in length. In some embodiments, the immobilized oligonucleotide is about 10 to about 45 nucleotides in length. In some embodiments, the immobilized oligonucleotide is about 15 to about 40 nucleotides in length. In some embodiments, the immobilized oligonucleotide is about 20 to about 35 nucleotides in length. In some embodiments, the immobilized oligonucleotide is about 20 to about 30 nucleotides in length. In some embodiments, the immobilized oligonucleotide is about 25 to about 30 nucleotides in length.

In embodiments, the immobilized oligonucleotide includes spacer nucleotides. Including spacer nucleotides in the linker puts the target polynucleotide in an environment having a greater resemblance to free solution. This can be beneficial, for example, in enzyme-mediated reactions such as sequencing-by-synthesis. It is believed that such reactions encounter less steric hindrance issues that can occur when the polynucleotide is directly attached to the particle or is attached through a very short linker (e.g., a linker including about 1 to 3 carbon atoms). Spacer nucleotides form part of the immobilized oligonucleotide but do not participate in any reaction carried out on or with the oligonucleotide (e.g., a hybridization or amplification reaction). In embodiments, the spacer nucleotides include 1 to 20 nucleotides. In embodiments, the linker includes 10 spacer nucleotides. In embodiments, the linker includes 12 spacer nucleotides. In embodiments, the linker includes 15 spacer nucleotides. It is preferred to use polyT spacers, although other nucleotides and combinations thereof can be used. In embodiments, the linker includes 10, 11, 12, 13, 14, or 15 T spacer nucleotides. In embodiments, the linker includes 12 T spacer nucleotides. Spacer nucleotides are typically included at the 5' ends of oligonucleotide which are attached to the particle. Attachment can be achieved via a phosphorothioate present at the 5' end of the oligonucleotide, an azide moiety, a dibenzocyclooctyne (DBCO) moiety, or any other bioconjugate reactive moiety. The linker may be a carbon-containing chain such as those of formula —$(CH_2)_n$- wherein "n" is from 1 to about 1000. However, a variety of other linkers may be used so long as the linkers are stable under conditions used in DNA sequencing. In embodiments, the linker includes polyethylene glycol (PEG) having a general formula of —$(CH_2$—$CH_2$—$O)_m$-, wherein m is from about 1 to 500, 2 to 24, 2 to 18, or 6 to 12.

In embodiments, the linker, or the oligonucleotides (e.g., primers) include a cleavable site. A cleavage site is a site which allows controlled cleavage of the immobilized polynucleotide strand (e.g., the linker, the primer, or the polynucleotide) by chemical, enzymatic or photochemical means. Any suitable enzymatic, chemical, or photochemical cleavage reaction may be used to cleave the cleavage site. The cleavage reaction may result in removal of a part or the whole of the strand being cleaved. Suitable cleavage means include, for example, restriction enzyme digestion, in which case the cleavage site is an appropriate restriction site for the enzyme which directs cleavage of one or both strands of a duplex template; RNase digestion or chemical cleavage of a bond between a deoxyribonucleotide and a ribonucleotide, in which case the cleavage site may include one or more ribonucleotides; chemical reduction of a disulfide linkage with a reducing agent (e.g., THPP or TCEP), in which case the cleavage site should include an appropriate disulfide linkage; chemical cleavage of a diol linkage with periodate, in which case the cleavage site should include a diol linkage; generation of an abasic site and subsequent hydrolysis, etc. In embodiments, the cleavage site is included in the oligonucleotide (e.g., within the oligonucleotide sequence of the primer). In embodiments, the linker or the oligonucleotide, includes a diol linkage which permits cleavage by treatment with periodate (e.g., sodium periodate). It will be appreciated that more than one diol can be included at the cleavage site. One or more diol units may be incorporated into a polynucleotide using standard methods for automated chemical DNA synthesis. Oligonucleotide nucleotide primers including one or more diol linkers can be conveniently prepared by chemical synthesis. The diol linker is cleaved by treatment with any substance which promotes cleavage of the diol (e.g., a diol-cleaving agent). In embodiments, the diol-cleaving agent is periodate, e.g., aqueous sodium periodate ($NaIO_4$). Following treatment with the diol-cleaving agent (e.g., periodate) to cleave the diol, the cleaved product may be treated with a "capping agent" in order to neutralize reactive species generated in the cleavage reaction. Suitable capping agents for this purpose include amines, e.g., ethanolamine or propanolamine. In embodiments, cleavage may be accomplished by using a modified nucleotide as the cleavable site (e.g., uracil, 8oxoG, 5-mC, 5-hmC) that is removed or nicked via a corresponding DNA glycosylase, endonuclease, or combination thereof.

In embodiments, each of the particle-immobilized oligonucleotides (e.g., immobilized primers) is about 5 to about 25 nucleotides in length. In embodiments, each of the particle-immobilized oligonucleotides (e.g., immobilized primers) is about 10 to about 40 nucleotides in length. In embodiments, each of the particle-immobilized oligonucleotides (e.g., immobilized primers) is about 5 to about 100 nucleotides in length. In embodiments, each of the particle-immobilized oligonucleotides (e.g., immobilized primers) is about 20 to 200 nucleotides in length. In embodiments, each of the particle-immobilized oligonucleotides (e.g., immobilized primers) about or at least about 5, 6, 7, 8, 9, 10, 12, 15, 18, 20, 25, 30, 35, 40, 50 or more nucleotides in length. In embodiments, one or more particle-immobilized oligonucleotides include blocking groups at their 3' ends that prevent polymerase extension. A blocking moiety prevents formation of a covalent bond between the 3' hydroxyl moiety of the nucleotide and the 5' phosphate of another nucleotide. In embodiments, the 3' modification is a 3'-phosphate modification includes a 3' phosphate moiety, which is removed by a PNK enzyme.

In embodiments, the immobilized oligonucleotide includes one or more phosphorothioate nucleotides. In embodiments, the immobilized oligonucleotide includes a plurality of phosphorothioate nucleotides. In embodiments, about or at least about 20%, 30%, 40%, 50%, 60%, 70%, 80%, 90%, or about 100% of the nucleotides in the immobilized oligonucleotide are phosphorothioate nucleotides. In embodiments, most of the nucleotides in the immobilized oligonucleotide are phosphorothioate nucleotides. In embodiments, all of the nucleotides in the immobilized oligonucleotide are phosphorothioate nucleotides. In embodiments, none of the nucleotides in the immobilized oligonucleotide are phosphorothioate nucleotides.

In some embodiments, the immobilized oligonucleotide is capable of hybridizing to a complementary sequence of a template nucleic acid. In embodiments, the immobilized oligonucleotide includes DNA. In embodiments, the immobilized oligonucleotide includes RNA. In embodiments, the immobilized oligonucleotide is DNA. In embodiments, the immobilized oligonucleotide is RNA. In embodiments, the immobilized oligonucleotide includes a single-stranded DNA. In embodiments, the immobilized oligonucleotide includes a single-stranded RNA. In embodiments, the immobilized oligonucleotide is a single-stranded DNA. In embodiments, the immobilized oligonucleotide is a single-stranded RNA. In embodiments, the immobilized oligonucleotide is a nucleic acid sequence complementary to a target polynucleotide.

In some embodiments, the particle includes a plurality of bioconjugate reactive moieties. In embodiments, the particle includes a plurality of azide moieties, alkyne moieties, dibenzocyclooctyne (DBCO) moieties, epoxy moieties, or isocyanate moieties. In some embodiments, the particle includes a plurality of immobilized oligonucleotides (e.g., ssDNA moieties).

In another aspect is provided a solid support including two or more wells, wherein each well includes a first immobilized oligonucleotide as described herein, including embodiments, and a second immobilized oligonucleotide as described herein, including embodiments. In embodiments, the first immobilized oligonucleotide includes a sequence capable of hybridizing to a sequence of a target polynucleotide, and wherein the second immobilized oligonucleotide includes a sequence capable of hybridizing to a complementary sequence of said target polynucleotide, wherein the target polynucleotide does not include a common primer binding sequence (e.g., a universal priming sequence shared throughout the plurality of target polynucleotides).

In an aspect is a kit, including the solid support as described herein. Generally, the kit includes one or more containers providing a composition and one or more additional reagents (e.g., a buffer suitable for polynucleotide extension). The kit may also include a template nucleic acid (DNA and/or RNA), one or more primer polynucleotides, nucleoside triphosphates (including, e.g., deoxyribonucleotides, ribonucleotides, particles, labeled nucleotides, and/or modified nucleotides), buffers, salts, and/or labels (e.g., fluorophores). In embodiments, the kit includes a solid support, where each well already includes a first plurality of immobilized oligonucleotides and a second plurality of immobilized oligonucleotides. In embodiments, the solid support is in a container. The container may be a storage device or other readily usable vessel capable of storing and protecting the solid support. In embodiments, the kit includes a solid support, wherein the solid support includes a polymer including the immobilized oligonucleotides (e.g., the first and second pluralities of immobilized oligonucleotides) as described herein.

In an aspect is a kit, including the plurality of particles as described herein. Generally, the kit includes one or more containers providing a composition and one or more additional reagents (e.g., a buffer suitable for polynucleotide extension). The kit may also include a template nucleic acid (DNA and/or RNA), one or more primer polynucleotides, nucleoside triphosphates (including, e.g., deoxyribonucleotides, ribonucleotides, particles, labeled nucleotides, and/or modified nucleotides), buffers, salts, and/or labels (e.g., fluorophores). In embodiments, the kit includes an array with particles already loaded into the wells. In embodiments, the particles are in a container. In embodiments, the particles are in aqueous suspension or as a powder within the container. The container may be a storage device or other readily usable vessel capable of storing and protecting the particles.

In embodiments, the kit includes a sequencing polymerase, and one or more amplification polymerases. In embodiments, the sequencing polymerase is capable of incorporating modified nucleotides. In embodiments, the polymerase is a DNA polymerase. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g., Therminator γ, 9° N polymerase (exo-), Therminator II, Therminator III, or Therminator IX). In embodiments, the DNA polymerase is a thermophilic nucleic acid polymerase. In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044, each of which are incorporated herein by reference for all purposes). In embodiments, the kit includes a strand-displacing polymerase. In embodiments, the kit includes a strand-displacing polymerase, such as a phi29 polymerase, phi29 mutant polymerase or a thermostable phi29 mutant polymerase.

In embodiments, the kit is to support analysis of single cells and tissue sections on the device described herein. In embodiments, the kits enable multiomics analysis, including RNA transcription, protein expression, and targeted gene sequencing. In embodiments, the kits include a microplate, and reagents for sample preparation, purification, amplification, and sequencing readout. In embodiments, the kit includes a solid support including a plurality of clusters of capture probes (e.g., clusters with a first and a second plurality of immobilized capture oligonucleotides as described herein). In embodiments, the kits for protein detection include DNA-conjugated antibodies.

In embodiments, the kit can further include one or more biological stain(s) (e.g., any of the biological stains as described herein). For example, the kit can further include eosin and hematoxylin. In other examples, the kit can include a biological stain such as acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, safranin, or any combination thereof.

In embodiments, the kit includes a buffered solution. Typically, the buffered solutions contemplated herein are made from a weak acid and its conjugate base or a weak base and its conjugate acid. For example, sodium acetate and acetic acid are buffer agents that can be used to form an acetate buffer. Other examples of buffer agents that can be used to make buffered solutions include, but are not limited to, Tris, bicine, tricine, HEPES, TES, MOPS, MOPSO and PIPES. Additionally, other buffer agents that can be used in enzyme reactions, hybridization reactions, and detection reactions are known in the art. In embodiments, the buffered solution can include Tris. With respect to the embodiments described herein, the pH of the buffered solution can be modulated to permit any of the described reactions. In some embodiments, the buffered solution can have a pH greater than pH 7.0, greater than pH 7.5, greater than pH 8.0, greater than pH 8.5, greater than pH 9.0, greater than pH 9.5, greater than pH 10, greater than pH 10.5, greater than pH 11.0, or greater than pH 11.5. In other embodiments, the buffered solution can have a pH ranging, for example, from about pH 6 to about pH 9, from about pH 8 to about pH 10, or from about pH 7 to about pH 9. In embodiments, the buffered solution can include one or more divalent cations. Examples of divalent cations can include, but are not limited to, $Mg^{2+}$, $Mn^{2+}$, $Zn^{2+}$, and $Ca^{2+}$. In embodiments, the buffered solution can contain one or more divalent cations at a concentration sufficient to permit hybridization of a nucleic acid.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay, etc.) from one location to another. For example, kits include one or more enclosures (e.g., boxes) containing the relevant reaction reagents and/or supporting materials. As used herein, the term "fragmented kit" refers to a delivery system including two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits. In embodiments, the kit includes, without limitation, nucleic acid primers, probes, adapters, enzymes, and the like, and are each packaged in a container, such as, without limitation, a vial, tube or bottle, in a package suitable for commercial distribution, such as, without limitation, a box, a sealed pouch, a blister pack and a carton. The package typically contains a label or packaging insert indicating the uses of the packaged materials. As used herein, "packaging materials" includes any article used in the packaging for distribution of reagents in a kit, including without limitation containers, vials, tubes, bottles, pouches, blister packaging, labels, tags, instruction sheets and package inserts.

III. Methods

In as aspect is provided a method of generating immobilized complements of a plurality of target polynucleotides, the method including: a) annealing a plurality of target polynucleotides to the first plurality of immobilized oligonucleotides as described herein; and b) extending the immobilized oligonucleotides with a polymerase (e.g., Bst large fragment (Bst LF) polymerase, Bst2.0 polymerase, Bsu polymerase, SD polymerase, Vent exo-polymerase, Phi29 polymerase, or a mutant thereof) to generate a plurality of immobilized complements of the plurality of target polynucleotides. In embodiments, the plurality of target polynucleotides do not include a common sequence (e.g., a sequence universal to a substantial majority of the plurality, such as for example a sequence of an adapter).

In embodiments, the target polynucleotides do not include a common sequence (e.g., the same sequence within the plurality). In embodiments, the target polynucleotides do not include a synthetic sequence (e.g., a primer binding sequence). In embodiments, the target polynucleotide does not include a universal primer binding sequence (e.g., a polynucleotide sequence that is common to a majority of the target polynucleotides). In embodiments, the target polynucleotide is a fragmented polynucleotide. In embodiments, the target polynucleotide is genomic DNA (gDNA). In embodiments, the target polynucleotide is genomic DNA (gDNA) including a sequence that encodes for a protein.

In embodiments, the polymerase is a strand-displacing polymerase. In embodiments, the strand-displacing polymerase is Bst large fragment (Bst LF) polymerase, Bst 3.0 polymerase, Bst2.0 polymerase, Bsu polymerase, SD polymerase, Vent exo-polymerase, Phi29 polymerase, or a mutant thereof. In embodiments, the polymerase is Bst DNA Polymerase, Vent (exo-) DNA Polymerase, Pfu DNA polymerase, Taq polymerase, Phusion High-Fidelity DNA Polymerase, Q5 High-Fidelity DNA Polymerase, or mutant of any one of the foregoing. In embodiments, the polymerase is Bst DNA Polymerase, Vent (exo-) DNA Polymerase, Phusion High-Fidelity DNA Polymerase, or Q5 High-Fidelity DNA Polymerase. In embodiments, the polymerase is a *Pyrococcus* polymerase (e.g., a polymerase described in WO 2018/148723 or WO 2020/056044, each of which are incorporated herein by reference for all purposes). In embodiments, the polymerase is a Bst DNA polymerase (e.g., exonuclease minus Bst), phi29 DNA polymerase, large fragment of Bsu DNA polymerase, and Bca (exo-) DNA polymerase, Klenow fragment of *E. coli* DNA polymerase, T5 polymerase, M-MuLV reverse transcriptase, HIV viral reverse transcriptase, or Deep Vent DNA polymerase. In embodiments, the polymerase is a phi29 DNA polymerase wild type phi29 DNA polymerase (e.g., MagniPhi from Expedeon), or variant EquiPhi29 DNA polymerase (e.g., from Thermo Fisher Scientific), or chimeric QualiPhi DNA polymerase (e.g., from 4basebio).

In an aspect is provided a method of amplifying a target polynucleotide, the method including: contacting a solid support (e.g., a solid support as described herein) with a plurality of target polynucleotides, wherein the target polynucleotides do not include a common primer binding sequence (e.g., does not include a synthetic sequence typically employed in library preparation); hybridizing a target polynucleotide to a first immobilized oligonucleotide from the first plurality, and extending with a polymerase the first immobilized oligonucleotide to generate a first extension product; hybridizing the first extension product to a second immobilized oligonucleotide from the second plurality, and extending with a polymerase the second immobilized oligonucleotide to generate a second extension product; and hybridizing the second extension product to a third immobilized oligonucleotide from the first plurality, and extending with a polymerase the third immobilized oligonucleotide to generate a third extension product. In embodiments, the solid support includes two or more wells including a first plurality of immobilized oligonucleotides and a second plurality of immobilized oligonucleotides. In embodiments, the method further includes sequencing the first extension product, the second extension product, and the third extension product. In embodiments, the method does not include substantial library preparation (e.g., DNA-preprocessing) methods.

In as aspect is provided a method of generating immobilized complements of a plurality of target polynucleotides, the method including: a) annealing a plurality of target polynucleotides to one or more particles including the first plurality of immobilized oligonucleotides as described herein; and b) extending the immobilized oligonucleotides with a polymerase to generate a plurality of immobilized complements of the plurality of target polynucleotides.

In embodiments, the method includes denaturing the target polynucleotides (e.g., separating the two or more target polynucleotides) and repeating steps a) and b). In embodiments, the method includes removing the target polynucleotides (e.g., denaturing, digesting, and/or washing away the target polynucleotides) and contacting the solid support with a second plurality of target polynucleotides, hybridizing two or more target polynucleotides to the immobilized oligonucleotides as described herein and extending the immobilized oligonucleotides with a polymerase. Hybridizing a target polynucleotide to a polynucleotide primer is an inherently stochastic event. For stochastic events occurring over a period of time (e.g., a seeding-amplification cycle) it may be convenient to use the Poisson approximation to better understand the probability of an event occurring during that time. For example, if one knows the average rate of a hybridization event, represented as $\lambda^{seed}$, (ie., how often a target polynucleotide hybridizes to a polynucleotide primer) occurring during a seeding-amplification cycle, it is possible to calculate the probability that an amplification site will contain an amplicon (e.g., a monoclonal amplicon) following a seeding-amplification cycle. Two variables affecting $\lambda^{seed}$ include the concentration of the target polynucleotide and the amount of time the target polynucleotide is exposed to the polynucleotide primer, $t_{seed}$, during a seeding-amplification cycle. Generally, increasing the concentration of the target polynucleotide or increasing $t_{seed}$ increases $\lambda^{seed}$. Conventional methods typically overseed the array, that is, the methods often employed ensure the concentration of the target polynucleotides are in abundance relative to the available amplification sites, to maximize the opportunity for a target polynucleotide to hybridize to the primer in the amplification site. Embodiments of the invention described herein suggest underseeding, that is limiting the concentration or limiting the contacting time between target polynucleotides and the primers (i.e., immobilized oligonucleotides), and repeating the cycle to promote capture efficiency.

In embodiments, the method further includes contacting the one or more particles with a degrading agent thereby decomposing the degradable particle core (e.g., a degradable particle core as described herein) and forming a polymer composition attached to the well. In embodiments, the polymer composition includes a plurality of polymerized units of shell monomers wherein one or more shell monomers includes the first plurality of immobilized oligonucleotides as described herein covalently linked to the shell monomer.

In as aspect is provided a method of generating immobilized complements of a plurality of target polynucleotides of a cell in situ, the method including: a) annealing a plurality of target polynucleotides to the first plurality of immobilized oligonucleotides as described herein; and b) extending the immobilized oligonucleotides with a polymerase to generate a plurality of immobilized complements of the plurality of target polynucleotides.

In embodiments, the method further includes: c) annealing the immobilized complements of the target polynucleotides to the second plurality of immobilized oligonucleotides; and d) extending the second plurality of immobilized oligonucleotides thereby generating a plurality of immobilized target polynucleotides. In embodiments, the methods further includes repeating steps a) to d), thereby amplifying the plurality of target polynucleotides. In embodiments, the method further includes sequencing the target polynucleotides (and amplification products thereof).

In embodiments, the target polynucleotides may be derived from any in vivo or in vitro source, including from one or multiple cells, tissues, organs, or organisms, whether living or dead, or from any biological or environmental source (e.g., water, air, soil). For example, in some embodiments, the target polynucleotides includes eukaryotic and/or prokaryotic dsDNA that originates or that is derived from humans, animals, plants, fungi, (e.g., molds or yeasts), bacteria, viruses, viroids, mycoplasma, or other microorganisms. In embodiments, the target polynucleotides includes genomic DNA, subgenomic DNA, chromosomal DNA (e.g., from an isolated chromosome or a portion of a chromosome, e.g., from one or more genes or loci from a chromosome), mitochondrial DNA, chloroplast DNA, plasmid or other episomal-derived DNA (or recombinant DNA contained therein), or double-stranded cDNA made by reverse transcription of RNA using an RNA-dependent DNA polymerase or reverse transcriptase to generate first-strand cDNA and then extending a primer annealed to the first-strand cDNA to generate dsDNA. In embodiments, the target polynucleotides is from an in vitro source. For example, in some embodiments, the target polynucleotides includes dsDNA that is prepared in vitro from single-stranded DNA (ssDNA) or from single-stranded or double-stranded RNA (e.g., using methods that are well-known in the art, such as primer extension using a suitable DNA-dependent and/or RNA-dependent DNA polymerase (reverse transcriptase). In some embodiments, the target polynucleotides includes dsDNA that is prepared from all or a portion of one or more double-stranded or single-stranded DNA or RNA molecules using any methods known in the art, including methods for: DNA or RNA amplification (e.g., PCR or reverse-transcriptase-PCR (RT-PCR), transcription-mediated amplification methods, with amplification of all or a portion of one or more nucleic acid molecules); molecular cloning of all or a portion of one or more nucleic acid molecules in a plasmid, fosmid, BAC or other vector that subsequently is replicated in a suitable host cell; or capture of one or more nucleic acid molecules by hybridization, such as by hybridization to DNA probes on an array or microarray.

In embodiments, prior to step a), the target polynucleotides do not include a primer binding sequence (or complementary sequence thereof) on a 5' or 3' end. In embodiments, prior to step a), the target polynucleotides do not include end-polishing (e.g., generating blunt-ends). In embodiments, prior to step a), the target polynucleotides do not include contacting the targeting polynucleotides with a ligase. In embodiments, prior to step a), the target polynucleotides do not include contacting the targeting polynucleotides with a transposase.

It will be appreciated that any of the amplification methodologies described herein or known in the art can be utilized with universal or target-specific primers to amplify the target polynucleotide. Suitable methods for amplification include, but are not limited to, the polymerase chain reaction (PCR), strand displacement amplification (SDA), transcription mediated amplification (TMA) and nucleic acid sequence-based amplification (NASBA), for example, as described in U.S. Pat. No. 8,003,354, which is incorporated herein by reference in its entirety. The above amplification methods can be employed to amplify one or more nucleic acids of interest. Additional examples of amplification processes include, but are not limited to, bridge-PCR, recombinase polymerase amplification (RPA), loop-mediated isothermal amplification (LAMP), rolling circle amplification (RCA), strand displacement amplification, RCA with exponential strand displacement amplification. In embodiments, amplification includes an isothermal amplification reaction. In embodiments, amplification includes bridge amplification. In general, bridge amplification uses repeated steps of annealing of primers to templates, primer extension, and separation of extended primers from templates. Because primers are attached within the core polymer, the extension products released upon separation from an initial template is also attached within the core. The 3' end of an amplification product is then permitted to anneal to a nearby reverse primer that is also attached within the core, forming a "bridge" structure. The reverse primer is then extended to produce a further template molecule that can form another bridge. In embodiments, forward and reverse primers hybridize to primer binding sites that are specific to a particular target nucleic acid. In embodiments, forward and reverse primers hybridize to primer binding sites that have been added to, and are common among, target polynucleotides. Examples of additional clonal amplification techniques include, but are not limited to, bridge PCR, solid-phase rolling circle amplification (RCA), solid-phase exponential rolling circle amplification, solid-phase recombinase polymerase amplification (RPA), solid-phase helicase dependent amplification (HDA), template walking amplification, emulsion PCR on particles (beads), or combinations of the aforementioned methods. Optionally, during clonal amplification, additional solution-phase primers can be supplemented in the flow cell for enabling or accelerating amplification.

In embodiments, amplifying includes contacting the solid support and/or the plurality of particles with one or more reagents for amplifying the target polynucleotide. Examples of reagents include but are not limited to polymerase, buffer, and nucleotides (e.g., an amplification reaction mixture). In certain embodiments the term "amplifying" refers to a method that includes a polymerase chain reaction (PCR). Conditions conducive to amplification (i.e., amplification conditions) are known and often include at least a suitable polymerase, a suitable template, a suitable primer or set of primers, suitable nucleotides (e.g., dNTPs), a suitable buffer, and application of suitable annealing, hybridization and/or extension times and temperatures. In embodiments, amplifying generates an amplicon. In embodiments, an amplicon contains multiple, tandem copies of the circularized nucleic acid molecule of the corresponding sample nucleic acid. The number of copies can be varied by appropriate modification of the amplification reaction including, for example, varying the number of amplification cycles run, using polymerases of varying processivity in the amplification reaction and/or varying the length of time that the amplification reaction is run, as well as modification of other conditions known in the art to influence amplification yield. Generally, the number of copies of a nucleic acid in an amplicon is at least 100, 200, 500, 1000, 2000, 3000, 4000, 5000, 6000, 7000, 8000, 9000 and 10,000 copies, and can be varied depending on the application. As disclosed herein, one form of an amplicon is as a nucleic acid "ball" localized to the particle and/or well of the array. The number of copies of the nucleic acid can therefore provide a desired size of a nucleic acid "ball" or a sufficient number of copies for subsequent analysis of the amplicon, e.g., sequencing.

In embodiments, the sample includes a plurality of target polynucleotides at a concentration selected such that a majority of the particles in which the amplification occurs includes amplicons of only one original target polynucleotide. In embodiments, about or at least about 60%, 70%, 80%, 90%, 95%, or more of the particles in which amplification occurs contains amplicons of only one original target polynucleotide.

In embodiments, the methods further include a step of separating particles that include amplicons from particles that do not include amplicons. For example, particles that do not include amplicon, also referred to as "blank" particles, can be separated from particles with amplicon by charge-based separation. Since DNA carries a negative charge, the particles that contain amplified products will be significantly charged compared to the "blank" particles. The particles containing amplicons can be separated from the "blank" particles by an electric field. By choosing a relatively low seeding ratio, e.g. <20%, or <10%, or <5%, the probability of having more than 1 template per particle (multiple seeding) can be greatly reduced. The large fraction of unseeded "blank" particles can then be removed by charge-based separation, resulting in nearly pure population of single-seeded particles for monoclonal amplification. In embodiments, the methods include amplifying a target polynucleotide in solution, separating particles containing amplicons from "blank" particles, and depositing the particles containing amplicons in a container (e.g., a flow cell) for sequencing. Alternatively, the particles may contain a magnetic core and may be separated by applying a magnetic field.

In embodiments, the methods further include repeating the contacting and amplifying steps using the separated particles that do not include an amplicon. In embodiments, the contacting is repeated with an aliquot of the same sample as in the original contacting, and particles from the repeated steps are pooled (e.g., in a container, such as a flow cell) prior to sequencing. In embodiments, repeating the contacting and amplifying steps does not involve separating particles that do not include an amplicon from those that do contain an amplicon.

In embodiments of the methods provided herein, arranging (e.g., arraying) the particles occurs prior to contacting the particles with a sample that includes a target polynucleotide. In other embodiments, arranging the particles occurs after contacting the particles with a sample that includes a target polynucleotide. In other embodiments, arranging the particles occurs after amplifying the target polynucleotide.

In embodiments of the methods provided herein, the contacting step is performed under non-hybridizing conditions. In embodiments of the methods provided herein, the contacting step is performed under non-hybridizing conditions initially, then the conditions are changed to hybridizing conditions. In embodiments of the methods provided herein, the contacting step is performed under hybridizing conditions initially, then the conditions are changed to non-hybridizing conditions. In general, contacting the sample under non-hybridizing conditions can facilitate distribution of target polynucleotides within a polymer particle prior to subsequent steps (e.g., amplification). Examples of non-hybridizing conditions include but are not limited to low salt, high temperature, and/or presence of additives such as formamide. The precise nature of non-hybridizing conditions (e.g., the temperature, or the amounts of salt or formamide) will vary with factors such as the length, GC-content, or melting temperature (Tm) of primers (or the target-hybridizing portion thereof) present in the reaction. In embodiments, primers are designed to have Tm's within 15, 10, 5, 3 or fewer degrees of one another. In embodiments, non-hybridizing conditions includes a temperature that is about or at least about 5, 10, 15, 20, or more degrees above the average Tm of primers in the reaction.

In embodiments, the method further includes contacting the immobilized target polynucleotides with a sequencing primer and sequencing the immobilized target polynucleotide, and amplification products thereof. In embodiments, sequencing includes generating one or more sequencing reads. Generating sequencing reads may be obtained via, for example, a sequencing-by-synthesis, sequencing-by-binding, or sequencing-by-ligation method.

In embodiments, the method further includes contacting the immobilized target polynucleotides with a sequencing primer, extending the sequencing primer to incorporate a detectable label that indicates the identity of a nucleotide in the target polynucleotides, detecting the detectable label, and repeating the extending and detecting steps, thereby sequencing the target polynucleotides. In embodiments, the methods include sequencing one or more bases of a target nucleic acid by extending a sequencing primer hybridized to a target nucleic acid (e.g., an amplification product of a target nucleic acid). In embodiments, the sequencing includes sequencing-by-synthesis, sequencing by ligation, or pyrosequencing, and generates a sequencing read.

In embodiments, generating a sequencing read includes executing a plurality of sequencing cycles, each cycle including extending the sequencing primer by incorporating a nucleotide or nucleotide analogue using a polymerase and detecting a characteristic signature indicating that the nucleotide or nucleotide analogue has been incorporated.

In embodiments, the method includes sequencing the first and/or the second strand of a amplification product by extending a sequencing primer hybridized thereto. A variety of sequencing methodologies can be used such as sequencing-by-synthesis (SBS), pyrosequencing, sequencing by ligation (SBL), or sequencing by hybridization (SBH). Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210,891; 6,258,568; and. 6,274,320, each of which is incorporated herein by reference in its entirety). In pyrosequencing, released PPi can be detected by being converted to adenosine triphosphate (ATP) by ATP sulfurylase, and the level of ATP generated can be detected via light produced by luciferase. In this manner, the sequencing reaction can be monitored via a luminescence detection system. In both SBL and SBH methods, target nucleic acids, and amplicons thereof, that are present at features of an array are subjected to repeated cycles of oligonucleotide delivery and detection. SBL methods, include those described in Shendure et al. Science 309:1728-1732 (2005); U.S. Pat. Nos. 5,599,675; and 5,750,341, each of which is incorporated herein by reference in its entirety; and the SBH methodologies are as described in Bains et al., Journal of Theoretical Biology 135(3), 303-7 (1988); Drmanac et al., Nature Biotechnology 16, 54-58 (1998); Fodor et al., Science 251(4995), 767-773 (1995); and WO 1989/10977, each of which is incorporated herein by reference in its entirety.

In SBS, extension of a nucleic acid primer along a nucleic acid template is monitored to determine the sequence of nucleotides in the template. The underlying chemical process can be catalyzed by a polymerase, wherein fluorescently labeled nucleotides are added to a primer (thereby extending the primer) in a template dependent fashion such that detection of the order and type of nucleotides added to the primer can be used to determine the sequence of the template. A plurality of different nucleic acid fragments that have been attached at different locations of an array can be subjected to an SBS technique under conditions where events occurring for different templates can be distinguished due to their location in the array. In embodiments, the sequencing step includes annealing and extending a sequencing primer to incorporate a detectable label that indicates the identity of a nucleotide in the target polynucleotide, detecting the detectable label, and repeating the extending and detecting steps. In embodiments, the methods include sequencing one or more bases of a target nucleic acid by extending a sequencing primer hybridized to a target nucleic acid (e.g., an amplification product produced by the amplification methods described herein). In embodiments, the sequencing step may be accomplished by a sequencing-by-synthesis (SBS) process. In embodiments, sequencing includes a sequencing by synthesis process, where individual nucleotides are identified iteratively, as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. Nos. 10,738,072, 7,541,444 and 7,057,026. Once such a modified nucleotide has been incorporated into the growing polynucleotide chain complementary to the region of the template being sequenced, there is no free 3'-OH group available to direct further sequence extension and therefore the polymerase cannot add further nucleotides. Once the identity of the base incorporated into the growing chain has been determined, the 3' block may be removed to allow addition of the next successive nucleotide. By ordering the products derived using these modified nucleotides it is possible to deduce the DNA sequence of the DNA template. Non-limiting examples of suitable labels are described in U.S. Pat. Nos. 8,178,360, 5,188,934 (4,7-dichlorofluorscein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthene dyes): U.S. Pat. No. 5,688,648 (energy transfer dyes); and the like.

Sequencing includes, for example, detecting a sequence of signals. Examples of sequencing include, but are not limited to, sequencing by synthesis (SBS) processes in which reversibly terminated nucleotides carrying fluorescent dyes are incorporated into a growing strand, complementary to the target strand being sequenced. In embodiments, the nucleotides are labeled with up to four unique fluorescent dyes. In embodiments, the nucleotides are labeled with at least two unique fluorescent dyes. In embodiments, the readout is accomplished by epifluorescence imaging. A variety of sequencing chemistries are available, non-limiting examples of which are described herein.

In embodiments, the method includes determining the nucleic acid sequence of the target polynucleotide. In embodiments, the molecule further includes quantifying the target nucleic acid molecule or amplicons. Methods for quantifying a target polynucleotide or amplicon are well known to one of skilled in the art. For example, during amplification of the target nucleic acid, quantitative techniques such as real-time polymerase chain reaction (RT-PCR) can be used to quantify the copy number of target nucleic acid molecules present in the clonal object as discussed in Logan et al. Real-Time PCR: Current Technology and Applications, Caister Academic Press. (2009). RT-PCR follows the general principle of polymerase chain reaction, however inclusion of detection molecules, such as non-specific fluorescent dyes that intercalate with any double-stranded DNA, or sequence-specific DNA probes consisting of oligonucleotides that are labeled with a fluorescent reporter, which permits detection only after hybridization of the probe with its complementary DNA target, allows for the detection of nucleic acid formed during amplification. The rate of detectable molecules is proportional to the copy number of target nucleic acid molecules present in the clonal object. Furthermore, quantifying the target nucleic acid molecule or amplicons can be done following amplification using standard gel electrophoresis and/or Southern blot techniques, which are well known in the art.

In embodiments, the method further includes sequencing the amplification product(s). Sequencing includes, for example, detecting a sequence of signals within the particle. Examples of sequencing include, but are not limited to, sequencing by synthesis (SBS) processes in which reversibly terminated nucleotides carrying fluorescent dyes are incorporated into a growing strand, complementary to the target strand being sequenced. In embodiments, the nucleotides are labeled with up to four unique fluorescent dyes. In embodiments, the readout is accomplished by epifluorescence imaging. A variety of sequencing chemistries are available, non-limiting examples of which are described herein.

In embodiments, the location of each cluster of capture probes (e.g., each cluster of a first plurality of immobilized capture oligonucleotides and a second plurality of immobilized capture oligonucleotides) on the surface of the solid support is determined during manufacture of the substrate itself. For example, the substrate may be manufactured by immobilizing one or more capture probes on the surface of the substrate (e.g., by binding to a surface probe on the substrate) and generating clusters (e.g., by bridge amplification), as described herein. The capture probes may include a spatial barcode and a capture domain, as described above. After cluster generation, the determination of the location of each cluster of capture probes on the surface may be determined by sequencing the capture probes on the substrate. In particular, sequencing primers targeting the spatial barcode may be utilized, and the sequence of the spatial barcode may be determined. The sequence of the spatial barcode for each cluster may be assigned to a specific location on the substrate (e.g., an XY coordinate on the substrate). In some embodiments, a high-resolution map of the substrate may be generated based upon the signal detected during sequencing (e.g., the fluorescent signal) and used to assign an XY coordinate to each cluster on the substrate. In some embodiments, the methods for spatial detection of nucleic acid (e.g. RNA) in a tissue sample further include correlating the sequence of the spatial barcode for each sequenced cDNA molecule with the location of the cluster of capture probes on the substrate having the corresponding spatial barcode. The first strand cDNA will contain the same spatial barcode as the capture probe, whereas the second strand cDNA will contain the complement to the spatial barcode of the capture probe. "Corresponding" as used herein covers each of these possibilities, depending on which cDNA strand is sequenced. For instance, if the second strand cDNA is sequenced, the sequence of the second strand cDNA is correlated with the location of the cluster of capture probes on the substrate having the complementary spatial barcode. Alternatively, if the first strand cDNA is sequenced (e.g., no intermittent steps of second strand synthesis and/or amplification are performed prior to sequencing the cDNA), the sequence of the first strand cDNA is correlated with the location of the cluster of capture probes on the substrate having the same spatial barcode.

In embodiments, the plurality of capture probes (e.g., the first plurality of immobilized capture probes and the second plurality of immobilized capture probes) is arranged in clusters on the surface of the substrate, each cluster including multiple capture probes. In embodiments, each capture probe in a cluster includes the same spatial barcode. Additionally, in embodiments, the spatial barcode for each cluster is unique. For example, cluster A contains probes including spatial barcode A, cluster B contains probes including spatial barcode B, cluster C contains probes including spatial barcode C, etc.

In some embodiments, the methods further include generating cDNA molecules from the bound RNA molecules. The cDNA generated is considered to be indicative of the RNA present in a cell at the time in which a tissue sample was taken. Therefore, cDNA represents all or some of the genes that were expressed in the cell at the time the tissue sample was taken. The capture probe acts as a primer for reverse transcription, such that the sequence of the capture probe is incorporated into the sequence of the first strand cDNA molecule along with the sequence complementary to the captured RNA strand. Accordingly, the spatial barcode of the capture probe is incorporated into the sequence of the first strand cDNA molecule. Generating cDNA molecules from the bound RNA molecules may be performed by any suitable method. For example, generating cDNA molecules from the bound RNA molecules may be performed by addition of a reverse transcriptase to facilitate reverse transcription of the RNA (e.g., mRNA) to generate a complementary or copy DNA (i.e., cDNA). The cDNA resulting from the reverse transcription of RNA is referred to herein as "first strand cDNA". First strand cDNA synthesis (e.g., reverse transcription) may be performed directly on the substrate.

In some embodiments, the reverse transcription reaction includes a reverse transcriptase, dNTPs and a suitable buffer. The reaction mixture may include other components, such as RNase inhibitor(s). Each dNTP is typically present in an amount ranging from about 10 to 5000 mM, usually from about 20 to 1000 mM. Any suitable reverse transcriptase enzyme may be used. Suitable enzymes include: M-MLV, MuLV, AMV, HIV, ArrayScript™, MultiScribe™, ThermoScript™, and Superscript® I, II, and III enzymes. The reverse transcriptase reaction may be carried out at any suitable temperature, which is dependent on the properties of the enzyme. Typically, reverse transcriptase reactions are performed between 37-55° C., although temperatures outside of this range may also be appropriate. The reaction time may be as little as 1, 2, 3, 4 or 5 minutes or as much as 48 hours. Typically, the reaction is carried out for between 3-12 hours, although other suitable reaction times (e.g., overnight) may be used.

In some embodiments, a strand complementary to the first strand cDNA may be synthesized. The strand complementary to the first strand cDNA is referred to herein as "second strand cDNA". The term "cDNA" as used herein is used in the broadest sense and refers to any cDNA, including first strand cDNA and second strand cDNA. In some embodiments, "generating cDNA" includes performing second strand synthesis (e.g., following the reverse transcription reaction) to generate second strand cDNA. In some embodiments, second strand cDNA synthesis may occur without increasing the number of copies of the second strand cDNA (e.g., without amplifying the second strand). In other embodiments, second strand cDNA may be synthesized and amplified, resulting in multiple copies of the second strand. Second strand cDNA synthesis, if performed, may be performed on the substrate (e.g., while the cDNA is immobilized on the substrate). Alternatively, the first strand cDNA may be released from the substrate and second strand cDNA synthesis may be performed in solution. The second strand cDNA includes a complement of the capture probe and therefore includes a complement of the spatial barcode sequence of the capture probe. The second strand cDNA may be amplified using a suitable primer or combination of primers upstream of the complement to the spatial barcode sequence, such that the complement of the spatial barcode sequence is presence in each amplified second strand cDNA. In some embodiments, second strand cDNA synthesis is performed using random primers. For example, the first strand cDNA may be incubated with random primers, such as hexamer primers, and a DNA polymerase, under conditions sufficient for synthesis of the complementary DNA strand (e.g., second strand cDNA) to form.

In some embodiments, the second strand cDNA may be isolated, purified and amplified following synthesis. For example, the second strand cDNA may be synthesized by a suitable method as described above (e.g., using random primers). In some embodiments, the secondary strand cDNA may be isolated through DNA denaturation in any solutions with high pH and/or organic solutions that can denature the DNA. In some embodiments, the secondary strand cDNA may be isolated through heat denaturation. The isolated second strand may be purified, and then amplified by PCR. Primers for PCR amplification of the second strand cDNA may be any suitable primers, including primers targeting the additional features (e.g., primer binding sites, sequencing barcodes, unique molecular identifiers) added to the second strand cDNA. Any suitable number of isolation, amplification, and purification steps may be performed to generate the final library of cDNA prior to sequencing. In some embodiments, the capture probes used for the initial capture of RNA (e.g., mRNA) may contain one or more additional features (e.g., additional to the spatial barcode and capture domain) that facilitate sequencing library preparation. For example, the capture probes may contain a sequencing handle (e.g., sequencing barcode). Therefore, the complement of the sequencing barcode will be present in the cDNA. Accordingly, cDNA generated by the methods described herein may include two distinct sequencing barcodes. For example, the cDNA may include sequencing barcode(s) compatible with a Singular Genomics' or Illuminam sequencing platform. In some embodiments, the cDNA includes sequencing barcode(s), a spatial barcode, and/or a unique molecular identifier. These additional features may facilitate library preparation, sequencing, and spatial detection of RNA by the methods described herein.

In some embodiments, the generated cDNA may be sequenced with no intervening treatment steps prior to sequencing. For example, in tissue samples that include large amounts of RNA, generating the cDNA may yield a sufficient amount of cDNA such that it may be sequenced directly. In other embodiments, it may be desirable to generate double stranded cDNA and/or generate multiple copies of the DNA prior to sequencing. Such methods may be performed while the cDNA is bound to the substrate, or the cDNA may be released from the substrate and subsequently treated to generate double stranded copies and/or amplify the DNA. In some embodiments, it may be desirable to generate double stranded DNA without increasing the number of double stranded DNA molecules. In other embodiments, it may be desirable to generate double stranded DNA and generate multiple copies of the second strand. For example, one or multiple amplification reactions may be conducted to generate multiple copies of single stranded or double stranded DNA.

In some embodiments, generation of cDNA (e.g., by reverse transcription of the RNA bound to the capture probes) may take place on the substrate and the generated cDNA maybe released from the substrate prior to subsequent treatment steps. For example, the cDNA may be generated on the substrate and the generated DNA may be released from the substrate and collected in a tube. Subsequent steps (e.g., second strand cDNA synthesis, amplification, sequencing, etc.) may be performed in solution. In some embodiments, RNA may be removed prior to subsequent treatment of the cDNA strand. For example, RNA may be removed using an RNA digesting enzyme (e.g., RNase). In some embodiments, no specific RNA removal step is necessary, as RNA will degrade naturally and/or removal of the tissue from the substrate is sufficient for RNA removal.

In some embodiments, the methods for spatial detection of nucleic acid (e.g. RNA) in a tissue sample further include sequencing the cDNA molecules. The cDNA molecules may be sequenced on the substrate or may be released and collected into a suitable device (e.g., a tube) prior to sequencing. Sequencing may be performed by any suitable method.

In some embodiments, the full length of the cDNA molecules may be sequenced. In some embodiments, less than the full length of the cDNA molecules may be sequenced. The claimed methods are not limited to sequencing the entire length of each cDNA molecule. For example, the first 100 nucleotides from each end of the cDNA molecules may be sequenced and used to identify the gene expressed. In some embodiments, sequencing may be performed to determine the sequence of the spatial barcode and at least about 20 bases of RNA transcript specific sequence data. For example, the sequencing may be performed to determine the sequence of the spatial barcode and at least 10, 25, 30, 35, 40, 45, 50 bases of RNA transcript specific sequence data. Additional bases of RNA transcript specific sequence data may be obtained. For example, the sequencing may be performed to determine the sequence of the spatial barcode and at least 50, 60, 70, 80, 90, or 100 bases of RNA transcript specific data.

In embodiments, the methods for spatial detection of nucleic acid (e.g. RNA) in a tissue sample further include imaging the tissue after contacting the tissue with the substrate (e.g., after immobilizing the tissue on the substrate). Imaging the tissue may assist in the determination of the spatial location of RNA molecules within the tissue sample. In embodiments, imaging the tissue is performed before generating cDNA. In embodiments, imaging the tissue is performed after generating cDNA. In embodiments, prior to imaging, the method further includes permeabilizing the immobilized tissue section. In embodiments, prior to imaging, the method does not include permeabilizing the immobilized tissue section. In embodiments, prior to imaging, the method further includes contacting the immobilized tissue section with one or more imaging reagents or stains. In embodiments, following permeabilization, the tissue section is contacted with one or more imaging reagents or stains. In embodiments, the tissue section is contacted with one or more imaging reagents or stains without permeabilization. In embodiments, the imaging reagents or stains include hematoxylin and eosin (H&E) staining reagents. In embodiments, the imaging includes phase-contrast microscopy, bright-field microscopy, Nomarski differential-interference-contrast microscopy, dark field microscopy, electron microscopy, or cryo-electron microscopy. In embodiments, the imaging reagents or stains include phase-contrast microscopy, bright-field microscopy, Nomarski differential-interference-contrast microscopy, or dark field microscopy imaging reagents. In embodiments, the light transmittance of the sample is measured. For example, light transmittance may be measured with a visible near-infrared optical fiber spectrometer, wherein a circular spot of light (e.g., diameter, 5 mm) is irradiated on the central part a sample and the transmitted light is collected using an optical sensor.

In embodiments, the imaging reagents or stains include electron microscopy (e.g., transmission electron microscopy or scanning electron microscopy) or cryo-electron microscopy imaging reagents. Examples of electron microscopy contrast agents may include one or more heavy metals (e.g., gold particles, colloidal gold particles, uranium, lead, platinum, and/or osmium) and/or antibodies bound to one or more types of heavy metals (e.g., gold particles, colloidal gold particles, uranium, lead, platinum, and/or osmium). For example, immunogold labels that may be used to contact the tissue section include may include different antibodies bound to gold particles of different sizes to image different molecules of interest. Optionally, the method may include contacting the tissue section with heavy metals. Heavy metals that may be used to stain additional features of interest and/or provide contrast between different structures in the tissue section may include uranium, lead, platinum, and/or osmium (see, e.g., U.S. Pat. Pubs. 2019/0355550 and 2013/0344500, each of which is incorporated herein by reference in its entirety).

In embodiments, the tissue section includes a tissue portion or a cell (e.g. plurality of cells such as blood cells). In embodiments, the tissue section includes one or more cells.

In embodiments, the tissue section is embedded in an embedding material including paraffin wax, polyepoxide polymer, polyacrylic polymer, agar, gelatin, celloidin, cryogel, optimal cutting temperature (OCT) compositions, glycols, or a combination thereof. In embodiments, the tissue section is embedded in an embedding material including paraffin wax. In embodiments, the OCT composition includes about 10% polyvinyl alcohol and about 4% polyethylene glycol. In embodiments, the OCT composition includes sucrose (e.g., 30% sucrose). In embodiments, the OCT composition is Tissue Freezing Medium (TFM) available from Leica Microsystems, Catalog #14020108926.

In embodiments, the tissue is immobilized to the substrate (e.g., the solid support including one or more clusters of the first plurality of capture probes and the second plurality of capture probes) by covalently binding the tissue to one or more bioconjugate reactive moieties of the substrate. In embodiments, the tissue is immobilized to the substrate by non-covalently binding the tissue to the substrate. For non-covalent binding, the tissue sections attach to the substrate surface due to surface interactions, such as Van der Waal forces, electrostatic forces, hydrophobic interactions and hydrogen bonds. The physical adsorption efficiency can be enhanced by treating the material with air plasma to increase its hydrophilicity.

In embodiments, the substrate includes a functionalized glass surface or a functionalized plastic surface. In embodiments, the functionalized glass surface includes (3-aminopropyl)triethoxysilane (APTES), (3-Aminopropyl)trimethoxysilane (APTMS), γ-Aminopropylsilatrane (APS), N-(6-aminohexyl)aminomethyltriethoxysilane (AHAMTES), polyethylenimine (PEI), 5,6-epoxyhexyltriethoxysilane, or triethoxysilylbutyraldehyde, or a combination thereof.

Tissue sections include tissue or organ samples obtained from a subject, e.g., a mammal. In certain embodiments, the subject is diagnosed with a disease or disorder, such as a cancerous tumor, or considered at risk of having or developing the disease or disorder. Tissue sections may also be obtained from healthy donors, e.g., as normal control samples. In certain embodiments, both a disease tissue (e.g., a tumor tissue) sample and a normal sample are obtained from the same subject. In particular embodiments, the tissue section is obtained from a patient, e.g., a mammal such as a human. In other embodiments, a tissue section is obtained from an animal model of disease. Various animal models of disease are known and available in the art. Particular animal models of cancer include but are not limited to xenograft, syngeneic, and PDx models, e.g., in mice or rats. Animal models may also include human cells, cancerous or otherwise, introduced into animal models wherein tumor properties, progress, and treatment may be assessed. In vitro 3D tissue arrangements, organoids, and stem or iPS-cell-derived 3D compositions are also relevant models, and these may include human or other animal cells, for example.

In embodiments, the tissue section includes a tissue or a cell. Biological tissue samples suitable for use with the methods and systems described herein generally include any type of tissue samples collected from living or dead subjects, such as, for example, tumor tissue and autopsy samples. Tissue samples may be collected and processed using the methods and systems described herein and subjected to microscopic analysis immediately following processing, or may be preserved and subjected to microscopic analysis at a future time, e.g., after storage for an extended period of time. In some embodiments, the methods described herein may be used to preserve tissue samples in a stable, accessible and fully intact form for future analysis. For example, tissue samples, such as, e.g., human tumor tissue samples, may be processed as described herein and cleared to remove a plurality of cellular components, such as, e.g., lipids, and then stored for future analysis. In some embodiments, the methods and systems described herein may be used to analyze a fresh tissue section. In some embodiments, the methods and systems described herein may be used to analyze a previously-preserved (e.g., previously fixed) or stored tissue section (e.g., tissue sample). For example, in some embodiments a previously-preserved tissue sample that has not been subjected to a sample preparation process described herein may be processed and analyzed as described herein. In particular methods, a tissue sample is frozen prior to being processed as described herein.

In certain embodiments, tissue sections are tumor tissue samples. Tumor samples may contain only tumor cells, or they may contain both tumor cells and non-tumor cells. In particular embodiments, a tissue section includes only non-tumor cells. In particular embodiments, the tumor is a solid tumor. In particular embodiments, the tissue section is obtained from or includes an adrenal cortical cancer, anal cancer, aplastic anemia, bileduct cancer, bladder cancer, bone cancer, bone metastasis, brain tumor, brain cancer, breast cancer, childhood cancer, cancer of unknown primary origin, Castleman disease, cervical cancer, colon/rectal cancer, endometrial cancer, esophagus cancer, Ewing family of tumors, eye cancer, gallbladder cancer, gastrointestinal carcinoid tumors, gastrointestinal stromal tumors, gestational trophoblastic disease, head or neck cancer, Kaposi sarcoma, renal cell carcinoma, laryngeal and hypopharyngeal cancer, liver cancer, non-small cell lung cancer, small cell lung cancer, lung carcinoid tumor, lymphoma of the skin, malignant mesothelioma, myelodysplasia syndrome, nasal cavity or paranasal sinus cancer, nasopharyngeal cancer, neuroblastoma, oral cavity or oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma in adult soft tissue, basal or squamous cell skin cancer, melanoma, small intestine cancer, stomach cancer, testicular cancer, throat cancer, thymus cancer, thyroid cancer, uterine sarcoma, vaginal cancer, vulvar cancer, Waldenstrom macroglobulinemia, Wilms tumor and secondary cancers caused by cancer treatment, is a tissue section obtained from a subject diagnosed with or suspected of having any of these tumors or cancers.

The methods of the invention can be used to characterize a cancer or metastasis thereof, including without limitation, a carcinoma, a sarcoma, a lymphoma or leukemia, a germ cell tumor, a blastoma, or other cancers. Carcinomas include without limitation epithelial neoplasms, squamous cell neoplasms squamous cell carcinoma, basal cell neoplasms basal cell carcinoma, transitional cell papillomas and carcinomas, adenomas and adenocarcinomas (glands), adenoma, adenocarcinoma, linitis plastica insulinoma, glucagonoma, gastrinoma, vipoma, cholangiocarcinoma, hepatocellular carcinoma, adenoid cystic carcinoma, carcinoid tumor of appendix, prolactinoma, oncocytoma, hurthle cell adenoma, renal cell carcinoma, grawitz tumor, multiple endocrine adenomas, endometrioid adenoma, adnexal and skin appendage neoplasms, mucoepidermoid neoplasms, cystic, mucinous and serous neoplasms, cystadenoma, pseudomyxoma peritonei, ductal, lobular and medullary neoplasms, acinar cell neoplasms, complex epithelial neoplasms, warthin's tumor, thymoma, specialized gonadal neoplasms, sex cord stromal tumor, thecoma, granulosa cell tumor, arrhenoblastoma, sertoli leydig cell tumor, glomus tumors, paraganglioma, pheochromocytoma, glomus tumor, nevi and melanomas, melanocytic nevus, malignant melanoma, melanoma, nodular melanoma, dysplastic nevus, lentigo maligna melanoma, superficial spreading melanoma, and malignant acral lentiginous melanoma. Sarcoma includes without limitation Askin's tumor, botryodies, chondrosarcoma, Ewing's sarcoma, malignant hemangio endothelioma, malignant schwannoma, osteosarcoma, soft tissue sarcomas including: alveolar soft part sarcoma, angiosarcoma, cystosarcoma phyllodes, dermatofibrosarcoma, desmoid tumor, desmoplastic small round cell tumor, epithelioid sarcoma, extraskeletal chondrosarcoma, extraskeletal osteosarcoma, fibrosarcoma, hemangiopericytoma, hemangiosarcoma, kaposi's sarcoma, leiomyosarcoma, liposarcoma, lymphangiosarcoma, lymphosarcoma, malignant fibrous histiocytoma, neurofibrosarcoma, rhabdomyosarcoma, and synovialsarcoma. Lymphoma and leukemia include without limitation chronic lymphocytic leukemia/small lymphocytic lymphoma, B-cell prolymphocytic leukemia, lymphoplasmacytic lymphoma (such as waldenstrom macroglobulinemia), splenic marginal zone lymphoma, plasma cell myeloma, plasmacytoma, monoclonal immunoglobulin deposition diseases, heavy chain diseases, extranodal marginal zone B cell lymphoma, also called malt lymphoma, nodal marginal zone B cell lymphoma (nmzl), follicular lymphoma, mantle cell lymphoma, diffuse large B cell lymphoma, mediastinal (thymic) large B cell lymphoma, intravascular large B cell lymphoma, primary effusion lymphoma, burkitt lymphoma/leukemia, T cell prolymphocytic leukemia, T cell large granular lymphocytic leukemia, aggressive NK cell leukemia, adult T cell leukemia/lymphoma, extranodal NK/T cell lymphoma, nasal type, enteropathy-type T cell lymphoma, hepatosplenic T cell lymphoma, blastic NK cell lymphoma, mycosis fungoides/sezary syndrome, primary cutaneous CD30-positive T cell lymphoproliferative disorders, primary cutaneous anaplastic large cell lymphoma, lymphomatoid papulosis, angioimmunoblastic T cell lymphoma, peripheral T cell lymphoma, unspecified, anaplastic large cell lymphoma, classical hodgkin lymphomas (nodular sclerosis, mixed cellularity, lymphocyte-rich, lymphocyte depleted or not depleted), and nodular lymphocyte-predominant hodgkin lymphoma. Germ cell tumors include without limitation germinoma, dysgerminoma, seminoma, nongerminomatous germ cell tumor, embryonal carcinoma, endodermal sinus turmor, choriocarcinoma, teratoma, polyembryoma, and gonadoblastoma. Blastoma includes without limitation nephroblastoma, medulloblastoma, and retinoblastoma. Other cancers include without limitation labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma.

In a further embodiment, the cancer under analysis may be a lung cancer including non-small cell lung cancer and small cell lung cancer (including small cell carcinoma (oat cell cancer), mixed small cell/large cell carcinoma, and combined small cell carcinoma), colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemia, lymphoma, myeloma, or a solid tumor.

Tissue sections may be obtained from a subject by any means known and available in the art. In particular embodiments, a tissue section, e.g., a tumor tissue sample, is obtained from a subject by fine needle aspiration, core needle biopsy, stereotactic core needle biopsy, vacuum-assisted core biopsy, or surgical biopsy. In particular embodiments, the surgical biopsy is an incisional biopsy, which removes only part of the suspicious area. In other embodiments, the surgical biopsy is an excisional biopsy, which removes the entire diseased tissue (e.g., tumor) or abnormal area. In particular embodiments, an excisional tumor tissue sample is obtained from a tumor that has been excised with the intent to "cure" a patient in the case of early stage disease, wherein in other embodiments, the excisional tumor tissue sample is obtained from an excised bulk of primary tumor in later stage disease. Tumor tissue samples may include primary tumor tissue, metastastic tumor tissue and/or secondary tumor tissue. Tumor tissue samples may be cell cultures, e.g., cultures of tumor-derived cell lines. In certain embodiments, a tissue section is a cell line, e.g., a cell pellet of a cultured cell line, such as a tumor cell line. In particular embodiments, the cell line or cell pellet is frozen or was previously frozen. Such cell lines and pellets are useful, e.g., as positive or negative controls for imaging with various reagents. Tumor tissue samples may also be xenograft tumors, e.g., tumors obtained from animals administered with tumor cells, e.g., a human tumor cell line. In certain embodiments, a first tumor tissue sample from a subject is a primary tumor tissue sample obtained during an initial surgery intended to remove the entire tumor, and a second tumor tissue sample is obtained from the same subject is a metastatic tumor tissue sample or a secondary tumor tissue sample obtained during a later surgery.

Tissue sections, e.g., tumor tissue samples, may be obtained surgically or using a laparoscope. A tissue section may be a tissue sample obtained from any part of the body to examine it for disease or injury, e.g., presence of cancer tissue or cells, or the extent or characteristics thereof. In particular embodiments, the tissue section includes abdominal tissue, bone, bone marrow, breast tissue, endometrial tissue, kidney tissue, liver tissue, lung or chest tissue, lymph node, nerve tissue, skin, testicular tissue, head or neck tissue, or thyroid tissue. In certain embodiments, the tissue is obtained from brain, breast, skin, bone, joint, skeletal muscle, smooth muscle, red bone marrow, thymus, lymphatic vessel, thoracic duct, spleen, lymph node, nasal cavity, pharynx, larynx, trachea, bronchus, lung, oral cavity, esophagus, liver, stomach, small intestine, large intestine, rectum, anus, spinal cord, nerve, pineal gland, pituitary gland, thyroid gland, thymus, adrenal gland, pancreas, ovary, testis, heart, blood vessel, kidney, uterus, urinary bladder, urethra, prostate gland, penis, prostate, testis, scrotum, ductus deferens, mammary glands, ovary, uterus, vagina, or uterine tube.

In particular embodiments, a tissue section has a size greater than sections typically examined by traditional pathology thin section or immunohistochemical analysis, which are typically in the range of 4-10 microns thick. In certain embodiments, a tissue section is greater than 20 microns, greater than 50 microns, greater than 100 microns, greater than 200 microns, greater than 500 microns, greater than 1 mm, greater than 2 mm, greater than 5 mm, greater than 10 mm or greater than 20 mm in thickness and/or length. In particular embodiments, the tissue section has a length and/or a thickness between 20 microns and 20 mm, between 20 microns and 10 mm, or between 50 microns and 1 mm. In certain embodiments, a tissue section is a cubic sample with each side greater than 10 microns, greater than 20 microns, greater than 50 microns, greater than 100 microns, greater than 200 microns, greater than 500 microns, greater than 1 mm, greater than 2 mm, greater than 5 mm, greater than 10 mm, or greater than 2 mm in thickness and/or length. In some embodiments, a tissue section is thinner, e.g., from about 4-10 or 4-20 microns in thickness.

RNA, including mRNA, is highly susceptible to degradation upon exposure to one or more RNAses. RNAses are present in a wide range of locations, including water, many reagents, laboratory equipment and surfaces, skin, and mucous membranes. Working with RNA often requires preparing an RNAse-free environment and materials, as well as taking precautions to avoid introducing RNAses into an RNAse-free environment. These precautions include, but are not limited to, cleaning surfaces with an RNAse cleaning product (e.g., RNASEZAP™ and other commercially available products or 0.5% sodium dodecyl sulfate [SDS] followed by 3% $H_2O_2$); using a designated workspace, materials, and equipment (e.g., pipets, pipet tips); using barrier tips; baking designated glassware (e.g., 300° C. for 2 hours) prior to use; treating enzymes, reagents, and other solutions (e.g., with diethyl pyrocarbonate [DEPC] or dimethyl pyrocarbonate [DMPC]) or using commercially available, certified RNAse-free water or solutions, or ultrafiltered water (e.g., for Tris-based solutions); including an RNAse inhibitor while avoiding temperatures or denaturing conditions that could deactivate the inhibitor); and wearing clean gloves (while avoiding contaminated surfaces) and a clean lab coat.

In embodiments, the tissue section forms part of a tissue in situ. In embodiments, the tissue section includes one or more prokaryotic cells. In embodiments, the tissue section includes one or more eukaryotic cells. In embodiments, the tissue section includes a bacterial cell (e.g., a bacterial cell or bacterial spore), a fungal cell (e.g., a fungal spore), a plant cell, or a mammalian cell. In embodiments, the tissue section includes a stem cell. In embodiments, the stem cell is an embryonic stem cell, a tissue-specific stem cell, a mesenchymal stem cell, or an induced pluripotent stem cell. In embodiments, the tissue section includes an endothelial cell, muscle cell, myocardial, smooth muscle cell, skeletal muscle cell, mesenchymal cell, epithelial cell; hematopoietic cell, such as lymphocytes, including T cell, e.g., (Th1 T cell, Th2 T cell, ThO T cell, cytotoxic T cell); B cell, pre-B cell; monocytes; dendritic cell; neutrophils; or a macrophage. In embodiments, the tissue section includes a stem cell, an immune cell, a cancer cell (e.g., a circulating tumor cell or cancer stem cell), a viral-host cell, or a cell that selectively binds to a desired target. In embodiments, the cell includes a T cell receptor gene sequence, a B cell receptor gene sequence, or an immunoglobulin gene sequence. In embodiments, the cell includes a Toll-like receptor (TLR) gene sequence. In embodiments, the cell includes a gene sequence corresponding to an immunoglobulin light chain polypeptide and a gene sequence corresponding to an immunoglobulin heavy chain polypeptide. In embodiments, the tissue section includes a genetically modified cell. In embodiments, the tissue section includes a circulating tumor cell or cancer stem cell.

In embodiments, the tissue section includes a prokaryotic cell. In embodiments, the tissue section includes a bacterial cell. In embodiments, the bacterial cell is a *Bacteroides, Clostridium, Faecalibacterium, Eubacterium, Ruminococcus, Peptococcus, Peptostreptococcus,* or *Bifidobacterium* cell. In embodiments, the bacterial cell is a *Bacteroides fragilis, Bacteroides melaninogenicus, Bacteroides oralis, Enterococcus faecalis, Escherichia coli, Enterobacter* sp., *Klebsiella* sp., *Bifidobacterium bifidum, Staphylococcus aureus, Lactobacillus, Clostridium perfringens, Proteus mirabilis, Clostridium tetani, Clostridium septicum, Pseudomonas aeruginosa, Salmonella enterica, Faecalibacterium prausnitzii, Peptostreptococcus* sp., or *Peptococcus* sp. cell. In embodiments, tissue section includes a fungal cell. In embodiments, the fungal cell is a *Candida, Saccharomyces, Aspergillus, Penicillium, Rhodotorula, Trametes, Pleospora, Sclerotinia, Bullera,* or *Galactomyces* cell.

In embodiments, the tissue section includes a viral-host cell. A "viral-host cell" is used in accordance with its ordinary meaning in virology and refers to a cell that is infected with a viral genome (e.g., viral DNA or viral RNA). The cell, prior to infection with a viral genome, can be any cell that is susceptible to viral entry. In embodiments, the viral-host cell is a lytic viral-host cell. In embodiments, the viral-host cell is capable of producing viral protein. In embodiments, the viral-host cell is a lysogenic viral-host cell. In embodiments, the cell is a viral-host cell including a viral nucleic acid sequence, wherein the viral nucleic acid sequence is from a Hepadnaviridae, Adenoviridae, Herpesviridae, Poxviridae, Parvoviridae, Reoviridae, Coronaviridae, Retroviridae virus.

In embodiments, the tissue section includes an adherent cell (e.g., epithelial cell, endothelial cell, or neural cell). Adherent cells are usually derived from tissues of organs and attach to a substrate (e.g., epithelial cells adhere to an extracellular matrix coated substrate via transmembrane adhesion protein complexes). Adherent cells typically require a substrate, e.g., tissue culture plastic, which may be coated with extracellular matrix (e.g., collagen and laminin) components to increase adhesion properties and provide other signals needed for growth and differentiation. In embodiments, the tissue section includes a neuronal cell, an endothelial cell, epithelial cell, germ cell, plasma cell, a muscle cell, peripheral blood mononuclear cell (PBMC), a myocardial cell, or a retina cell. In embodiments, the tissue section includes a suspension cell (e.g., a cell free-floating in the culture medium, such a lymphoblast or hepatocyte). In embodiments, the tissue section includes a glial cell (e.g., astrocyte, radial glia), pericyte, or stem cell (e.g., a neural stem cell). In embodiments, the tissue section includes a neuronal cell. In embodiments, the tissue section includes an endothelial cell. In embodiments, the tissue section includes an epithelial cell. In embodiments, the tissue section includes a germ cell. In embodiments, the tissue section includes a plasma cell. In embodiments, the tissue section includes a muscle cell. In embodiments, the tissue section includes a peripheral blood mononuclear cell (PBMC). In embodiments, the tissue section includes a myocardial cell. In embodiments, the tissue section includes a retina cell. In embodiments, the tissue section includes a lymphoblast. In embodiments, the tissue section includes a hepatocyte. In embodiments, the tissue section includes a glial cell. In embodiments, the tissue section includes an astrocyte. In embodiments, the tissue section includes a radial glia. In embodiments, the tissue section includes a pericyte. In embodiments, the tissue section includes a stem cell. In embodiments, the tissue section includes a neural stem cell.

In embodiments, the tissue section includes a cell bound to a known antigen. In embodiments, the cell is a cell that selectively binds to a desired target, wherein the target is an antibody, or antigen binding fragment, an aptamer, affimer, non-immunoglobulin scaffold, small molecule, or genetic modifying agent. In embodiments, the cell is a leukocyte (i.e., a white-blood cell). In embodiments, leukocyte is a granulocyte (neutrophil, eosinophil, or basophil), monocyte, or lymphocyte (T cells and B cells). In embodiments, the cell is a lymphocyte. In embodiments, the cell is a T cell, an NK cell, or a B cell.

In embodiments, the tissue section includes an immune cell. In embodiments, the immune cell is a granulocyte, a mast cell, a monocyte, a neutrophil, a dendritic cell, or a natural killer (NK) cell. In embodiments, the immune cell is an adaptive cell, such as a T cell, NK cell, or a B cell. In embodiments, the cell includes a T cell receptor gene sequence, a B cell receptor gene sequence, or an immunoglobulin gene sequence. In embodiments, the immune cell is a granulocyte. In embodiments, the immune cell is a mast cell. In embodiments, the immune cell is a monocyte. In embodiments, the immune cell is a neutrophil. In embodiments, the immune cell is a dendritic cell. In embodiments, the immune cell is a natural killer (NK) cell. In embodiments, the immune cell is a T cell. In embodiments, the immune cell is a B cell. In embodiments, the cell includes a T cell receptor gene sequence. In embodiments, the cell includes a B cell receptor gene sequence. In embodiments, the cell includes an immunoglobulin gene sequence. In embodiments, the plurality of target nucleic acids includes non-contiguous regions of a nucleic acid molecule. In embodiments, the non-contiguous regions include regions of a VDJ recombination of a B cell or T cell.

In embodiments, the tissue section includes a cancer cell. In embodiments, the cancer is lung cancer, colorectal cancer, skin cancer, colon cancer, pancreatic cancer, breast cancer, cervical cancer, lymphoma, leukemia, or a cancer associated with aberrant K-Ras, aberrant APC, aberrant Smad4, aberrant p53, or aberrant TGFβ. In embodiments, the cancer cell includes a ERBB2, KRAS, TP53, PIK3CA, or FGFR2 gene. In embodiments, the cancer cell includes a cancer-associated gene (e.g., an oncogene associated with kinases and genes involved in DNA repair) or a cancer-associated biomarker. A "biomarker" is a substance that is associated with a particular characteristic, such as a disease or condition. A change in the levels of a biomarker may correlate with the risk or progression of a disease or with the susceptibility of the disease to a given treatment. In embodiments, the cancer is Acute Myeloid Leukemia, Adrenocortical Carcinoma, Bladder Urothelial Carcinoma, Breast Ductal Carcinoma, Breast Lobular Carcinoma, Cervical Carcinoma, Cholangiocarcinoma, Colorectal Adenocarcinoma, Esophageal Carcinoma, Gastric Adenocarcinoma, Glioblastoma Multiforme, Head and Neck Squamous Cell Carcinoma, Hepatocellular Carcinoma, Kidney Chromophobe Carcinoma, Kidney Clear Cell Carcinoma, Kidney Papillary Cell Carcinoma, Lower Grade Glioma, Lung Adenocarcinoma, Lung Squamous Cell Carcinoma, Mesothelioma, Ovarian Serous Adenocarcinoma, Pancreatic Ductal Adenocarcinoma, Paraganglioma & Pheochromocytoma, Prostate Adenocarcinoma, Sarcoma, Skin Cutaneous Melanoma, Testicular Germ Cell Cancer, Thymoma, Thyroid Papillary Carcinoma, Uterine Carcinosarcoma, Uterine Corpus Endometrioid Carcinoma, or Uveal Melanoma. In embodiments, the cancer-associated gene is a nucleic acid sequence identified within The Cancer Genome Atlas Program, accessible at www.cancer.gov/tcga.

In embodiments, the cancer-associated biomarker is MDC, NME-2, KGF, P1GF, Flt-3L, HGF, MCP1, SAT-1, MIP-1-b, GCLM, OPG, TNF RII, VEGF-D, ITAC, MMP-10, GPI, PPP2R4, AKR1B1, AmylA, MIP-1b, P-Cadherin, or EPO. In embodiments, the cancer-associated gene is a AKT1, AKT2, AKT3, ALK, AR, ARAF, ARID1A, ATM, ATR, ATRX, AXL, BAP1, BRAF, BRCA1, BRCA2, BTK, CBL, CCND1, CCND2, CCND3, CCNE1, CDK12, CDK2, CDK4, CDK6, CDKN1B, CDKN2A, CDKN2B, CHEK1, CHEK2, CREBBP, CSF1R, CTNNB1, DDR2, EGFR, ERBB2, ERBB3, ERBB4, ERCC2, ERG, ESR1, ETV1, ETV4, ETV5, EZH2, FANCA, FANCD2, FANCI, FBXW7, FGF19, FGF3, FGFR1, FGFR2, FGFR3, FGFR4, FGR, FLT3, FOXL2, GATA2, GNA11, GNAQ, GNAS, H3F3A, HIST1H3B, HNF1A, HRAS, IDH1, IDH2, IGF1R, JAK1, JAK2, JAK3, KDR, KIT, KNSTRN, KRAS, MAGOH, MAP2K1, MAP2K2, MAP2K4, MAPK1, MAX, MDM2, MDM4, MED12, MET, MLH1, MRE11A, MSH2, MSH6, MTOR, MYB, MYBL1, MYC, MYCL, MYCN, MYD88, NBN, NF1, NF2, NFE2L2, NOTCH1, NOTCH2, NOTCH3, NOTCH4, NRAS, NRG1, NTRK1, NTRK2, NTRK3, NUTM1, PALB2, PDGFRA, PDGFRB, PIK3CA, PIK3CB, PIK3R1, PMS2, POLE, PPARG, PPP2R1A, PRKACA, PRKACB, PTCH1, PTEN, PTPN11, RAC1, RAD50, RAD51, RAD51B, RAD51C, RAD51D, RAF1, RB1, RELA, RET, RHEB, RHOA, RICTOR, RNF43, ROS1, RSPO2, RSPO3, SETD2, SF3B1, SLX4, SMAD4, SMARCA4, SMARCB1, SMO, SPOP, SRC, STAT3, STK11, TERT, TOP1, TP53, TSC1, TSC2, U2AF1, or XPO1 gene. In embodiments, the cancer-associated gene is a ABL1, AKT1, ALK, APC, ATM, BRAF, CDH1, CDKN2A, CSF1R, CTNNB1, EGFR, ERBB2, ERBB4, EZH2, FBXW7, FGFR1, FGFR2, FGFR3, FLT3, GNA11, GNAQ, GNAS, HNF1A, HRAS, IDH1, IDH2, JAK2, JAK3, KDR, KIT, KRAS, MET, MLH1, MPL, NOTCH1, NPM1, NRAS, PDGFRA, PIK3CA, PTEN, PTPN11, RB1, RET, SMAD4, SMARCB1, SMO, SRC, STK11, TP53, or VHL gene. In embodiments, the tissue section includes a cell (e.g., a T cell) within a tumor. In embodiments, the tissue section includes a non-allogenic cell (i.e., native cell to the subject) within a tumor. In embodiments, the tissue section includes a tumor infiltrating lymphocyte (TIL). In embodiments, the tissue section includes an allogenic cell. In embodiments, the tissue section includes a circulating tumor cell.

In embodiments, the tissue section is obtained from a subject (e.g., human or animal tissue). Once obtained, the tissue section is placed in an artificial environment in plastic or glass containers supported with specialized medium containing essential nutrients and growth factors to support proliferation. In embodiments, the tissue section is permeabilized and immobilized to a solid support surface. In embodiments, the tissue section is permeabilized and immobilized to an array (i.e., to discrete locations arranged in an array). In embodiments, the tissue section is immobilized to a solid support surface. In embodiments, the surface includes a patterned surface (e.g., suitable for immobilization of a plurality of cells in an ordered pattern. The discrete regions of the ordered pattern may have defined locations in a regular array, which may correspond to a rectilinear pattern, circular pattern, hexagonal pattern, or the like. These discrete regions are separated by interstitial regions. As used herein, the term "interstitial region" refers to an area in a substrate or on a surface that separates other areas of the substrate or surface. In embodiments, a plurality of cells are immobilized on a patterned surface that have a mean or median separation from one another of about 10-20 μm. In embodiments, a plurality of cells are immobilized on a patterned surface that have a mean or median separation from one another of about 10-20; 10-50; or 100 μm. In embodiments, a plurality of cells are arrayed on a substrate. In embodiments, a plurality of cells are immobilized in a 96-well microplate having a mean or median well-to-well spacing of about 8 mm to about 12 mm (e.g., about 9 mm). In embodiments, a plurality of cells are immobilized in a 384-well microplate having a mean or median well-to-well spacing of about 3 mm to about 6 mm (e.g., about 4.5 mm).

In embodiments, the tissue section is attached to the receiving substrate via a bioconjugate reactive linker. In embodiments, the tissue section is attached to the substrate via a specific binding reagent. In embodiments, the specific binding reagent includes an antibody, single-chain Fv fragment (scFv), antibody fragment-antigen binding (Fab), or an aptamer. In embodiments, the specific binding reagent includes an antibody, or antigen binding fragment, an aptamer, affimer, or non-immunoglobulin scaffold. In embodiments, the specific binding reagent is a peptide, a cell penetrating peptide, an aptamer, a DNA aptamer, an RNA aptamer, an antibody, an antibody fragment, a light chain antibody fragment, a single-chain variable fragment (scFv), a lipid, a lipid derivative, a phospholipid, a fatty acid, a triglyceride, a glycerolipid, a glycerophospholipid, a sphingolipid, a saccharolipid, a polyketide, a polylysine, polyethyleneimine, diethylaminoethyl (DEAE)-dextran, cholesterol, or a sterol moiety. Substrates may be prepared for selective capture of particular cells of the tissue section. For example, a substrate containing a plurality of bioconjugate reactive moieties or a plurality of specific binding reagents, optionally in an ordered pattern, contacts a plurality of cells of the tissue section. Only cells of the tissue section containing complementary bioconjugate reactive moieties or complementary specific binding reagents are capable of reacting, and thus adhering, to the substrate.

In embodiments, the methods are performed in situ in tissue sections that have been prepared according to methodologies known in the art. Methods for permeabilization and fixation of cells and tissue samples are known in the art, as exemplified by Cremer et al., The Nucleus: Volume 1: Nuclei and Subnuclear Components, R. Hancock (ed.) 2008; and Larsson et al., Nat. Methods (2010) 7:395-397, the content of each of which is incorporated herein by reference in its entirety. In embodiments, the tissue section is cleared (e.g., digested) of proteins, lipids, or proteins and lipids.

In embodiments, the tissue section is exposed to paraformaldehyde (i.e., by contacting the cell with paraformaldehyde). Any suitable permeabilization and fixation technologies can be used for making the cell available for the detection methods provided herein. In embodiments the method includes affixing single cells or tissues to a transparent substrate. Exemplary tissue include those from skin tissue, muscle tissue, bone tissue, organ tissue and the like. In embodiments, the method includes immobilizing the tissue section in situ to a substrate and permeabilized for delivering probes, enzymes, nucleotides and other components required in the reactions. In embodiments, the tissue section includes many cells from a tissue section in which the original spatial relationships of the cells are retained. In embodiments, the tissue section in situ is within a Formalin-Fixed Paraffin-Embedded (FFPE) sample. In embodiments, the tissue section is subjected to paraffin removal methods, such as methods involving incubation with a hydrocarbon solvent, such as xylene or hexane, followed by two or more washes with decreasing concentrations of an alcohol, such as ethanol. The tissue section may be rehydrated in a buffer, such as PBS, TBS or MOPs. In embodiments, the FFPE sample is incubated with xylene and washed using ethanol to remove the embedding wax, followed by treatment with Proteinase K to permeabilized the tissue. In embodiments, the tissue section is fixed with a chemical fixing agent. In embodiments, the chemical fixing agent is formaldehyde or glutaraldehyde. In embodiments, the chemical fixing agent is glyoxal or dioxolane. In embodiments, the chemical fixing agent includes one or more of ethanol, methanol, 2-propanol, acetone, and glyoxal. In embodiments, the chemical fixing agent includes formalin, Greenfix®, Greenfix® Plus, UPM, CyMol®, HOPE®, CytoSkelFix™, F-Solv®, FineFIX®, RCL2/KINFix, UMFIX, Glyo-Fixx®, Histochoice®, or PAXgene®. In embodiments, the tissue section is fixed within a synthetic three-dimensional matrix (e.g., polymeric material). In embodiments, the synthetic matrix includes polymeric-crosslinking material. In embodiments, the material includes polyacrylamide, poly-ethylene glycol (PEG), poly(acrylate-co-acrylic acid) (PAA), or Poly(N-isopropylacrylamide) (NIPAM).

In embodiments, the fixed tissue may be frozen tissue. The frozen biological tissue can be fixed using a fixing agent, which is suitably an organic fixing agent. In some embodiments, the fixing agent can be chilled and can be at a temperature of about 0° C. to about 100° C., suitably about zero to about 50° C., or about 1° C. to about 50° C. The fixing agent can be chilled by placing it over a bed of ice to maintain its temperature as close to 0° C. as possible. The frozen biological tissue can be treated with the fixing agent using any suitable technique, suitably by immersing it in the fixing agent for a period of time. Depending on the type and size of the biological tissue sample, the treatment time can range from about 5 minutes to about 60 minutes, suitably about 10 minutes to about 30 minutes, or about 15 minutes to about 25 minutes, or about 20 minutes. In some embodiments, treatment time may be overnight. During fixing, the snap-frozen tissue will thaw but will suitably remain at a low temperature due to the low temperature environment of the fixing agent.

In some embodiments, the type/identity of a fixation agent, the amount/concentration of a fixation agent, the temperature at which it is used, the duration for which it is used, and the like, may be empirically determined or titrated. These parameters, and others, may need to be varied to obtain optimal results for different tissues, for different organisms, or for different days on which an experiment is performed. Insufficient fixation (e.g., too little fixing agent, too low temperature, too short duration) may not, for example, stabilize/preserve the cells/organelles/analytes of tissues. Excess fixation (e.g., too much fixing agent, too high temperature, too long duration) may result in the single biological samples (e.g., cells/nuclei) obtained from the methods not yielding good results in single biological sample (e.g., single-cell or single nucleus) workflows or assays in which the biological samples (e.g., cells or nuclei) are used. Generally, the quality of data obtained in these workflows/assays may be a good measure of the extent of the fixation process.

In some embodiments, the fixative can be diluted in a buffer, e.g., saline, phosphate buffer (PB), phosphate buffered saline (PBS), citric acid buffer, potassium phosphate buffer, etc., usually at a concentration of about 1-10%, e.g. 1%, 2%, 3%, 4%, 5%, 6%, 7%, 8%, or 10%, for example, 4% paraformaldehyde/0.1 M phosphate buffer; 2% paraformaldehyde/0.2% picric acid/0.1 M phosphate buffer; 4% paraformaldehyde/0.2% periodate/1.2% lysine in 0.1 M phosphate buffer; 4% paraformaldehyde/0.05% glutaraldehyde in phosphate buffer; etc. The type of fixative used and the duration of exposure to the fixative can depend on the sensitivity of the molecules of interest in the tissue section to denaturation by the fixative, and can be readily determined using conventional histochemical or immunohistochemical techniques, for example as described in Buchwalow and Bocker. Immunohistochemistry: Basics and Methods. Springer-Verlag Berlin Heidelberg 2010.

During the fixing, the biological tissue sample can be periodically cut into successively smaller segments while it is submerged in the fixation solution, to facilitate perfusion and fixation of the biological tissue sample by the organic fixing agent. For example, the tissue sample may have an initial length, width and/or diameter of about 0.25 cm to about 1.5 cm or may be initially cut into segments having such suitable dimensions. After a first periodic interval, the tissue sample or segments can be cut into smaller segments, and the smaller segments can remain immersed in the fixing agent. This process can be repeated after a second periodic interval, after a third periodic interval, after a fourth periodic interval, and so on. The periodic intervals can range from about 1 to about 10 minutes, or about 2 to about 8 minutes, or about 4 to about 6 minutes. The sum of the periodic intervals can equal the entire fixing time and can range from about 5 to about 60 minutes, or about 10 to about 30 minutes, or about 15 to about 25 minutes, for example. The resulting fixed tissue segments can have a length, width and/or diameter in a range of less than 1 mm to about 10 mm, by way of example. In some embodiments, the tissue is not cut into smaller segments during fixation. In some embodiments, this may be performed prior to fixation. In some embodiments, this may be performed after fixation.

Once the biological tissue segments have been sufficiently fixed, the fixation process may be stopped and/or the tissue may be removed from the fixation and the tissue may be washed. Generally, fixation is stopped to cease additional activity of the fixative on the tissue. Fixation may also be stopped so that any subsequent biochemical reactions performed on the tissue (e.g., enzymatic cell dissociation) can function. In some embodiments, the tissue segments may be treated or contacted with a quenching medium to quench the fixation. The term "quenching" means to stop the fixation reaction, i.e., the chemical interactions that cause the fixation. Quenching the fixation can be accomplished by immersing the fixed tissue segments in a suitable quenching medium. The fixation quenching medium can be chilled and can have a temperature of about 0° C. to about 100° C., or about 1° C. to about 50° C. In embodiments, the quenching medium is a phosphate buffer solution (PBS). One suitable phosphate buffer solution is 1×PBS, available from Sigma Aldrich Corp. 1×PBS has a pH of about 7.4 and the following composition in water: NaCl—137 mM, KCl—2.7 mM, $Na_2HPO_4$—10 mM, $KH_2PO_4$—1.8 mM. In one embodiment, the phosphate buffer solution can be combined with fetal bovine serum (FBS) to aid in quenching the fixation reaction. FBS is the liquid fraction of clotted blood from fetal calves, depleted of cells, fibrin and clotting factors, but containing many nutritional and macromolecular factors essential for cell growth. Bovine serum albumin (BSA) is the major component of FBS. The fetal bovine serum can be combined with the phosphate buffer solution at a concentration of about 1% to about 25% by weight FBS and about 75% to about 99% by weight PBS, suitably about 5% to about 15% by weight FBS and about 85% to about 95% by weight PBS, or about 10% by weight FBS and about 90% by weight PBS. In another embodiment, a solution of concentrated ethanol in water can be used instead of the PBS in the quenching medium. The ethanol solution can contain about 50% to about 90% by weight ethanol, or about 55% to about 85% by weight ethanol, or about 60% to about 80% by weight ethanol, or about 70% by weight ethanol. In some embodiments, fixation may be quenched using a quenching solution that does not contain serum. In some examples, Tris-based buffers may be used. In some examples, PBS+50 mM Tris pH 8.0+0.02% BSA (RNAse free)+0.1 U/ul of RNAse Inhibitor may be used. In some examples, the tissue may be removed from the fixative and washed using a quenching solution or biological buffer.

In embodiments, the tissue section is lysed to release nucleic acid or other materials from the cells. For example, the tissue section may be lysed using reagents (e.g., a surfactant such as Triton-X or SDS, an enzyme such as lysozyme, lysostaphin, zymolase, cellulase, mutanolysin, glycanases, proteases, mannase, proteinase K, etc.) or a physical lysing mechanism a physical condition (e.g., ultrasound, ultraviolet light, mechanical agitation, etc.). The cells may release, for instance, DNA, RNA, mRNA, proteins, or enzymes. The cells may arise from any suitable source. For instance, the cells may be any cells for which nucleic acid from the cells is desired to be studied or sequenced, etc., and may include one, or more than one, cell type. The cells may be for example, from a specific population of cells, such as from a certain organ or tissue (e.g., cardiac cells, immune cells, muscle cells, cancer cells, etc.), cells from a specific individual or species (e.g., human cells, mouse cells, bacteria, etc.), cells from different organisms, cells from a naturally-occurring sample (e.g., pond water, soil, etc.), or the like. In some cases, the cells may be dissociated from tissue. In embodiments, the method does not include dissociating the cell from the tissue or the cellular microenvironment. In embodiments, the method does not include lysing the tissue section.

In embodiments, a permeabilization solution can contain additional reagents or a biological sample may be treated with additional reagents in order to optimize biological sample permeabilization. In some embodiments, an additional reagent is an RNA protectant. As used herein, the term "RNA protectant" typically refers to a reagent that protects RNA from RNA nucleases (e.g., RNases). Any appropriate RNA protectant that protects RNA from degradation can be used. A non-limiting example of an RNA protectant includes organic solvents (e.g., at least 60%, 65%, 70%, 75%, 80%, 85%, 90%, or 95% v/v organic solvent), which includes ethanol, methanol, propan-2-ol, acetone, trichloroacetic acid, propanol, polyethylene glycol, acetic acid, or a combination thereof. In embodiments, the RNA protectant includes ethanol, methanol and/or propan-2-ol, or a combination thereof. In embodiments, the RNA protectant includes RNAlater ICE (ThermoFisher Scientific). In embodiments, the RNA protectant includes a salt. The salt may include ammonium sulfate, ammonium bisulfate, ammonium chloride, ammonium acetate, cesium sulfate, cadmium sulfate, cesium iron (II) sulfate, chromium (III) sulfate, cobalt (II) sulfate, copper (II) sulfate, lithium chloride, lithium acetate, lithium sulfate, magnesium sulfate, magnesium chloride, manganese sulfate, manganese chloride, potassium chloride, potassium sulfate, sodium chloride, sodium acetate, sodium sulfate, zinc chloride, zinc acetate and zinc sulfate. In some embodiments, the biological sample is treated with one or more RNA protectants before, contemporaneously with, or after permeabilization.

In embodiments, the method includes imaging the immobilized tissue section. In embodiments, the method further includes an imaging modality, immunofluorescence (IF), or immunohistochemistry modality (e.g., immunostaining). In embodiments, the method includes ER staining (e.g., contacting the tissue section with a cell-permeable dye which localizes to the endoplasmic reticula), Golgi staining (e.g., contacting the tissue section with a cell-permeable dye which localizes to the Golgi), F-actin staining (e.g., contacting the tissue section with a phalloidin-conjugated dye that binds to actin filaments), lysosomal staining (e.g., contacting the tissue section with a cell-permeable dye that accumulates in the lysosome via the lysosome pH gradient), mitochondrial staining (e.g., contacting the tissue section with a cell-permeable dye which localizes to the mitochondria), nucleolar staining, or plasma membrane staining. For example, the method includes live cell imaging (e.g., obtaining images of the tissue section) prior to or during fixing, immobilizing, and permeabilizing the tissue section. Immunohistochemistry (IHC) is a powerful technique that exploits the specific binding between an antibody and antigen to detect and localize specific antigens in cells and tissue, commonly detected and examined with the light microscope. Known IHC modalities may be used, such as the protocols described in Magaki, S., Hojat, S. A., Wei, B., So, A., & Yong, W. H. (2019). Methods in molecular biology (Clifton, N.J.), 1897, 289-298, which is incorporated herein by reference. In embodiments, the additional imaging modality includes bright field microscopy, phase contrast microscopy, Nomarski differential-interference-contrast microscopy, or dark field microscopy. In embodiments, the method further includes determining the cell morphology of the tissue section (e.g., the cell boundary or cell shape) using known methods in the art. For example, to determining the cell boundary includes comparing the pixel values of an image to a single intensity threshold, which may be determined quickly using histogram-based approaches as described in Carpenter, A. et al Genome Biology 7, R100 (2006) and Arce, S., Sci Rep 3, 2266 (2013)). By "microscopic analysis" is meant the analysis of a specimen using techniques that provide for the visualization of aspects of a specimen that cannot be seen with the unaided eye, i.e., that are not within the resolution range of the normal human eye. Such techniques may include, without limitation, optical microscopy, e.g., bright field, oblique illumination, dark field, phase contrast, differential interference contrast, interference reflection, epifluorescence, confocal microscopy, CLARITY-optimized light sheet microscopy (COLM), light field microscopy, tissue expansion microscopy, etc., laser microscopy, such as, two photon microscopy, electron microscopy, and scanning probe microscopy. By "preparing a biological specimen for microscopic analysis" is generally meant rendering the specimen suitable for microscopic analysis at an unlimited depth within the specimen. In embodiments, the immobilized tissue section is imaged using "optical sectioning" techniques, such as laser scanning confocal microscopes, laser scanning 2-Photon microscopy, parallelized confocal (i.e. spinning disk), computational image deconvolution methods, and light sheet approaches. Optical sectioning microscopy methods provide information about single planes of a volume by minimizing contributions from other parts of the volume and do so without physical sectioning. The resulting "stack" of such optically sectioned images, represents a full reconstruction of the 3-dimensional features of a tissue volume. A typical confocal microscope includes a 10×/0.5 objective (dry; working distance, 2.0 mm) and/or a 20×/0.8 objective (dry; working distance, 0.55 mm), with a s z-step interval of 1 to 5 µm. A typical light sheet fluorescence microscope includes an sCMOS camera, a 2×/0.5 objective lens, and zoom microscope body (magnification range of ×0.63 to ×6.3). For entire scanning of whole samples, the z-step interval is 5 or 10 µm, and for image acquisition in the regions of interest, an interval in the range of 2 to 5 µm may be used.

To microscopically visualize tissue sections prepared by the subject methods, in some embodiments the tissue section is embedded in a mounting medium. Mounting medium is typically selected based on its suitability for the reagents used to visualize the cellular biomolecules, the refractive index of the tissue section, and the microscopic analysis to be performed. For example, for phase-contrast work, the refractive index of the mounting medium should be different from the refractive index of the specimen, whereas for bright-field work the refractive indexes should be similar. As another example, for epifluorescence work, a mounting medium should be selected that reduces fading, photobleaching or quenching during microscopy or storage. In certain embodiments, a mounting medium or mounting solution may be selected to enhance or increase the optical clarity of the cleared tissue specimen. Nonlimiting examples of suitable mounting media that may be used include glycerol, CC/Mount™, Fluoromount™ Fluoroshield™, ImmunHistoMount™, Vectashield™, Permount™, Acrytol™, CureMount™, FocusClear™, or equivalents thereof.

The biological targets or molecules to be detected can be any biological molecules including but not limited to proteins, nucleic acids, lipids, carbohydrates, ions, or multicomponent complexes containing any of the above. Examples of subcellular targets include organelles, e.g., mitochondria, Golgi apparatus, endoplasmic reticulum, chloroplasts, endocytic vesicles, exocytic vesicles, vacuoles, lysosomes, etc. Exemplary nucleic acid targets can include genomic DNA of various conformations (e.g., A-DNA, B-DNA, Z-DNA), mitochondria DNA (mtDNA), mRNA, tRNA, rRNA, hRNA, miRNA, and piRNA. For example, following immobilization on the receiving substrate, the sections may be fixed with methanol, permeabilized with 0.025% Triton in PBS solution, and stained with primary antibodies directed against vimentin (fibroblasts) and macrophages, followed by secondary antibody labeling (e.g., Alexa-594 conjugated secondary antibodies). Additional counterstaining may be performed, for example using 4,6-diamidino-2-phenylindole (DAPI) mounting media to counterstain nuclei.

In embodiments, the collection of information (e.g., sequencing information and cell morphology) is referred to as a signature. The term "signature" may encompass any gene or genes, protein or proteins, or epigenetic element(s) whose expression profile or whose occurrence is associated with a specific cell type, subtype, or cell state of a specific cell type or subtype within a population of cells. It is to be understood that also when referring to proteins (e.g., differentially expressed proteins), such may fall within the definition of "gene" signature. Levels of expression or activity or prevalence may be compared between different cells in order to characterize or identify for instance signatures specific for cell (sub)populations. Increased or decreased expression or activity of signature genes may be compared between different cells in order to characterize or identify for instance specific cell (sub)populations.

In embodiments, the methods described herein may further include constructing a 3-dimensional pattern of abundance, expression, and/or activity of each target from spatial patterns of abundance, expression, and/or activity of each target of multiple samples. In embodiments, the multiple samples can be consecutive tissue sections of a 3-dimensional tissue sample.

In embodiments, the method further includes digesting the tissue section by contacting the sample-carrier construct with an endopeptidase. In embodiments, the endopeptidase is pepsin.

In embodiments, the method further includes removing the embedding material from the sample. For example, if the embedding material is paraffin wax, the embedding material is removed by contacting the sample-carrier construct with a hydrocarbon solvent, such as xylene or hexane, followed by two or more washes with decreasing concentrations of an alcohol, such as ethanol.

In embodiments, the method includes measuring changes in the amount of biomaterial present in a well relative to a control (e.g., a sample obtained at a different time point or exposed to alternate conditions). As used herein, "biomaterial" refers to any biological material produced by an organism. In some embodiments, biomaterial includes secretions, extracellular matrix, proteins, lipids, organelles, membranes, cells, portions thereof, and combinations thereof. In some embodiments, cellular material includes secretions, extracellular matrix, proteins, lipids, organelles, membranes, cells, portions thereof, and combinations thereof. In some embodiments, biomaterial includes viruses. In some embodiments, the biomaterial is a replicating virus and thus includes virus infected cells.

In embodiments, additional methods may be performed to further characterize the sample. For example, in addition to sequencing, the method includes protein analysis, lipid analysis, metabolite analysis (e.g., glucose analysis), or measuring the transcriptomic profile, gene expression activity, genomic profile, protein expression activity, proteomic profile, protein interaction activity, cellular receptor expression activity, lipid profile, lipid activity, carbohydrate profile, microvesicle activity, glucose activity, and combinations thereof.

In some embodiments, determining the spatial location of RNA molecules within a tissue sample includes correlating the location of the cluster of capture probes (e.g., the cluster including the first plurality of immobilized capture probes and second plurality of immobilized capture probes) on the substrate with a corresponding location within the tissue sample. In some embodiments, the spatial location of the RNA molecules in the tissue sample may allow identification of a single cell expressing the RNA molecules.

In some embodiments, the methods described herein may include each of the following steps (in no particular order): a. providing a solid support as described herein (e.g., a solid support including clusters including a first plurality of immobilized capture probes and a second plurality of immobilized capture probes); b. determining the sequence of the spatial barcode for at least one capture probe in each cluster on the solid support; c. assigning each cluster a location (e.g., XY coordinate) on the solid support based upon the sequence of the spatial barcode; d. contacting the solid support with a tissue sample and allowing RNA molecules in the tissue sample to bind to the capture probes; e. imaging the tissue sample while the sample is bound to the solid support; f. generating cDNA molecules from the RNA molecules bound to the capture probes; g. determining the sequence of the spatial barcode for the cDNA molecules and correlating this sequence with the location of a corresponding cluster on the substrate (e.g., cluster of capture probes containing the corresponding spatial barcode); h. correlating the location of the corresponding cluster of capture probes on the solid support with a corresponding location within the tissue sample, thus identifying the spatial location of RNA (e.g., gene) expression in the sample.

In representative embodiments, the methods described herein may include each of the following steps (in no particular order): a. providing a solid support as described herein (e.g., a solid support including clusters including a first plurality of immobilized capture probes and a second plurality of immobilized capture probes); b. determining the sequence of the spatial barcode for at least one capture probe in each cluster on the solid support; c. assigning each cluster a location (e.g., XY coordinate) on the solid support based upon the sequence of the spatial barcode; d. contacting the solid support with a tissue sample and allowing RNA molecules in the tissue sample to bind to the capture probes; e. imaging the tissue sample while the sample is bound to the solid support; f. generating first strand cDNA molecules from the RNA molecules bound to the capture probes (e.g., by reverse transcription) g. generating, isolating, purifying, and amplifying second strand cDNA molecules from the first strand cDNA molecules, thus creating multiple second strand cDNA molecules from each first strand cDNA molecules; h. determining the sequence of the spatial barcode for the second strand cDNA molecules and correlating this sequence with the location of a corresponding cluster on the solid support (e.g., cluster of capture probes containing the complementary spatial barcode to the spatial barcode of the second strand cDNA); i. correlating the location of the corresponding cluster of capture probes on the solid support with a corresponding location within the tissue sample, thus identifying the spatial location of RNA (e.g., gene) expression in the sample.

Sequencing of the cDNA molecules enables determination of gene expression in the tissue sample, as cDNA is considered indicative of RNA expression in the tissue at the time it was isolated. Accordingly, determining the location within the tissue to which the sequence of the spatial barcode for the cDNA molecules corresponds allows for localized, spatial detection of RNA expression in the tissue sample. In some embodiments, the methods described herein have a high enough resolution to enable determination of gene expression in a single cell.

In some embodiments, the methods may further include analyzing the tissue sample for the presence of one or more additional targets, such as targets bound to the additional capture moieties on the substrate. For example, the methods may further include determining whether the tissue sample additionally contains one or more proteins of interest, which may be detected by an antibody conjugated capture moiety on the substrate. In some embodiments, the location of the additional capture moieties on the substrate may be known and thus used to determine the corresponding location of the additional target in the tissue sample. For example, the location of the additional capture moieties on the substrate may be known based upon the location of the cluster of capture probes in which the additional capture moieties are integrated.

In embodiments, generating a first sequencing read or a second sequencing read includes sequencing-by-binding (see, e.g., U.S. Pat. Pubs. US2017/0022553, US2019/0048404, and US2021/0373000, each of which is incorporated herein by reference in its entirety). As used herein, "sequencing-by-binding" refers to a sequencing technique wherein specific binding of a polymerase and cognate nucleotide to a primed template nucleic acid molecule (e.g., blocked primed template nucleic acid molecule) is used for identifying the next correct nucleotide to be incorporated into the primer strand of the primed template nucleic acid molecule. The specific binding interaction need not result in chemical incorporation of the nucleotide into the primer. In some embodiments, the specific binding interaction can precede chemical incorporation of the nucleotide into the primer strand or can precede chemical incorporation of an analogous, next correct nucleotide into the primer. Thus, detection of the next correct nucleotide can take place without incorporation of the next correct nucleotide. As used herein, the "next correct nucleotide" (sometimes referred to as the "cognate" nucleotide) is the nucleotide having a base complementary to the base of the next template nucleotide. The next correct nucleotide will hybridize at the 3'-end of a primer to complement the next template nucleotide. The next correct nucleotide can be, but need not necessarily be, capable of being incorporated at the 3' end of the primer. For example, the next correct nucleotide can be a member of a ternary complex that will complete an incorporation reaction or, alternatively, the next correct nucleotide can be a member of a stabilized ternary complex that does not catalyze an incorporation reaction. A nucleotide having a base that is not complementary to the next template base is referred to as an "incorrect" (or "non-cognate") nucleotide.

Flow cells provide a convenient format for housing an array of clusters produced by the methods described herein, in particular when subjected to an SBS or other detection technique that involves repeated delivery of reagents in cycles. For example, to initiate a first SBS cycle, one or more labeled nucleotides and a DNA polymerase in a buffer, can be flowed into/through a flow cell that houses an array of clusters. The clusters of an array where primer extension causes a labeled nucleotide to be incorporated can then be detected. Optionally, the nucleotides can further include a reversible termination moiety that temporarily halts further primer extension once a nucleotide has been added to a primer. For example, a nucleotide analog having a reversible terminator moiety can be added to a primer such that subsequent extension cannot occur until a deblocking agent (e.g., a reducing agent) is delivered to remove the moiety. Thus, for embodiments that use reversible termination, a deblocking reagent (e.g., a reducing agent) can be delivered to the flow cell (before, during, or after detection occurs). Washes can be carried out between the various delivery steps as needed. The cycle can then be repeated N times to extend the primer by N nucleotides, thereby detecting a sequence of length N. Example SBS procedures, fluidic systems and detection platforms that can be readily adapted for use with an array produced by the methods of the present disclosure are described, for example, in Bentley et al., Nature 456: 53-59 (2008), US Patent Publication 2018/0274024, WO 2017/205336, US Patent Publication 2018/0258472, each of which are incorporated herein in their entirety for all purposes.

Use of the sequencing method outlined above is a non-limiting example, as essentially any sequencing methodology which relies on successive incorporation of nucleotides into a polynucleotide chain can be used. Suitable alternative techniques include, for example, pyrosequencing methods, FISSEQ (fluorescent in situ sequencing), MPSS (massively parallel signature sequencing), or sequencing by ligation-based methods.

In embodiments, each particle core includes a silica, magnetic, or paramagnetic material, such as in the form of a bead or particle. For example, the particle shell layers may be formed around and encapsulating a supporting bead, for example, a silica, magnetic, or paramagnetic bead.

In embodiments, the particle is a functionalized particle including a particle core and a particle shell, wherein the particle shell includes the plurality of bioconjugate reactive moieties, the plurality of immobilized oligonucleotides, or a combination thereof, wherein each of the bioconjugate reactive moieties and each of the immobilized oligonucleotides include a linker binding the bioconjugate reactive moieties and oligonucleotide to the particle core. In embodiments, the functionalized particle is a silica particle.

In embodiments of the methods provided herein, the particle is a polymer particle. In embodiments of the methods provided herein, the particle is a functionalized particle including a particle core and a particle shell, wherein the particle shell includes the plurality of bioconjugate reactive moieties, the plurality of immobilized oligonucleotides, or a combination thereof, wherein each of the bioconjugate reactive moieties and each of the immobilized oligonucleotides include a linker binding the bioconjugate reactive moieties and oligonucleotide to the particle core.

In embodiments, arraying the particles includes contacting the surface with a first solution including the plurality of particles in an anti-solvent. In embodiments, the particle includes acrylamide and the anti-solvent is an aqueous ethanol solution. In embodiments, the particle includes sulfobetaine acrylate (SBA), carboxybetaine acrylate (CBA), phosphorylcholine acrylate (PCA), sulfobetaine methacrylate (SBMA), carboxybetaine methacrylate (CBMA), or phosphorylcholine methacrylate (PCMA) and the anti-solvent is an aqueous acetone solution. In embodiments, arraying the particles further includes removing the first solution and contacting the surface with a second solution, wherein the second solution is an aqueous solution capable of expanding the volume of the particle. In embodiments, the second solution includes water. In embodiments of the methods provided herein, the second solution expands the volume of the particles by up to 10%, up to 20%, up to 30%, up to 40%, up to 50%, up to 60%, up to 70%, up to 80%, up to 100%, up to 150%, up to 200%, or more relative to particle in an anti-solvent. In embodiments of the methods provided herein, the solvent expands the volume of the particles by 10-200%, 30-150%, or 50-100%, relative to particle in an anti-solvent. In embodiments of the methods provided herein, the presence of the solvent expands the volume of the particles by up to 90% relative to particle in an anti-solvent.

In embodiments, the polymers of the present disclosure (e.g., polymer particles,) swell with a solvent in which they are suspended, and the refractive index of the suspension is about the same as the solvent. In embodiments of the methods provided herein, the polymer particle or the shell polymer, have a refractive index of about 1.2-1.6, 1.25-1.5, or 1.3-1.4 when hydrated. In embodiments, the polymer particle or the shell polymer have a refractive index of about 1.3 when hydrated.

In an aspect, provided herein are methods of sequencing target polynucleotides, the methods including contacting a polymer particle with a sample that includes target polynucleotides, amplifying the target polynucleotides to produce discrete amplicon clusters, and sequencing the amplicon clusters. In embodiments, the polymer particle includes a polymer covalently attached to polynucleotide primers. In embodiments, amplifying the target includes extension of primers along the target polynucleotides within the polymer particle. In embodiments, each amplicon cluster originates from amplification of a single target polynucleotide. In embodiments, sequencing includes detecting sequences of signals within the polymer particle.

In embodiments of the methods provided herein, the target polynucleotides are at a concentration in the sample selected to produce amplicon clusters having a desired density. For example, the concentration of target polynucleotides is selected based on a calculation of (a) the average size of a cluster of amplicons that will result from amplification under selected conditions (e.g., a selected duration and number of extension steps), and (b) a desired separation between adjacent amplicon clusters in the array.

In embodiments of the methods provided herein, the amplicon clusters have a mean or median separation from one another of about 0.5-5 µm. In embodiments, the mean or median separation is about 0.1-10 microns, 0.25-5 microns, 0.5-2 microns, 1 micron, or a number or a range between any two of these values. In embodiments, the mean or median separation is about or at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 µm or a number or a range between any two of these values. The mean or median separation may be measured center-to-center (i.e., the center of one amplicon cluster to the center of a second amplicon cluster). In embodiments of the methods provided herein, the amplicon clusters have a mean or median separation (measured center-to-center) from one another of about 0.5-5 µm. The mean or median separation may be measured edge-to-edge (i.e., the edge of one amplicon cluster to the edge of a second amplicon cluster). In embodiments of the methods provided herein, the amplicon clusters have a mean or median separation (measured edge-to-edge) from one another of about 0.2-5 µm.

Neighboring features of an array can be discrete one from the other in that they do not overlap. Accordingly, the features can be adjacent to each other or separated by a gap (e.g., an interstitial space). In embodiments where features are spaced apart, neighboring sites can be separated, for example, by a distance of less than 10 µm, 5 µm, 1 µm, 0.9 µm, 0.8 m, 0.7 µm, 0.6 µm, 0.5 µm or less. The layout of features on an array can also be understood in terms of center-to-center distances between neighboring features. An array useful in the invention can have neighboring features with center-to-center spacing of less than about 10 µm, 5 µm, 1 µm, 0.9 µm, 0.8 µm, 0.7 µm, 0.6 µm, 0.5 µm or less. Furthermore, it will be understood that the distance values described above and elsewhere herein can represent an average distance between neighboring features of an array. As such, not all neighboring features need to fall in the specified range unless specifically indicated to the contrary, for example, by a specific statement that the distance constitutes a threshold distance between all neighboring features of an array.

In embodiments, each feature generated on the surface of an array can be of similar or smaller size than the area of the surface occupied by the particle from which the feature was produced, and all the features will typically be of similar size and intensity to each other. The uniform size, uniform intensity, and lack of overlap provides a convenient density of features per unit area. Detection of tightly packed non-overlapping arrays with features of uniform size and intensity are typically easier to analyze than images where a subset of the features overlap with each other.

In embodiments of the methods provided herein, the amplicon clusters have a mean or median diameter of about 100-2000 nm, or about 200-1000 nm. In embodiments, the mean or median diameter is about 100-3000 nanometers, about 500-2500 nanometers, about 1000-2000 nanometers, or a number or a range between any two of these values. In embodiments, the mean or median diameter is about or at most about 100, 200, 300, 400, 500, 600, 700, 800, 900, 1000, 1100, 1200, 1300, 1400, 1500, 1600, 1700, 1800, 1900, 2000 nanometers or a number or a range between any two of these values.

In embodiments, the arrays include about 10,000,000 features/cm$^2$ to about 5,000,000,000 features/cm$^2$. In embodiments, the arrays include about 100,000,000 features/cm$^2$ to about 1,000,000,000 features/cm$^2$. In embodiments, the arrays include about 100,000 features/cm$^2$ to about 100,000,000 features/cm$^2$. In embodiments, the arrays include about or about 10,000,000 features/cm$^2$ to about 50,000,000 features/cm$^2$.

In embodiments, the method does not include ligating an adapter to the target polynucleotide. The terms "ligating", "ligation" and their derivatives refer generally to the process for covalently linking two or more molecules together, for example covalently linking two or more nucleic acid molecules to each other. In some embodiments, ligation includes joining nicks between adjacent nucleotides of nucleic acids. In some embodiments, ligation includes forming a covalent bond between an end of a first and an end of a second nucleic acid molecule. In some embodiments, the ligation can include forming a covalent bond between a 5' phosphate group of one nucleic acid and a 3' hydroxyl group of a second nucleic acid thereby forming a ligated nucleic acid molecule.

In an aspect is provided a method of immobilizing a first oligonucleotide and a second oligonucleotide to a particle, the method including: i) annealing a first primer to the first oligonucleotide, wherein the first primer includes, from 5' to 3', a bioconjugate reactive moiety and a first primer binding sequence, and wherein the first oligonucleotide includes, from 3' to 5', a sequence complementary to the first primer binding sequence and a sequence capable of hybridizing to the complement of the first endogenous region of the target polynucleotide; ii) annealing a second primer to the second oligonucleotide, wherein the second primer includes, from 5' to 3', a bioconjugate reactive moiety and a second primer binding sequence, and wherein the second oligonucleotide includes, from 3' to 5', a sequence complementary to the second primer binding sequence and a sequence capable of hybridizing to the second region of the target polynucleotide; iii) extending the first and second primers with a polymerase to generate first and second extension products, thereby forming a first double-stranded oligonucleotide and a second double-stranded oligonucleotide; iv) contacting the bioconjugate moiety of the double-stranded oligonucleotides with a particle including one or more complementary bioconjugate moieties and forming a bioconjugate linker, thereby immobilizing the first oligonucleotide and the second oligonucleotide to the particle. In embodiments, the second primer includes, from 5' to 3', a bioconjugate reactive moiety and a second primer binding sequence, and wherein the second oligonucleotide includes, from 3' to 5', a sequence complementary to the second primer binding sequence and a sequence capable of hybridizing to the second endogenous region of the target polynucleotide. In embodiments, the method further comprises repeating steps i) to iv) for a third oligonucleotide and a fourth oligonucleotide, thereby immobilizing the third and fourth oligonucleotide to the particle. In embodiments, the method further comprises repeating steps i) to iv) for a fifth oligonucleotide and a sixth oligonucleotide, thereby immobilizing the fifth and sixth oligonucleotide to the particle. In embodiments, the method further comprises repeating steps i) to iv) for a seventh oligonucleotide and an eighth oligonucleotide, thereby immobilizing the seventh and eighth oligonucleotide to the particle. In embodiments, the method further comprises repeating steps i) to iv) for a ninth oligonucleotide and a tenth oligonucleotide, thereby immobilizing the ninth and tenth oligonucleotide to the particle. In embodiments, the method further comprises repeating steps i) to iv) for one or more pairs of oligonucleotides (e.g., one or more forward and reverse primers), thereby immobilizing the one or more pairs of oligonucleotides to the particle.

In embodiments, the method further includes contacting a solid support with the particle.

In some embodiments, the first oligonucleotide is about 5 to about 50 nucleotides in length. In some embodiments, the first oligonucleotide is about 5 to about 40 nucleotides in length. In some embodiments, the first oligonucleotide is about 10 to about 45 nucleotides in length. In some embodiments, the first oligonucleotide is about 15 to about 40 nucleotides in length. In some embodiments, the first oligonucleotide is about 20 to about 35 nucleotides in length. In some embodiments, the first oligonucleotide is about 20 to about 30 nucleotides in length. In some embodiments, the first oligonucleotide is about 25 to about 30 nucleotides in length. In some embodiments, the second oligonucleotide is about 5 to about 50 nucleotides in length. In some embodiments, the second oligonucleotide is about 5 to about 40 nucleotides in length. In some embodiments, the second oligonucleotide is about 10 to about 45 nucleotides in length. In some embodiments, the second oligonucleotide is about 15 to about 40 nucleotides in length. In some embodiments, the second oligonucleotide is about 20 to about 35 nucleotides in length. In some embodiments, the second oligonucleotide is about 20 to about 30 nucleotides in length. In some embodiments, the second oligonucleotide is about 25 to about 30 nucleotides in length.

In embodiments, the average longest dimension of the particle is from about 100 nm to about 3000 nm. In embodiments, the average longest dimension of the particle is from about 100 nm to about 1000 nm. In embodiments, the average longest dimension of the particle is from about 150 nm to about 600 nm. In some embodiments, the average longest dimension of the particle is from about 200 nm to about 1000 nm. In embodiments, the average longest dimension of the particle is from about 150 nm to about 600 nm. In some embodiments, the average longest dimension of the particle is from about 350 nm to about 600 nm. In some embodiments, the average longest dimension of the particle is from about 400 nm to about 500 nm. In some embodiments, the average longest dimension of the particle is from about 500 nm to about 1200 nm. In some embodiments, the average longest dimension of the particle is from about 1000 nm to about 1500 nm. In some embodiments, the average longest dimension of the particle is from about 1500 nm to about 2500 nm. In some embodiments, the average longest dimension of the particle is from about 2500 nm to about 3000 nm. In some embodiments, the average longest dimension of the particle is about 500 nm. In some embodiments, the average longest dimension of the particle is about 400 nm. In some embodiments, the average longest dimension of the particle is about 400 nm, 450 nm, 500 nm, or 550 nm. In embodiments, the average longest dimension of the particle is at least, about, or at most 100, 200, 300, 400, 500, 600, 700, 800, 900, 1000 nm or a number or a range between any two of these values. In embodiments, the average longest dimension of the particle is at least, about, or at most 1000, 1100, 1200, 1300, 1400, 1500, 1600, 1700, 1800, 1900, 2000, 2100, 2200, 2300, 2400, 2500, 2600, 2700, 2800, 2900, 3000 nm or a number or a range between any two of these values.

In embodiments, the particle includes a metal-organic framework (MOF) particle. In embodiments, the particle has a degradable particle core that includes a metal-organic framework (MOF) particle. In embodiments, the degradable particle core includes a polystyrene (PS) particle, or polymethyl methacrylate (PMMA) particle, or latex particle. In embodiments, the MOF particle is any metal-organic framework particle that can be degraded by a change in external conditions, including a change in pH, temperature, or other chemical degrading agent. In embodiments, the MOF particle is a Zeolitic Imidazolate Framework 8 (ZIF-8) particle. In embodiments, the MOF particle is UiO-66. In embodiments, the MOF particle is a Zr based MOFs, mesoporous iron (III) carboxylate MIL-100(Fe). In embodiments, the degrading the degradable particle core does not destroy or damage the oligonucleotide. In embodiments, the MOF particle is as described in Furukawa et al. (see Science, vol. 341, No. 6149, 1230444, 2013) or Cohen (see Chem. Reviews, Vol. 112, No. 2, p. 970-1000, 2012).

In embodiments, the first oligonucleotide is a single-stranded nucleic acid. In embodiments, the second oligonucleotide is a single-stranded nucleic acid. In embodiments, each immobilized oligonucleotide is a single-stranded nucleic acid.

In an aspect is provided, a method of sequencing two or more RNA molecules (i.e., target polynucleotides), the method including: a) contacting the array as described herein with a sample including a plurality of RNA molecules (e.g., a sample including a plurality of different RNA molecules); and b) immobilizing the plurality of RNA molecules (e.g., hybridizing the plurality of RNA molecules to a first plurality of immobilized oligonucleotides and extending the immobilized oligonucleotides with a reverse transcriptase), thereby generating a plurality of immobilized complements of the plurality of RNA molecules. In embodiments, the method further includes: c) annealing the immobilized complements of the plurality of RNA molecules to a second plurality of immobilized oligonucleotides; and d) extending the second plurality of immobilized oligonucleotides with a DNA polymerase thereby generating a plurality of immobilized target polynucleotides. In embodiments, the method further includes further includes repeating steps a) to d), thereby amplifying the plurality of RNA molecules. In embodiments, the method further includes contacting the immobilized polynucleotides with a sequencing primer, extending the sequencing primer to incorporate a detectable label that indicates the identity of a nucleotide in the target polynucleotides, detecting the detectable label, and repeating the extending and detecting steps, thereby sequencing the two or more RNA molecules.

In an aspect is provided, a method of sequencing two or more cfDNA molecules (i.e., target polynucleotides), the method including: a) contacting the array as described herein with a sample including a plurality of cfDNA molecules (e.g., a sample including a plurality of different cfDNA molecules); and b) immobilizing the plurality of cfDNA molecules (e.g., hybridizing the plurality of cfDNA molecules to a first plurality of immobilized oligonucleotides and extending the immobilized oligonucleotides), thereby generating a plurality of immobilized complements of the plurality of cfDNA molecules. In embodiments, the method further includes: c) annealing the immobilized complements to a second plurality of immobilized oligonucleotides; and d) extending the second plurality of immobilized oligonucleotides thereby generating a plurality of immobilized target polynucleotides. In embodiments, the method further includes further includes repeating steps a) to d), thereby amplifying the plurality of cfDNA molecules. In embodiments, the method further includes contacting the immobilized polynucleotides with a sequencing primer, extending the sequencing primer to incorporate a detectable label that indicates the identity of a nucleotide in the target polynucleotides, detecting the detectable label, and repeating the extending and detecting steps, thereby sequencing the two or more cfDNA molecules.

In an aspect is provided, a method of sequencing two or more V, D, and/or J segment DNA molecules (i.e., target polynucleotides), the method including: a) contacting the array as described herein with a sample including a plurality of V, D, and/or J segment DNA molecules (e.g., a sample including a plurality of different V, D, and/or J segment DNA molecules); and b) immobilizing the plurality of V, D, and/or J segment DNA molecules (e.g., hybridizing the plurality of V, D, and/or J segment DNA molecules to a first plurality of immobilized oligonucleotides and extending the immobilized oligonucleotides), thereby generating a plurality of immobilized complement polynucleotides. In embodiments, the method further includes: c) annealing the plurality of immobilized complements to a second plurality of immobilized oligonucleotides; and d) extending the second plurality of immobilized oligonucleotides thereby generating a plurality of immobilized target polynucleotides. In embodiments, the method further includes further includes repeating steps a) to d), thereby amplifying the plurality of V, D, and/or J segment DNA molecules. In embodiments, the method further includes contacting the immobilized polynucleotides with a sequencing primer, extending the sequencing primer to incorporate a detectable label that indicates the identity of a nucleotide in the target polynucleotides, detecting the detectable label, and repeating the extending and detecting steps, thereby sequencing the two or more V, D, and/or J segment DNA molecules.

In an aspect is provided a method of generating immobilized complements of a plurality of target polynucleotides, the method including: a) contacting a solid support as described herein and in embodiments with a sample including a plurality of target polynucleotides and annealing two or more target polynucleotides to the first plurality of immobilized oligonucleotides; and b) extending the immobilized oligonucleotides with a polymerase to generate a plurality of immobilized complements of the plurality of target polynucleotides. In embodiments, the method further includes c) annealing the immobilized complements of the target polynucleotides to the second plurality of immobilized oligonucleotides; and d) extending the second plurality of immobilized oligonucleotides thereby generating a plurality of immobilized target polynucleotides. In embodiments, the method further includes repeating steps a) to d), thereby amplifying the plurality of target polynucleotides.

In an aspect is provided a method of detecting cancer in a sample. In embodiments, the method includes contacting the array as described herein with a sample including a plurality of polynucleotides and immobilizing the plurality of polynucleotides (e.g., hybridizing the plurality of polynucleotide molecules to a first plurality of immobilized oligonucleotides and extending the immobilized oligonucleotides), thereby generating a plurality of immobilized complements of the plurality of polynucleotide molecules. In embodiments, the method includes amplifying and sequencing the polynucleotides, and detecting cancer when one or more of the polynucleotides includes a cancer-associated gene or cancer-associated biomarker.

In embodiments, the method further includes: c) annealing the immobilized complements to a second plurality of immobilized oligonucleotides; and d) extending the second plurality of immobilized oligonucleotides thereby generating a plurality of immobilized target polynucleotides. In embodiments, the method further includes further includes repeating steps a) to d), thereby amplifying the plurality of molecules. In embodiments, the method further includes contacting the immobilized polynucleotides with a sequencing primer, extending the sequencing primer to incorporate a detectable label that indicates the identity of a nucleotide in the target polynucleotides, detecting the detectable label, and repeating the extending and detecting steps, thereby sequencing the molecules.

A sample may include material obtained from cells or tissues that are normal, healthy, diseased (e.g., infected), and/or cancerous (e.g., cancer cells). A sample obtained from a subject may include cells or cellular material (e.g., nucleic acids) of multiple organisms (e.g., virus nucleic acid, fetal nucleic acid, bacterial nucleic acid, parasite nucleic acid).

In embodiments, the sample includes a cancer-associated gene (e.g., an oncogene associated with kinases and genes involved in DNA repair) or a cancer-associated biomarker. A "biomarker" is a substance that is associated with a particular characteristic, such as a disease or condition. A change in the levels of a biomarker may correlate with the risk or progression of a disease or with the susceptibility of the disease to a given treatment. In embodiments, the cancer is Acute Myeloid Leukemia, Adrenocortical Carcinoma, Bladder Urothelial Carcinoma, Breast Ductal Carcinoma, Breast Lobular Carcinoma, Cervical Carcinoma, Cholangiocarcinoma, Colorectal Adenocarcinoma, Esophageal Carcinoma, Gastric Adenocarcinoma, Glioblastoma Multiforme, Head and Neck Squamous Cell Carcinoma, Hepatocellular Carcinoma, Kidney Chromophobe Carcinoma, Kidney Clear Cell Carcinoma, Kidney Papillary Cell Carcinoma, Lower Grade Glioma, Lung Adenocarcinoma, Lung Squamous Cell Carcinoma, Mesothelioma, Ovarian Serous Adenocarcinoma, Pancreatic Ductal Adenocarcinoma, Paraganglioma & Pheochromocytoma, Prostate Adenocarcinoma, Sarcoma, Skin Cutaneous Melanoma, Testicular Germ Cell Cancer, Thymoma, Thyroid Papillary Carcinoma, Uterine Carcinosarcoma, Uterine Corpus Endometrioid Carcinoma, or Uveal Melanoma. In embodiments, the cancer-associated gene is a nucleic acid sequence identified within The Cancer Genome Atlas Program, accessible at www.cancer.gov/tcga.

In embodiments, the cancer-associated biomarker is a gene selected from the following: MDC, NME-2, KGF, P1GF, Flt-3L, HGF, MCP1, SAT-1, MIP-1-b, GCLM, OPG, TNF RII, VEGF-D, ITAC, MMP-10, GPI, PPP2R4, AKR1B1, AmylA, MIP-1b, P-Cadherin, or EPO. In embodiments, the cancer-associated gene is a AKT1, AKT2, AKT3, ALK, AR, ARAF, ARID1A, ATM, ATR, ATRX, AXL, BAP1, BRAF, BRCA1, BRCA2, BTK, CBL, CCND1, CCND2, CCND3, CCNE1, CDK12, CDK2, CDK4, CDK6, CDKN1B, CDKN2A, CDKN2B, CHEK1, CHEK2, CREBBP, CSF1R, CTNNB1, DDR2, EGFR, ERBB2, ERBB3, ERBB4, ERCC2, ERG, ESR1, ETV1, ETV4, ETV5, EZH2, FANCA, FANCD2, FANCI, FBXW7, FGF19, FGF3, FGFR1, FGFR2, FGFR3, FGFR4, FGR, FLT3, FOXL2, GATA2, GNA11, GNAQ, GNAS, H3F3A, HIST1H3B, HNF1A, HRAS, IDH1, IDH2, IGF1R, JAK1, JAK2, JAK3, KDR, KIT, KNSTRN, KRAS, MAGOH, MAP2K1, MAP2K2, MAP2K4, MAPK1, MAX, MDM2, MDM4, MED12, MET, MLH1, MRE11A, MSH2, MSH6, MTOR, MYB, MYBL1, MYC, MYCL, MYCN, MYD88, NBN, NF1, NF2, NFE2L2, NOTCH1, NOTCH2, NOTCH3, NOTCH4, NRAS, NRG1, NTRK1, NTRK2, NTRK3, NUTM1, PALB2, PDGFRA, PDGFRB, PIK3CA, PIK3CB, PIK3R1, PMS2, POLE, PPARG, PPP2R1A, PRKACA, PRKACB, PTCH1, PTEN, PTPN11, RAC1, RAD50, RAD51, RAD51B, RAD51C, RAD51D, RAF1, RB1, RELA, RET, RHEB, RHOA, RICTOR, RNF43, ROS1, RSPO2, RSPO3, SETD2, SF3B1, SLX4, SMAD4, SMARCA4, SMARCB1, SMO, SPOP, SRC, STAT3, STK11, TERT, TOP1, TP53, TSC1, TSC2, U2AF1, or XPO1 gene. In embodiments, the cancer-associated gene is a ABL1, AKT1, ALK, APC, ATM, BRAF, CDH1, CDKN2A, CSF1R, CTNNB1, EGFR, ERBB2, ERBB4, EZH2, FBXW7, FGFR1, FGFR2, FGFR3, FLT3, GNA11, GNAQ, GNAS, HNF1A, HRAS, IDH1, IDH2, JAK2, JAK3, KDR, KIT, KRAS, MET, MLH1, MPL, NOTCH1, NPM1, NRAS, PDGFRA, PIK3CA, PTEN, PTPN11, RB1, RET, SMAD4, SMARCB1, SMO, SRC, STK11, TP53, or VHL gene.

In embodiments, the cancer is a lymphoid hematological malignancy, wherein the lymphoid hematological malignancy is acute T-cell lymphoblastic leukemia (T-ALL), acute B-cell lymphoblastic leukemia (B-ALL), multiple myeloma, plasmacytoma, macroglobulinemia, chronic lymphocytic leukemia (CLL), acute lymphoblastic leukemia (ALL), Hodgkins lymphoma, non-Hodgkins lymphoma, cutaneous T-cell lymphoma, mantle cell lymphoma, peripheral T-cell lymphoma, hairy cell leukemia, T prolymphocytic lymphoma, angioimmunoblastic T-cell lymphoma, T lymphoblastic leukemia/lymphoma, peripheral T-cell lymphoma, adult T cell leukemia/lymphoma, mycosis fungoides, Sezary syndrome, T lymphoblastic leukemia, myeloproliferative neoplasm, and myelodysplastic syndrome.

In embodiments, the gene is associated with a pediatric cancer. In embodiments, the gene is associated with an adult cancer. In embodiments, the gene is associated with cancer in an animal (e.g., a mammal). In embodiments, the cancer is a pilocytic astrocytoma, Ewing sarcoma, supratentorial ependymoma, infantile fibrosarcoma, cholangiocarcinoma, infantile spindle cell sarcoma, infiltrating glioma, ganglioglioma, or acute lymphocytic leukemia.

As used herein, the term "cancer" refers to all types of cancer, neoplasm or malignant tumors found in mammals, including leukemia, carcinomas and sarcomas. Exemplary cancers that may be detected with a method provided herein include cancer of the thyroid, endocrine system, brain, breast, cervix, colon, head & neck, liver, kidney, lung, non-small cell lung, melanoma, mesothelioma, ovary, pancreas, sarcoma, stomach, uterus or Medulloblastoma. Additional examples include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be detected with a method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be detected with a method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be detected with a method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be detected with a method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatinifori carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

The term "aberrant" as used herein refers to different from normal. When used to described enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound), results in reduction of the disease or one or more disease symptoms.

EXAMPLES

Example 1. NIPT Chromosome Counting

Non-invasive prenatal testing (NIPT), for example, trisomy detection, relies on the accurate representation of genetic material originating on a chromosome compared to genetic material originating from other chromosomes. In prenatal care, cell-free DNA (cfDNA) of fetal origin obtained from maternal blood is used to detect fetal aneuploidies as early as the 10th week of gestation (Norton M E et al. N. Engl. J. Med. 2015; 372:1589-97). Typical single-gene NIPT analyses recover the dosage of pathogenic alleles, the fraction of cfDNA isolated from maternal blood that is of fetal origin, the number of DNA molecules assayed, and paternal inheritance of variants not found in the mother's genotype (Tsao D S et al. Scientific Reports 2019; 9: 14382). Whole-genome sequencing of fetal cfDNA fragments has been demonstrated to be efficacious in detecting fetal aneuploidy for multiple chromosomes across the genome, with high sensitivity and specificity for the detection of trisomies 21, 18, 13, and monosomy X (Bianchi D W et al. Obstetrics & Gynecology 2012; 119(5): 890-901). These non-invasive prenatal tests (NIPT) are routinely used in clinical care and are also covered by health insurance (van Schendel R V et al. BMC Health Services Research 2017; 17:670).

NIPT routinely infers copy number alterations (CNAs) through routine shallow-depth whole-genome sequencing (sWGS) data (0.1× to 1× coverage) (Raman L et al. Nucleic Acids Research 2018; 47(4): 1605-14). Studies into the influence of read counts on CNA prediction accuracy have found that higher number of reads allow for further increasing of accuracy, with some sources recommending the use of approximately 16M-17M reads for analyses (i.e., 0.35× genome coverage for 2×35 bp reads), due to the fact that the detection rate reaches a plateau for a 10% fetal fraction and >3 Mb deletion sizes, which is the average fetal fraction in pregnant women in the most relevant weeks of pregnancy for NIPT (Kucharik M et al. PLoS ONE 2020; 15(8): e0238245). Using more reads may be beneficial, especially for small deletions and in circumstances where there is a low fetal fraction and low read counts may prevent accurate detection events. In addition to low read counts, sample loss during typical NGS library preparation can further impact detection rates, especially where there is a low fetal fraction.

Before a target nucleic acid is sequenced, some degree of DNA pre-processing into a library is typically required. For example, these steps may involve fragmenting input polynucleotides into an appropriate platform-specific size range, followed by an end-polishing step to generate blunt ended DNA fragments. Specific adapters are then ligated to these fragments. A functional library typically includes having specific adapter sequences (e.g., P5 and or P7 adapters, or complements thereof) added to the 3' and 5' ends of the target polynucleotide to ensure compatibility with the underlying flow cell, so it may be amplified appropriately. PCR is often used to overcome sample loss during the library prep process, but this can lead to underrepresentation of low abundance targets in the final analysis. Prior to this disclosure, adapter ligation has been a critical step in the library prep workflow, where poor ligation efficiency across nucleic acid species dramatically skews sequencing results. Some commercial library prep kits have been reported to have very low (<15%) ligation efficiency, while different kits were found to have high sample loss during preparation (>50%) (see, e.g., Aigrain L et al. BMC Genomics. 2016; 17:458, which is incorporated herein by reference in its entirety). Commercial library prep kits for targeted sequencing have also displayed significant variability with regards to library complexity, coverage uniformity, and errors in the UMIs (see, e.g., Chung J et al. BMC Genomics. 2019; 20(1); 216, which is hereby incorporated by reference in its entirety). Targeted NIPT would therefore benefit, both in data quality and for the user experience, from a sequencing workflow that did not require the extensive library prep that existing commercial kits offer.

Figure 3A:
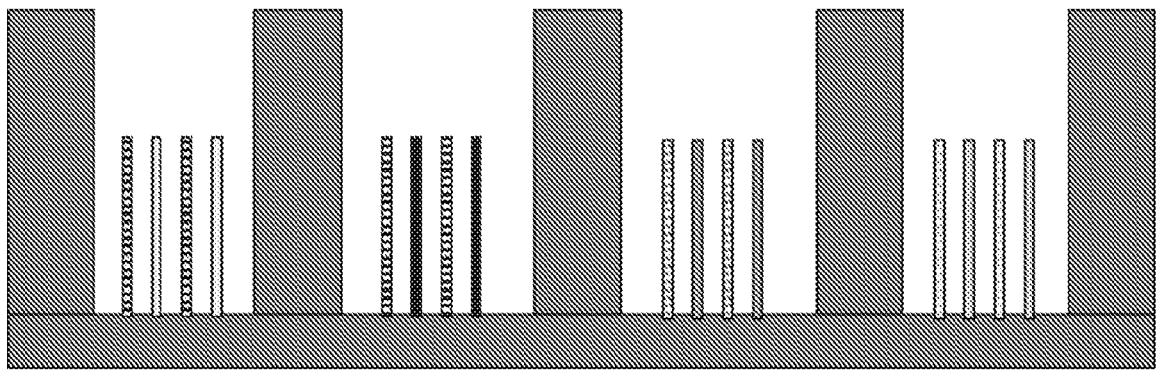
FIGS. 3A-3B illustrate different embodiments of the array.
Figure 3B:
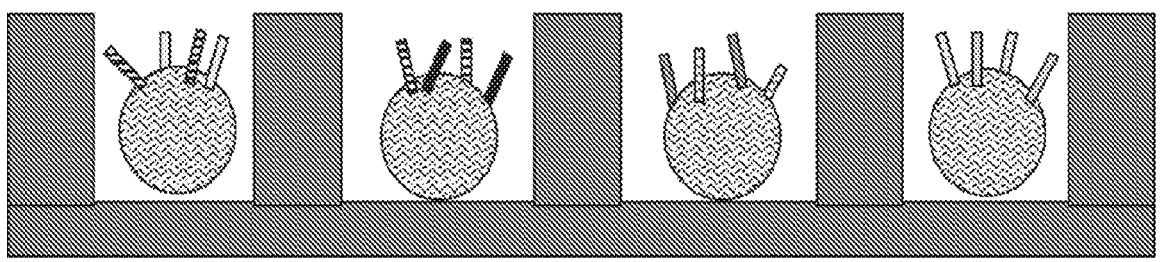
Figure 4:
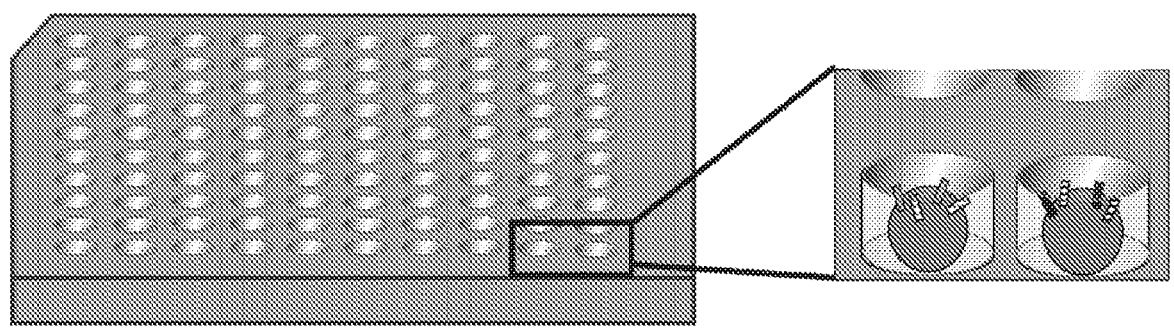
FIG. 4 illustrates an embodiment of the array, wherein the set of immobilized oligonucleotides are immobilized to particles, wherein at least one particle occupies a feature in an individual well of the array. Each well contains different sets of primers, such that each feature is capable of capturing different target polynucleotides from a sample containing a plurality of different target sequences.
Figure 5A:
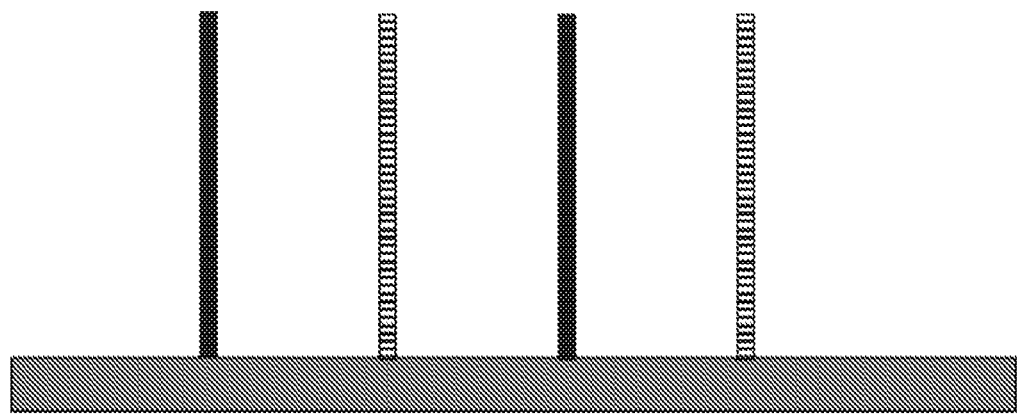
FIGS. 5A-5C provide a detailed view of three different configurations of primers for one feature. For example, each feature may include a plurality of all targeted capture primers (FIG. 5A). Alternatively, the immobilized oligonucleotides may include a primer binding sequence (PB1 or PB2) in addition to the target capture sequence (TC or TC') as shown in FIG. 5B.
Figure 5B:
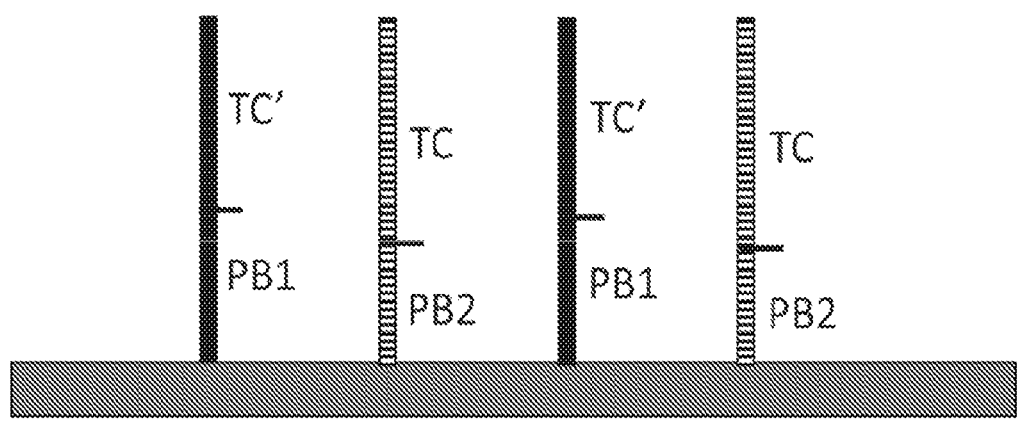
Figure 5C:
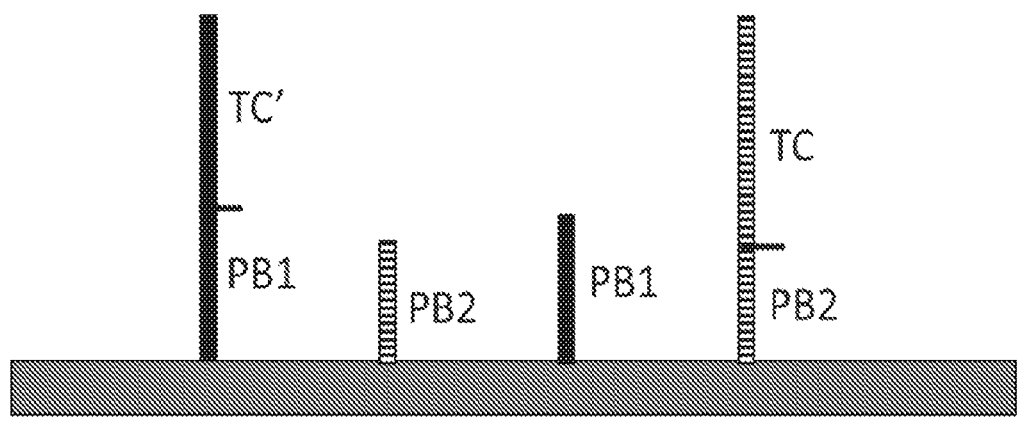

Described herein is a method of targeted nucleic acid sequencing that reduces sample loss by bypassing the typical library preparation workflow prior to hybridization of polynucleotide fragments to an array. An additional advantage of this method is normalization of a multiplexed sample, i.e., the simultaneous detection of low abundance targets along with high abundance targets. For example, an array of features is provided (see, FIG. 1), wherein within each feature there is a plurality of a first type of immobilized oligonucleotide (solid bar) and a plurality of a second type of immobilized oligonucleotide (striped bar), collectively referred to as a set of primers. The array may be a patterned array, wherein the set of immobilized oligonucleotides occupy distinct feature surrounded by interstitial regions of the surface (e.g., a well) (see, FIG. 3A). Alternatively, the array may be a patterned array of particles, wherein the set of immobilized oligonucleotides are immobilized to particles, wherein one particle occupies a feature (see, FIG. 3B). The particles may be localized in an individual well of an array, wherein each well containing a distinct set of immobilized oligonucleotides (see, FIG. 4). For example, each feature may include a plurality of all targeted capture primers (FIG. 5A). Alternatively, the immobilized oligonucleotides may include a primer binding sequence (PB1 or PB2) in addition to the target capture sequence (TC or TC') as shown in FIG. 5B. FIG. 5C depicts a feature containing immobilized oligonucleotide that includes a first type of immobilized oligonucleotide that includes a primer binding sequence (e.g., PB1) along with a complementary target capture sequence (TC'), a second type of immobilized oligonucleotides that includes a second primer binding sequence (PB2) and a sequence homologous to a sequence of the target fragment, and also includes additional immobilized oligonucleotide binding sequences (e.g., PB1 and PB2).

Figure 6A:
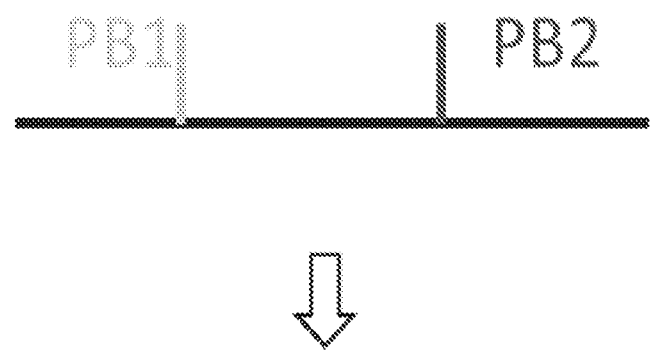
FIGS. 6A-6B illustrate an embodiment of assembling a target capture feature. For clarity only a subset of immobilized oligonucleotides are shown, however it is understood that a plurality of immobilized oligonucleotides are present.
Figure 6A:
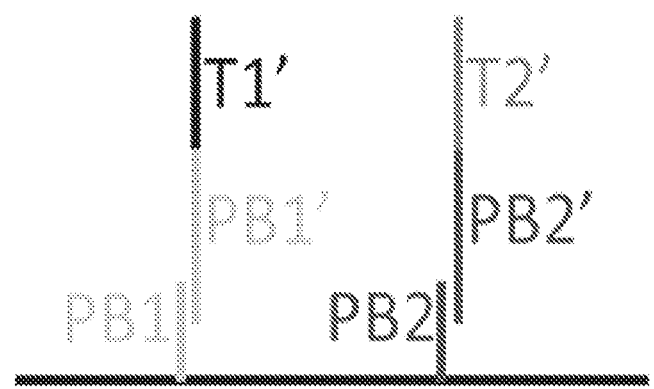
Figure 6B:
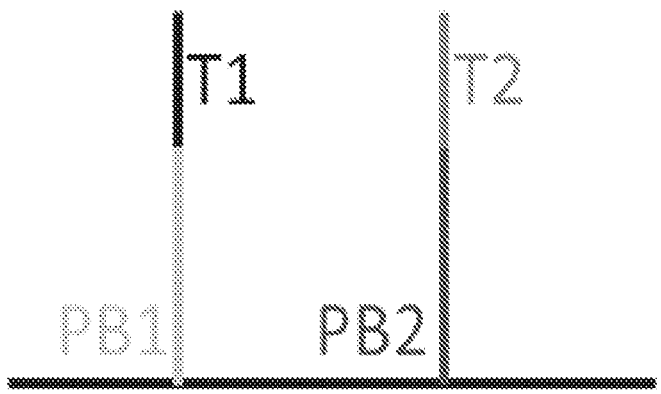

Prior to applying a sample to the array, the immobilized target capture features may be assembled, for example, to attach target capture primers to the primer binding sites. In some embodiments, immobilized target capture features including a primer binding sequence and a target capture sequence are synthesized and attached directly to the array surface using known methods in the art (e.g., conjugation between a first bioconjugate reactive group and a second bioconjugate reactive group). FIG. 6A depicts a first immobilized oligonucleotide (PB1) and a second immobilized oligonucleotide (PB2). A first oligo containing a target capture sequence (i.e., a sequence complementary to a target, T1') and a region of complementarity to the first immobilized oligonucleotide (PB1') is allowed to contact the immobilized oligonucleotides. Similarly, a second oligo containing a target capture sequence (i.e., a sequence complementary to a target, T2') and a region of complementarity to the second immobilized oligonucleotide (PB2') is brought into contact with the immobilized oligonucleotides. A polymerase (not shown) extends the first and second immobilized oligonucleotide to generate immobilized oligonucleotides (FIG. 6B). For example, following primer extension the first immobilized oligonucleotide contains a first primer binding sequence (PB1) and a target sequence (T1) and the second immobilized oligonucleotide contains a second primer binding sequence (PB2) and a different target sequence (T2). The primer binding sequences each independently include a complementary sequence to one or more primers (e.g., an amplification primer, a sequencing primer, or both).

Figure 10A:
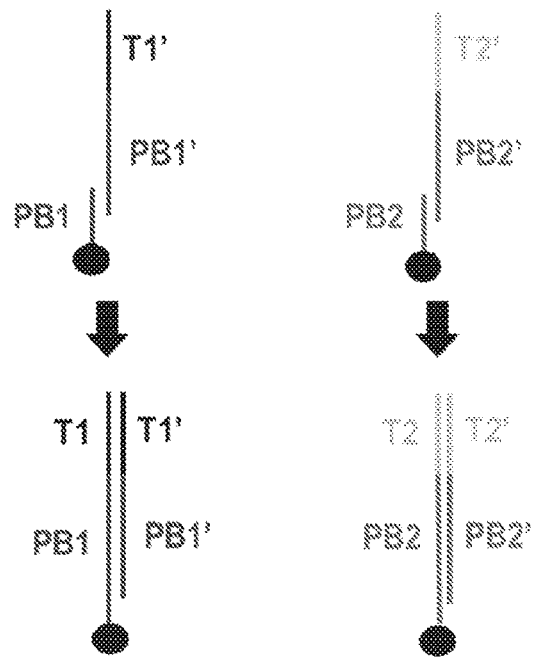
FIGS. 10A-10B illustrate an alternate embodiment of assembling a target capture feature. For clarity only a subset of oligonucleotides are shown, however it is understood that a plurality of oligonucleotides are present.
Figure 10B:
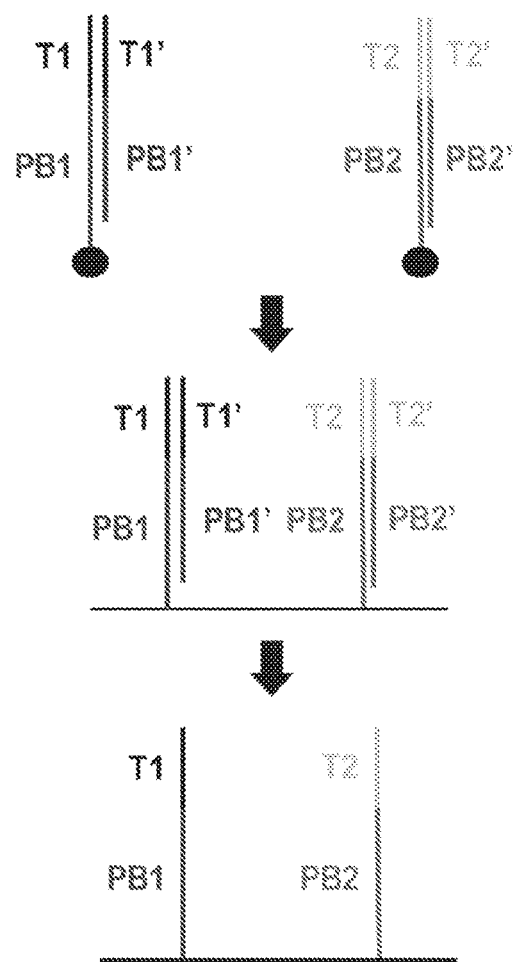

An alternate embodiment of assembling a target capture feature is illustrated in FIGS. 10A-10B. In some embodiments, target capture features including a primer binding sequence and a target capture sequence are generated away from the array surface and attached directly to the array surface in double-stranded form using known methods in the art (e.g., conjugation between a first bioconjugate reactive group and a second bioconjugate reactive group). FIG. 10A depicts a first oligonucleotide (PB1) and a second oligonucleotide (PB2), wherein each oligonucleotide is labeled on the 5' end with a bioconjugate reactive moiety (e.g., a dibenzocyclooctyne (DBCO) moiety), depicted as a sphere. A first oligo containing a target capture sequence (i.e., a sequence complementary to a target, T1') and a region of complementarity to the first labeled oligonucleotide (PB1') is allowed to contact the labeled oligonucleotide. Similarly, a second oligo containing a target capture sequence (i.e., a sequence complementary to a target, T2') and a region of complementarity to the second labeled oligonucleotide (PB2') is brought into contact with the labeled oligonucleotide. A polymerase (not shown) extends the first and second labeled oligonucleotides to generate double-stranded labeled oligonucleotides. For example, following primer extension the first labeled oligonucleotide contains a first primer binding sequence (PB1) and a target sequence (T1) and the second labeled oligonucleotide contains a second primer binding sequence (PB2) and a different target sequence (T2). The primer binding sequences each independently include a complementary sequence to one or more primers (e.g., an amplification primer, a sequencing primer, or both). Subsequently, the double-stranded oligonucleotides are covalently linked to a surface, as shown in FIG. 10B. Following surface deposition, chemical and/or heat denaturation is applied to release the non-immobilized strand, leaving behind the immobilized target capture features.

In contrast to existing methods of making oligonucleotide-conjugated arrays, the particles of the invention may be prepared away from the array surface (i.e., the surface of the solid support), mixed and/or pooled, yielding increased flexibility in the diversity of immobilized capture oligonucleotides that may be applied to the wells of an array. Typically, an array is coated with a lawn of immobilized oligonucleotides which may be amplified to generate target-specific capture probes, or the immobilized oligonucleotides may be provided to the array already including target-specific sequences. For example, U.S. Patent Application No. US2011/0172119 describes a method of selectively amplifying template polynucleotides on a solid support, which leads to a solid support with an identical set of capture polynucleotides. As described herein, the particles may be prepared with oligonucleotides specific for a set of different targets, and then an array including a plurality of the particles may be assembled. Providing flexibility in the diversity and production of the target polynucleotides present in an array allows for greater support of multiplex sequencing and targeting of greater numbers of specific template polynucleotide regions.

Figure 1B:
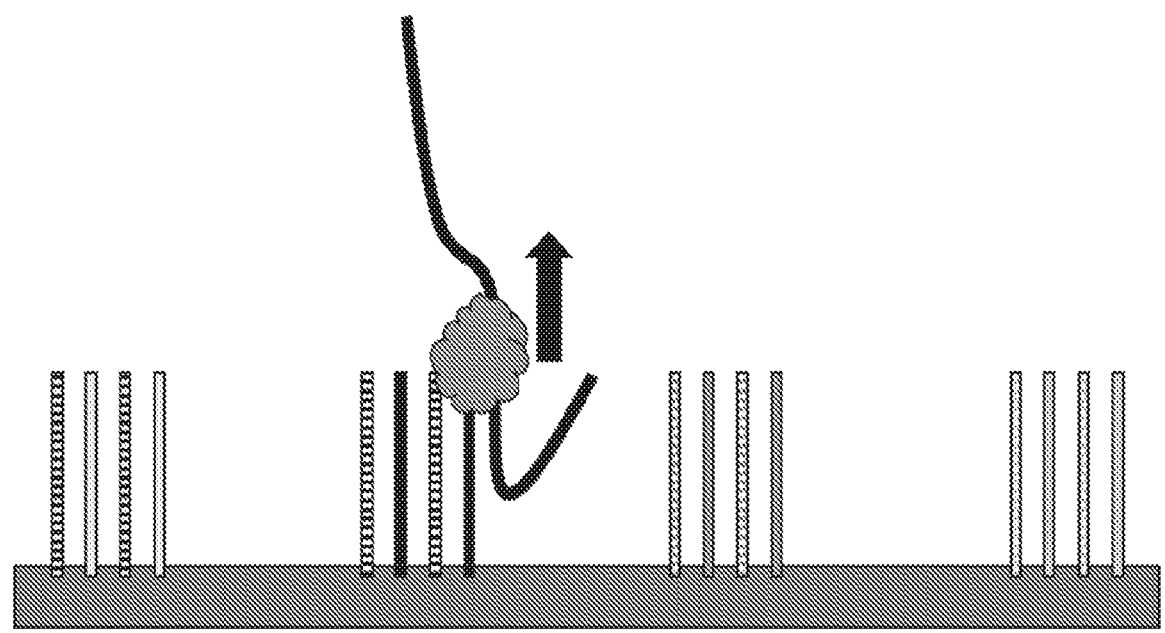
Figure 2A:
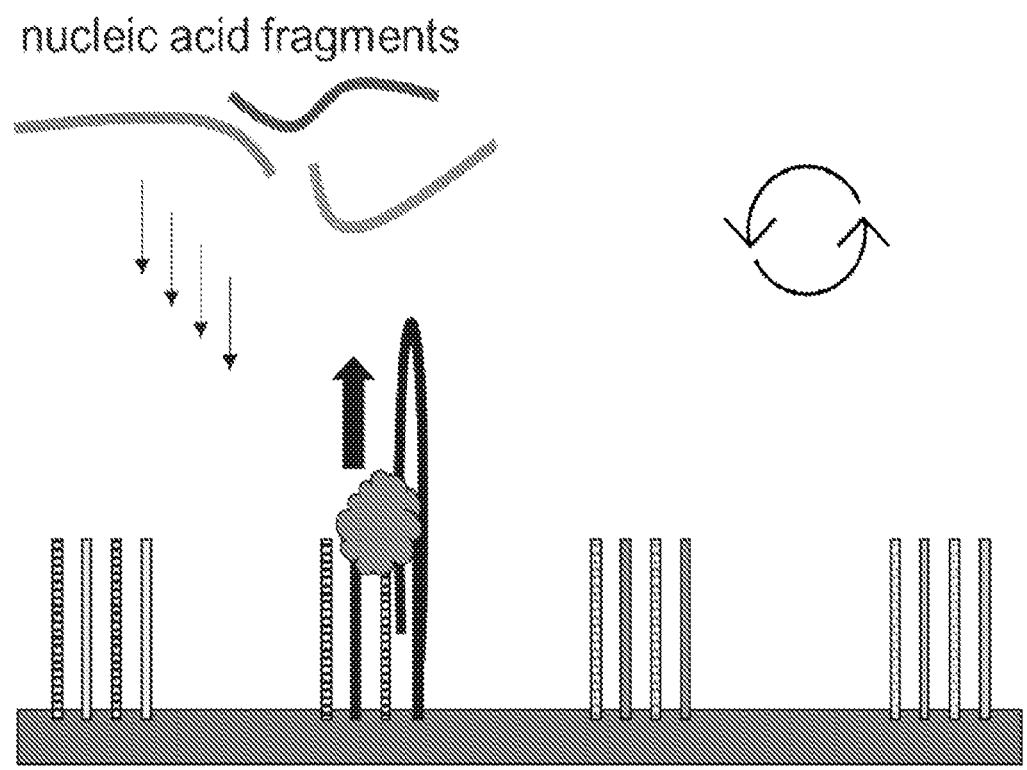
FIGS. 2A-2B depict an illustration of a bridge PCR amplification cycle, where the immobilized extended complement hybridizes to the second type of immobilized oligonucleotide within the same feature and in the presence of a polymerase (depicted as the squishy cloud in FIG. 2A) and nucleotides the second type of immobilized oligonucleotide is extended to generate an immobilized portion of the captured fragment. The process is repeated, that is, under suitable conditions allowing multiple polynucleotide fragments to hybridize to a complementary sequence within a feature, and extending to generate a copies of the captured fragment and complements thereof. Following a plurality of bridge PCR amplification cycles, each feature that captured a polynucleotide includes a cluster of polynucleotides, as illustrated in FIG. 2B.
Figure 2B:
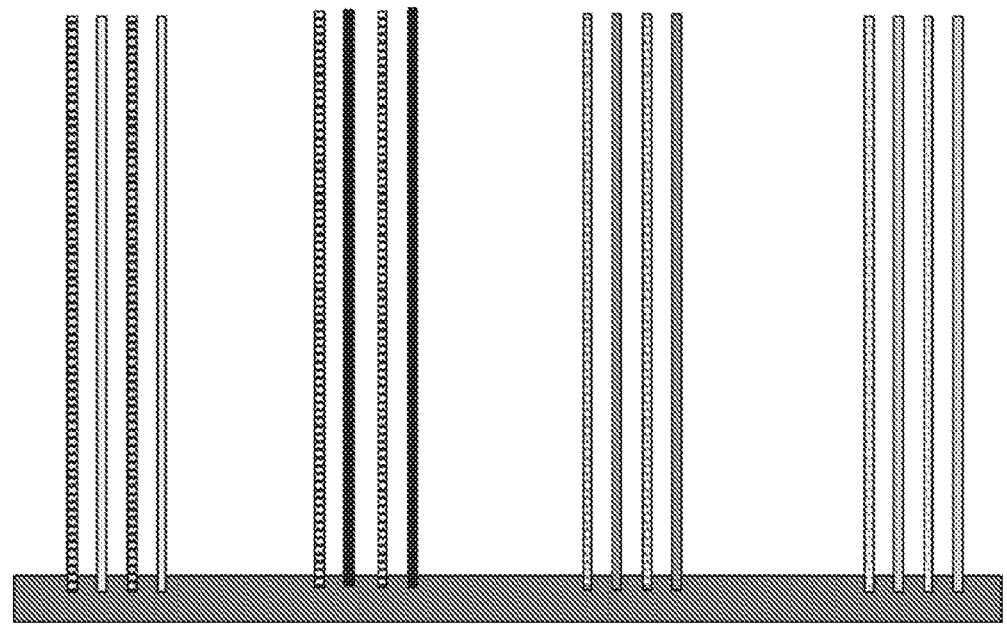

A fetal fraction sample including a plurality of nucleic acid fragments is applied to the array, wherein one primer type is complementary to a first sequence of the nucleic acid fragment, whereas the second primer type is homologous to a second sequence of the fragment, indicated in the figure as different color/textures (see, FIG. 1). Each feature on the array can include a different set of primers. Polynucleotide fragments are allowed to contact the array. If the fragment includes a complementary region to one of the immobilized oligonucleotides in the set, it is captured by hybridization to the first type of immobilized oligonucleotide under suitable conditions. In the presence of a polymerase and nucleotides, the immobilized oligonucleotide is extended to generate a complement of a portion of the captured fragment.

Following hybridization and immobilization of the targeted panel of nucleic acid fragments, bridge PCR (bPCR) amplification is performed (see, FIG. 2 and FIGS. 7A-7E). During the bPCR cycle, the immobilized extended complement hybridizes to the second type of immobilized oligonucleotide within the same feature and in the presence of a polymerase (depicted as the cloud) and nucleotides the second type of immobilized oligonucleotide is extended to generate an immobilized portion of the captured fragment. The process is repeated, that is, under suitable conditions allowing multiple polynucleotide fragments to hybridize to a complementary sequence within a feature and extended to generate copies of the captured fragment and complements thereof. Following a plurality of bridge PCR amplification cycles, each feature that captured a polynucleotide includes a cluster of polynucleotides. The cluster of polynucleotides can then be subjected to sequencing, for example, sequencing-by-synthesis. A plurality of sequencing cycles then occur, wherein each cycle includes extension and detection of an incorporated nucleotide. The entire array may be selectively sequenced by choosing the appropriate initiator, i.e., the appropriate sequencing primer.

Example 2. Multiplexed RNA-Seq

Sequencing RNA (e.g., mRNA, rRNA, and tRNA) allows for transcriptome investigation and discovery, and provides useful insight informing scientists which genes are turned on in a cell, what their level of expression is, and at what times they are activated or shut off. Methods for sequencing of RNA are known in the art. RNA sequencing (RNA-seq) uses massively parallel sequencing to allow, for example, transcriptome analyses of genomes at a far higher resolution than is available with Sanger sequencing- and microarray-based methods. In RNA-seq methods, complementary DNAs (cDNAs) and copies of cDNAs generated from the RNA of interest are directly sequenced using next-generation sequencing technologies. RNA-seq has been used successfully to precisely quantify transcript levels, confirm, or revise previously annotated 5' and 3' ends of genes, and map exon/intron boundaries (Eminaga S et al., Curr. Protoc. in Mol. Biol., 2013, 103:4.17.1-4.17.14). RNA-seq has been widely applied to both well-studied model organisms and non-model organisms, to provide information on transcript profile of organisms, and to give important insights into biological processes. For organisms with known reference genomes, researchers usually take advantage of a mapping-first strategy to analyze transcriptome data. However, a mapping-first strategy is not suitable when reference sequence is not available or incomplete. Thus, for organisms with un-sequenced genome or cancer cells with widespread chimeric RNAs (Kannan K et al. Proc. Natl. Acad. Sci. U.S.A., 2011, 108(22):9172-77, and Maher C A et al. Nature, 2009, 458(7234):97-101), de novo assembly is essential to provide a workable solution for transcriptome analysis. With optimized transcriptome assembly methods, de novo assembly of short sequence reads into transcripts allows researchers to reconstruct the sequences of a full transcriptome, identify and catalog all expressed genes, separate isoforms, and capture the expression levels of transcripts (Zhao Q Y et al. BMC Bioinformatics, 2011, 12:S2).

Preparing a library for RNA-seq can introduce various means for reducing signal quality and bias, including low input amounts and differentially expressed transcripts, and gene length (see, e.g., Mandelboum S et al. PLoS Biol. 2019; 17(11): e3000481). Comparison of various commercial RNA-Seq library prep methods have highlighted the difference in quality of libraryies produced by different RNA input amounts, specifically when performing differential expression analysis (see, e.g., Sarantopoulou D et al. Scientific Reports. 2019; 9:13477, which is herein incorporated by reference in its entirety). Described in the invention herein is a method of targeted nucleic acid sequencing that reduces sample loss by bypassing the typical library preparation workflow prior to hybridization of polynucleotide fragments to an array. An additional advantage of this method is normalization of a multiplexed sample, i.e., the simultaneous detection of low abundance targets along with high abundance targets.

The nucleic acid sample used for this experiment contains total RNA or mRNA, preferably purified RNA or mRNA, from an organism (e.g., human). Total RNA includes, but is not limited to, protein coding RNA also called coding RNA such as messenger RNA (mRNA) and non-protein coding RNA (non-coding RNA or ncRNA), such as ribosomal RNA (rRNA), transfer RNA (tRNA), micro RNA (miRNA), small interfering RNA (siRNA), piwi-interacting RNA (piRNA), small nuclear RNA (snRNA) and small nucleolar RNA (snoRNA). Each one of these RNA types may be used as input. Optionally, and preferably, the RNA will include a poly(A) tail, however the RNA molecule may not have a poly(A) tail (e.g., non-protein coding RNAs (ncRNA) such as ribosomal RNA (rRNA), transfer RNA (tRNA), micro RNA (miRNA), small interfering RNA (siRNA), piwi-interacting RNA (piRNA) and small nuclear RNA (snRNA)).

For example, prokaryotic mRNA does not have a poly(A) tail. In RNA molecules that do not have a poly A tail, a poly(A) tail may be added synthetically (e.g. enzymatically) to validate these studies. In embodiments, a poly(A) tail is enzymatically added to the RNA molecule using known techniques in the art.

A multiplexed targeted capture approach for RNA is described herein, wherein the target RNA molecule can hybridize to a complementary surface oligo (gene specific and/or poly T), which is then extended by a reverse transcriptase (RT), followed by bridge PCR, etc. There are many applications that are especially suited for RNA, such as gene fusion detection. A derivative to this technique could include the use of an RT like M-MLV RT, which adds terminal Gs to the extended cDNA, which can then be copied by a surface-bound polyC "helper oligo". This approach could eliminate the need for a second gene-specific primer.

A multiplexed targeted capture approach for RNA is described herein, wherein an isolated RNA molecule (e.g., mRNA), may be further purified and captured by hybridization to gene-specific complementary surface oligos on an array. In the presence of a reverse transcriptase, complementary DNA (cDNA) is generated, followed by a DNA polymerase-mediated second strand synthesis to yield an input DNA molecule. The RNA is then removed and bridge PCR is performed, for example. As an alternative approach, following cDNA production of the captured target RNA, terminal Gs may be added to the extended cDNA using a reverse transcriptase, e.g., M-MLV reverse transcriptase. This G-tailed cDNA may then hybridize to a surface-bound polyC oligo for subsequent bridge PCR. This method has the advantage of, for example, eliminating the need for a second gene-specific primer.

For example, an array of features is provided (see, FIG. 1), wherein within each feature there is a plurality of a first type of immobilized oligonucleotide (solid bar) and a plurality of a second type of immobilized oligonucleotide (striped bar), collectively referred to as a set of primers. The array may be a patterned array, wherein the set of immobilized oligonucleotides occupy distinct feature surrounded by interstitial regions of the surface (e.g., a well) (see, FIG. 3A). Alternatively, the array may be a patterned array, wherein the set of immobilized oligonucleotides are immobilized to particles, wherein one particle occupies a feature (see, FIG. 3B). The particles may be localized in an individual well of an array, wherein each well contains a distinct set of immobilized oligonucleotides (see, FIG. 4).

A plurality of RNA fragments are applied to the array, wherein one primer type is complementary to a first sequence of the nucleic acid fragment, whereas the second primer type is homologous to a second sequence of the fragment, indicated in the figure as different color/textures (see, FIG. 1). Each feature on the array can include a different set of primers. Polynucleotide fragments are allowed to contact the array. If the fragment includes a complementary region to one of the immobilized oligonucleotides in the set, it is captured by hybridization to the first type of immobilized oligonucleotide under suitable conditions. In the presence of a polymerase and nucleotides, the immobilized oligonucleotide is extended to generate a complement of a portion of the captured fragment.

Following hybridization, reverse transcription, and immobilization of the targeted panel of RNA fragments, bridge PCR (bPCR) amplification is performed (see, FIG. 2 and FIGS. 7A-7E). During the bPCR cycle, the immobilized extended complement hybridizes to the second type of immobilized oligonucleotide within the same feature and in the presence of a polymerase (depicted as the cloud) and nucleotides the second type of immobilized oligonucleotide is extended to generate an immobilized portion of the captured fragment. The process is repeated, that is, under suitable conditions allowing multiple polynucleotide fragments to hybridize to a complementary sequence within a feature and extended to generate copies of the captured fragment and complements thereof. Following a plurality of bridge PCR amplification cycles, each feature that captured a polynucleotide includes a cluster of polynucleotides. The cluster of polynucleotides can then be subjected to sequencing, for example, sequencing-by-synthesis. A plurality of sequencing cycles then occur, wherein each cycle includes extension and detection of an incorporated nucleotide. The entire array may be selectively sequenced by choosing the appropriate initiator, i.e., the appropriate sequencing primer.

Example 3. Targeted Infectious Agent Testing

Rapid and definitive microbial identification is desirable for a variety of industrial, medical, environmental, quality, and research reasons. Traditionally, the microbiology laboratory has functioned to identify the etiologic agents of infectious diseases through direct examination and culture of specimens. Since the mid-1980s, researchers have repeatedly demonstrated the practical utility of molecular biology techniques, many of which form the basis of clinical diagnostic assays. Some of these techniques include nucleic acid hybridization analysis, restriction enzyme analysis, genetic sequence analysis, and separation and purification of nucleic acids (See, e.g., J. Sambrook, E. F. Fritsch, and T. Maniatis, Molecular Cloning: A Laboratory Manual, 2nd Ed., Cold Spring Harbor Laboratory Press, Cold Spring Harbor, N.Y., 1989). These procedures, in general, are time-consuming and tedious. Another option is the polymerase chain reaction (PCR) or other amplification procedure that amplifies a specific target DNA sequence based on the flanking primers used. Finally, detection and data analysis convert the hybridization event into an analytical result.

The concept of a universal detection system has been forwarded for identification of bacterial pathogens, and speaks most directly to the possible clinical implications of a broad-based screening tool for clinical use. Exploiting the existence of highly conserved regions of DNA common to all bacterial species in a PCR assay, for example, would empower physicians to rapidly identify the presence of bacteremia, which would profoundly impact patient care. Previous empiric decision making could be abandoned in favor of educated practice, allowing appropriate and expeditious decision-making regarding need for antibiotic therapy and hospitalization.

"High yield" clinical setting diagnostic testing where expeditious identification of the presence of systemic bacterial infection is performed can have immediate high morbidity and mortality consequences. Notable clinical infections have included evaluation of febrile infants at risk for sepsis, detection of bacteremia in febrile neutropenic cancer patients, and examination of critically ill patients in the intensive care unit. While several of these studies have reported promising results (with sensitivity and specificity well over 90%), significant technical difficulties (described below) remain, and have prevented general acceptance of this assay in clinics and hospitals (which remain dependent on standard blood culture methodologies). Even the advantages of the real-time PCR technique, which offers a quantitative, more reproducible, and technically simpler system, remains encumbered by inherent technical limitations of the PCR assay (see, e.g., Yang S and Rothman R E. Lancet Infect. Dis. 2004; 4(6):337-348, which is incorporated herein by reference in its entirety).

The principal shortcomings of applying PCR assays to the clinical setting include: inability to eliminate background DNA contamination; interference with the PCR amplification by substrates present in the reaction; and limited capacity to provide rapid reliable speciation, antibiotic resistance and subtype identification. Some laboratories have recently made progress in identifying and removing inhibitors; however, background contamination remains problematic, and methods directed towards eliminating exogenous sources of DNA report significant diminution in assay sensitivity. Finally, while product identification and detailed characterization has been achieved using sequencing techniques, these approaches are laborious and time-intensive thus detracting from its clinical applicability.

With multidrug-resistant pathogens on the rise, early antimicrobial resistance profiling is crucial both for timely, objective treatment of infected patients, as well as for broader public-health surveillance. Conventional tests of this type are limited by prolonged culturing time (48-72 h) and poor accuracy due to variability in inoculum size and culturing conditions. To address these shortcomings, nucleic-acid-based assays are being advanced as genetic mechanisms of drug resistance are elucidated. Antimicrobial (i.e., antibacterial) resistance occurs when a microbe (i.e., bacteria and/or bacterial strain) acquires a genetic mutation, either spontaneously or by gene transfer, rendering it resistant to the effect of one or more anti-bacterial agents, i.e., antibiotics. Drug-resistant organisms may acquire resistance to first-line antibiotics, necessitating the use of a second-line agent to which the microbe is sensitive. In the case of some bacterial strains that have gained resistance to multiple drugs, resistance to second- and even third-line antibiotics is sequentially acquired. Tuberculosis (TB) is one of the top ten causes of death worldwide and the leading cause of death from a single infectious agent (Chakaya J et al. Int. J. Infect. Dis. 2021; 51201-9712(21): 00193-4). TB is caused by the pathogenic bacteria species *Mycobacterium tuberculosis* (MTb), which infects cells of the upper airway of an organism. Macrophages internalize invading MTb cells by phagocytosis, which are then believed to reside within the endosomes of the macrophage. The immune system attempts to isolate the infection and aggregates infected macrophages into a granuloma. In a minority of cases, the integrity of the granuloma is compromised and MTb cells infect other parts of the lung and/or enter the lymph system and reach other organs or systems, rapidly deteriorating patient outcomes.

Existing clinical diagnostics, such as Cepheid's Xpert® MTB/RIF, focus on differentiating whether a patient presenting with symptoms of TB is infected with a multi-drug resistant and rifampicin resistant strain, which simultaneously detects both. Such diagnostic tests provide key decision metrics for the type of isolation and treatment that would be most efficacious for a patient. Tests such as these, though useful for point-of-case diagnostic purposes, do not provide information on the factors regulating the development of the granuloma. Rifampicin resistance may occur alone or in association with resistance to isoniazid and other drugs (Steingart K R et al. Cochrane Database Syst. Rev. 2014; 2014(1): C009593). Rifampicin inhibits bacterial DNA-dependent RNA polymerase, encoded by the RNA polymerase gene rpoB, and resistance has mainly been associated with mutations in an 81-base pair region of the rpoB gene, including the mutations Q513P, Q513K, H256R, S531L, or S531W (Al-Mutairi N M et al. BMC Infect. Dis. 2019; 19: 3). Resistance to ethambutol (EMB), isoniazid (INH), and pyrazinamide (PZA) include mutations in the embB, inhA, and pncA genes, respectively. Mutations in one or more of these genes are frequently found in multi-drug resistant MTb strains.

Mycobacteria other than the tubercle *Bacillus* sometimes infect humans (see, e.g., Tierney D and Nardell E A. Merck Manual. "Nontuberculous Mycobacterial Infections"; 2018). These organisms (called nontuberculous mycobacteria) are commonly present in soil and water and are much less virulent in humans than is *Mycobacterium tuberculosis*. Infections with these organisms have been called atypical, environmental, and nontuberculous mycobacterial infections. Most exposures and infections by these organisms do not cause disease, which usually requires a defect in local or systemic host defenses; the frail elderly and immunocompromised people are at the highest risk. *M. avium* complex (MAC)—the closely related species of *M. avium* and *M. intracellulare*—accounts for most diseases. Other causative species are *M. kansasii, M. xenopi, M. marinum, M. ulcerans, M. fortuitum, M. abscessus,* and *M. chelonae*. Person-to-person transmission has not been documented. The lungs are the most common site of disease; most of these lung infections involve MAC but may be due to *M. kansasii, M. xenopi,* or *M. abscessus*. Occasional cases involve lymph nodes, bones and joints, the skin, and wounds. However, incidence of disseminated MAC disease is increasing in HIV-infected patients, and resistance to anti-TB drugs is the rule (except for *M. kansasii* and *M. xenopi*). Diagnosis of nontuberculous mycobacterial infections is typically made via acid-fast stain and culture of samples, time-consuming and labor-intensive processes. There is a need for comprehensive, efficient, and accurate diagnostic methods that can discriminate between the various species of *Mycobacterium*, and simultaneously assess for the presence of antimicrobial resistance genes.

Described in the invention herein is a method of targeted nucleic acid sequencing that enables multiplexed detection of infectious agents in broad general panels. Further, the method allows for sequencing of relevant antimicrobial resistance genes within the same sequencing run. For example, an array of features (see, FIG. 1) designed for detecting *Mycobacterium* species (*M. tuberculosis, M. avium,* and *M. intracellulare*) and related-antimicrobial resistance genes (e.g., rpoB, embB, inhA, and pncA) is provided, wherein within each feature there is a plurality of a first type of immobilized oligonucleotide (solid bar) and a plurality of a second type of immobilized oligonucleotide (striped bar), collectively referred to as a set of primers. The array may be a patterned array, wherein the set of immobilized oligonucleotides occupy distinct feature surrounded by interstitial regions of the surface (e.g., a well) (see, FIG. 3A). Alternatively, the array may be a patterned array, wherein the set of immobilized oligonucleotides are immobilized to particles, wherein one particle occupies a feature (see, FIG. 3B). The particles may be localized in an individual well of an array, wherein each well contains a distinct set of immobilized oligonucleotides (see, FIG. 4).

A patient experiencing symptoms of Mycobacterial infection may seek treatment for several clinical patterns including pulmonary disease, skin, and soft tissue infections, musculoskeletal infections, disseminated disease, catheter-associated disease, and lymphadenitis. A sputum sample is obtained from the patient, and bacterial DNA is isolated using methods known in the art. A plurality of bacterial DNA fragments are optionally fragmented, end-repaired, and applied to the array, wherein one primer type is complementary to a first sequence of the nucleic acid fragment, whereas the second primer type is homologous to a second sequence of the fragment, indicated in the figure as different color/textures (see, FIG. 1). Alternatively, no significant library preparation is employed, i.e., a plurality of bacterial DNA fragments are applied to the array. Each feature on the array can include a different set of primers, e.g., primers specific to rpoB, embB, inhA, etc. Polynucleotide fragments are allowed to contact the array. If the fragment includes a complementary region to one of the immobilized oligonucleotides in the set, it is captured by hybridization to the first type of immobilized oligonucleotide under suitable conditions. In the presence of a polymerase and nucleotides, the immobilized oligonucleotide is extended to generate a complement of a portion of the captured fragment.

Following hybridization and immobilization of the targeted panel of RNA fragments, bridge PCR (bPCR) amplification is performed (see, FIG. 2 and FIGS. 7A-7E). During the bPCR cycle, the immobilized extended complement hybridizes to the second type of immobilized oligonucleotide within the same feature and in the presence of a polymerase (depicted as the cloud) and nucleotides the second type of immobilized oligonucleotide is extended to generate an immobilized portion of the captured fragment. The process is repeated, that is, under suitable conditions allowing multiple polynucleotide fragments to hybridize to a complementary sequence within a feature and extended to generate copies of the captured fragment and complements thereof. Following a plurality of bridge PCR amplification cycles, each feature that captured a polynucleotide includes a cluster of polynucleotides. The cluster of polynucleotides can then be subjected to sequencing, for example, sequencing-by-synthesis. A plurality of sequencing cycles then occur, wherein each cycle includes extension and detection of an incorporated nucleotide. The entire array may be selectively sequenced by choosing the appropriate initiator, i.e., the appropriate sequencing primer. The method described herein can be applied to sequence targeted panels of pathogenic infectious agents and increase the quality and efficiency of clinical diagnostics.

Example 4. Compartmentalization-Free Target Nucleic Acid Quantification

Digital polymerase chain reaction (dPCR) is a refinement of conventional PCR methods that can be used to directly quantify and clonally amplify nucleic acids. Conventional PCR assumes that amplification is exponential. Therefore, nucleic acids may be quantified by comparing the number of amplification cycles and amount of PCR end-product to those of a reference sample. Digital PCR is designed to quantitate target nucleic acid sequences by dividing the sample into many independent partitions such that each contains either a few or no target sequences. Typically, the accuracy and more importantly the precision of determination by dPCR may be improved by using a greater number of partitions. For example, dPCR may be carried out identically in an array having between at least 100-100,000 partitions, e.g., between at least 1,000-100,000 reaction sites, or between at least 10,000-100,000 reaction sites. The capture or isolation of individual nucleic acid molecules can be performed in micro well plates, capillaries, the dispersed phase of an emulsion, and arrays of miniaturized chambers, as well as on nucleic acid binding surfaces. For example, the Digital LightCycler® System from Roche reportedly offers three different solid-state partition plates with varying numbers of nanowell compartments (e.g., partition plate types including approximately 20 k, 28 k, or 100 k partitions, with each partition type accepting approximately 45 μL, 30 μL, or 15 μL, respectively).

The distribution of target sequences in the partitions can be approximated with a Poisson's distribution. Each partition acts as an individual PCR microreactor and partitions containing amplified target sequences are detected by fluorescence. The ratio of positive partitions (presence of fluorescence) over the total number allows one to determine the concentration of the target in the sample (see, e.g., Quan P L et al. Sensors. 2018; 18(4):1271, which is incorporated herein by reference in its entirety). False-positive signal, for example, is an error that may manifest during dPCR assays that employ a compartmentalization approach, as further described in U.S. Pat. Pub. No. 2016/0310949 and International Application No. PCT/EP2021/061040, each of which is incorporated herein by reference in its entirety. As a sample is partitioned in an array, the partitioning process may lead to partially filled or unfilled partitions, i.e., a reaction volume deviation, and the partially filled or unfilled partitions are alternatively referred to as voids or fill-voids. The fluorescent signal from a void may be difficult to distinguish from the signal observed from an otherwise filled partition containing low or no target molecule. In addition, bright spots may be observed in void partitions, which may be mistaken for positive signal from filled partitions.

Figure 11:
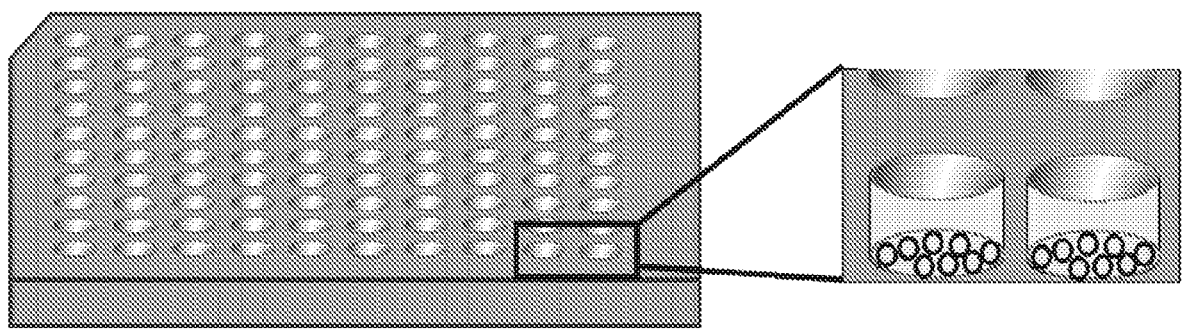
FIG. 11 illustrates an embodiment of the array, wherein the individual wells of the array include a plurality of nanowells (illustrated as several round features at the bottom of the wells). Each plurality of nanowells in each well contains different sets of primers, such that each well is capable of capturing different target polynucleotides from a sample containing a plurality of different target sequences.

The methods of the invention described herein provide an alternate way to obtain digital quantification of original target nucleic acids in a sample while at the same time obtaining sequence information, without the need to perform any compartmentalization as is required by existing digital PCR offerings. Advantageously, the methods described herein do not require detecting reaction volume deviations to correct for false-positive signals. For example, an array of features (see, FIG. 1) designed for detecting trisomy 21 in cell-free fetal DNA in maternal plasma is provided (e.g., detecting a SNP on PLAC4 mRNA, a placenta-expressed transcript on chromosome 21, as described in Dennis Lo Y M et al. Proc. Natl. Acad. Sci. USA. 2007; 104(32):13116-13121, which is incorporated herein by reference in its entirety), wherein within each feature there is a plurality of a first type of immobilized oligonucleotide (solid bar) and a plurality of a second type of immobilized oligonucleotide (striped bar), collectively referred to as a set of primers. The array may be a patterned array, wherein the set of immobilized oligonucleotides occupy distinct feature surrounded by interstitial regions of the surface (e.g., a well) (see, FIG. 3A). Alternatively, the array may be a patterned array, wherein the set of immobilized oligonucleotides are immobilized to particles, wherein one particle occupies a feature (see, FIG. 3B). The particles may be localized in an individual well of an array, wherein each well contains a distinct set of immobilized oligonucleotides (see, FIG. 4). In embodiments, the array includes wells, wherein each well includes a plurality of nanowells (see, FIG. 11), wherein the plurality of nanowells of each well contain a distinct set of immobilized oligonucleotides useful for capturing and amplifying specific targets within each well.

A blood sample is obtained from a patient, and cfDNA is isolated using methods known in the art. A plurality of DNA molecules are optionally fragmented, end-repaired, and applied to the array, wherein one primer type is complementary to a first sequence of the nucleic acid fragment, whereas the second primer type is homologous to a second sequence of the fragment, indicated in the figure as different color/textures (see, FIG. 1). Alternatively, no significant library preparation is employed, i.e., a plurality of cfDNA molecules are applied to the array. Each feature on the array can include a different set of primers, e.g., primers for detecting a SNP on PLAC4 mRNA or other known chromosome 21 SNPs, such as rs1735976-rs2827016 and others described in Ghanta S et al. PLoS One. 2010; 5(10):e13184, which is incorporated herein by reference in its entirety. Polynucleotide fragments are allowed to contact the array. If the fragment includes a complementary region to one of the immobilized oligonucleotides in the set, it is captured by hybridization to the first type of immobilized oligonucleotide under suitable conditions. In the presence of a polymerase and nucleotides, the immobilized oligonucleotide is extended to generate a complement of a portion of the captured fragment.

Following hybridization and immobilization of the targeted panel of DNA fragments, bridge PCR (bPCR) amplification is performed (see, FIG. 2 and FIGS. 7A-7E). During the bPCR cycle, the immobilized extended complement hybridizes to the second type of immobilized oligonucleotide within the same feature and in the presence of a polymerase (depicted as the cloud) and nucleotides the second type of immobilized oligonucleotide is extended to generate an immobilized portion of the captured fragment. The process is repeated, that is, under suitable conditions allowing multiple polynucleotide fragments to hybridize to a complementary sequence within a feature and extended to generate copies of the captured fragment and complements thereof. Following a plurality of bridge PCR amplification cycles, each feature that captured a polynucleotide includes a cluster of polynucleotides. The cluster of polynucleotides can then be subjected to sequencing, for example, sequencing-by-synthesis. A plurality of sequencing cycles then occur, wherein each cycle includes extension and detection of an incorporated nucleotide. The entire array may be selectively sequenced by choosing the appropriate initiator, i.e., the appropriate sequencing primer. The method described herein can be applied to sequence targeted panels for fetal cfDNA sequencing, while obtaining quantitative information about the original nucleic acids in the sample, increasing the quality and efficiency of clinical diagnostics.

Example 5. Immune Cell Profiling

The functions of immune cells such as B- and T-cells are predicated on the recognition through specialized receptors of specific targets (antigens) in pathogens. There are approximately $10^{10}$-$10^{11}$ B-cells and $10^{11}$ T-cells in a human adult (Ganusov V V, De Boer R J. Trends Immunol. 2007; 28(12):514-8; and Bains I, Antia R, Callard R, Yates A J. Blood. 2009; 113(22):5480-5487). Immune cells are critical components of adaptive immunity in humans. Immune cells (e.g., T cells, B cells, NK cells, neutrophils, and monocytes) directly bind to pathogens through antigen-binding regions present on the cells. Within lymphoid organs (e.g., bone marrow for B cells and the thymus for T cells) the gene segments variable (V), joining (J), and diversity (D) rearrange to produce a novel amino acid sequence in the antigen-binding regions of antibodies that allow for the recognition of antigens from a range of pathogens (e.g., bacteria, viruses, parasites, and worms) as well as antigens arising from cancer cells. The large number of possible V-D-J segments, combined with additional (junctional) diversity, lead to a theoretical diversity of >$10^{14}$, which is further increased during adaptive immune responses. Overall, the result is that each B- and T-cell expresses a practically unique receptor, whose sequence is the outcome of both germline and somatic diversity. These antibodies also contain a constant (C) region, which confers the isotype to the antibody. In most mammals, there are five antibody isotypes: IgA, IgD, IgE, IgG, and IgM. For example, each antibody in the IgA isotype shares the same constant region.

While parts of the B-cell immunoglobulin receptor (BCR) can be traced back to segments encoded in the germline (i.e., the V, D and J segments), the set of segments used by each receptor is something that needs to be determined as it is coded in a highly repetitive region of the genome (Yaari G, Kleinstein S H. Practical guidelines for B-cell receptor repertoire sequencing analysis. Genome Med. 2015; 7:121. (2015)).

In embodiments, the methods described herein may be utilized for B cell heavy and light chain sequencing by targeting the combination of variable and constant gene segments that make up a given heavy and light chain. These methods provide unique insight into the recombination efforts of a cell's heavy and light chain genes. Likewise, the methods can be applied for T-cell receptor (TCR) alpha and beta chain sequencing. The genes encoding alpha (TCRA) and beta (TCRB) chains are composed of multiple non-contiguous gene segments which include V, D, and J segments for TCRB and V and J for TCRA. As with B cell receptor diversity, the enormous diversity of TCR repertoires is generated by random combinatorial gene events. The methods described here can be used to provide a comprehensive view of TCR diversity in intact T cells.

Described in the invention herein is a method of targeted nucleic acid sequencing that enables multiplexed detection of a cell's heavy and light chain genes. For example, an array of features (see, FIG. 1) designed for detecting V and J segments for T-cell receptor (TCR) alpha and beta chain sequencing is provided, wherein within each feature there is a plurality of a first type of immobilized oligonucleotide (solid bar) and a plurality of a second type of immobilized oligonucleotide (striped bar), collectively referred to as a set of primers. The array may be a patterned array, wherein the set of immobilized oligonucleotides occupy distinct feature surrounded by interstitial regions of the surface (e.g., a well) (see, FIG. 3A). Alternatively, the array may be a patterned array, wherein the set of immobilized oligonucleotides are immobilized to particles, wherein one particle occupies a feature (see, FIG. 3B). The particles may be localized in an individual well of an array, wherein each well contains a distinct set of immobilized oligonucleotides (see, FIG. 4).

A blood sample is obtained from a patient, and PBMCs (including T-cells) are isolated using methods known in the art. A plurality of DNA molecules are optionally fragmented, end-repaired, and applied to the array, wherein one primer type is complementary to a first sequence of the nucleic acid fragment, whereas the second primer type is homologous to a second sequence of the fragment, indicated in the figure as different color/textures (see, FIG. 1). Alternatively, no significant library preparation is employed, i.e., a plurality of DNA molecules are applied to the array. Each feature on the array can include a different set of primers, e.g., primers specific to any V segment or J segment of TCRA. Polynucleotide fragments are allowed to contact the array. If the fragment includes a complementary region to one of the immobilized oligonucleotides in the set, it is captured by hybridization to the first type of immobilized oligonucleotide under suitable conditions. In the presence of a polymerase and nucleotides, the immobilized oligonucleotide is extended to generate a complement of a portion of the captured fragment.

Following hybridization and immobilization of the targeted panel of DNA fragments, bridge PCR (bPCR) amplification is performed (see, FIG. 2 and FIGS. 7A-7E). During the bPCR cycle, the immobilized extended complement hybridizes to the second type of immobilized oligonucleotide within the same feature and in the presence of a polymerase (depicted as the cloud) and nucleotides the second type of immobilized oligonucleotide is extended to generate an immobilized portion of the captured fragment. The process is repeated, that is, under suitable conditions allowing multiple polynucleotide fragments to hybridize to a complementary sequence within a feature and extended to generate copies of the captured fragment and complements thereof. Following a plurality of bridge PCR amplification cycles, each feature that captured a polynucleotide includes a cluster of polynucleotides. The cluster of polynucleotides can then be subjected to sequencing, for example, sequencing-by-synthesis. A plurality of sequencing cycles then occur, wherein each cycle includes extension and detection of an incorporated nucleotide. The entire array may be selectively sequenced by choosing the appropriate initiator, i.e., the appropriate sequencing primer. The method described herein can be applied to sequence targeted panels for immune receptor repertoire sequencing and increase the quality and efficiency of clinical diagnostics.

Example 6. Tumor DNA Detection

It is a major challenge to distinguish true variants from background noise for rare variant discovery. Typically, large amounts of sequencing data (high sequencing depth) are required to differentiate a true variant from an amplification and/or sequencing error using previous methods. In addition, the heterogeneity of mutations within populations of rare cells in liquid biopsy samples, such as plasma or saliva, make it difficult to distinguish between sequencing-related errors and true somatic mutations originating from tumors. Methods and constructs provided herein do not necessarily require such large sequencing depths, thereby dramatically reducing the costs associated with sequencing.

Studying cell-free DNA (cfDNA) proves to be a useful test case for testing the capabilities of the linked duplex sequencing methods described herein, for recovering sequencing depth and for detecting rare mutations in a clinical application. Nucleic acids, e.g., cfDNA, are released into the bloodstream and other body fluids as part of natural cell apoptosis, necrosis, and secretion, and includes both single- and double-stranded DNA fragments that are relatively short (overwhelmingly less than 200 base-pairs) and are normally at a low concentration (e.g. 1-100 ng/mL in plasma). It is known that the concentration of cfDNA and ctDNA in plasma correlates with tumor size and stage. For example, patients having stage I cancer types had fewer than 10 copies per 5 ml of tumor mutations in plasma. In contrast, the copy number increased 10 to 100 times among late-stage patients (Haque et al. bioRxiv. 2017; 237578.). Thus, ctDNA assays used for early cancer diagnosis should be highly sensitive. Commercial solutions require UMIs on both strands of the double-stranded template, followed by low-error sequencing. To determine a true variant using previous commercial solutions, large amounts of sequencing data (high sequencing depth) is required to generate a consensus sequencing read to confidently ascertain a single nucleotide change.

Recent cancer genome sequencing studies have shown that virtually all cancers harbor somatic genetic alterations. These alterations include insertions, deletions, single-base substitutions, and translocations (Vogelstein et al Science. 2013 Mar. 29; 339(6127): 1546-1558). In cancer, a proportion of cfDNA circulating in plasma can come from the tumor, with the relative contribution of cfDNA coming from the tumor increases with cancer severity. The rate of these chromosomal changes in cancer cells is elevated and mutations can be challenging to detect accurately (Pietrasz et al Clin Cancer Res. 2017 Jan. 1; 23(1):116-123). While typical commercial sequencing instruments have a sequencing error rate that varies from about 0.05-1% (Quail et al Nat Methods. 2008 December; 5(12):1005-10), and can reveal comprehensive genomic alterations, it remains a challenge to distinguish variants at such low fraction from background errors of sequencing. Nonetheless, identifying cfDNA harboring these genetic alterations serves as valuable biomarkers and accurately detecting these variants will significantly improve current methods of cancer diagnosis, cancer progression monitoring, therapy effectiveness, and early-stage detection.

Described in the invention herein is a method of targeted nucleic acid sequencing that enables multiplexed detection of cfDNA genetic alterations. For example, an array of features (see, FIG. 1) designed for detecting the HER2 gene and the reference gene RPP30 is provided (for additional information, see, Yang S R et al. Mod. Pathol. 2020; 33: 1546-56, which is incorporated herein by reference in its entirety), wherein within each feature there is a plurality of a first type of immobilized oligonucleotide (solid bar) and a plurality of a second type of immobilized oligonucleotide (striped bar), collectively referred to as a set of primers. The array may be a patterned array, wherein the set of immobilized oligonucleotides occupy distinct feature surrounded by interstitial regions of the surface (e.g., a well) (see, FIG. 3A). Alternatively, the array may be a patterned array, wherein the set of immobilized oligonucleotides are immobilized to particles, wherein one particle occupies a feature (see, FIG. 3B). The particles may be localized in an individual well of an array, wherein each well contains a distinct set of immobilized oligonucleotides (see, FIG. 4).

Alternatively, or in addition to multiplexed detection of cfDNA genetic alterations, the methods described herein are also used for targeted exome sequence. In embodiments, the target polynucleotide includes complements to exon genomic sequences (i.e., nucleic acids encoding for proteins). For example, in tumor exome sequencing, only the coding regions of genes are assessed, which frequently contain mutations that affect tumor progression. Depending on experimental needs, cancer exome sequencing can also be expanded to untranslated regions and microRNA (miRNA) binding sites. For example, an array of features (see, FIG. 1) designed for detecting a panel of cancer gene exomes is provided, for example, wherein individual features include oligonucleotides targeting a specific cancer gene exome (e.g., TP53, KRAS, PIK3CA, or other cancer-associated gene, for example as described in Reda M et al. EBioMedicine. 2020; 51: 102624; McCabe M J et al. Sci. Rep. 2019; 9(1): 17052; Zhou C et al. Ann. Transl. Med. 2021; 9(18): 1437; and Klevebring D et al. PLoS One. 2014; 9(8):e104417, each of which is incorporated herein by reference in its entirety). For example, within each feature there is a plurality of a first type of immobilized oligonucleotide (solid bar) and a plurality of a second type of immobilized oligonucleotide (striped bar), collectively referred to as a set of primers. The array may be a patterned array, wherein the set of immobilized oligonucleotides occupy distinct feature surrounded by interstitial regions of the surface (e.g., a well) (see, FIG. 3A). Alternatively, the array may be a patterned array, wherein the set of immobilized oligonucleotides are immobilized to particles, wherein one particle occupies a feature (see, FIG. 3B). The particles may be localized in an individual well of an array, wherein each well contains a distinct set of immobilized oligonucleotides (see, FIG. 4). Performing targeted exome sequencing with the methods described herein results in average coverage from between 30× to 100×, or greater.

A blood sample is obtained from a patient, and cfDNA is isolated using methods known in the art. A plurality of cfDNA molecules are fragmented, end-repaired, and applied to the array, wherein one primer type is complementary to a first sequence of the nucleic acid fragment, whereas the second primer type is homologous to a second sequence of the fragment, indicated in the figure as different color/textures (see, FIG. 1). Alternatively, no significant library preparation is employed, i.e., a plurality of cfDNA molecules are applied to the array. Each feature on the array can include a different set of primers, e.g., primers specific to HER2 or RPP30. Polynucleotide fragments are allowed to contact the array. If the fragment includes a complementary region to one of the immobilized oligonucleotides in the set, it is captured by hybridization to the first type of immobilized oligonucleotide under suitable conditions. In the presence of a polymerase and nucleotides, the immobilized oligonucleotide is extended to generate a complement of a portion of the captured fragment.

Following hybridization and immobilization of the targeted panel of DNA fragments, bridge PCR (bPCR) amplification is performed (see, FIG. 2 and FIGS. 7A-7E). During the bPCR cycle, the immobilized extended complement hybridizes to the second type of immobilized oligonucleotide within the same feature and in the presence of a polymerase (depicted as the cloud) and nucleotides the second type of immobilized oligonucleotide is extended to generate an immobilized portion of the captured fragment. The process is repeated, that is, under suitable conditions allowing multiple polynucleotide fragments to hybridize to a complementary sequence within a feature and extended to generate copies of the captured fragment and complements thereof. Following a plurality of bridge PCR amplification cycles, each feature that captured a polynucleotide includes a cluster of polynucleotides. The cluster of polynucleotides can then be subjected to sequencing, for example, sequencing-by-synthesis. A plurality of sequencing cycles then occur, wherein each cycle includes extension and detection of an incorporated nucleotide. The entire array may be selectively sequenced by choosing the appropriate initiator, i.e., the appropriate sequencing primer. The method described herein can be applied to sequence targeted panels for cfDNA oncogene sequencing, including targeted cancer exome gene panels, and increase the quality and efficiency of clinical diagnostics.

Example 7. Spatially Barcoded Arrays

The position of any given cell, relative to its neighbors and non-cellular structures, can provide useful information for defining cellular phenotype, cell state, and ultimately cell and tissue function. Location can determine the signals to which cells are exposed. While endocrine signals act at macroscopic scales, many other types of signals act upon neighboring cells via cell-cell interactions or via soluble signals acting in the vicinity. One form these signals can take is of cell surface-bound protein receptors and ligand pairs, the mRNA for which can be detected by transcriptomics (see, e.g., Armingol E et al. Nat. Rev. Genet. 2021; 22(2): 71-88). The expansion of protein-protein interaction databases and recent advances in RNA sequencing technologies have enabled routine analyses of intercellular signaling from gene expression measurements of bulk and single-cell data sets. Single-cell RNA sequencing (scRNA-seq) has greatly advanced our understanding of cellular heterogeneity by profiling individual cell transcriptomes. However, cell dissociation from the tissue structure causes a loss of spatial information, which hinders the identification of intercellular communication networks and global transcriptional patterns present in the tissue architecture. To overcome this limitation, novel transcriptomic platforms that preserve spatial information have been actively developed. Significant achievements in imaging technologies have enabled in situ targeted transcriptomic profiling in single cells at single molecule resolution (see, e.g., Lee J et al. BMB Rep. 2022; 55(3): 113-124).

Standard immunohistochemistry and RNA in situ hybridization (ISH), for example, can examine only one or a handful of target molecular species at a time; therefore, the amount of information obtained from a single experimental session is limited. To overcome this, emerging spatial transcriptomics techniques aim to examine all genes expressed from the genome from a single histological slide (see, e.g., Asp M et al. Bioessays. 2020; 42(10): e1900221). There are three major methodologies to experimentally implement spatial transcriptomics. First, the sequential in situ hybridization method, often combined with combinatorial multiplexing, can increase the number of RNA species that can be detected from a single histological section. Second, in situ sequencing can identify RNA sequences from the tissue through fluorescence-based direct sequencing. Finally, spatial barcoding methods associate RNA sequences and their spatial locations by capturing tissue RNA using a spatially barcoded oligonucleotide array.

There are a growing number of in situ capture technologies being developed and commercialized to perform such examinations on a single histological slide. For example, one iteration of the 10× Genomics Visium platform includes the use of glass slides containing marked 6.5×6.5 mm areas where thin tissue sections are placed and imaged. Each area contains 5000 printed regions of barcoded mRNA capture probes with the dimensions of 55 μm in diameter and a center-to-center distance of 100 μm. Tissue is permeabilized and mRNAs are hybridized to the barcoded capture probes directly underneath. cDNA synthesis connects the spatial barcode and the captured mRNA, and sequencing reads are later overlaid with the captured tissue image. Another example includes NanoString's GeoMX Digital Spatial Profiler, wherein a slide-fixed tissue section is first exposed to a pre-known panel of barcoded hybridization probes, after which regions of interest (ROIs) are manually selected. The ROIs are then subjected to UV light and target specific barcodes are cleaved off and digital counting performed with the nCounter system.

The techniques for spatial transcriptomics with barcoded oligonucleotide capture arrays described, however, have limitations in the spatial resolution of up to 55-100 μm due to the physical size of capturing spots. To resolve the issue of low spatial resolution in capture-based sequencing methodology, bead-based capturing sequencing was developed. In 2019, Rodriques et al. developed Slide-seq (see, e.g., Rodriques S G et al. Science. 2019; 363(6434): 1463-67) for higher cellular resolution genome-wide analysis using DNA-barcoded 10 m beads onto a rubber-coated glass slide. In Slide-seq, each bead's distinct barcoded sequence is determined via SBL (sequencing-by-ligation) methods.

Using the beads, the resolution comparable to the size of an individual cell was achieved by NGS of barcoded RNA-seq libraries and successfully applied to the hippocampus area in mice. Additionally, high-definition spatial transcriptomics (HDST) was developed as another effort to accomplish higher resolution for barcoded transcripts (see, e.g., Vickovic S et al. Nat. Methods. 2019; 16(10): 987-990). HDST randomly deposits barcoded poly(d)T oligonucleotides into a 2 µm well with bead array-based fabrication. Mouse brain and primary breast cancers were profiled with 25× higher resolution than that of Slide-seq using this method, resulting in a reconstruction of the spatial architecture of mouse brain and primary breast cancer tissues.

Cho et al. developed a high-resolution spatial barcoding technology, Seq-Scope, with a 0.5-0.8 µm center-to-center resolution (see, e.g., Cho C S et al. Cell. 2021; 184(13): 3559-3572). This technique was developed based on the NGS technology that utilizes randomly barcoded single-molecule oligonucleotides with a transcriptome capture capacity of approximately 4,700 UMIs/cell on average, comparable to conventional scRNA-seq methods. This technical improvement enabled visualizing the histological organization of the transcriptome architecture in liver tissues at subcellular level. More recently, another high-resolution spatial barcoding technology, SpaTial Enhanced Re-solution Omics-sequencing (Stereo-seq) was introduced with a center-to-center resolution of 500-715 nm (see, Chen A et al. Cell. 2022; 185(10): 1777-1792). This method applies microfluidic channels perpendicularly for unique pair-wise barcoding on each spot of the tissue section. Stereo-seq can capture up to 133,775 UMIs per 100 µm diameter bin, and was capable of profiling a whole mouse embryo. Stereo-seq is currently undergoing commercial development by BGI as its STOmics platform, currently in early access.

While most of these techniques are designed for fresh frozen tissues stored below the temperature at which mRNAs degrade, some methods such as Visium FFPE are compatible with tissues that are fixed with formalin and embedded in paraffin wax, although this requires extra steps to prepare the tissue for profiling and a different, gene-specific probe-set (although all genes in the genome are nonetheless profiled). Independently developed techniques to adapt Visium reagents to FFPE-preserved tissues are also available but it is unclear whether these are in active commercial development (see, e.g., Gracia Villacampa E et al. Cell Genomics. 2021; 1(3): 100065).

A common approach for in situ spatial transcriptomic analysis of mRNAs is to use a capture array including poly-d(T) capture probes which then hybridize to polyadenylated RNA species. The Seq-Scope method, for example, relies on the targeting of poly-A tails of mRNA molecules for capture onto a physical array of spatially barcoded RNA-capture molecules, and a spatial map of barcodes where each barcoded sequence is associated with a spatial coordinate. In this system, the RNA-capture molecules include a poly-d(T) capture domain for associating with the mRNA molecules. The poly-d(T) approach introduces several limitations, including, for example, the inability to target RNA species which are not poly-A tailed (e.g., non-polyadenylated), for example, histone mRNAs, lncRNAs, rRNAs, and snRNAs (see, e.g., Yang L et al. Genome Biol. 2011; 12(2): R16, which is incorporated herein by reference in its entirety). Additionally, biases may be introduced towards polyadenylated RNA molecules due to the varying degree of lengths of poly-A tails present. For example, a recent study identified a population of mRNAs (>10% of genes' mRNAs) that were inconsistently captured by poly (A) selection due to highly variable poly(A) tails (see, Viscardi M J and Arribere J A. BMC Genomics. 2022; 23:530, which is incorporated herein by reference in its entirety). Variable tail length genes (genes with mRNAs exhibiting a large difference in mean poly(A) tail lengths in poly(A)-selected samples compared to unselected samples) were found to be preferentially lost upon poly(A) selection, indicating that poly(A) selection may cause gene-specific recovery biases, and also added unnecessary noise to sample replicates. Recently, a method for performing in situ polyadenylation of non-polyadenylated RNAs followed by poly (A) selection and sequencing was described (see, McKellar D W et al. bioRxiv. 2022; 2022.03.20.488964), although the biases described supra for poly(A) selection may still need to be considered with such an approach.

The methods described herein provide a solution for specifically targeting a broad range of RNA species in situ regardless of polyadenylation status, for example, or length of poly(A) tails. This approach offers users an opportunity to customize the tissue nucleic acid capture arrays of existing and future spatial transcriptomic platforms towards a large number of nucleic acid types. For example, the methods described herein include a first plurality of immobilized capture probes and a second plurality of immobilized capture probes, wherein one or more of the first plurality include a first sequence capable of hybridizing to a first endogenous region of a target polynucleotide of a cell in situ, and wherein one or more of the second plurality include a second sequence capable of hybridizing to the complement of a second region of the target polynucleotide of the cell in situ, may be used with any of the spatial transcriptomics platforms described or referenced supra. For example, the Seq-Scope method described in Cho et al. used capture probes including an oligo-dT tail for targeting mRNA molecules in cells. One could instead use the first and second pluralities of capture probes as described herein, thereby avoiding any biases and underrepresentation of mRNA species, while also targeting non-polyadenylated RNA types using the same spatially barcode array.

Briefly, a first plurality of capture probes and a second plurality of capture probes each including a spatial barcode, a capture domain (e.g., a first sequence capable of hybridizing to a first endogenous region of a target polynucleotide, or a second sequence capable of hybridizing to the complement of a second region of the target polynucleotide), and a cleavage domain are immobilized on a solid support. The capture probes include a platform primer binding sequence and are bound to the solid support by interactions with a corresponding platform primer attached to the solid support. Capture probes are then amplified, for example, by bridge amplification, resulting in the generation of multiple clusters including immobilized first and second pluralities of capture probes on the surface of the solid support. The resulting substrate includes millions of clusters, each cluster containing first and second pluralities of immobilized capture probes including the same spatial barcode.

Sequencing is performed to determine the sequence of the spatial barcodes for each cluster. The sequence is then used to assign each cluster to a specific location on the solid support. Following amplification and determination of the spatial barcode sequence, the capture domain may be exposed. For example, the capture domain may be exposed by the addition of suitable restriction enzymes (e.g., XbaI) to cut the cleavage domain, and one or more wash steps (e.g., NaOH wash) or enzymatic steps (e.g., exonuclease digestion) may be performed. In embodiments, the resulting capture probe includes the platform primer sequence bound to the surface of the solid support (e.g., tethered to the solid support via a bioconjugate reactive moiety), the spatial barcode sequence, and an exposed capture domain. In other embodiments, the capture domain may be synthesized on the spatial barcode sequence by hybridizing a separate oligonucleotide that encodes a complement of the capture domain sequence (e.g., a complement of the of a first endogenous region of a target polynucleotide, or a second region of the target polynucleotide). In yet other embodiments, the clusters may be replicated onto a new substrate by PCR or isothermal amplification, which may then be further processed to expose the capture domain.

After determining the spatial barcode sequences of each cluster, the solid support is then further processed (e.g., removing unused platform primer oligonucleotides and other non-specific ssDNA) to generate a spatial barcode array that can capture target nucleic acids (e.g., mRNAs) released from a tissue section or plurality of cells, as described in PCT Pub. No. WO2022/015913, which is incorporated by reference herein in its entirety. The quality of the clustered array may be inspected by staining with a DNA dye, such as SYBR Gold.

Tissue, for example OCT-mounted fresh frozen tissue, is sectioned in a cryostat using methods known in the art. The tissue sections are then placed on the spatial capture array and fixed, for example using 4% formaldehyde. The tissues may then be hematoxylin and eosin stained using methods known in the art and imaged under a light microscope. To release RNAs from the fixed tissues, the tissues are treated, for example, with 0.2 U/uL collagenase I at 37° C. 20 min, and then with 1 mg/mL pepsin in 0.1M HCl at 37° C. 10 min, as previously described (see, Salmen F et al. Nat. Protoc. 2018; 13(11): 2501-34, which is incorporated herein by reference in its entirety).

The tissue is then washed with a reverse-transcription buffer including, for example, Maxima 5×RT Buffer (Cat. No. EP0751, Thermofisher) and RNase Inhibitor (Cat. No. 30281, Lucigen). Subsequently, reverse transcription is performed by incubating the tissue-attached spatial barcode array in an RT buffered reaction solution containing, for example, Maxima 5×RT Buffer (Cat. No. EP0751, Thermofisher), 20% Ficoll PM-400 (Cat. No. F4375-10G, Sigma), dNTPs (Cat. No. N0477L, NEB), RNase Inhibitor (Cat. No. 30281, Lucigen), Maxima H-RTase (Cat. No. EP0751, Thermofisher), and Actinomycin D (500 ng/pl, Cat. No. A1410, Sigma-Aldrich). The RT reaction solution is then incubated at 42° C. overnight.

The following day, the RT solution is removed and the tissue is submerged in an exonuclease I cocktail (1 U Exo I enzyme (Cat. No. M2903, NEB) in IX Exo I buffer) and incubated at 37° C. for 45 min, to eliminate DNA that did not hybridize with mRNA, for example. Then the cocktail is removed, and the tissues are submerged in 1× tissue digestion buffer (100 mM Tris pH 8.0, 100 mM NaCl, 2% SDS, 5 mM EDTA, 16 U/mL Proteinase K (Cat. No. P8107S, NEB) and incubated at 37° C. for 40 min. After tissue digestion, the array is washed with water 3 times, 0. IN NaOH 3 times (each with 5 min incubation at room temperature), 0.1M Tris (pH7.5) 3 times (each with a brief wash), and then water 3 times (each with brief wash). This will eliminate all mRNA from the spatially barcoded array.

After the washing steps, second strand synthesis is performed by adding to the tissue a second strand synthesis mix including a sequencing primer-conjugated random primer, dNTP mix (Cat. No. N0477, NEB), and Klenow Fragment (exonuclease-deficient; Cat. No. M0212, NEB). Then the spatially barcoded array is incubated at 37° C. for 2 hr in a humidity-controlled chamber. After second strand synthesis, the array is washed with water to remove all DNAs that are taken off from the array, so that each spatial barcode molecule corresponds to each single copy of second strand. Then the array is treated with 0.1 N NaOH to elute the second strand. The elution step is duplicated and combined with the first elution. The second strand product elution is then neutralized by mixing with 3 M potassium acetate, pH 5.5. The neutralized secondary strand product is then subjected to AMPure XP purification (Cat. No. A63881, Beckman Coulter) using 1.8× bead/sample ratio, according to the manufacturer's protocol. The final elution is performed using water. Sequencing libraries are then prepared according to manufacturer's protocols. The libraries are subjected to, for example, paired-end (e.g., 100-150 bp) sequencing processes on, for example, a Singular Genomics™ sequencer (e.g., the G4™ system) or Illumina™ sequencer (e.g., HiSeq™, MiSeq™, NextSeq™, or NovaSeq™ systems). A plurality of sequencing cycles then occur, wherein each cycle includes extension and detection of an incorporated nucleotide. The entire array may be selectively sequenced by choosing the appropriate initiator, i.e., the appropriate sequencing primer.

P-Embodiments

The present disclosure provides the following illustrative embodiments.

Embodiment P1. A particle comprising a first plurality of immobilized oligonucleotides and a second plurality of immobilized oligonucleotides, wherein one or more of the first plurality comprise a first sequence capable of hybridizing to a first endogenous region of a target polynucleotide, and wherein one or more of the second plurality comprise a second sequence capable of hybridizing to the complement of a second region of said target polynucleotide.

Embodiment P2. The particle of Embodiment P1, wherein the 3' end of the first sequence is complementary to said first endogenous region of said target polynucleotide, and wherein the 3' end of the second sequence is complementary to said complement of said second region of said target polynucleotide.

Embodiment P3. The particle of Embodiment P1 or Embodiment P2, wherein the second sequence is at least 80% identical to a second endogenous region of said target polynucleotide.

Embodiment P4. The particle of any one of Embodiment P1 to Embodiment P3, wherein the second sequence is 80%, 90%, 95%, 99%, or 100% identical to a second region of said target polynucleotide.

Embodiment P5. The particle of any one of Embodiment P1 to Embodiment P4, wherein the first sequence and the second sequence further each independently comprise a primer binding sequence.

Embodiment P6. The particle of any one of Embodiment P1 to Embodiment P5, wherein the first sequence comprises, from 5' to 3', a primer binding sequence and sequence complementary to a first endogenous region of the target polynucleotide.

Embodiment P7. The particle of any one of Embodiment P1 to Embodiment P6, wherein the second sequence comprises, from 5' to 3', a primer binding sequence and a second sequence at least 80% identical to a second region of said target polynucleotide.

Embodiment P8. The particle of any one of Embodiment P1 to Embodiment P7, wherein said particle is bound to a solid support.

Embodiment P9. The particle of any one of Embodiment P1 to Embodiment P7, wherein said particle is bound to a discrete site on a solid support.

Embodiment P10. The particle of any one of Embodiment P1 to Embodiment P7, wherein said particle is in a well of a multiwell container.

Embodiment P11. The particle of any one of Embodiment P1 to Embodiment P10, wherein the target polynucleotide does not comprise a universal primer binding sequence.

Embodiment P12. The particle of any one of Embodiment P1 to Embodiment P11, further comprising an immobilized target polynucleotide comprising, from 5' to 3', the target polynucleotide sequence or a complement thereof, and a sequence complementary the second sequence.

Embodiment P13. The particle of any one of Embodiment P1 to Embodiment P12, wherein each particle further comprises a plurality of azide moieties, alkyne moieties, dibenzocyclooctyne (DBCO) moieties, epoxy moieties, or isocyanate moieties.

Embodiment P14. The particle of any one of Embodiment P1 to Embodiment P13, wherein the average longest dimension of said particle is from about 100 nm to about 1000 nm.

Embodiment P15. The particle of any one of Embodiment P1 to Embodiment P13, wherein the average longest dimension of said particle is from about 150 nm to about 600 nm.

Embodiment P16. The particle of any one of Embodiment P1 to Embodiment P15, wherein said particle comprises glass, ceramic, metal, silica, magnetic material, or a paramagnetic material.

Embodiment P17. The particle of any one of Embodiment P1 to Embodiment P15, wherein said particle is a polymer particle comprising polymerized units of polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, polyethylene glycol (PEG)-thiol/PEG-acrylate, acrylamide/N,N'-bis(acryloyl) cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly (vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof.

Embodiment P18. The particle of any one of Embodiment P1 to P13, wherein said particle comprises a particle core and a particle shell, wherein said particle shell comprises a plurality of bioconjugate reactive moieties, wherein each of said bioconjugate reactive moieties and each of said immobilized oligonucleotides comprise a linker binding said bioconjugate reactive moieties and oligonucleotide to said particle core.

Embodiment P19. The particle of Embodiment P18, wherein said particle core comprises glass, ceramic, metal, silica, magnetic material, or a paramagnetic material, and further wherein said particle shell comprises polymerized units of polyacrylamide (AAm), glicydyl methacrylate (GMA), glicydyl methacrylate (GMA)-azide, polyethylene glycol methacrylate (PEGMA), polyethylene glycol methacrylate (PEGMA), isocyanatoethyl methacrylate (IEM), or a copolymer thereof.

Embodiment P20. A plurality of particles, wherein each of said particles comprises a particle of any one of Embodiment P1 to Embodiment P19.

Embodiment P21. The plurality of Embodiment P20, wherein one or more particles comprise a first sequence complementary to a first endogenous region of different target polynucleotides.

Embodiment P22. The plurality of Embodiment P20 or Embodiment P21, wherein at least 1%, 5%, 10%, 15%, 20%, 25% or more of said particles comprise a first sequence complementary to a first endogenous region of different target polynucleotides.

Embodiment P23. The plurality of Embodiment P20 or Embodiment P21, wherein at least 10%, 20%, 30%, 40%, 50% or more of said particles comprise a first sequence complementary to a first endogenous region of different target polynucleotides.

Embodiment P24. The plurality of Embodiment P20 or Embodiment P21, wherein at least 50%, 75%, 90%, 95%, 99% or more of said particles comprise a first sequence complementary to a first endogenous region of different target polynucleotides.

Embodiment P25. The plurality of any one of Embodiment P20 to Embodiment P24, wherein each particle of the plurality is bound to a solid support.

Embodiment P26. The plurality of any one of Embodiment P20 to Embodiment P24, wherein one or more particles of the plurality is in a well of a multiwell container.

Embodiment P27. The plurality of Embodiment P26, wherein greater than 50%, 60%, 70%, 80%, 90% or 95% of the wells comprise a particle.

Embodiment P28. The plurality of Embodiment P26, wherein each of the wells are separated from each other by about 0.2 μm to about 2.0 μm.

Embodiment P29. The plurality of Embodiment P26, wherein each the wells are from about 0.2 m to about 2 μm in diameter, and wherein the wells are about 0.5 μm to about 2 μm in depth.

Embodiment P30. The plurality of any one of Embodiment P20 to Embodiment P24, wherein each particle is bound to a discrete site on solid support, wherein each discrete site of the solid support is separated by an interstitial region.

Embodiment P31. A solid support comprising the plurality of any one of Embodiment P20 to Embodiment P24.

Embodiment P32. A microfluidic device comprising the plurality of any one of Embodiment P20 to Embodiment P24.

Embodiment P33. A method of generating immobilized complements of a plurality of target polynucleotides, the method comprising: a) annealing a plurality of target polynucleotides to one or more particles comprising the first plurality of immobilized oligonucleotides of any one of Embodiment P1 to Embodiment P32; and b) extending the immobilized oligonucleotides with a polymerase to generate a plurality of immobilized complements of the plurality of target polynucleotides.

Embodiment P34. The method of Embodiment P33, further comprising: c) annealing the immobilized complements of the target polynucleotides to the second plurality of immobilized oligonucleotides; and d) extending the second plurality of immobilized oligonucleotides thereby generating a plurality of immobilized target polynucleotides.

Embodiment P35. The method of Embodiment P34, further comprising repeating steps a) to d), thereby amplifying the plurality of target polynucleotides.

Embodiment P36. The method of any one of Embodiment P32 to Embodiment P35, further comprising contacting the immobilized target polynucleotides with a sequencing primer, extending the sequencing primer to incorporate a detectable label that indicates the identity of a nucleotide in the target polynucleotides, detecting the detectable label, and repeating the extending and detecting steps, thereby sequencing the target polynucleotides.

Embodiment P37. A method of immobilizing a first oligonucleotide and a second oligonucleotide to a particle, the method comprising: i) annealing a first primer to a first oligonucleotide, wherein said first primer comprises, from 5' to 3', a bioconjugate reactive moiety and a first primer binding sequence, and wherein said first oligonucleotide comprises, from 3' to 5', a sequence complementary to the first primer binding sequence and a sequence capable of hybridizing to the complement of the first endogenous region of the target polynucleotide; ii) annealing a second primer to a second oligonucleotide, wherein said second primer comprises, from 5' to 3', a bioconjugate reactive moiety and a second primer binding sequence, and wherein said second oligonucleotide comprises, from 3' to 5', a sequence complementary to the second primer binding sequence and a sequence capable of hybridizing to the second region of the target polynucleotide; iii) extending the first and second primers with a polymerase to generate first and second extension products, thereby forming a first double-stranded oligonucleotide and a second double-stranded oligonucleotide; iv) contacting the bioconjugate moiety of the double-stranded oligonucleotides with a particle comprising one or more complementary bioconjugate moieties and forming a bioconjugate linker, thereby immobilizing the first oligonucleotide and the second oligonucleotide to the particle.

Embodiment P38. A solid support comprising two or more wells, wherein each well comprises a first plurality of immobilized oligonucleotides and a second plurality of immobilized oligonucleotides, wherein one or more of the first plurality comprise a first sequence capable of hybridizing to a first endogenous region of a target polynucleotide, and wherein one or more of the second plurality comprise a second sequence capable of hybridizing to the complement of a second endogenous region of said target polynucleotide.

Embodiment P39. The solid support of Embodiment P38, wherein both the first endogenous region and the second endogenous region comprise a gene or a fragment thereof.

Embodiment P40. The solid support of Embodiment P38 or Embodiment P39, wherein one or more wells comprise a first sequence complementary to a first endogenous region of different target polynucleotides.

Embodiment P41. The solid support of any one of Embodiment P38 to Embodiment P40, wherein at least 1%, 5%, 10%, 15%, 20%, 25% or more of the wells comprise a first sequence complementary to a first endogenous region of different target polynucleotides.

Embodiment P42. The solid support of any one of Embodiment P38 to Embodiment P40, wherein at least 10%, 20%, 30%, 40%, 50% or more of the wells comprise a first sequence complementary to a first endogenous region of different target polynucleotides.

Embodiment P43. The solid support of any one of Embodiment P38 to Embodiment P40, wherein at least 50%, 75%, 90%, 95%, 99% or more of the wells comprise a first sequence complementary to a first endogenous region of different target polynucleotides.

Embodiment P44. The solid support of any one of Embodiment P38 to Embodiment P43, wherein each well of the solid support is separated by an interstitial region.

Embodiment P45. The solid support of any one of Embodiment P38 to Embodiment P44, wherein the solid support is a flow cell.

Embodiment P46. The solid support of any one of Embodiment P38 to Embodiment P45, wherein the solid support comprises about 0.2 wells to about 4.0 wells per $\mu m^2$.

Embodiment P47. The solid support of any one of Embodiment P38 to Embodiment P46, wherein each well is from about 0.2 μm to about 2 μm in diameter, and from about 0.5 μm to about 2 μm in depth.

Embodiment P48. The solid support of any one of Embodiment P38 to Embodiment P47, wherein each of the wells are separated from each other by about 0.2 μm to about 2.0 μm.

Embodiment P49. A particle comprising a first plurality of immobilized oligonucleotides and a second plurality of immobilized oligonucleotides, wherein one or more of the first plurality comprise a first sequence capable of hybridizing to a first endogenous region of a target polynucleotide, and wherein one or more of the second plurality comprise a second sequence capable of hybridizing to the complement of a second endogenous region of said target polynucleotide.

Embodiment P50. The particle of Embodiment P49, wherein both the first endogenous region and the second endogenous region comprise a gene or a fragment thereof.

Embodiment P51. A plurality of particles, wherein each of said particles comprises the particle of Embodiment P49 or Embodiment P50.

Embodiment P52. The plurality of Embodiment P51, wherein one or more particles comprise a first sequence complementary to a first endogenous region of different target polynucleotides.

Embodiment P53. The plurality of Embodiment P51 or Embodiment P52, wherein at least 1%, 5%, 10%, 15%, 20%, 25% or more of said particles comprise a first sequence complementary to a first endogenous region of different target polynucleotides.

Embodiment P54. The plurality of Embodiment P51 or Embodiment P52, wherein at least 10%, 20%, 30%, 40%, 50% or more of said particles comprise a first sequence complementary to a first endogenous region of different target polynucleotides.

Embodiment P55. The plurality of Embodiment P51 or Embodiment P52, wherein at least 50%, 75%, 90%, 95%, 99% or more of said particles comprise a first sequence complementary to a first endogenous region of different target polynucleotides.

Embodiment P56. A solid support comprising the plurality of any one of Embodiment P51 to Embodiment P55.

Embodiment P57. A microfluidic device comprising the solid support of any one of Embodiment P38 to Embodiment P48 or Embodiment P56 or the plurality of any one of Embodiment P51 to Embodiment P55.

Embodiment P58. A method of immobilizing a first oligonucleotide and a second oligonucleotide to a particle, the method comprising: i) annealing a first primer to the first oligonucleotide, wherein said first primer comprises, from 5' to 3', a bioconjugate reactive moiety and a first primer binding sequence, and wherein said first oligonucleotide comprises, from 3' to 5', a sequence complementary to the first primer binding sequence and a sequence capable of hybridizing to the complement of a first endogenous region of a target polynucleotide; ii) annealing a second primer to the second oligonucleotide, wherein said second primer comprises, from 5' to 3', a bioconjugate reactive moiety and a second primer binding sequence, and wherein said second oligonucleotide comprises, from 3' to 5', a sequence complementary to the second primer binding sequence and a sequence capable of hybridizing to a second endogenous region of the target polynucleotide; iii) extending the first and second primers with a polymerase to generate first and second extension products, thereby forming a first double-stranded oligonucleotide and a second double-stranded oligonucleotide; and iv) contacting the bioconjugate moieties of the double-stranded oligonucleotides with a particle comprising one or more complementary bioconjugate moieties and forming a bioconjugate linker, thereby immobilizing the first oligonucleotide and the second oligonucleotide to the particle.

Embodiment P59. A method of generating immobilized complements of a plurality of target polynucleotides, the method comprising: a) contacting the solid support of any one of Embodiment P38 to Embodiment P48 with a sample comprising a plurality of target polynucleotides and annealing two or more target polynucleotides to the first plurality of immobilized oligonucleotides; and b) extending the immobilized oligonucleotides with a polymerase to generate a plurality of immobilized complements of the plurality of target polynucleotides.

Embodiment P60. The method of Embodiment P59, further comprising c) annealing the immobilized complements of the target polynucleotides to the second plurality of immobilized oligonucleotides; and d) extending the second plurality of immobilized oligonucleotides thereby generating a plurality of immobilized target polynucleotides.

Embodiment P61. The method of Embodiment P60, further comprising repeating steps a) to d), thereby amplifying the plurality of target polynucleotides.

Additional Embodiments

The present disclosure provides the following additional illustrative embodiments.

Embodiment 1. A solid support comprising two or more wells, wherein each well comprises a first plurality of immobilized oligonucleotides and a second plurality of immobilized oligonucleotides, wherein one or more of the immobilized oligonucleotides of said first plurality comprise a first sequence capable of hybridizing to a first endogenous region of a target polynucleotide, and wherein one or more of the immobilized oligonucleotides of said second plurality comprise a second sequence capable of hybridizing to the complement of a second endogenous region of said target polynucleotide; optionally wherein said target polynucleotide does not comprise an adapter (e.g., an engineered sequence), and said first endogenous region and said second endogenous region are polynucleotide sequences of a biological sample.

Embodiment 2. The solid support of Embodiment 1, wherein both the first endogenous region and the second endogenous region comprise a gene or a fragment thereof.

Embodiment 3. The solid support of Embodiment 1 or 2, wherein one or more wells comprise a first sequence complementary to a first endogenous region of different target polynucleotides.

Embodiment 4. The solid support of any one of Embodiments 1 to 3, wherein at least 1%, 5%, 10%, 15%, 20%, 25% or more of the wells comprise a first sequence complementary to a first endogenous region of different target polynucleotides.

Embodiment 5. The solid support of any one of Embodiments 1 to 3, wherein at least 10%, 20%, 30%, 40%, 50% or more of the wells comprise a first sequence complementary to a first endogenous region of different target polynucleotides.

Embodiment 6. The solid support of any one of Embodiments 1 to 3, wherein at least 50%, 75%, 90%, 95%, 99% or more of the wells comprise a first sequence complementary to a first endogenous region of different target polynucleotides.

Embodiment 7. The solid support of any one of Embodiments 1 to 6, wherein each well of the solid support is separated by an interstitial region.

Embodiment 8. The solid support of any one of Embodiments 1 to 7, wherein the solid support is a flow cell.

Embodiment 9. The solid support of any one of Embodiments 1 to 7, wherein the solid support comprises 2, 4, 6, 12, 24, 48, 96, 384, or 1536 wells.

Embodiment 10. The solid support of Embodiment 9, wherein each well is about 5 mm to about 8 mm in diameter.

Embodiment 11. The solid support of any one of Embodiments 1 to 8, wherein each well comprises a plurality of nanowells.

Embodiment 12. The solid support of Embodiment 11, wherein each nanowell is about 0.1 m to about 3 2 µm in depth, and wherein the nanowells are about 0.1 µm to about 2 µm in depth.

Embodiment 13. The solid support of any one of Embodiments 1 to 8, 11, or 12, wherein the solid support comprises about 0.2 wells to about 4.0 wells per µm$^2$.

Embodiment 14. The solid support of any one of Embodiments 1 to 8, or 11-13, wherein each well is from about 0.2 µm to about 2 µm in diameter, and from about 0.5 µm to about 2 µm in depth.

Embodiment 15. The solid support of any one of Embodiments 1 to 8, or 11-15, wherein each of the wells are separated from each other by about 0.2 µm to about 2.0 µm.

Embodiment 16. A particle comprising a first plurality of immobilized oligonucleotides and a second plurality of immobilized oligonucleotides, wherein one or more of the immobilized oligonucleotides of said first plurality comprise a first sequence capable of hybridizing to a first endogenous region of a target polynucleotide, and wherein one or more of the immobilized oligonucleotides of said second plurality comprise a second sequence capable of hybridizing to the complement of a second endogenous region of said target polynucleotide optionally wherein said target polynucleotide does not comprise an adapter, and said first endogenous region and said second endogenous region are polynucleotide sequences of a biological sample.

Embodiment 17. The particle of Embodiment 16, wherein both the first endogenous region and the second endogenous region comprise a gene or a fragment thereof.

Embodiment 18. A plurality of particles, wherein each of said particles comprises the particle of Embodiment 16 or 17.

Embodiment 19. The plurality of Embodiment 18, wherein one or more particles comprise a first sequence complementary to a first endogenous region of different target polynucleotides.

Embodiment 20. The plurality of Embodiment 18 or 19, wherein at least 1%, 5%, 10%, 15%, 20%, 25% or more of said particles comprise a first sequence complementary to a first endogenous region of different target polynucleotides.

Embodiment 21. The plurality of Embodiment 18 or 19, wherein at least 10%, 20%, 30%, 40%, 50% or more of said particles comprise a first sequence complementary to a first endogenous region of different target polynucleotides.

Embodiment 22. The plurality of claim 18, wherein at least 50%, 75%, 90%, 95%, 99% or more of said particles comprise a first sequence complementary to a first endogenous region of different target polynucleotides.

Embodiment 23. A solid support comprising the plurality of any one of Embodiments 18 to 22.

Embodiment 24. A microfluidic device comprising the solid support of any one of Embodiments 1 to 15 or 23.

Embodiment 25. A solid support comprising a first well and a second well, wherein said first well comprises a plurality of immobilized oligonucleotides comprising a first sequence capable of hybridizing to an endogenous region of a first target polynucleotide, and a plurality of immobilized oligonucleotides comprising a second sequence capable of hybridizing to the complement of an endogenous region of said first target polynucleotide; and wherein said second well comprises a plurality of immobilized oligonucleotides comprising a third sequence capable of hybridizing to an endogenous region of a second target polynucleotide, and a plurality of immobilized oligonucleotides comprising a fourth sequence capable of hybridizing to the complement of an endogenous region of said second target polynucleotide; optionally wherein said target polynucleotide does not comprise an adapter, and said first endogenous region and said second endogenous region are polynucleotide sequences of a biological sample.

Embodiment 26. The solid support of Embodiment 25, wherein both the first endogenous region and the second endogenous region comprise a gene or a fragment thereof.

Embodiment 27. The solid support of Embodiment 25 or 26, wherein one or more wells comprise a first sequence complementary to a first endogenous region of different target polynucleotides.

Embodiment 28. The solid support of any one of Embodiments 25 to 27, wherein at least 1%, 5%, 10%, 15%, 20%, 25% or more of the wells comprise a first sequence complementary to a first endogenous region of different target polynucleotides.

Embodiment 29. The solid support of any one of Embodiments 25 to 27, wherein at least 10%, 20%, 30%, 40%, 50% or more of the wells comprise a first sequence complementary to a first endogenous region of different target polynucleotides.

Embodiment 30. The solid support of any one of Embodiments 25 to 27, wherein at least 50%, 75%, 90%, 95%, 99% or more of the wells comprise a first sequence complementary to a first endogenous region of different target polynucleotides.

Embodiment 31. The solid support of any one of Embodiments 25 to 30, wherein each well of the solid support is separated by an interstitial region.

Embodiment 32. The solid support of any one of Embodiments 25 to 31, wherein the solid support is a flow cell.

Embodiment 33. The solid support of any one of Embodiments 25 to 31, wherein the solid support comprises 2, 4, 6, 12, 24, 48, 96, 384, or 1536 wells.

Embodiment 34. The solid support of Embodiment 33, wherein each well is about 5 mm to about 8 mm in diameter.

Embodiment 35. The solid support of any one of Embodiments 25 to 32, wherein each well comprises a plurality of nanowells.

Embodiment 36. The solid support of Embodiment 35, wherein each nanowell is about 0.1 m to about 3 2 µm in depth, and wherein the nanowells are about 0.1 µm to about 2 µm in depth.

Embodiment 37. The solid support of any one of Embodiments 25 to 32, 35, or 36, wherein the solid support comprises about 0.2 wells to about 4.0 wells per $µm^2$.

Embodiment 38. The solid support of any one of Embodiments 25 to 32, or 35-37, wherein each well is from about 0.2 µm to about 2 µm in diameter, and from about 0.5 µm to about 2 µm in depth.

Embodiment 39. The solid support of any one of Embodiments 25 to 32, or 35-38, wherein each of the wells are separated from each other by about 0.2 µm to about 2.0 µm.

Embodiment 40. A microfluidic device comprising the solid support of any one of Embodiments 25 to 39.

Embodiment 41. A method of immobilizing a first oligonucleotide and a second oligonucleotide to a particle, the method comprising: i) annealing a first primer to the first oligonucleotide, wherein said first primer comprises, from 5' to 3', a bioconjugate reactive moiety and a first primer binding sequence, and wherein said first oligonucleotide comprises, from 3' to 5', a sequence complementary to the first primer binding sequence and a sequence capable of hybridizing to the complement of a first endogenous region of a target polynucleotide; ii) annealing a second primer to the second oligonucleotide, wherein said second primer comprises, from 5' to 3', a bioconjugate reactive moiety and a second primer binding sequence, and wherein said second oligonucleotide comprises, from 3' to 5', a sequence complementary to the second primer binding sequence and a sequence capable of hybridizing to a second endogenous region of the target polynucleotide; iii) extending the first and second primers with a polymerase to generate first and second extension products, thereby forming a first double-stranded oligonucleotide and a second double-stranded oligonucleotide; and iv) contacting the bioconjugate moieties of the double-stranded oligonucleotides with a particle comprising one or more complementary bioconjugate moieties and forming a bioconjugate linker, thereby immobilizing the first oligonucleotide and the second oligonucleotide to the particle.

Embodiment 42. The method of Embodiment 41, wherein the average longest dimension of the particle is about 100 nm to about 3000 nm.

Embodiment 43. The method of Embodiment 41 or 42, wherein said particle comprises a metal-organic framework (MOF) particle.

Embodiment 44. The method of any one of Embodiment 41 to 43, further comprising contacting a solid support with the particle.

Embodiment 45. A method of generating immobilized complements of a plurality of target polynucleotides, the method comprising: a) contacting the solid support of any one of Embodiments 1 to 15, 23, or 25 to 39 with a sample comprising a plurality of target polynucleotides and annealing two or more target polynucleotides to the first plurality of immobilized oligonucleotides; and b) extending the immobilized oligonucleotides with a polymerase to generate a plurality of immobilized complements of the plurality of target polynucleotides, optionally wherein said target polynucleotide does not comprise an adapter, and said first endogenous region and said second endogenous region are polynucleotide sequences of a biological sample.

Embodiment 46. The method of Embodiment 45, further comprising c) annealing the immobilized complements of the target polynucleotides to the second plurality of immobilized oligonucleotides; and d) extending the second plurality of immobilized oligonucleotides thereby generating a plurality of immobilized target polynucleotides.

Embodiment 47. The method of Embodiment 46, further comprising repeating steps a) to d), thereby amplifying the plurality of target polynucleotides.

Embodiment 48. The method of any one of Embodiments 45 to 47, further comprising sequencing the target polynucleotides.

Embodiment 49. The method of any one of Embodiments 45 to 48, further comprising denaturing the two or more target polynucleotides and repeating steps a) and b).

Embodiment 50. A solid support comprising two or more wells, wherein each well comprises a first immobilized oligonucleotide and a second immobilized oligonucleotide, wherein the first immobilized oligonucleotide comprises a sequence capable of hybridizing to a sequence of a target polynucleotide, and wherein the second immobilized oligonucleotide comprises a sequence capable of hybridizing to a complementary sequence of said target polynucleotide, wherein said target polynucleotide does not comprise a common primer binding sequence, optionally wherein said target polynucleotide does not comprise an adapter, and said first endogenous region and said second endogenous region are polynucleotide sequences of a biological sample.

Embodiment 51. A method of amplifying a target polynucleotide, said method comprising: contacting a solid support of with a plurality of target polynucleotides, wherein said target polynucleotides do not include a common primer binding sequence, wherein the solid support comprises two or more wells comprising a first plurality of immobilized oligonucleotides and a second plurality of immobilized oligonucleotides; hybridizing a target polynucleotide to a first immobilized oligonucleotide from the first plurality, and extending with a polymerase the first immobilized oligonucleotide to generate a first extension product; hybridizing the first extension product to a second immobilized oligonucleotide from the second plurality, and extending with a polymerase the second immobilized oligonucleotide to generate a second extension product; and hybridizing the second extension product to a third immobilized oligonucleotide from the first plurality, and extending with a polymerase the third immobilized oligonucleotide to generate a third extension product, optionally wherein said target polynucleotide does not comprise an adapter, and said first endogenous region and said second endogenous region are polynucleotide sequences of a biological sample.

Embodiment 52. The method of Embodiment 51, further comprising sequencing the first extension product, the second extension product, and the third extension product.

---

What is claimed is:

1. A method of sequencing, said method comprising
contacting a solid support with a sample comprising a first target polynucleotide and a second target polynucleotide, wherein said first target polynucleotide is different from said second target polynucleotide, and wherein said solid support comprises
a first oligonucleotide attached to wells of the solid support at its 5' end, comprising a sequence capable of hybridizing to a first endogenous region of the first target polynucleotide and a sequencing primer binding sequence, and a second oligonucleotide comprising a sequence capable of hybridizing to the complement of a second endogenous region of said first target polynucleotide; and
a third oligonucleotide attached to wells of the solid support at its 5' end, comprising a sequence capable of hybridizing to a first endogenous region of the second target polynucleotide and the sequencing primer binding sequence, and a fourth oligonucleotide comprising a sequence capable of hybridizing to the complement of a second endogenous region of said second target polynucleotide;
forming a first extension product comprising the sequencing primer binding sequence by hybridizing the first target polynucleotide to the first oligonucleotide and extending the first oligonucleotide; forming a second extension product comprising the sequencing primer binding sequence by a hybridizing the second target polynucleotide to the third oligonucleotide and extending the third oligonucleotide; and
sequencing the first extension product and sequencing the second extension product, wherein said sequencing the first extension product and sequencing the second extension product comprises hybridizing a sequencing primer to the sequencing primer binding sequence of each of the first extension product and sequencing the second extension product, binding one or more labeled nucleotides to the hybridized sequencing primer, and detecting the bound labeled nucleotides,
wherein the solid support comprises 2, 4, 6, 12, 24, 48, 96, 384, or 1536 wells, wherein each of the wells comprises a plurality of nanowells, wherein each of the nanowells is about 0.1 µm to about 2.0 µm in depth, and about 0.1 µm to about 2.0 µm in diameter.

2. The method of claim 1, wherein both the first endogenous region and the second endogenous region of the first target polynucleotide comprise a gene or its fragment thereof.

3. The method of claim 1, wherein each of the wells is about 5 mm to about 8 mm in diameter.

4. The method of claim 1, wherein the wells of the solid support comprises a density of about 0.2 wells to about 4.0 wells per µm.

5. The method of claim 1, wherein each of the nanowells is separated from each other by a distance from about 0.2 µm to about 2.0 µm.

6. The method of claim 1, wherein said sequencing the first extension product and said sequencing the second extension product are performed by sequencing-by-synthesis, sequencing-by-ligation, or sequencing-by-binding.

7. The method of claim 1, wherein said sequencing the first extension product and said sequencing the second extension product are performed by sequencing-by-synthesis.

8. The method of claim 1, wherein the sequencing primer binding sequence comprises SEQ ID NO:1, or its full complement thereof, or SEQ ID NO:2, or its full complement thereof, or SEQ ID NO:3, or its full complement thereof, or SEQ ID NO:4, or its full complement thereof.

9. The method of claim 1, wherein the first target polynucleotide and the second target polynucleotide do not comprise a common primer binding sequence.

10. The method of claim 1, wherein the first oligonucleotide, second oligonucleotide, third oligonucleotide, and fourth oligonucleotide comprise about 30, about 35, about 40, about 45, about 50, or about 55 nucleotides.

11. The method of claim 1, wherein the first oligonucleotide, second oligonucleotide, third oligonucleotide, and fourth oligonucleotide comprise 30 or more than 30 nucleotides.

12. The method of claim 1, prior to said sequencing the first extension product and said sequencing the second extension product, generating amplification products by amplifying the first extension product and the second extension product.

13. The method of claim 12, further comprising sequencing the amplification products.

14. The method of claim 1, wherein the first target polynucleotide is a linear single stranded DNA polynucleotide and the second target polynucleotide is a linear single stranded DNA polynucleotide.

15. The method of claim 1, wherein the sequencing primer binding sequence comprises SEQ ID NO: 1, or its full complement thereof, or SEQ ID NO:4, or its full complement thereof.

16. A method of sequencing, said method comprising
contacting a solid support with a first target polynucleotide and a second target polynucleotide which is different from the first target polynucleotide, wherein the solid support comprises 2, 4, 6, 12, 24, 48, 96, 384, or 1536 wells, wherein each of the wells comprises a plurality of nanowells, wherein each of the nanowells is about 0.1 µm to about 2.0 µm in depth, and about 0.1 µm to about 2.0 µm in diameter;
forming a first extension product by hybridizing the first target polynucleotide to a first oligonucleotide and extending the first oligonucleotide; wherein the first oligonucleotide is attached to the wells of the solid support at its 5' end and comprises a sequence capable of hybridizing to an endogenous region of the first target polynucleotide and a sequencing primer binding sequence;

forming a second extension product by hybridizing the second target polynucleotide to a second oligonucleotide and extending the second oligonucleotide; wherein the second oligonucleotide is attached to the wells of the solid support at its 5' end and comprises a sequence capable of hybridizing to an endogenous region of the second target polynucleotide and the sequencing primer binding sequence; and sequencing the first extension product and sequencing the second extension product, wherein each of the first extension product and the second extension product comprises the sequencing primer binding sequence and said sequencing the first extension product and sequencing the second extension product comprises hybridizing a sequencing primer to the sequencing primer binding sequence of each of the first extension product and the second extension product, binding one or more labeled nucleotides to the hybridized sequencing primer, and detecting the bound labeled nucleotides.

17. The method of claim 16, wherein the endogenous region of each of said first target polynucleotide and said second target polynucleotide comprises a gene or its fragment thereof.

18. The method of claim 16, wherein the first target polynucleotide and the second target polynucleotide do not comprise a common primer binding sequence.

19. A method of sequencing, said method comprising contacting a solid support with a sample comprising a first target polynucleotide and a second target polynucleotide, wherein said first target polynucleotide is different from said second target polynucleotide, and wherein said solid support comprises a first oligonucleotide attached to the solid support at its 5' end a sequence capable of hybridizing to an endogenous region of the first target polynucleotide and a sequencing primer binding sequence; and a second oligonucleotide attached to the solid support at its 5' end a sequence capable of hybridizing to an endogenous region of the second target polynucleotide and the sequencing primer binding sequence;

forming a first extension product comprising the sequencing primer binding sequence by hybridizing the first target polynucleotide to the first oligonucleotide and extending the first oligonucleotide; forming a second extension product comprising the sequencing primer binding sequence by hybridizing the second target polynucleotide to the second oligonucleotide and extending the second oligonucleotide; and sequencing the first extension product and sequencing the second extension product, wherein said sequencing the first extension product and sequencing the second extension product comprises hybridizing a sequencing primer to the sequencing primer binding sequence, binding one or more labeled nucleotides to the hybridized sequencing primer, and detecting the bound labeled nucleotides, wherein the sequencing primer binding sequence comprises SEQ ID NO:1, or its full complement thereof, or SEQ ID NO:2, or its full complement thereof, or SEQ ID NO:3, or its full complement thereof.

20. The method of claim 19, wherein the endogenous region of each of said first target polynucleotide and said second target polynucleotide comprises a gene or its fragment thereof.

21. The method of claim 19, wherein the first target polynucleotide and the second target polynucleotide do not comprise a common primer binding sequence.

* * * * *

SEQUENCE LISTING

```
Sequence total quantity: 6
SEQ ID NO: 1            moltype = DNA  length = 31
FEATURE                 Location/Qualifiers
source                  1..31
                        mol_type = other DNA
                        organism = synthetic construct
SEQUENCE: 1
gatcggaaga gcacacgtct gaactccagt c                                31

SEQ ID NO: 2            moltype = DNA  length = 29
FEATURE                 Location/Qualifiers
source                  1..29
                        mol_type = other DNA
                        organism = synthetic construct
SEQUENCE: 2
agtggttggt gagggtcatc tcgctggag                                   29

SEQ ID NO: 3            moltype = DNA  length = 29
FEATURE                 Location/Qualifiers
source                  1..29
                        mol_type = other DNA
                        organism = synthetic construct
SEQUENCE: 3
acaaaggcag ccacgcactc cttccctgt                                   29

SEQ ID NO: 4            moltype = DNA  length = 33
FEATURE                 Location/Qualifiers
source                  1..33
                        mol_type = other DNA
                        organism = synthetic construct
SEQUENCE: 4
acactctttc cctacacgac gctcttccga tct                              33

SEQ ID NO: 5            moltype = DNA  length = 19
FEATURE                 Location/Qualifiers
source                  1..19
                        mol_type = other DNA
                        organism = synthetic construct
SEQUENCE: 5
aatgatacgg cgaccaccg                                              19
```

```
SEQ ID NO: 6           moltype = DNA   length = 21
FEATURE                Location/Qualifiers
source                 1..21
                       mol_type = other DNA
                       organism = synthetic construct
SEQUENCE: 6
caagcagaag acggcatacg a                                                       21
```